(12) United States Patent
Ikeda et al.

(10) Patent No.: US 11,155,525 B2
(45) Date of Patent: Oct. 26, 2021

(54) AZOLE DERIVATIVES AS APELIN RECEPTOR AGONIST

(71) Applicant: Sanford Burnham Prebys Medical Discovery Institute, La Jolla, CA (US)

(72) Inventors: Takuya Ikeda, Tokyo (JP); Yoshiyuki Kobayashi, Tokyo (JP); Naoki Miyoshi, Tokyo (JP); Osamu Suzuki, Tokyo (JP); Takahiro Nagayama, Tokyo (JP); Takashi Tsuji, Tokyo (JP); Layton H. Smith, Orlando, FL (US); Anthony B. Pinkerton, Rancho Santa Fe, CA (US)

(73) Assignee: SANFORD BURNHAM PREBYS MEDICAL DISCOVERY INSTITUTE, La Jolla, CA (US)

( * ) Notice: Subject to any disclaimer, the term of this patent is extended or adjusted under 35 U.S.C. 154(b) by 0 days.

(21) Appl. No.: 16/853,604

(22) Filed: Apr. 20, 2020

(65) Prior Publication Data
US 2020/0347022 A1 Nov. 5, 2020

Related U.S. Application Data

(62) Division of application No. 15/778,168, filed as application No. PCT/US2016/063152 on Nov. 21, 2016, now Pat. No. 10,626,096.

(60) Provisional application No. 62/259,336, filed on Nov. 24, 2015.

(51) Int. Cl.
| C07D 249/12 | (2006.01) |
| G16B 25/00 | (2019.01) |
| G16C 99/00 | (2019.01) |
| C07D 403/12 | (2006.01) |
| C07D 403/06 | (2006.01) |
| G16C 20/50 | (2019.01) |
| A61P 9/10 | (2006.01) |
| A61P 3/10 | (2006.01) |
| A61P 9/12 | (2006.01) |
| A61P 13/12 | (2006.01) |
| A61P 9/04 | (2006.01) |
| C07D 401/04 | (2006.01) |
| C07D 405/04 | (2006.01) |
| C07D 405/14 | (2006.01) |
| C07D 409/04 | (2006.01) |
| C07D 409/14 | (2006.01) |
| C07D 413/14 | (2006.01) |
| C07D 417/14 | (2006.01) |
| C07D 487/04 | (2006.01) |

(52) U.S. Cl.
CPC .............. *C07D 249/12* (2013.01); *A61P 3/10* (2018.01); *A61P 9/04* (2018.01); *A61P 9/10* (2018.01); *A61P 9/12* (2018.01); *A61P 13/12* (2018.01); *C07D 401/04* (2013.01); *C07D 403/06* (2013.01); *C07D 403/12* (2013.01); *C07D 405/04* (2013.01); *C07D 405/14* (2013.01); *C07D 409/04* (2013.01); *C07D 409/14* (2013.01); *C07D 413/14* (2013.01); *C07D 417/14* (2013.01); *C07D 487/04* (2013.01); *G16B 25/00* (2019.02); *G16C 20/50* (2019.02); *G16C 99/00* (2019.02)

(58) Field of Classification Search
CPC .................................................. C07D 249/12
See application file for complete search history.

(56) References Cited

U.S. PATENT DOCUMENTS

| 6,046,227 A | 4/2000 | Crowell et al. |
| 10,626,096 B2 | 4/2020 | Ikeda et al. |

(Continued)

FOREIGN PATENT DOCUMENTS

| WO | WO-2006044602 A2 | 4/2006 |
| WO | WO-2007034277 A1 | 3/2007 |

(Continued)

OTHER PUBLICATIONS

Ferreira et al. Synthesis and evaluation of new difluoromethyl azoles as antileishmanial agents. Eur J Med Chem 42(11-12):1388-1395 (2007).

(Continued)

*Primary Examiner* — Paul V Ward
(74) *Attorney, Agent, or Firm* — Wilson Sonsini Goodrich & Rosati

(57) ABSTRACT

The present invention relates to a novel azole derivative as an apelin receptor agonist and a method for treating cardiovascular disease, diabetic disease, renal disease, hypertension, and arteriosclerosis, etc., using the same. The present invention provides a compound represented by formula (I) or a pharmacologically acceptable salt thereof wherein $X^1$ represents —N= or —CH=, $X^2$ represents —CH= or —N=, $R^1$ and $R^2$ each represent a $C_1$ to $C_6$ alkoxy group or the like, $R^3$ represents a heteroaryl group (the heteroaryl group is optionally substituted by a methyl group or the like) or the like, and $R^4$ represents a $C_1$ to $C_6$ alkylthio group or a $C_2$ to $C_6$ alkenyl group (the $C_1$ to $C_6$ alkylthio group and the $C_2$ to $C_6$ alkenyl group are each optionally substituted by one carboxy group or the like) or the like.

(I)

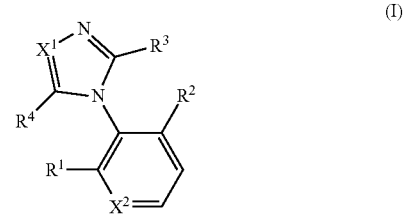

19 Claims, No Drawings

(56) References Cited

U.S. PATENT DOCUMENTS

| | | |
|---|---|---|
| 2002/0072614 A1 | 6/2002 | Luengo et al. |
| 2005/0288347 A1 | 12/2005 | Hodge et al. |
| 2010/0099683 A1 | 4/2010 | Tomkinson et al. |
| 2011/0009397 A1 | 1/2011 | Ying et al. |
| 2011/0101854 A1 | 5/2011 | Inoue et al. |
| 2011/0198988 A1 | 8/2011 | Inoue et al. |
| 2011/0268801 A1 | 11/2011 | Quart et al. |
| 2014/0031374 A1 | 1/2014 | Holsworth et al. |
| 2014/0155370 A1 | 6/2014 | Shacham et al. |

FOREIGN PATENT DOCUMENTS

| | | |
|---|---|---|
| WO | WO-2007047394 A2 | 4/2007 |
| WO | WO-2009070740 A2 | 6/2009 |
| WO | WO-2012154403 A2 | 11/2012 |
| WO | WO-2014044738 A1 | 3/2014 |
| WO | WO-2014085296 A1 | 6/2014 |
| WO | WO-2017091513 A1 | 6/2017 |

OTHER PUBLICATIONS

Modzelewska-Banachiewicz et al. Synthesis and biological activity of (Z) and (E) isomers of 3-(3,4-diary)-1,2,4-triazole-5-yl)prep-2-enoic acid. Monatsh Chem 140:439-444 (2009).

PCT/US2016/063152 International Preliminary Report on Patentability dated Jun. 7, 2018.

PCT/US2016/63152 International Search Report and Written Opinion dated Apr. 28, 2017.

PUBCHEM-CID 1248839 Create Date: Jul. 10, 2005 (Jul. 10, 2005) (12 pgs.).

PUBCHEM-CID 58240243 Create Date: Aug. 19, 2012 (Aug. 19, 2012) (8 pgs.).

U.S. Appl. No. 15/778,168 Office Action dated Aug. 15, 2019.

AZOLE DERIVATIVES AS APELIN RECEPTOR AGONIST

CROSS REFERENCE TO RELATED APPLICATIONS

This application is a divisional of U.S. patent application Ser. No. 15/778,168 filed on May 22, 2018, now U.S. Pat. No. 10,626,096, which was filed pursuant to 35 U.S.C. § 371 as a United States National Phase Application of International Application No. PCT/US2016/063152, filed Nov. 21, 2016, and claims the benefit of U.S. Application No. 62/259,336, filed Nov. 24, 2015, all of which are hereby incorporated by reference in their entirety.

STATEMENT OF JOINT RESEARCH AGREEMENT

The subject matter of the claimed invention was made as a result of activities undertaken within the scope of a joint research agreement, within the meaning of 35 U.S.C. § 102(c), by, or on behalf of, Daiichi Sankyo Company, Limited and Sanford-Burnham Medical Research Institute that was in effect on or before the effective filing date of the claimed invention.

BACKGROUND OF THE INVENTION

Field of the Invention

The present invention relates to a novel azole derivative as apelin receptor agonist, and a method for treating cardiovascular disease, diabetic disease, renal disease, hypertension, and arteriosclerosis, etc., using the same.

Description of the Related Art

With improvement in living standard, circulatory diseases (e.g., cardiovascular disease, diabetic disease, renal disease, and arteriosclerosis) caused by hypertension, hyperlipidemia, hyperglycemia, or the like have become a major problem in recent years. The treatment of the hypertension, the hyperlipidemia, and the hyperglycemia employs antihypertensive drugs, antilipemic drugs, and antidiabetic drugs, respectively. In clinical practice, $\alpha$ and $\beta$ blockers, diuretics, calcium antagonists, ACE inhibitors, and A-II antagonists, etc., are used as the antihypertensive drugs; HMG-CoA reductase inhibitors, anion-exchange resins, nicotinic acid derivatives, probucol, and fibrates, etc., are used as the antilipemic drug; and insulins, sulfonylureas, metformin, and glitazones, etc., are used as the antidiabetic drugs. These drugs contribute to the adjustment of blood pressure and lipid or glucose levels in blood. The rates of death from cardiovascular disease and renal disease, however, have not been largely improved even by use of these pharmaceutical drugs. Thus, there has been a demand for the development of superior therapeutic drugs.

An apelin receptor (also referred to as APJ, APLNR, or AGTRL-1) was identified as a G protein coupled receptor in 1993 (Non Patent Literature 1) and is widely distributed in various tissues in the whole body (Non Patent Literature 2). An endogenous ligand for the apelin receptor was identified in 1998 and is called apelin (Non Patent Literature 3). Apelin is known to include apelin-36 composed of 36 amino acids, apelin-17 composed of 17 amino acids, apelin-13 composed of 13 amino acids, and apelin-12 composed of 12 amino acids. All of these apelins are produced from a precursor (pre-pro-apelin) composed of 77 amino acids through enzymatic cleavage reaction. Apelin has been reported to exhibit a wide range of physiological effects such as a hypotensive effect, a diuretic effect, an effect of enhancing the strength of heart contraction, an antifibrotic effect, a glucose metabolism improving effect, an anti-inflammatory or anti-oxidative stress effect, and an angiogenic effect. Thus, a substance having apelin receptor agonist activity may serve as a therapeutic agent for hypertension, hyperglycemia, and thus circulatory diseases including cardiovascular disease, diabetic disease, renal disease, and arteriosclerosis, etc. (Non Patent Literatures 4 to 21).

Benzimidazole derivatives (Patent Literature 1) are known as low-molecular compounds having apelin receptor agonist activity, but structurally differ from the compound of the present invention.

CITATION LIST

Patent Literature

[Patent Literature 1] International Publication No. WO 2014/044738

Non Patent Literature

[Non Patent Literature 1] Gene 136, 355-360, 1993
[Non Patent Literature 2] Journal of Endocrinology (2013), 219, R13-R35
[Non Patent Literature 3] Biochemical and Biophysical Research Communications 251 (1998) 471-476
[Non Patent Literature 4] Circ Res. 2007; 101: e32-e42
[Non Patent Literature 5] Biochemical and Biophysical Research Communications 308 (2003) 480-485
[Non Patent Literature 6] Circulation 2003; 108: 1432-1439
[Non Patent Literature 7] Cell Metabolism 8, 437-445, Nov. 5, 2008
[Non Patent Literature 8] Regulatory Peptides 131 (2005) 12-17
[Non Patent Literature 9] Endocrinology 152: 59-68, 2011
[Non Patent Literature 10] Am J Physiol Renal Physiol 304: F788-F800, 2013
[Non Patent Literature 11] J Physiol 592.3 (2014) pp 505-521
[Non Patent Literature 12] Am J Physiol Heart Circ Physiol 296: H1329-H1335, 2009
[Non Patent Literature 13] J Am Heart Assoc. 2013; 2: e000249
[Non Patent Literature 14] J Mol Neurosci (2012) 48: 201-208
[Non Patent Literature 15] Experimental and Therapeutic Medicine, 3: 908-914, 2012
[Non Patent Literature 16] Proc. Natl. Acad. Sci. USA, Jul. 13, 2004, vol 101, no. 28 10464-10469
[Non Patent Literature 17] Journal of Neurochemistry, 2001, 77, 1085-1096
[Non Patent Literature 18] Circ Res. 2002; 91: 434-440
[Non Patent Literature 19] Circulation. 2004; 110[suppl II]:II-187-II-193
[Non Patent Literature 20] Circulation 2010; 121: 1818-1827
[Non Patent Literature 21] The journal of biological Chemistry vol 279, No 25, (2004), 26274-26279

An object of the present invention is to provide a novel azole derivative as an apelin receptor agonist, and a method

SUMMARY OF THE INVENTION

The present inventors have found a novel azole derivative as an apelin receptor agonist.

Specifically, the present invention encompasses the following aspects:

[1]

A compound represented by formula (I) or a pharmacologically acceptable salt thereof:

(I)

wherein $X^1$ represents —N= or —CH=,
$X^2$ represents —CH= or —N=,
$R^1$ and $R^2$ each independently represent a $C_1$ to $C_6$ alkyl group, a $C_1$ to $C_6$ alkoxy group, or a halogeno group (the $C_1$ to $C_6$ alkyl group and the $C_1$ to $C_6$ alkoxy group are each optionally substituted by 1 to 3 fluoro groups),
$R^3$ represents an aryl group, a heteroaryl group, a $C_1$ to $C_6$ alkyl group, or a $C_3$ to $C_8$ cycloalkyl group (the aryl group and the heteroaryl group are each optionally substituted by 1 to 3 identical or different groups selected from a $C_1$ to $C_6$ alkyl group, a $C_1$ to $C_6$ alkoxy group, a trifluoromethyl group, and a halogeno group), and
$R^4$ represents a $C_1$ to $C_6$ alkylthio group, an aryl-$C_1$ to $C_6$ alkylthio group, a heteroaryl-$C_1$ to $C_6$ alkylthio group, a $C_3$ to $C_8$ cycloalkyl-$C_1$ to $C_6$ alkylthio group, a heterocycloalkyl-$C_1$ to $C_6$ alkylthio group, a $C_2$ to $C_6$ alkenyl group, an aryl-$C_2$ to $C_6$ alkenyl group, a heteroaryl-$C_2$ to $C_6$ alkenyl group, a $C_3$ to $C_8$ cycloalkyl-$C_2$ to $C_6$ alkenyl group, a heterocycloalkyl-$C_2$ to $C_6$ alkenyl group, a $C_2$ to $C_6$ alkynyl group, an aryl-$C_2$ to $C_6$ alkynyl group, a heteroaryl-$C_2$ to $C_6$ alkynyl group, a $C_3$ to $C_8$ cycloalkyl-$C_2$ to $C_6$ alkynyl group, a heterocycloalkyl-$C_2$ to $C_6$ alkynyl group, a $C_1$ to $C_6$ alkyl group, an aryl-$C_1$ to $C_6$ alkyl group, a heteroaryl-$C_1$ to $C_6$ alkyl group, a $C_3$ to $C_8$ cycloalkyl-$C_1$ to $C_6$ alkyl group, a heterocycloalkyl-$C_1$ to $C_6$ alkyl group, a $C_1$ to $C_6$ alkoxy group, an aryl-$C_1$ to $C_6$ alkoxy group, a heteroaryl-$C_1$ to $C_6$ alkoxy group, a $C_3$ to $C_8$ cycloalkyl-$C_1$ to $C_6$ alkoxy group, a heterocycloalkyl-$C_1$ to $C_6$ alkoxy group, an aryl group, a heteroaryl group, a heterocycloalkyl group, a thiol group, a methylsulfonyl group, a halogeno group, or a hydrogen (the $C_1$ to $C_6$ alkylthio group, the aryl-$C_1$ to $C_6$ alkylthio group, the heteroaryl-$C_1$ to $C_6$ alkylthio group, the $C_3$ to $C_8$ cycloalkyl-$C_1$ to $C_6$ alkylthio group, the heterocycloalkyl-$C_1$ to $C_6$ alkylthio group, the $C_2$ to $C_6$ alkenyl group, the aryl-$C_2$ to $C_6$ alkenyl group, the heteroaryl-$C_2$ to $C_6$ alkenyl group, the $C_3$ to $C_8$ cycloalkyl-$C_2$ to $C_6$ alkenyl group, the heterocycloalkyl-$C_2$ to $C_6$ alkenyl group, the $C_2$ to $C_6$ alkynyl group, the aryl-$C_2$ to $C_6$ alkynyl group, the heteroaryl-$C_2$ to $C_6$ alkynyl group, the $C_3$ to $C_8$ cycloalkyl-$C_2$ to $C_6$ alkynyl group, the heterocycloalkyl-$C_2$ to $C_6$ alkynyl group, the $C_1$ to $C_6$ alkyl group, the aryl-$C_1$ to $C_6$ alkyl group, the heteroaryl-$C_1$ to $C_6$ alkyl group, the $C_3$ to $C_8$ cycloalkyl-$C_1$ to $C_6$ alkyl group, the heterocycloalkyl-$C_1$ to $C_6$ alkyl group, the $C_1$ to $C_6$ alkoxy group, the aryl-$C_1$ to $C_6$ alkoxy group, the heteroaryl-$C_1$ to $C_6$ alkoxy group, the $C_3$ to $C_8$ cycloalkyl-$C_1$ to $C_6$ alkoxy group, the heterocycloalkyl-$C_1$ to $C_6$ alkoxy group, the aryl group, the heteroaryl group, and the heterocycloalkyl group are each optionally substituted by one group, and the heteroaryl-$C_1$ to $C_6$ alkylthio group, the heteroaryl-$C_2$ to $C_6$ alkenyl group, the heteroaryl-$C_2$ to $C_6$ alkynyl group, the heteroaryl-$C_1$ to $C_6$ alkyl group, the heteroaryl-$C_1$ to $C_6$ alkoxy group, and the heteroaryl group are each optionally substituted at the heteroaryl group moiety by 1 to 4 identical or different groups selected from an oxo group, a $C_1$ to $C_6$ alkyl group, and a halogeno group).

[2]

The compound according to [1] or a pharmacologically acceptable salt thereof, wherein $X^1$ is —N=.

[3]

The compound according to [1] or a pharmacologically acceptable salt thereof, wherein $X^2$ is —CH=.

[4]

The compound according to [1] or a pharmacologically acceptable salt thereof, wherein $R^1$ and $R^2$ are each independently a $C_1$ to $C_6$ alkoxy group or a $C_1$ to $C_6$ alkyl group.

[5]

The compound according to [1] or a pharmacologically acceptable salt thereof, wherein $R^1$ and $R^2$ are each independently a methoxy group or an ethyl group.

[6]

The compound according to [1] or a pharmacologically acceptable salt thereof, wherein each of $R^1$ and $R^2$ is a methoxy group.

[7]

The compound according to [1] or a pharmacologically acceptable salt thereof, wherein $R^3$ is a furyl group, a thienyl group, a pyridyl group, a phenyl group, a n-butyl group, or a cyclopentyl group (the furyl group, the thienyl group, the pyridyl group, and the phenyl group are each optionally substituted by 1 or 2 identical or different groups selected from a methyl group and a halogeno group).

[8]

The compound according to [1] or a pharmacologically acceptable salt thereof, wherein $R^3$ is a furyl group or a thienyl group (the furyl group and the thienyl group are each optionally substituted by 1 or 2 identical or different groups selected from a methyl group and a halogeno group).

[9]

The compound according to [1] or a pharmacologically acceptable salt thereof, wherein $R^3$ is a furyl group (the furyl group is optionally substituted by 1 or 2 identical or different groups selected from a methyl group and a halogeno group).

[10]

The compound according to [1] or a pharmacologically acceptable salt thereof, wherein $R^3$ is a 5-methylfuran-2-yl group.

[11]

A compound represented by formula (II) or a pharmacologically acceptable salt thereof:

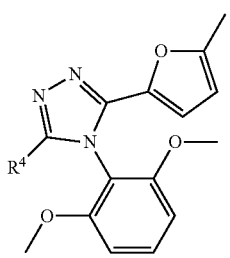
(II)

wherein R[4] represents a $C_1$ to $C_6$ alkylthio group, an aryl-$C_1$ to $C_6$ alkylthio group, a heteroaryl-$C_1$ to $C_6$ alkylthio group, a $C_3$ to $C_8$ cycloalkyl-$C_1$ to $C_6$ alkylthio group, a heterocycloalkyl-$C_1$ to $C_6$ alkylthio group, a $C_2$ to $C_6$ alkenyl group, an aryl-$C_2$ to $C_6$ alkenyl group, a heteroaryl-$C_2$ to $C_6$ alkenyl group, a $C_3$ to $C_8$ cycloalkyl-$C_2$ to $C_6$ alkenyl group, a heterocycloalkyl-$C_2$ to $C_6$ alkenyl group, a $C_2$ to $C_6$ alkynyl group, an aryl-$C_2$ to $C_6$ alkynyl group, a heteroaryl-$C_2$ to $C_6$ alkynyl group, a $C_3$ to $C_8$ cycloalkyl-$C_2$ to $C_6$ alkynyl group, a heterocycloalkyl-$C_2$ to $C_6$ alkynyl group, a $C_1$ to $C_6$ alkyl group, an aryl-$C_1$ to $C_6$ alkyl group, a heteroaryl-$C_1$ to $C_6$ alkyl group, a $C_3$ to $C_8$ cycloalkyl-$C_1$ to $C_6$ alkyl group, a heterocycloalkyl-$C_1$ to $C_6$ alkyl group, a $C_1$ to $C_6$ alkoxy group, an aryl-$C_1$ to $C_6$ alkoxy group, a heteroaryl-$C_1$ to $C_6$ alkoxy group, a $C_3$ to $C_8$ cycloalkyl-$C_1$ to $C_6$ alkoxy group, a heterocycloalkyl-$C_1$ to $C_6$ alkoxy group, an aryl group, a heteroaryl group, a heterocycloalkyl group, a thiol group, a methylsulfonyl group, a halogeno group, or a hydrogen (the $C_1$ to $C_6$ alkylthio group, the aryl-$C_1$ to $C_6$ alkylthio group, the heteroaryl-$C_1$ to $C_6$ alkylthio group, the $C_3$ to $C_8$ cycloalkyl-$C_1$ to $C_6$ alkylthio group, the heterocycloalkyl-$C_1$ to $C_6$ alkylthio group, the $C_2$ to $C_6$ alkenyl group, the aryl-$C_2$ to $C_6$ alkenyl group, the heteroaryl-$C_2$ to $C_6$ alkenyl group, the $C_3$ to $C_8$ cycloalkyl-$C_2$ to $C_6$ alkenyl group, the heterocycloalkyl-$C_2$ to $C_6$ alkenyl group, the $C_2$ to $C_6$ alkynyl group, the aryl-$C_2$ to $C_6$ alkynyl group, the heteroaryl-$C_2$ to $C_6$ alkynyl group, the $C_3$ to $C_8$ cycloalkyl-$C_2$ to $C_6$ alkynyl group, the heterocycloalkyl-$C_2$ to $C_6$ alkynyl group, the $C_1$ to $C_6$ alkyl group, the aryl-$C_1$ to $C_6$ alkyl group, the heteroaryl-$C_1$ to $C_6$ alkyl group, the $C_3$ to $C_8$ cycloalkyl-$C_1$ to $C_6$ alkyl group, the heterocycloalkyl-$C_1$ to $C_6$ alkyl group, the $C_1$ to $C_6$ alkoxy group, the aryl-$C_1$ to $C_6$ alkoxy group, the heteroaryl-$C_1$ to $C_6$ alkoxy group, the $C_3$ to $C_8$ cycloalkyl-$C_1$ to $C_6$ alkoxy group, the heterocycloalkyl-$C_1$ to $C_6$ alkoxy group, the aryl group, the heteroaryl group, and the heterocycloalkyl group are each optionally substituted by one group, and the heteroaryl-$C_1$ to $C_6$ alkylthio group, the heteroaryl-$C_2$ to $C_6$ alkenyl group, the heteroaryl-$C_2$ to $C_6$ alkynyl group, the heteroaryl-$C_1$ to $C_6$ alkyl group, the heteroaryl-$C_1$ to $C_6$ alkoxy group, and the heteroaryl group are each optionally substituted at the heteroaryl group moiety by 1 to 4 identical or different groups selected from an oxo group, a $C_1$ to $C_6$ alkyl group, and a halogeno group).

[12]

The compound according to any one of [1] to [11] or a pharmacologically acceptable salt thereof, wherein R[4] is a $C_1$ to $C_6$ alkylthio group, an aryl-$C_1$ to $C_6$ alkylthio group, a heteroaryl-$C_1$ to $C_6$ alkylthio group, a $C_3$ to $C_8$ cycloalkyl-$C_1$ to $C_6$ alkylthio group, a heterocycloalkyl-$C_1$ to $C_6$ alkylthio group, a $C_2$ to $C_6$ alkenyl group, an aryl-$C_2$ to $C_6$ alkenyl group, a heteroaryl-$C_2$ to $C_6$ alkenyl group, a $C_3$ to $C_8$ cycloalkyl-$C_2$ to $C_6$ alkenyl group, a heterocycloalkyl-$C_2$ to $C_6$ alkenyl group, a $C_2$ to $C_6$ alkynyl group, an aryl-$C_2$ to $C_6$ alkynyl group, a heteroaryl-$C_2$ to $C_6$ alkynyl group, a $C_3$ to $C_8$ cycloalkyl-$C_2$ to $C_6$ alkynyl group, a heterocycloalkyl-$C_2$ to $C_6$ alkynyl group, a $C_1$ to $C_6$ alkyl group, an aryl-$C_1$ to $C_6$ alkyl group, a heteroaryl-$C_1$ to $C_6$ alkyl group, a $C_3$ to $C_8$ cycloalkyl-$C_1$ to $C_6$ alkyl group, a heterocycloalkyl-$C_1$ to $C_6$ alkyl group, a $C_1$ to $C_6$ alkoxy group, an aryl-$C_1$ to $C_6$ alkoxy group, a heteroaryl-$C_1$ to $C_6$ alkoxy group, a $C_3$ to $C_8$ cycloalkyl-$C_1$ to $C_6$ alkoxy group, a heterocycloalkyl-$C_1$ to $C_6$ alkoxy group, an aryl group, a heteroaryl group, or a heterocycloalkyl group (the $C_1$ to $C_6$ alkylthio group, the aryl-$C_1$ to $C_6$ alkylthio group, the heteroaryl-$C_1$ to $C_6$ alkylthio group, the $C_3$ to $C_8$ cycloalkyl-$C_1$ to $C_6$ alkylthio group, the heterocycloalkyl-$C_1$ to $C_6$ alkylthio group, the $C_2$ to $C_6$ alkenyl group, the aryl-$C_2$ to $C_6$ alkenyl group, the heteroaryl-$C_2$ to $C_6$ alkenyl group, the $C_3$ to $C_8$ cycloalkyl-$C_2$ to $C_6$ alkenyl group, the heterocycloalkyl-$C_2$ to $C_6$ alkenyl group, the $C_2$ to $C_6$ alkynyl group, the aryl-$C_2$ to $C_6$ alkynyl group, the heteroaryl-$C_2$ to $C_6$ alkynyl group, the $C_3$ to $C_8$ cycloalkyl-$C_2$ to $C_6$ alkynyl group, the heterocycloalkyl-$C_2$ to $C_6$ alkynyl group, the $C_1$ to $C_6$ alkyl group, the aryl-$C_1$ to $C_6$ alkyl group, the heteroaryl-$C_1$ to $C_6$ alkyl group, the $C_3$ to $C_8$ cycloalkyl-$C_1$ to $C_6$ alkyl group, the heterocycloalkyl-$C_1$ to $C_6$ alkyl group, the $C_1$ to $C_6$ alkoxy group, an aryl-$C_1$ to $C_6$ alkoxy group, a heteroaryl-$C_1$ to $C_6$ alkoxy group, a $C_3$ to $C_8$ cycloalkyl-$C_1$ to $C_6$ alkoxy group, a heterocycloalkyl-$C_1$ to $C_6$ alkoxy group, an aryl group, a heteroaryl group, or a heterocycloalkyl group (the $C_1$ to $C_6$ alkylthio group, the aryl-$C_1$ to $C_6$ alkylthio group, the heteroaryl-$C_1$ to $C_6$ alkylthio group, the $C_3$ to $C_8$ cycloalkyl-$C_1$ to $C_6$ alkylthio group, the heterocycloalkyl-$C_1$ to $C_6$ alkylthio group, the $C_2$ to $C_6$ alkenyl group, the aryl-$C_2$ to $C_6$ alkenyl group, the heteroaryl-$C_2$ to $C_6$ alkenyl group, the $C_3$ to $C_8$ cycloalkyl-$C_2$ to $C_6$ alkenyl group, the heterocycloalkyl-$C_2$ to $C_6$ alkenyl group, the $C_2$ to $C_6$ alkynyl group, the aryl-$C_2$ to $C_6$ alkynyl group, the heteroaryl-$C_2$ to $C_6$ alkynyl group, the $C_3$ to $C_8$ cycloalkyl-$C_2$ to $C_6$ alkynyl group, the heterocycloalkyl-$C_2$ to $C_6$ alkynyl group, the $C_1$ to $C_6$ alkyl group, the aryl-$C_1$ to $C_6$ alkyl group, the heteroaryl-$C_1$ to $C_6$ alkyl group, the $C_3$ to $C_8$ cycloalkyl-$C_1$ to $C_6$ alkyl group, the heterocycloalkyl-$C_1$ to $C_6$ alkyl group, the $C_1$ to $C_6$ alkoxy group, the aryl-$C_1$ to $C_6$ alkoxy group, a heteroaryl-$C_1$ to $C_6$ alkoxy group, a $C_3$ to $C_8$ cycloalkyl-$C_1$ to $C_6$ alkoxy group, a heterocycloalkyl-$C_1$ to $C_6$ alkoxy group, an aryl group, a heteroaryl group, or a heterocycloalkyl group (the $C_1$ to $C_6$ alkylthio group, the aryl-$C_1$ to $C_6$ alkylthio group, the heteroaryl-$C_1$ to $C_6$ alkylthio group, the $C_3$ to $C_8$ cycloalkyl-$C_1$ to $C_6$ alkylthio group, the heterocycloalkyl-$C_1$ to $C_6$ alkylthio group, the $C_2$ to $C_6$ alkenyl group, the aryl-$C_2$ to $C_6$ alkenyl group, the heteroaryl-$C_2$ to $C_6$ alkenyl group, the $C_3$ to $C_8$ cycloalkyl-$C_2$ to $C_6$ alkenyl group, the heterocycloalkyl-$C_2$ to $C_6$ alkenyl group are each optionally substituted by one group selected from a carboxy group, a triazolylsulfonyl group, a carboxymethoxy group, a methylsulfonylamino group, a 4-methylbenzenesulfonylamino group, a (2S)-2-carboxypyrrolidin-1-ylcarbonyl group, a (2S, 4R)-2-carboxy-4-hydroxypyrrolidin-1-ylcarbonyl group, a benzenesulfonylaminocarbonyl group, a phosphoryl group, an amino group, a carbamoyl group, a dimethylcarbamoyl group, an oxo group, a hydroxy group, and a cyano group, and the heteroaryl-$C_1$ to $C_6$ alkylthio group, the heteroaryl-$C_2$ to $C_6$ alkenyl group, the heteroaryl-$C_2$ to $C_6$ alkynyl group, the heteroaryl-$C_1$ to $C_6$ alkyl group, the heteroaryl-$C_1$ to $C_6$ alkoxy group, and the heteroaryl group are each optionally substituted at the heteroaryl group moiety by 1 to 4 identical or different groups selected from an oxo group, a $C_1$ to $C_6$ alkyl group, and a halogeno group).

[13]

The compound according to any one of [1] to [11] or a pharmacologically acceptable salt thereof, wherein R[4] is a $C_1$ to $C_6$ alkylthio group, an aryl-$C_1$ to $C_6$ alkylthio group, a heteroaryl-$C_1$ to $C_6$ alkylthio group, a $C_3$ to $C_8$ cycloalkyl-$C_1$ to $C_6$ alkylthio group, a heterocycloalkyl-$C_1$ to $C_6$ alkylthio group, a $C_2$ to $C_6$ alkenyl group, an aryl-$C_2$ to $C_6$ alkenyl group, a heteroaryl-$C_2$ to $C_6$ alkenyl group, a $C_3$ to $C_8$ cycloalkyl-$C_2$ to $C_6$ alkenyl group, a heterocycloalkyl-$C_2$ to $C_6$ alkenyl group, a $C_2$ to $C_6$ alkynyl group, an aryl-$C_2$ to $C_6$ alkynyl group, a heteroaryl-$C_2$ to $C_6$ alkynyl group, a $C_3$ to $C_8$ cycloalkyl-$C_2$ to $C_6$ alkynyl group, a heterocycloalkyl-$C_2$ to $C_6$ alkynyl group, a $C_1$ to $C_6$ alkyl group, an aryl-$C_1$ to $C_6$ alkyl group, a heteroaryl-$C_1$ to $C_6$ alkyl group, a $C_3$ to $C_8$ cycloalkyl-$C_1$ to $C_6$ alkyl group, a heterocycloalkyl-$C_1$ to $C_6$ alkyl group, a $C_1$ to $C_6$ alkoxy group, an aryl-$C_1$ to $C_6$ alkoxy group, a heteroaryl-$C_1$ to $C_6$ alkoxy group, a $C_3$ to $C_8$ cycloalkyl-$C_1$ to $C_6$ alkoxy group, a heterocycloalkyl-$C_1$ to $C_6$ alkoxy group, an aryl group, a heteroaryl group, or a heterocycloalkyl group (the $C_1$ to $C_6$ alkylthio group, the aryl-$C_1$ to $C_6$ alkylthio group, the heteroaryl-$C_1$ to $C_6$ alkylthio group, the $C_3$ to $C_8$ cycloalkyl-$C_1$ to $C_6$ alkylthio group, the heterocycloalkyl-$C_1$ to $C_6$ alkylthio group, the $C_2$ to $C_6$ alkenyl group, the aryl-$C_2$ to $C_6$ alkenyl group, the heteroaryl-$C_2$ to $C_6$ alkenyl group, the $C_3$ to $C_8$ cycloalkyl-$C_2$ to $C_6$ alkenyl group, the heterocycloalkyl-$C_2$ to $C_6$ alkenyl group, the $C_2$ to $C_6$ alkynyl group, the aryl-$C_2$ to $C_6$ alkynyl group, the heteroaryl-$C_2$ to $C_6$ alkynyl group, the $C_3$ to $C_8$ cycloalkyl-$C_2$ to $C_6$ alkynyl group, the heterocycloalkyl-$C_2$ to $C_6$ alkynyl group, the $C_1$ to $C_6$ alkyl group, the aryl-$C_1$ to $C_6$ alkyl group, the heteroaryl-$C_1$ to $C_6$ alkyl group, the $C_3$ to $C_8$ cycloalkyl-$C_1$ to $C_6$ alkyl group, the heterocycloalkyl-$C_1$ to $C_6$ alkyl group, the $C_1$ to $C_6$ alkoxy group, the aryl-$C_1$ to $C_6$ alkoxy group, the heteroaryl-$C_1$ to $C_6$ alkoxy group, the $C_3$ to $C_8$ cycloalkyl-$C_1$ to $C_6$ alkoxy group, the heterocycloalkyl-$C_1$ to $C_6$ alkoxy group, the aryl group, the heteroaryl group, and the heterocycloalkyl group are each substituted by one group selected from a carboxy group, a triazolylsulfonyl group, a carboxymethoxy group, a methylsulfonylamino group, a 4-methylbenzenesulfonylamino group, a (2S)-2-carboxypyrrolidin-1-ylcarbonyl group, a (2S,4R)-2-carboxy-4-hydroxypyrrolidin-1-ylcarbonyl group, a benzenesulfonylaminocarbonyl group, and a phosphoryl group).

[14]

The compound according to any one of [1] to [11] or a pharmacologically acceptable salt thereof, wherein $R^4$ is a $C_1$ to $C_6$ alkylthio group, an aryl-$C_1$ to $C_6$ alkylthio group, a heteroaryl-$C_1$ to $C_6$ alkylthio group, a $C_3$ to $C_8$ cycloalkyl-$C_1$ to $C_6$ alkylthio group, a heterocycloalkyl-$C_1$ to $C_6$ alkylthio group, a $C_1$ to $C_6$ alkoxy group, an aryl-$C_1$ to $C_6$ alkoxy group, a heteroaryl-$C_1$ to $C_6$ alkoxy group, a $C_3$ to $C_8$ cycloalkyl-$C_1$ to $C_6$ alkoxy group, or a heterocycloalkyl-$C_1$ to $C_6$ alkoxy group (the $C_1$ to $C_6$ alkylthio group, the aryl-$C_1$ to $C_6$ alkylthio group, the heteroaryl-$C_1$ to $C_6$ alkylthio group, the $C_3$ to $C_8$ cycloalkyl-$C_1$ to $C_6$ alkylthio group, the heterocycloalkyl-$C_1$ to $C_6$ alkylthio group, the $C_1$ to $C_6$ alkoxy group, the aryl-$C_1$ to $C_6$ alkoxy group, the heteroaryl-$C_1$ to $C_6$ alkoxy group, the $C_3$ to $C_8$ cycloalkyl-$C_1$ to $C_6$ alkoxy group, and the heterocycloalkyl-$C_1$ to $C_6$ alkoxy group are each substituted by one group selected from a carboxy group, a benzenesulfonylaminocarbonyl group, and a phosphoryl group).

[15]

The compound according to any one of [1] to [11] or a pharmacologically acceptable salt thereof, wherein $R^4$ is a $C_1$ to $C_6$ alkylthio group, an aryl-$C_1$ to $C_6$ alkylthio group, a heteroaryl-$C_1$ to $C_6$ alkylthio group, or a $C_1$ to $C_6$ alkoxy group (the $C_1$ to $C_6$ alkylthio group, the aryl-$C_1$ to $C_6$ alkylthio group, the heteroaryl-$C_1$ to $C_6$ alkylthio group, and the $C_1$ to $C_6$ alkoxy group are each substituted by one group selected from a carboxy group, a benzenesulfonylaminocarbonyl group, and a phosphoryl group).

[16]

The compound according to any one of [1] to [11] or a pharmacologically acceptable salt thereof, wherein $R^4$ is a group

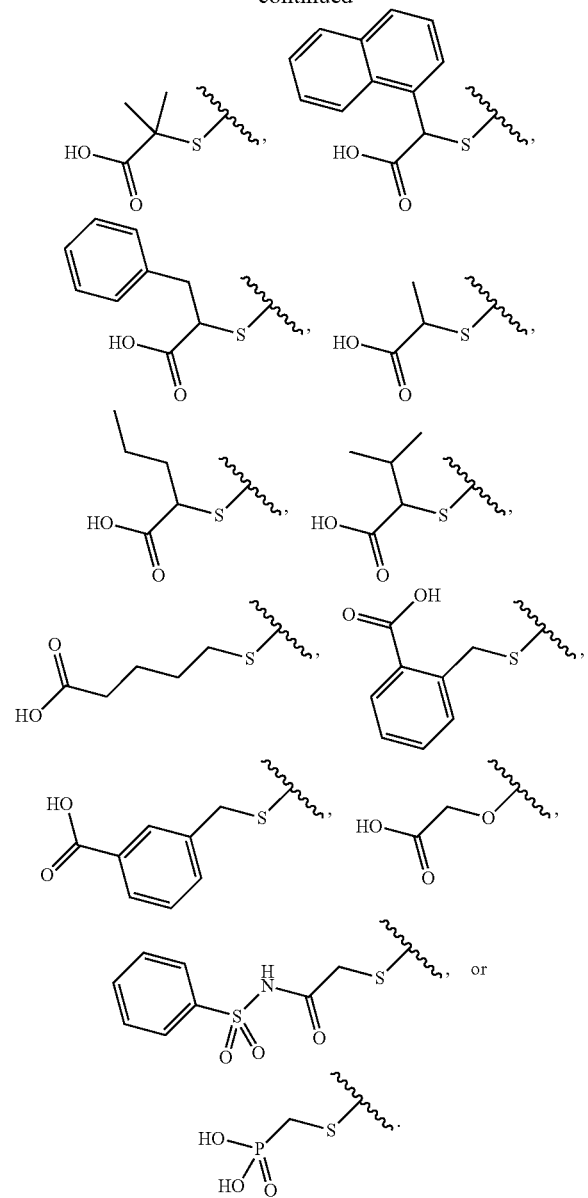

The compound according to any one of [1] to [11] or a pharmacologically acceptable salt thereof, wherein $R^4$ is a group

[18]

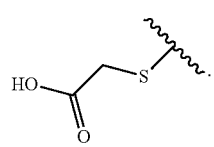 [SMILES: *SCC(=O)O]

The compound according to any one of [1] to [11] or a pharmacologically acceptable salt thereof, wherein $R^4$ is a $C_2$ to $C_6$ alkenyl group, an aryl-$C_2$ to $C_6$ alkenyl group, a heteroaryl-$C_2$ to $C_6$ alkenyl group, a $C_3$ to $C_8$ cycloalkyl-$C_2$ to $C_6$ alkenyl group, a heterocycloalkyl-$C_2$ to $C_6$ alkenyl group, a $C_2$ to $C_6$ alkynyl group, an aryl-$C_2$ to $C_6$ alkynyl group, a heteroaryl-$C_2$ to $C_6$ alkynyl group, a $C_3$ to $C_8$ cycloalkyl-$C_2$ to $C_6$ alkynyl group, a heterocycloalkyl-$C_2$ to $C_6$ alkynyl group, a $C_1$ to $C_6$ alkyl group, an aryl-$C_1$ to $C_6$ alkyl group, a heteroaryl-$C_1$ to $C_6$ alkyl group, a $C_3$ to $C_8$ cycloalkyl-$C_1$ to $C_6$ alkyl group, a heterocycloalkyl-$C_1$ to $C_6$ alkyl group, an aryl group, a heteroaryl group, or a heterocycloalkyl group (the $C_2$ to $C_6$ alkenyl group, the aryl-$C_2$ to $C_6$ alkenyl group, the heteroaryl-$C_2$ to $C_6$ alkenyl group, the $C_3$ to $C_e$ cycloalkyl-$C_2$ to $C_6$ alkenyl group, the heterocycloalkyl-$C_2$ to $C_6$ alkenyl group, the $C_2$ to $C_6$ alkynyl group, the aryl-$C_2$ to $C_6$ alkynyl group, the heteroaryl-$C_2$ to $C_6$ alkynyl group, the $C_3$ to $C_8$ cycloalkyl-$C_2$ to $C_6$ alkynyl group, the heterocycloalkyl-$C_2$ to $C_6$ alkynyl group, the $C_1$ to $C_6$ alkyl group, the aryl-$C_1$ to $C_6$ alkyl group, the heteroaryl-$C_1$ to $C_6$ alkyl group, the $C_3$ to $C_8$ cycloalkyl-$C_1$ to $C_6$ alkyl group, the heterocycloalkyl-$C_1$ to $C_6$ alkyl group, the aryl group, the heteroaryl group, and the heterocycloalkyl group are each substituted by one group selected from a carboxy group, a triazolylsulfonyl group, a carboxymethoxy group, a methylsulfonylamino group, a 4-methylbenzenesulfonylamino group, a (2S)-2-carboxypyrrolidin-1-ylcarbonyl group, and a (2S, 4R)-2-carboxy-4-hydroxypyrrolidin-1-ylcarbonyl group).

[19]

The compound according to any one of [1] to [11] or a pharmacologically acceptable salt thereof, wherein $R^4$ is a $C_2$ to $C_6$ alkenyl group, a $C_1$ to $C_6$ alkyl group, or an aryl group (the $C_2$ to $C_6$ alkenyl group, the $C_1$ to $C_6$ alkyl group, and the aryl group are each substituted by one group selected from a carboxy group, a triazolylsulfonyl group, a carboxymethoxy group, a methylsulfonylamino group, a 4-methylbenzenesulfonylamino group, a (2S)-2-carboxypyrrolidin-1-ylcarbonyl group, and a (2S, 4R)-2-carboxy-4-hydroxypyrrolidin-1-ylcarbonyl group).

[20]

The compound according to any one of [1] to [11] or a pharmacologically acceptable salt thereof, wherein $R^4$ is a vinyl group, an ethyl group, or a phenyl group (the vinyl group, the ethyl group, and the phenyl group are each substituted by one group selected from a carboxy group, a triazolylsulfonyl group, a carboxymethoxy group, a methylsulfonylamino group, a 4-methylbenzenesulfonylamino group, a (2S)-2-carboxypyrrolidin-1-ylcarbonyl group, and a (2S,4R)-2-carboxy-4-hydroxypyrrolidin-1-ylcarbonyl group).

[21]

The compound according to any one of [1] to [11] or a pharmacologically acceptable salt thereof, wherein $R^4$ is a group

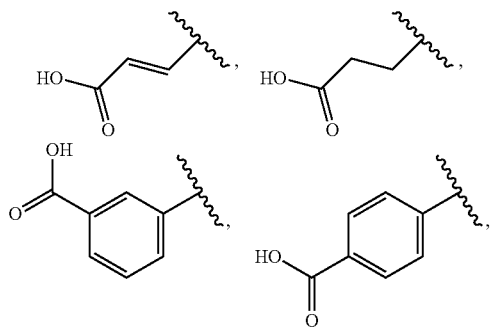

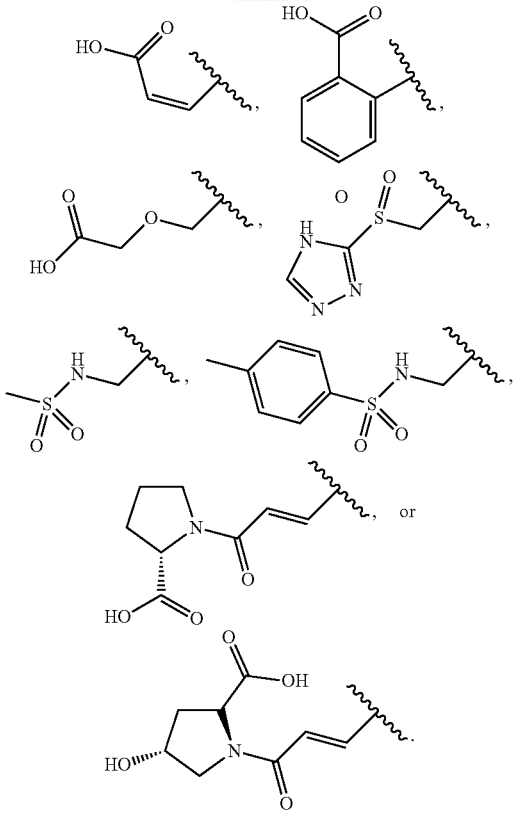

The compound according to any one of [1] to [11] or a pharmacologically acceptable salt thereof, wherein $R^4$ is a group

[23]

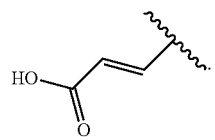

The compound according to any one of [1] to [11] or a pharmacologically acceptable salt thereof, wherein $R^4$ is a heteroaryl-$C_1$ to $C_6$ alkylthio group, a heteroaryl-$C_2$ to $C_6$ alkenyl group, a heteroaryl-$C_2$ to $C_6$ alkynyl group, a heteroaryl-$C_1$ to $C_6$ alkyl group, a heteroaryl-$C_1$ to $C_6$ alkoxy group, or a heteroaryl group (the heteroaryl-$C_1$ to $C_6$ alkylthio group, the heteroaryl-$C_2$ to $C_6$ alkenyl group, the heteroaryl-$C_2$ to $C_6$ alkynyl group, the heteroaryl-$C_1$ to $C_6$ alkyl group, the heteroaryl-$C_1$ to $C_6$ alkoxy group, and the heteroaryl group are each optionally substituted at the heteroaryl group moiety by 1 to 4 identical or different groups selected from an oxo group, a $C_1$ to $C_6$ alkyl group, and a halogeno group).

[24]

The compound according to any one of [1] to [11] or a pharmacologically acceptable salt thereof, wherein $R^4$ is a heteroaryl-$C_1$ to $C_6$ alkylthio group, a heteroaryl-$C_2$ to $C_6$ alkenyl group, a heteroaryl-$C_2$ to $C_6$ alkynyl group, a heteroaryl-$C_1$ to $C_6$ alkyl group, a heteroaryl-$C_1$ to $C_6$ alkoxy group, or a heteroaryl group (the heteroaryl-$C_1$ to $C_6$ alkylthio group, the heteroaryl-$C_2$ to $C_6$ alkenyl group, the heteroaryl-$C_2$ to $C_6$ alkynyl group, the heteroaryl-$C_1$ to $C_6$ alkyl group, the heteroaryl-$C_1$ to $C_6$ alkoxy group, and the heteroaryl group are each optionally substituted at the heteroaryl group moiety by 1 or 2 oxo groups).

[25]

The compound according to any one of [1] to [11] or a pharmacologically acceptable salt thereof, wherein $R^4$ is a heteroaryl-$C_1$ to $C_6$ alkylthio group, or a heteroaryl-$C_2$ to $C_6$ alkenyl group (the heteroaryl-$C_1$ to $C_6$ alkylthio group and the heteroaryl-$C_2$ to $C_6$ alkenyl group are each optionally substituted at the heteroaryl group moiety by 1 or 2 oxo groups).

[26]

The compound according to any one of [1] to [11] or a pharmacologically acceptable salt thereof, wherein $R^4$ is a group

[27]

The compound according to any one of [1] to [11] or a pharmacologically acceptable salt thereof, wherein $R^4$ is a group

[28]

The compound according to any one of [1] to [11] or a pharmacologically acceptable salt thereof, wherein $R^4$ is a group

[29]

The compound according to [1] or a pharmacologically acceptable salt thereof, wherein the compound is selected from the group consisting of
{[4-(2,6-Dimethoxyphenyl)-5-(5-methylfuran-2-yl)-4H-1,2,4-triazol-3-yl]sulfanyl}acetic acid,
4-{[4-(2,6-Dimethoxyphenyl)-5-(5-methylfuran-2-yl)-4H-1,2,4-triazol-3-yl]sulfanyl}butanoic acid,
{[5-(5-Bromofuran-2-yl)-4-(2,6-dimethoxyphenyl)-4H-1,2,4-triazol-3-yl]sulfanyl}acetic acid,
{[4-(2,6-Diethylphenyl)-5-(5-methylfuran-2-yl)-4H-1,2,4-triazol-3-yl]sulfanyl}acetic acid,
{[4-(2,4-Dimethoxypyridin-3-yl)-5-(5-methylfuran-2-yl)-4H-1,2,4-triazol-3-yl]sulfanyl}acetic acid,
{[4-(2,6-Dimethoxyphenyl)-5-(5-methylfuran-2-yl)-4H-1,2,4-triazol-3-yl]sulfanyl}(phenyl)acetic acid,
2-{[4-(2,6-Dimethoxyphenyl)-5-(5-methylfuran-2-yl)-4H-1,2,4-triazol-3-yl]sulfanyl}-2-methylpropanoic acid,
{[4-(2,6-Dimethoxyphenyl)-5-(5-methylfuran-2-yl)-4H-1,2,4-triazol-3-yl]sulfanyl}(naphthalen-1-yl)acetic acid,
2-{[4-(2,6-Dimethoxyphenyl)-5-(5-methylfuran-2-yl)-4H-1,2,4-triazol-3-yl]sulfanyl}-3-phenylpropanoic acid,
2-{[4-(2,6-Dimethoxyphenyl)-5-(5-methylfuran-2-yl)-4H-1,2,4-triazol-3-yl]sulfanyl}propanoic acid,
2-{[4-(2,6-Dimethoxyphenyl)-5-(5-methylfuran-2-yl)-4H-1,2,4-triazol-3-yl]sulfanyl}pentanoic acid,
2-{[4-(2,6-Dimethoxyphenyl)-5-(5-methylfuran-2-yl)-4H-1,2,4-triazol-3-yl]sulfanyl}-3-methylbutanoic acid,
{[4-(2,6-Dimethoxyphenyl)-5-(5-methylfuran-2-yl)-4H-1,2,4-triazol-3-yl]oxy}acetic acid,
2-{[4-(2,6-Dimethoxyphenyl)-5-(5-methylfuran-2-yl)-4H-1,2,4-triazol-3-yl]sulfanyl}-N-(phenylsulfonyl)acetamide, and
({[4-(2,6-Dimethoxyphenyl)-5-(5-methylfuran-2-yl)-4H-1,2,4-triazol-3-yl]sulfanyl}methyl)phosphonic acid.

[30]

The compound according to [1] or a pharmacologically acceptable salt thereof, wherein the compound is selected from the group consisting of
(2E)-3-[4-(2,6-Dimethoxyphenyl)-5-(5-methylfuran-2-yl)-4H-1,2,4-triazol-3-yl]prop-2-enoic acid,
3-[4-(2,6-Dimethoxyphenyl)-5-(5-methylfuran-2-yl)-4H-1,2,4-triazol-3-yl]propanoic acid,
3-[4-(2,6-Dimethoxyphenyl)-5-(5-methylfuran-2-yl)-4H-1,2,4-triazol-3-yl]benzoic acid, 4-[4-(2,6-Dimethoxyphenyl)-5-(5-methylfuran-2-yl)-4H-1,2,4-triazol-3-yl]benzoic acid,
(2Z)-3-[4-(2,6-Dimethoxyphenyl)-5-(5-methylfuran-2-yl)-4H-1,2,4-triazol-3-yl]prop-2-enoic acid,
{[4-(2,6-Dimethoxyphenyl)-5-(5-methylfuran-2-yl)-4H-1,2,4-triazol-3-yl]methoxy}acetic acid,
4-(2,6-Dimethoxyphenyl)-3-(5-methylfuran-2-yl)-5-[(4H-1,2,4-triazol-3-ylsulfanyl)methyl]-4H-1,2,4-triazole,
N-{[4-(2,6-Dimethoxyphenyl)-5-(5-methylfuran-2-yl)-4H-1,2,4-triazol-3-yl]methyl}methanesulfonamide,
N-{[4-(2,6-Dimethoxyphenyl)-5-(5-methylfuran-2-yl)-4H-1,2,4-triazol-3-yl]methyl}-4-methylbenzenesulfonamide,
1-{(2E)-3-[4-(2,6-Dimethoxyphenyl)-5-(5-methylfuran-2-yl)-4H-1,2,4-triazol-3-yl]prop-2-enoyl}-L-proline, and
(4R)-1-{(2E)-3-[4-(2,6-Dimethoxyphenyl)-5-(5-methylfuran-2-yl)-4H-1,2,4-triazol-3-yl]prop-2-enoyl}-4-hydroxy-L-proline.

[31]
The compound according to [1] or a pharmacologically acceptable salt thereof, wherein the compound is selected from the group consisting of
6-({[4-(2,6-Dimethoxyphenyl)-5-(5-methylfuran-2-yl)-4H-1,2,4-triazol-3-yl]sulfanyl}methyl)pyrimidine-2,4(1H,3H)-dione,
5-({[4-(2,6-Dimethoxyphenyl)-5-(5-methylfuran-2-yl)-4H-1,2,4-triazol-3-yl]sulfanyl}methyl)pyrazolo[1,5-a]pyrimidin-7(4H)-one,
4-({[4-(2,6-Dimethoxyphenyl)-5-(5-methylfuran-2-yl)-4H-1,2,4-triazol-3-yl]sulfanyl}methyl)pyridin-2(1H)-one,
5-({[4-(2,6-Dimethoxyphenyl)-5-(5-methylfuran-2-yl)-4H-1,2,4-triazol-3-yl]sulfanyl}methyl)-1H-tetrazole,
3-({[4-(2,6-Dimethoxyphenyl)-5-(5-methylfuran-2-yl)-4H-1,2,4-triazol-3-yl]sulfanyl}methyl)-1,2,4-oxadiazol-5(2H)-one,
5-({[4-(2,6-Dimethoxyphenyl)-5-(5-methylfuran-2-yl)-4H-1,2,4-triazol-3-yl]sulfanyl}methyl)-2,4-dihydro-3H-1,2,4-triazol-3-one,
5-({[4-(2,6-Dimethoxyphenyl)-5-(5-methylfuran-2-yl)-4H-1,2,4-triazol-3-yl]sulfanyl}methyl)-1,3,4-oxadiazol-2(3H)-one,
and
5-({[4-(2,6-Dimethoxyphenyl)-5-(5-methylfuran-2-yl)-4H-1,2,4-triazol-3-yl]sulfanyl}methyl)-1,2-dihydro-3H-pyrazol-3-one.

[32]
A pharmaceutical composition comprising a compound according to any one of [1] to [11], or a pharmacologically acceptable salt thereof, as an active ingredient.

[33]
A method for treating or preventing a disease, comprising administering a pharmacologically effective amount of a compound according to any one of [1] to [11], or a pharmacologically acceptable salt thereof.

[34]
The method according to [33], wherein the disease is cardiovascular disease, coronary heart disease, stroke, heart failure, systolic heart failure, diastolic heart failure, diabetic heart failure, heart failure with preserved ejection fraction, cardiomyopathy, myocardial infarction, left ventricular dysfunction, left ventricular dysfunction after myocardial infarction, cardiac hypertrophy, myocardial remodeling, myocardial remodeling after infarction, myocardial remodeling after cardiac surgery, or valvular heart disease.

[35]
The method according to [33], wherein the disease is metabolic disease, metabolic syndrome, insulin resistance, diabetes mellitus, diabetic late complications, diabetic macrovasculopathy, diabetic microvasculopathy, diabetic nephropathy, diabetic retinopathy, diabetic neuropathies, or cardiac autonomic neuropathy.

[36]
The method according to [33], wherein the disease is CNS-dependent disturbed fluid homeostasis, CNS-independent disturbed fluid homeostasis, acute renal failure, chronic renal failure, hypertension, pulmonary hypertension, portal hypertension, or systolic hypertension.

[37]
The method according to [33], wherein the disease is vascular disease, vascular hypertrophy, vascular remodeling, vascular stiffness, atherosclerosis, peripheral arterial occlusive disease (PAOD), restenosis, thrombosis, vascular permeability disorder, cardiac, renal, or retinal disorder caused by ischemia, or cardiac, renal, or retinal disorder caused by reperfusion.

[38]
A method for agonizing apelin receptor activity in a subject, comprising administering a compound according to any one of [1] to [11], or a pharmacologically acceptable salt thereof, to a subject.

[39]
A method for treating a disease or condition treatable by agonizing apelin receptor, comprising administering to a subject in need thereof a therapeutically effective amount of a compound according to any one of [1] to [11], or a pharmacologically acceptable salt thereof.

Hereinafter, the substituents in the present specification will be described.

In the present invention, the "$C_1$ to $C_6$ alkyl group" refers to a linear or branched alkyl group having 1 to 6 carbon atoms. Examples thereof can include a methyl group, an ethyl group, a n-propyl group, an isopropyl group, a n-butyl group, an isobutyl group, a s-butyl group, a tert-butyl group, a n-pentyl group, an isopentyl group, a 2-methylbutyl group, a neopentyl group, a 1-ethylpropyl group, a n-hexyl group, an isohexyl group, a 4-methylpentyl group, a 3-methylpentyl group, a 2-methylpentyl group, a 1-methylpentyl group, a 3,3-dimethylbutyl group, a 2,2-dimethylbutyl group, a 1,1-dimethylbutyl group, a 1,2-dimethylbutyl group, a 1,3-dimethylbutyl group, a 2,3-dimethylbutyl group, and a 2-ethylbutyl group. Preferred examples of the "$C_1$ to $C_6$ alkyl group" for $R^1$ and $R^2$ can include an ethyl group. Preferred examples of the "$C_1$ to $C_6$ alkyl group" for $R^3$ can include a n-butyl group. Preferred examples of the "$C_1$ to $C_6$ alkyl group" for $R^4$ can include an ethyl group.

In the present invention, the "$C_1$ to $C_6$ alkoxy group" refers to a group in which the aforementioned "$C_1$ to $C_6$ alkyl group" is bonded to an oxygen atom. Examples thereof can include a methoxy group, an ethoxy group, a n-propoxy group, an isopropoxy group, a n-butoxy group, an isobutoxy group, a s-butoxy group, a tert-butoxy group, a n-pentoxy group, an isopentoxy group, a 2-methylbutoxy group, a neopentoxy group, a 1-ethylpropoxy group, a n-hexyloxy group, an isohexyloxy group, a 4-methylpentoxy group, a 3-methylpentoxy group, a 2-methylpentoxy group, a 1-methylpentoxy group, a 3,3-dimethylbutoxy group, a 2,2-dimethylbutoxy group, a 1,1-dimethylbutoxy group, a 1,2-dimethylbutoxy group, a 1,3-dimethylbutoxy group, a 2,3-dimethylbutoxy group, and a 2-ethylbutoxy group. Preferred examples of the "$C_1$ to $C_6$ alkoxy group" for $R^1$ and $R^2$ can include a methoxy group. Preferred examples of the "$C_1$ to $C_6$ alkoxy group" for $R^4$ can include a methoxy group and an ethoxy group.

In the present invention, the "halogeno group" refers to a fluoro group, a chloro group, a bromo group, or an iodo group.

In the present invention, the "aryl group" refers to an aromatic hydrocarbon group having a 6- to 10-membered ring composed of carbon atoms. Examples thereof can include a phenyl group, an indenyl group, and a naphthyl group. Preferred examples of the "aryl group" for $R^3$ can include a phenyl group. Preferred examples of the "aryl group" for $R^4$ can include a phenyl group.

In the present invention, the "heteroaryl group" refers to an aromatic heterocyclic group having a 5- to 10-membered ring containing 1 to 4 nitrogen, oxygen, and/or sulfur atoms. Examples thereof can include a furyl group, a thienyl group, a pyrrolyl group, a pyrazolyl group, an imidazolyl group, an oxazolyl group, an oxadiazolyl group, an isoxazolyl group, a thiazolyl group, an isothiazolyl group, a 1,2,3-triazolyl group, a 1,2,4-triazolyl group, a thiadiazolyl group, a tetrazolyl group, a pyranyl group, a pyridyl group, a pyridazinyl group, a pyrimidinyl group, a pyrazinyl group, and a triazinyl group. Also, this group may be condensed with another cyclic group. Examples thereof can include a benzofuranyl group, a chromenyl group, an indolizinyl group, an isoindolyl group, an indolyl group, an indazolyl group, a purinyl group, a quinolizinyl group, an isoquinolyl group, a quinolyl group, a phthalazinyl group, a naphthyridinyl group, a quinoxalinyl group, a quinazolinyl group, an isoquinazolinyl group, a pyridopyrimidinyl group, a pyridopyridazinyl group, a pyridopyrazinyl group, a pyrrolopyridinyl group, an imidazopyridinyl group, a pyrazolopyridinyl group, a pyrazolopyrimidinyl group, and a triazolopyridinyl group. Preferred examples of the "heteroaryl group" for $R^3$ can include a furyl group, a thienyl group, and a pyridyl group, more preferably a furyl group, most preferably a furan-2-yl group. Preferred examples of the "heteroaryl group" for $R^4$ can include a pyridyl group, a pyrimidinyl group, a pyridopyrimidinyl group, and a pyrazolopyrimidinyl group, more preferably a pyridopyrimidinyl group, most preferably a pyridopyrimidin-2-yl group.

In the present invention, the "$C_3$ to $C_8$ cycloalkyl group" refers to a 3- to 8-membered saturated cyclic hydrocarbon group. Examples thereof can include a cyclopropyl group, a cyclobutyl group, a cyclopentyl group, a cyclohexyl group, a cycloheptyl group, and a cyclooctyl group. Preferred examples of the "$C_3$ to $C_8$ cycloalkyl group" for $R^3$ can include a cyclopentyl group.

In the present invention, the "heterocycloalkyl group" refers to a saturated heterocyclic group having a 4- to 7-membered ring containing 1 or 2 nitrogen, oxygen, and/or sulfur atoms. Examples thereof can include an azetidinyl group, a pyrrolidinyl group, a piperidinyl group, an azepanyl group, an oxetanyl group, a tetrahydrofuranyl group, a tetrahydropyranyl group, a morpholinyl group, a thiomorpholinyl group, a piperazinyl group, an imidazolidinyl group, a pyrazolidinyl group, a hexahydropyrimidinyl group, a hexahydropyridazinyl group, a [1,4]-diazepanyl group, and a [1,4]-oxazepanyl group.

In the present invention, the "$C_1$ to $C_6$ alkylthio group" refers to a group in which the aforementioned "$C_1$ to $C_6$ alkyl group" is bonded to a sulfur atom. Examples thereof can include a methylthio group, an ethylthio group, a n-propylthio group, an isopropylthio group, a n-butylthio group, an isobutylthio group, a s-butylthio group, a tert-butylthio group, a n-pentylthio group, an isopentylthio group, a 2-methylbutylthio group, a neopentylthio group, a 1-ethylpropylthio group, a n-hexylthio group, an isohexylthio group, a 4-methylpentylthio group, a 3-methylpentylthio group, a 2-methylpentylthio group, a 1-methylpentylthio group, a 3,3-dimethylbutylthio group, a 2,2-dimethylbutylthio group, a 1,1-dimethylbutylthio group, a 1,2-dimethylbutylthio group, a 1,3-dimethylbutylthio group, a 2,3-dimethylbutylthio group, and a 2-ethylbutylthio group. Preferred examples of the "$C_1$ to $C_6$ alkylthio group" for $R^4$ can include a methylthio group.

In the present invention, the "$C_2$ to $C_6$ alkenyl group" refers to a linear or branched alkenyl group having 2 to 6 carbon atoms. Examples thereof can include a vinyl group, a propenyl group, a butenyl group, a pentenyl group, and a hexenyl group. Preferred examples of the "$C_2$ to $C_6$ alkenyl group" for $R^4$ can include a vinyl group.

In the present invention, the "$C_2$ to $C_6$ alkynyl group" refers to a linear or branched alkynyl group having 2 to 6 carbon atoms. Examples thereof can include an ethynyl group, a propynyl group, a butynyl group, a pentynyl group, and a hexynyl group.

In the present invention, the "aryl-$C_1$ to $C_6$ alkylthio group" refers to the aforementioned "$C_1$ to $C_6$ alkylthio group" substituted by one aforementioned "aryl group".

In the present invention, the "heteroaryl-$C_1$ to $C_6$ alkylthio group" refers to the aforementioned "$C_1$ to $C_6$ alkylthio group" substituted by one aforementioned "heteroaryl group".

In the present invention, the "$C_3$ to $C_8$ cycloalkyl-$C_1$ to $C_6$ alkylthio group" refers to the aforementioned "$C_1$ to $C_6$ alkylthio group" substituted by one aforementioned "$C_3$ to $C_8$ cycloalkyl group".

In the present invention, the "heterocycloalkyl-$C_1$ to $C_6$ alkylthio group" refers to the aforementioned "$C_1$ to $C_6$ alkylthio group" substituted by one aforementioned "heterocycloalkyl group".

In the present invention, the "aryl-$C_2$ to $C_6$ alkenyl group" refers to the aforementioned "$C_2$ to $C_6$ alkenyl group" substituted by one aforementioned "aryl group".

In the present invention, the "heteroaryl-$C_2$ to $C_6$ alkenyl group" refers to the aforementioned "$C_2$ to $C_6$ alkenyl group" substituted by one aforementioned "heteroaryl group".

In the present invention, the "$C_3$ to $C_8$ cycloalkyl-$C_2$ to $C_6$ alkenyl group" refers to the aforementioned "$C_2$ to $C_6$ alkenyl group" substituted by one aforementioned "$C_3$ to $C_8$ cycloalkyl group".

In the present invention, the "heterocycloalkyl-$C_2$ to $C_6$ alkenyl group" refers to the aforementioned "$C_2$ to $C_6$ alkenyl group" substituted by one aforementioned "heterocycloalkyl group".

In the present invention, the "aryl-$C_2$ to $C_6$ alkynyl group" refers to the aforementioned "$C_2$ to $C_6$ alkynyl group" substituted by one aforementioned "aryl group".

In the present invention, the "heteroaryl-$C_2$ to $C_6$ alkynyl group" refers to the aforementioned "$C_2$ to $C_6$ alkynyl group" substituted by one aforementioned "heteroaryl group".

In the present invention, the "$C_3$ to $C_8$ cycloalkyl-$C_2$ to $C_6$ alkynyl group" refers to the aforementioned "$C_2$ to $C_6$ alkynyl group" substituted by one aforementioned "$C_3$ to $C_8$ cycloalkyl group".

In the present invention, the "heterocycloalkyl-$C_2$ to $C_6$ alkynyl group" refers to the aforementioned "$C_2$ to $C_6$ alkynyl group" substituted by one aforementioned "heterocycloalkyl group".

In the present invention, the "aryl-$C_1$ to $C_6$ alkyl group" refers to the aforementioned "$C_1$ to $C_6$ alkyl group" substituted by one aforementioned "aryl group".

In the present invention, the "heteroaryl-$C_1$ to $C_6$ alkyl group" refers to the aforementioned "$C_1$ to $C_6$ alkyl group" substituted by one aforementioned "heteroaryl group".

In the present invention, the "$C_3$ to $C_8$ cycloalkyl-$C_1$ to $C_6$ alkyl group" refers to the aforementioned "$C_1$ to $C_6$ alkyl group" substituted by one aforementioned "$C_3$ to $C_8$ cycloalkyl group".

In the present invention, the "heterocycloalkyl-$C_1$ to $C_6$ alkyl group" refers to the aforementioned "$C_1$ to $C_6$ alkyl group" substituted by one aforementioned "heterocycloalkyl group".

Hereinafter, preferred substituents for the compound represented by formula (I) or (II) of the present invention will be described.

$X^1$ is preferably —N=.

$X^2$ is preferably —CH=.

$R^1$ and $R^2$ are preferably each independently a $C_1$ to $C_6$ alkyl group or a $C_1$ to $C_6$ alkoxy group, more preferably each independently a methoxy group or an ethyl group, most preferably each a methoxy group, as a whole.

$R^3$ is preferably a furyl group, a thienyl group, a pyridyl group, a phenyl group, a n-butyl group, or a cyclopentyl group (the furyl group, the thienyl group, the pyridyl group, and the phenyl group are each optionally substituted by 1 or 2 identical or different groups selected from a methyl group and a halogeno group), more preferably a furyl group or a thienyl group (the furyl group and the thienyl group are each optionally substituted by 1 or 2 identical or different groups selected from a methyl group and a halogeno group), further preferably a furyl group (the furyl group is optionally substituted by 1 or 2 identical or different groups selected from a methyl group and a halogeno group), most preferably a 5-methylfuran-2-yl group, as a whole.

$R^4$ is preferably substituent having acidic functional group. Compounds having such substituent are expected to exhibit largely reduced hydrophobicity and improved metabolic stability, water solubility, and oral absorbability, etc.

According to the first embodiment, the substituent having such an acidic functional group is preferably a $C_1$ to $C_6$ alkylthio group, an aryl-$C_1$ to $C_6$ alkylthio group, a heteroaryl-$C_1$ to $C_6$ alkylthio group, a $C_3$ to $C_8$ cycloalkyl-$C_1$ to $C_6$ alkylthio group, a heterocycloalkyl-$C_1$ to $C_6$ alkylthio group, a $C_1$ to $C_6$ alkoxy group, an aryl-$C_1$ to $C_6$ alkoxy group, a heteroaryl-$C_1$ to $C_6$ alkoxy group, a $C_3$ to $C_8$ cycloalkyl-$C_1$ to $C_6$ alkoxy group, or a heterocycloalkyl-$C_1$ to $C_6$ alkoxy group (the $C_1$ to $C_6$ alkylthio group, the aryl-$C_1$ to $C_6$ alkylthio group, the heteroaryl-$C_1$ to $C_6$ alkylthio group, the $C_3$ to $C_8$ cycloalkyl-$C_1$ to $C_6$ alkylthio group, the heterocycloalkyl-$C_1$ to $C_6$ alkylthio group, the $C_1$ to $C_6$ alkoxy group, the aryl-$C_1$ to $C_6$ alkoxy group, the heteroaryl-$C_1$ to $C_6$ alkoxy group, the $C_3$ to $C_8$ cycloalkyl-$C_1$ to $C_6$ alkoxy group, and the heterocycloalkyl-$C_1$ to $C_6$ alkoxy group are each substituted by one group selected from a carboxy group, a benzenesulfonylaminocarbonyl group, and a phosphoryl group), more preferably a $C_1$ to $C_6$ alkylthio group, an aryl-$C_1$ to $C_6$ alkylthio group, a heteroaryl-$C_1$ to $C_6$ alkylthio group, or a $C_1$ to $C_6$ alkoxy group (the $C_1$ to $C_6$ alkylthio group, the aryl-$C_1$ to $C_6$ alkylthio group, the heteroaryl-$C_1$ to $C_6$ alkylthio group, and the $C_1$ to $C_6$ alkoxy group are each substituted by one group selected from a carboxy group, a benzenesulfonylaminocarbonyl group, and a phosphoryl group), further preferably a group

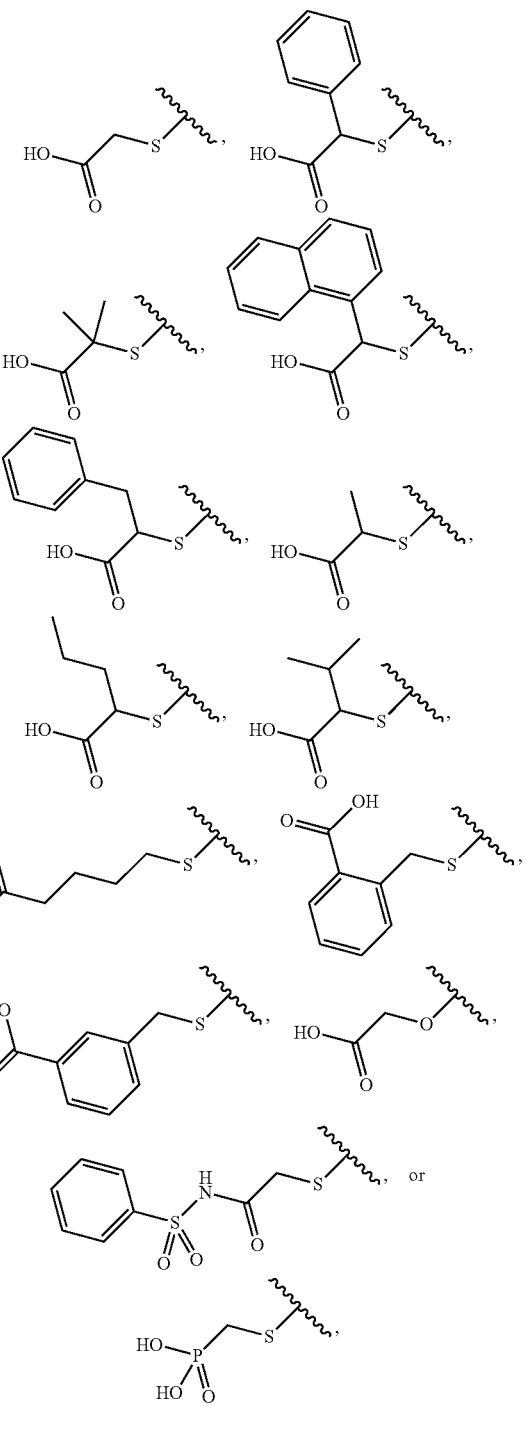

most preferably a group

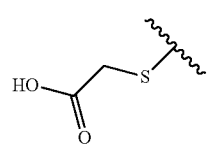

According to the second embodiment, the substituent having such an acidic functional group is preferably a $C_2$ to $C_6$ alkenyl group, an aryl-$C_2$ to $C_6$ alkenyl group, a heteroaryl-$C_2$ to $C_6$ alkenyl group, a $C_3$ to $C_8$ cycloalkyl-$C_2$ to $C_6$ alkenyl group, a heterocycloalkyl-$C_2$ to $C_6$ alkenyl group, a $C_2$ to $C_6$ alkynyl group, an aryl-$C_2$ to $C_6$ alkynyl group, a heteroaryl-$C_2$ to $C_6$ alkynyl group, a $C_3$ to $C_8$ cycloalkyl-$C_2$ to $C_6$ alkynyl group, a heterocycloalkyl-$C_2$ to $C_6$ alkynyl group, a $C_1$ to $C_6$ alkyl group, an aryl-$C_1$ to $C_6$ alkyl group, a heteroaryl-$C_1$ to $C_6$ alkyl group, a $C_3$ to $C_8$ cycloalkyl-$C_1$ to $C_6$ alkyl group, a heterocycloalkyl-$C_1$ to $C_6$ alkyl group, an aryl group, a heteroaryl group, or a heterocycloalkyl group (the $C_2$ to $C_6$ alkenyl group, the aryl-$C_2$ to $C_6$ alkenyl group, the heteroaryl-$C_2$ to $C_6$ alkenyl group, the $C_3$ to $C_8$ cycloalkyl-$C_2$ to $C_6$ alkenyl group, the heterocycloalkyl-$C_2$ to $C_6$ alkenyl group, the $C_2$ to $C_6$ alkynyl group, the aryl-$C_2$ to $C_6$ alkynyl group, the heteroaryl-$C_2$ to $C_6$ alkynyl group, the $C_3$ to $C_8$ cycloalkyl-$C_2$ to $C_6$ alkynyl group, the heterocycloalkyl-$C_2$ to $C_6$ alkynyl group, the $C_1$ to $C_6$ alkyl group, the aryl-$C_1$ to $C_6$ alkyl group, the heteroaryl-$C_1$ to $C_6$ alkyl group, the $C_3$ to $C_8$ cycloalkyl-$C_1$ to $C_6$ alkyl group, the heterocycloalkyl-$C_1$ to $C_6$ alkyl group, the aryl group, the heteroaryl group, and the heterocycloalkyl group are each substituted by one group selected from a carboxy group, a triazolylsulfonyl group, a carboxymethoxy group, a methylsulfonylamino group, a 4-methylbenzenesulfonylamino group, a (2S)-2-carboxypyrrolidin-1-ylcarbonyl group, and a (2S,4R)-2-carboxy-4-hydroxypyrrolidin-1-ylcarbonyl group), more preferably a $C_2$ to $C_6$ alkenyl group, a $C_1$ to $C_6$ alkyl group, or an aryl group (the $C_2$ to $C_6$ alkenyl group, the $C_1$ to $C_6$ alkyl group, and the aryl group are each substituted by one group selected from a carboxy group, a triazolylsulfonyl group, a carboxymethoxy group, a methylsulfonylamino group, a 4-methylbenzenesulfonylamino group, a (2S)-2-carboxypyrrolidin-1-ylcarbonyl group, and a (2S, 4R)-2-carboxy-4-hydroxypyrrolidin-1-ylcarbonyl group), further preferably a vinyl group, an ethyl group, or a phenyl group (the vinyl group, the ethyl group, and the phenyl group are each substituted by one group selected from a carboxy group, a triazolylsulfonyl group, a carboxymethoxy group, a methylsulfonylamino group, a 4-methylbenzenesulfonylamino group, a (2S)-2-carboxypyrrolidin-1-ylcarbonyl group, and a (2S, 4R)-2-carboxy-4-hydroxypyrrolidin-1-ylcarbonyl group), still further preferably a group

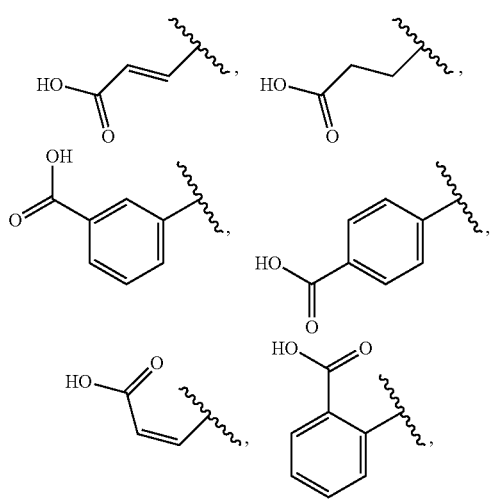

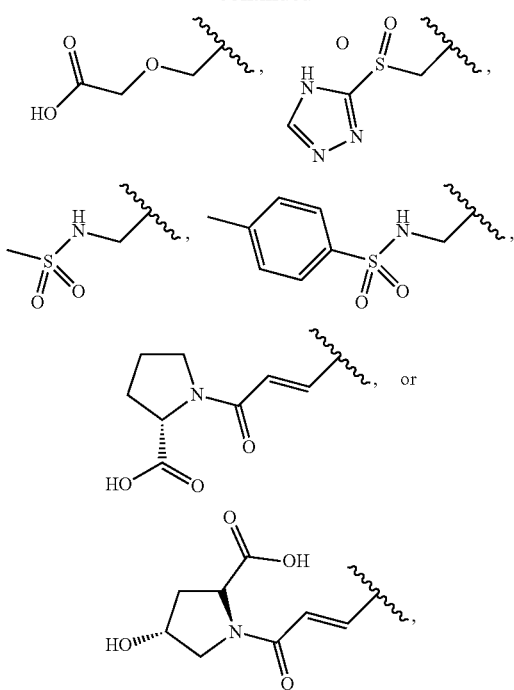

most preferably a group

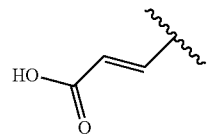

According to the third embodiment, the substituent having such an acidic functional group is preferably a heteroaryl-$C_1$ to $C_6$ alkylthio group, a heteroaryl-$C_2$ to $C_6$ alkenyl group, a heteroaryl-$C_2$ to $C_6$ alkynyl group, a heteroaryl-$C_1$ to $C_6$ alkyl group, a heteroaryl-$C_1$ to $C_6$ alkoxy group, or a heteroaryl group (the heteroaryl-$C_1$ to $C_6$ alkylthio group, the heteroaryl-$C_2$ to $C_6$ alkenyl group, the heteroaryl-$C_2$ to $C_6$ alkynyl group, the heteroaryl-$C_1$ to $C_6$ alkyl group, the heteroaryl-$C_1$ to $C_6$ alkoxy group, and the heteroaryl group are each optionally substituted at the heteroaryl group moiety by 1 or 2 oxo groups), more preferably a heteroaryl-$C_1$ to $C_6$ alkylthio group, or a heteroaryl-$C_2$ to $C_6$ alkenyl group (the heteroaryl-$C_1$ to $C_6$ alkylthio group and the heteroaryl-$C_2$ to $C_6$ alkenyl group are each optionally substituted at the heteroaryl group moiety by 1 or 2 oxo groups), further preferably a group

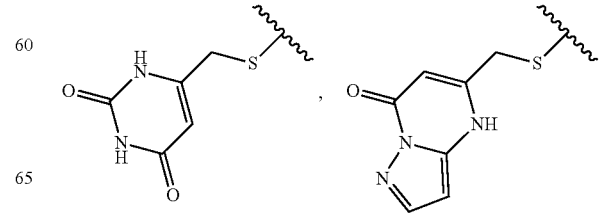

-continued

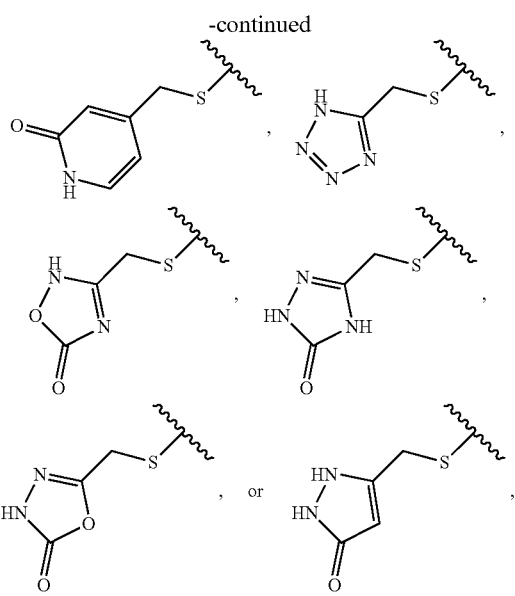

further preferably a group

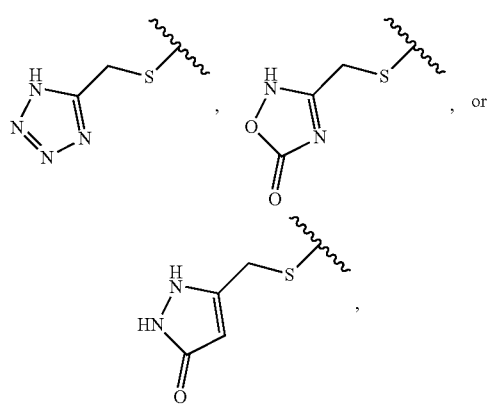

most preferably a group

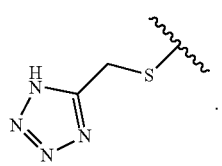 [SMILES: *SCc1nnn[nH]1]

When the compound represented by formula (I) or (II) of the present invention or a pharmacologically acceptable salt thereof has a substituent such as a carboxy group, this compound or salt can be converted to a prodrug (compound that is converted in vivo through metabolism to the compound represented by formula (I) or (II)). The present invention also encompasses such a prodrug.

As for the pharmacologically acceptable salt of the compound represented by formula (I) or (II) of the present invention, examples of acid addition salts formed with acids can include: hydrohalides such as hydrofluoride, hydrochloride, hydrobromide, and hydroiodide; inorganic acid salts such as nitrate, perchlorate, sulfate, and phosphate; lower alkanesulfonates such as methanesulfonate, trifluoromethanesulfonate, and ethanesulfonate; arylsulfonates such as benzenesulfonate and p-toluenesulfonate; organic acid salts such as acetate, malate, fumarate, succinate, citrate, tartrate, oxalate, and maleate; and amino acid salts such as ornithine salts, glutamate, and aspartate.

Examples of the base addition salts formed with bases can include: alkali metal salts such as sodium salt, potassium salt, and lithium salt; alkaline earth metal salts such as calcium salt and magnesium salt; inorganic salts such as ammonium salt; organic amine salts such as dibenzylamine salt, morpholine salt, phenylglycine alkyl ester salt, ethylenediamine salt, N-methylglucamine salt, diethylamine salt, triethylamine salt, cyclohexylamine salt, dicyclohexylamine salt, N,N'-dibenzylethylenediamine salt, diethanolamine salt, N-benzyl-N-(2-phenylethoxy)amine salt, piperazine salt, tetramethylammonium salt, and tris(hydroxymethyl) aminomethane salt; and amino acid salts such as arginine salt.

The compound represented by formula (I) or (II) of the present invention or the pharmacologically acceptable salt thereof may be present as a solvate. Such a solvent is also included in the compound represented by formula (I) or (II) of the present invention or the pharmacologically acceptable salt thereof. The solvate is not particularly limited as long as the solvate is pharmacologically acceptable. Specifically, the solvate is preferably hydrate, ethanol solvate, or the like, more preferably hydrate.

When the compound represented by formula (I) or (II) of the present invention or the pharmacologically acceptable salt thereof has at least one chiral center, carbon-carbon double bond, axial chiral, tautomerism, or the like, optical isomers (including enantiomers and diastereomers), geometric isomers, rotational isomers, and tautomers may exist. The present invention encompasses each of these isomers and mixtures (including racemates) thereof at arbitrary ratios.

The compound represented by formula (I) or (II) of the present invention or the pharmacologically acceptable salt thereof can form an isotopic compound by the replacement of one or more atoms constituting the compound or the salt with isotopes at nonnatural ratios. The isotopes can be radioactive or nonradioactive. Examples thereof include deuterium ($^2$H; D), tritium ($^3$H; T), carbon-14 ($^{14}$C), and iodine-125 ($^{125}$I). The radioactive or nonradioactive isotopic compound can be used as a pharmaceutical drug for the treatment or prevention of a disease, a reagent for research (e.g., a reagent for assay), a diagnostic agent (e.g., a diagnostic imaging agent), or the like. The present invention encompasses these radioactive or nonradioactive isotopic compounds.

The compound represented by formula (I) or (II) of the present invention or the pharmacologically acceptable salt thereof can be produced according to, for example, the following methods A to E.

Method A:

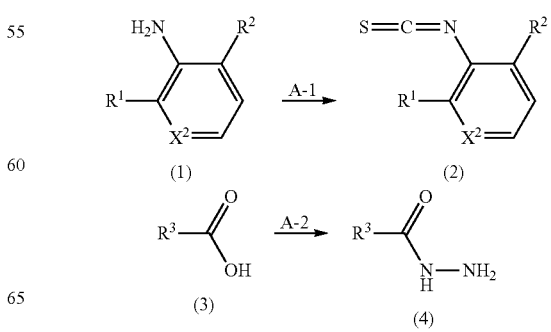

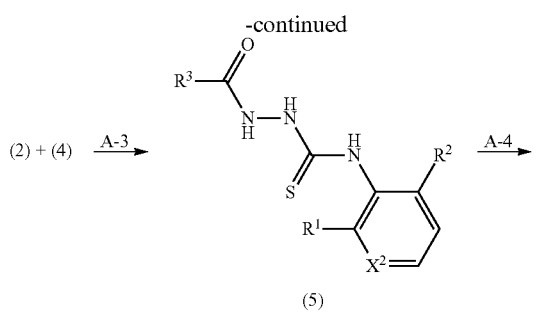
(5)
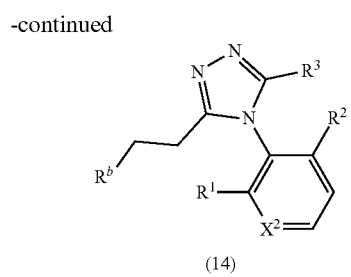
(14)
Method C:
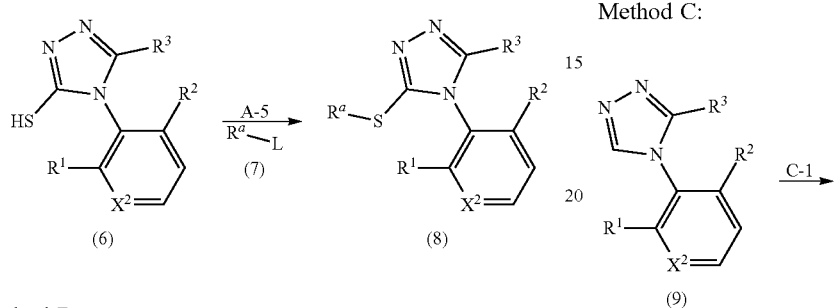
Method B:
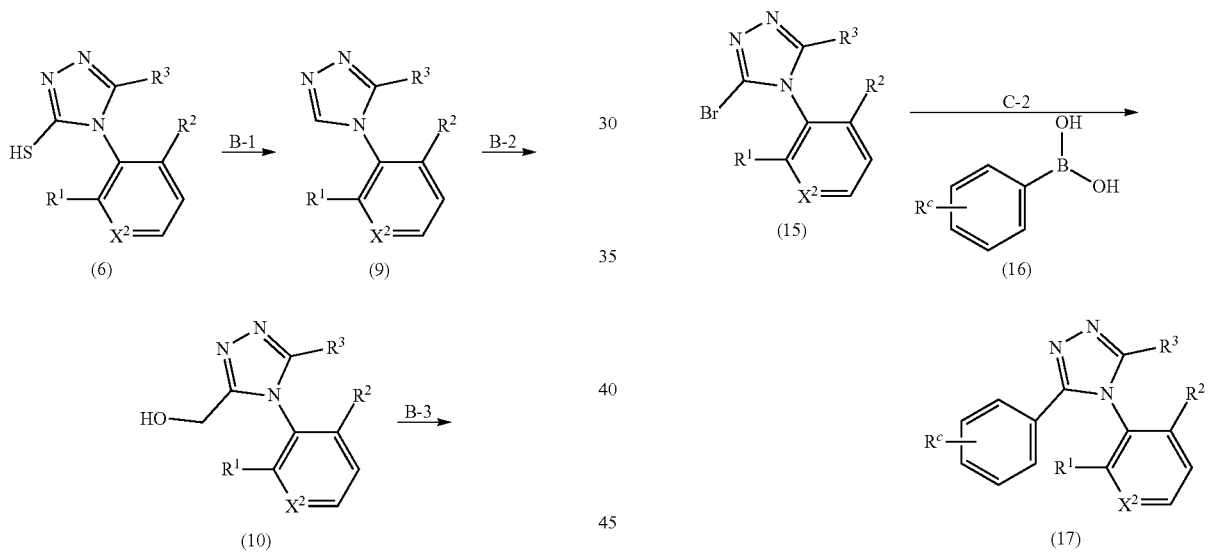
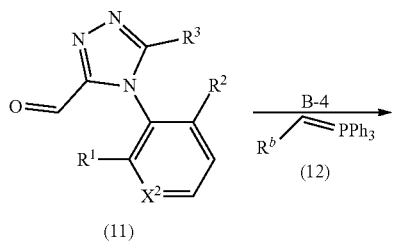
Method D:
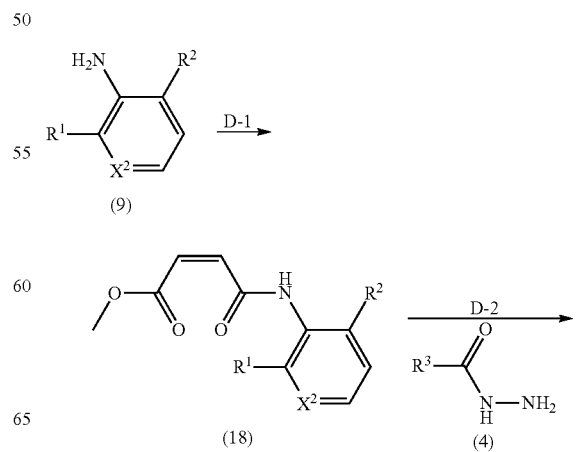

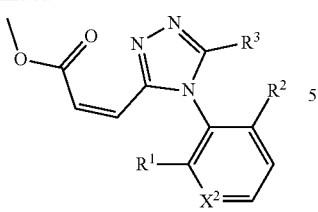

(19)

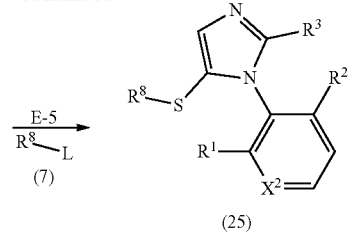

Method E:

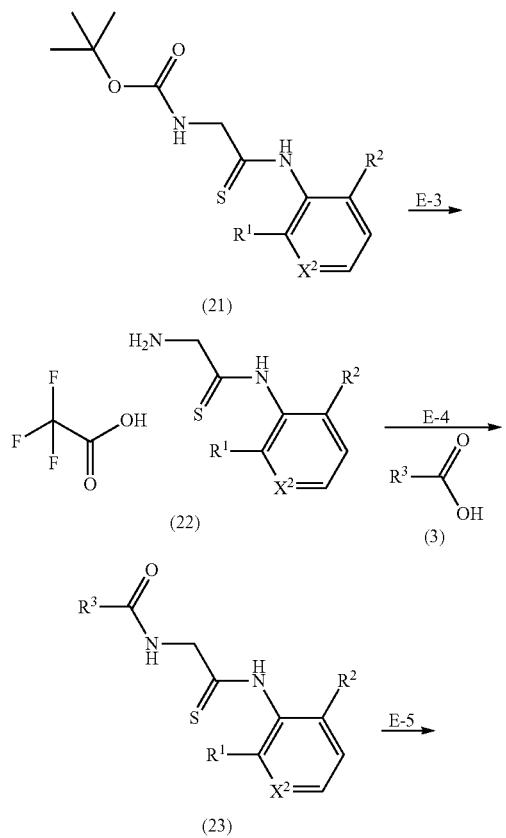

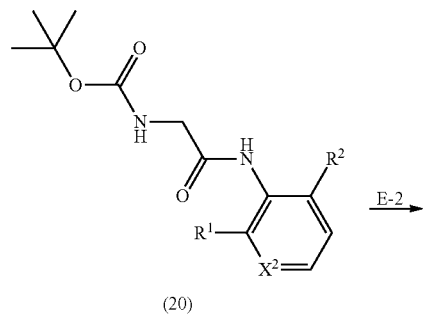

In the description of the methods A to E, $X^1$, $X^2$, $R^1$, $R^2$, and $R^3$ are as defined in formulas (I) and (II), $R^a$ represents a substituent such as a $C_1$ to $C_6$ alkyl group, an aryl-$C_1$ to $C_6$ alkyl group, or a heteroaryl-$C_1$ to $C_6$ alkyl group, the substituent being optionally substituted, L represents a leaving group such as a halogeno group, $R^b$ represents a substituent such as a methoxycarbonyl group, or an ethoxycarbonyl group, and $R^C$ represents a substituent such as a methoxycarbonyl group or an ethoxycarbonyl group.

A compound obtained through the reaction of each step in the methods A to E can be further converted to a derivative by a method well known in the field of organic chemistry (e.g., oxidation reaction, reduction reaction, deprotection reaction, and condensation reaction).

The acid for use in the reaction of each step in the methods A to E and in the reaction of the step of further conversion to a derivative is not particularly limited as long as the acid does not inhibit the reaction. The acid is selected from, for example, the following acid group: organic acids such as acetic acid, propionic acid, trifluoroacetic acid, and pentafluoropropionic acid; and organic sulfonic acids such as p-toluenesulfonic acid, camphorsulfonic acid, and trifluoromethanesulfonic acid; and inorganic acids such as hydrochloric acid, hydrobromic acid, hydroiodic acid, phosphoric acid, sulfuric acid, and nitric acid.

The base for use in the reaction of each step in the methods A to E and in the reaction of the step of further conversion to a derivative is not particularly limited as long as the base does not inhibit the reaction. The base is selected from, for example, the following base group: alkali metal carbonates such as lithium carbonate, sodium carbonate, potassium carbonate, and cesium carbonate; alkali metal bicarbonates such as lithium bicarbonate, sodium bicarbonate, and potassium bicarbonate; alkali metal hydroxides such as lithium hydroxide, sodium hydroxide, and potassium hydroxide; alkaline earth metal hydroxides such as calcium hydroxide and barium hydroxide; alkali metal hydrides such as lithium hydride, sodium hydride, and potassium hydride; alkali metal amides such as lithium amide, sodium amide, and potassium amide; alkali metal alkoxides such as lithium methoxide, sodium methoxide, sodium ethoxide, sodium tert-butoxide, and potassium tert-butoxide; lithium akylamides such as lithium diisopropylamide; alkali metal silylamides such as lithium bistrimethylsilylamide and sodium bistrimethylsilylamide; alkyllithiums such as n-butyllithium, sec-butyllithium, and tert-butyllithium; and organic amines such as triethylamine, tributylamine, diisopropylethylamine, N-methylmorpholine, pyridine, picoline, lutidine, 4-(N,N-dimethylamino)pyridine, 4-pyrrolidinopyridine, quinoline, N,N-dimethylaniline, 1,5-diazabicyclo[4.3.0]non-5-ene (DBN), 1,4-diazabicyclo[2.2.2]octane (DABCO), and 1,8-diazabicyclo[5.4.0]undec-7-ene (DBU).

The solvent for use in the reaction of each step in the methods A to E and in the reaction of the step of further conversion to a derivative is not particularly limited as long as the solvent does not inhibit the reaction. The solvent is selected from, for example, the following solvent group: aliphatic hydrocarbons such as n-hexane, n-pentane, n-heptane, petroleum ether, and cyclohexane; aromatic hydrocarbons such as benzene, toluene, xylene, and ethylbenzene; halogenated hydrocarbons such as dichloromethane, chloroform, carbon tetrachloride, dichloroethane, chlorobenzene, and dichlorobenzene; ethers such as diethyl ether, diisopropyl ether, tetrahydrofuran, 2-methyltetrahydrofuran, 1,4-dioxane, dimethoxyethane, and diethylene glycol dimethyl ether; ketones such as acetone, methyl ethyl ketone, methyl isobutyl ketone, and cyclohexanone; esters such as methyl acetate, ethyl acetate, propyl acetate, isopropyl acetate, and butyl acetate; nitriles such as acetonitrile, propionitrile, butyronitrile, and isobutyronitrile; carboxylic acids such as acetic acid and propionic acid; alcohols such as methanol, ethanol, 1-propanol, 2-propanol, 1-butanol, 2-butanol, 2-methyl-1-propanol, tert-butanol, and 1,2-propanediol; amides such as formamide, N,N-dimethylformamide, N,N-dimethylacetamide, 1-methyl-2-pyrrolidone, dimethylimidazolone, and hexamethylphosphortriamide; sulfoxides such as dimethyl sulfoxide; sulfones such as sulfolane; water; and mixtures thereof.

In the reaction of each step in the methods A to E and in the reaction of the step of further conversion to a derivative, the reaction temperature differs depending on solvents, starting materials, or reagents, etc., and the reaction time differs depending on solvents, starting materials, reagents, or reaction temperatures, etc.

After the completion of the reaction of each step in the methods A to E and the reaction of the step of further conversion to a derivative, the compound of interest of each step can be isolated from the reaction mixture according to a method well known in the field of organic chemistry. The compound of interest is obtained, for example, by: (i) if necessary, filtering off insoluble matter such as a catalyst; (ii) adding water and a water-immiscible solvent (e.g., dichloromethane, diethyl ether, or ethyl acetate) to the reaction mixture to extract the compound of interest; (iii) washing the organic layer with water, followed by drying using a desiccant such as anhydrous magnesium sulfate; and (iv) distilling off the solvent. The obtained compound of interest can be further purified, if necessary, by a method well known in the field of organic chemistry, for example, recrystallization, reprecipitation, or silica gel column chromatography. Alternatively, the compound of interest of each step may be used directly in the next reaction without being purified.

When a compound serving as a starting material in the reaction of each step in the methods A to E and in the reaction of the step of further conversion to a derivative has a group inhibiting the reaction of interest, such as an amino group, a hydroxy group, or a carboxy group, an appropriate protective group may be introduced to these groups and the introduced protective group may be removed, if necessary. Such a protective group is not particularly limited as long as the protective group is one usually used. The protective group can be a protective group described in, for example, Peter G. M. Wuts, Theodora W. Greene, Greene's Protective Groups in Organic Synthesis 4th Edition (2007), Wiley-InterScience. The reactions for the introduction and removal of these protective groups can be carried out according to methods well known in the field of organic chemistry (e.g., methods described in the literature).

In each step in the methods A to E and in the step of further conversion to a derivative, a diastereomeric mixture can be resolved into single diastereomers by, for example, column chromatography or a crystallization method, and a racemate can be resolved into single enantiomers by, for example, optically active column chromatography or a fractional crystallization method using an optically active compound (e.g., an optically active carboxylic acid compound or an optically active amine compound).

The pharmacologically acceptable salt of the compound represented by formula (I) or (II) of the present invention can be produced by, for example, the following method: (i) dissolving the compound represented by formula (I) or (II) of the present invention in a solvent; (ii) adding an acid or a base to the reaction solution and stirring the reaction mixture; (iii) if necessary, carrying out the heating and cooling of the reaction mixture, the distilling off of the solvent, the addition of a poor solvent, or the addition of seed crystals of the salt compound of interest; and (iv) collecting the deposited solid by filtration.

Hereinafter, the reaction of each step in the methods A to E will be described.

Method A:

Step A-1:

This step is the step of contacting compound (1) with thiophosgene to produce compound (2). The compound (1) can be obtained by a method known in the art or a method similar thereto, or a commercially available one can be used. The solvent used in this step is preferably a 1:1 mixed solvent of dichloromethane and water. The amount of the thiophosgene used in this step is preferably 1 to 1.2 equivalents with respect to the compound (1). This step preferably employs a base. The base is preferably sodium bicarbonate. The amount of the base is preferably 2 to 3 equivalents with respect to the compound (1). The reaction temperature of this step is preferably −20° C. to 40° C. The reaction time of this step is preferably 30 minutes to 4 hours.

Step A-2:

This step is the step of converting compound (3) to acid chloride (step A-2-1), further esterifying the acid chloride (step A-2-2), and then contacting the resulting compound with hydrazine (step A-2-3) to produce compound (4).

The compound (3) can be obtained by a method known in the art or a method similar thereto, or a commercially available one can be used.

The solvent used in step A-2-1 is preferably dichloromethane. The conversion to acid chloride in step A-2-1 is preferably carried out using oxalyl chloride in the presence of a small amount of N,N-dimethylformamide. The amount of the oxalyl chloride is preferably 1.9 to 2.1 equivalents with respect to the compound (3). The reaction temperature of step A-2-1 is preferably −20° C. to 40° C. The reaction time of step A-2-1 is preferably 1 hour to 12 hours.

The solvent used in step A-2-2 is preferably methanol. The reaction temperature of step A-2-2 is preferably 0° C. to 40° C. The reaction time of step A-2-2 is preferably 30 minutes to 4 hours.

The solvent used in step A-2-3 is preferably ethanol. The hydrazine used in A-2-3 is preferably hydrazine monohydrate. The amount of the hydrazine monohydrate is preferably 1 to 4 equivalents with respect to the compound (3). The reaction temperature of this step is preferably 80° C. to 120° C. The reaction time of this step is preferably 1 hour to 12 hours.

Step A-3:

This step is the step of contacting compound (2) with compound (4) to produce compound (5). The compound (2) used can be obtained by the method of step A-1 or a method similar thereto. The compound (4) can be obtained by the method of step A-2 or a method similar thereto, or a commercially available one can be used. The amount of the compound (2) used in this step is preferably 0.9 to 1.1 equivalents with respect to the compound (4). The solvent used in this step is preferably tetrahydrofuran. The reaction temperature of this step is preferably 50° C. to 90° C. The reaction time of this step is preferably 30 minutes to 4 hours.

Step A-4:

This step is the step of constructing a triazole ring by the treatment of compound (5) with a base to produce compound (6). The compound (5) used can be obtained by the method of step A-3 or a method similar thereto. The base used in this step is preferably 1 mol/L aqueous sodium hydroxide solution. The amount of the base is preferably 2 to 3 equivalents with respect to the compound (5). The reaction temperature of this step is preferably 85° C. to 115° C. The reaction time of this step is preferably 30 minutes to 4 hours.

Step A-5:

This step is the step of contacting compound (6) with compound (7) to produce compound (8). The compound (6) used can be obtained by the method of step A-4 or a method similar thereto. The compound (7) can be obtained by a method known in the art or a method similar thereto, or a commercially available one can be used. The amount of the compound (7) used in this step is preferably 1 to 1.3 equivalents with respect to the compound (6). This step preferably employs a base. The base is preferably potassium carbonate. The amount of the base is preferably 1 to 1.5 equivalents with respect to the compound (6) The solvent used in this step is preferably acetone. The reaction temperature of this step is preferably 0° C. to 70° C. The reaction time of this step is preferably 30 minutes to 4 hours.

Method B:

Step B-1:

This step is the step of desulfurizing compound (6) to produce compound (9). The compound (6) used can be obtained by the method of step A-4 or a method similar thereto. The desulfurization in this step is preferably carried out using a solution of hydrogen peroxide in acetic acid. The amount of the hydrogen peroxide is preferably 2 to 3 equivalents with respect to the compound (6). The solvent used in this step is preferably dichloromethane. The reaction temperature of this step is preferably −20° C. to 30° C. The reaction time of this step is preferably 30 minutes to 4 hours.

Step B-2:

This step is the step of condensing compound (9) with formaldehyde to produce compound (10). The compound (9) used can be obtained by the method of step B-1 or a method similar thereto. The formaldehyde used in this step is preferably a 36% aqueous formaldehyde solution. The amount of the formaldehyde is preferably 15 to 30 equivalents with respect to the compound (9). The reaction temperature of this step is preferably 70° C. to 110° C. The reaction time of this step is preferably 30 minutes to 4 hours.

Step B-3:

This step is the step of oxidizing compound (10) to produce compound (11). The compound (10) used can be obtained by the method of step B-2 or a method similar thereto. The oxidizing agent used in this step is preferably Dess-Martin periodinane. The amount of the oxidizing agent is preferably 1 to 1.5 equivalents with respect to the compound (10). The solvent used in this step is preferably dichloromethane. The reaction temperature of this step is preferably −20° C. to 20° C. The reaction time of this step is preferably 30 minutes to 4 hours.

Step B-4:

This step is the step of condensing compound (11) with compound (12) through Wittig reaction to produce compound (13). The compound (11) used can be obtained by the method of step B-3 or a method similar thereto. The compound (12) can be obtained by a method known in the art or a method similar thereto, or a commercially available one can be used. The amount of the compound (12) used in this step is preferably 1 to 1.5 equivalents with respect to the compound (11). The solvent used in this step is preferably toluene. The reaction temperature of this step is preferably 70° C. to 120° C. The reaction time of this step is preferably 30 minutes to 4 hours.

Step B-5:

This step is the step of hydrogenating compound (13) using a catalyst under the hydrogen atmosphere to produce compound (14). The compound (13) used can be obtained by the method of step B-4 or a method similar thereto. The catalyst used in this step is preferably a 10% palladium carbon catalyst. The amount of the catalyst is preferably 0.05 to 0.2 equivalents with respect to the compound (13). The solvent used in this step is preferably methanol. The reaction temperature of this step is preferably 0° C. to 40° C. The reaction time of this step is preferably 1 hour to 12 hours.

Method C:

Step C-1:

This step is the step of brominating compound (9) to produce compound (15). The compound (9) used can be obtained by the method of step B-1 or a method similar thereto. The brominating agent used in this step is preferably N-bromosuccinimide. The amount of the brominating agent is preferably 1 to 1.5 equivalents with respect to the compound (13). The solvent used in this step is preferably tetrahydrofuran. The reaction temperature of this step is preferably 50° C. to 90° C. The reaction time of this step is preferably 30 minutes to 4 hours.

Step C-2:

This step is the step of condensing compound (15) with compound (16) through Suzuki-Miyaura coupling to produce compound (17). The compound (15) used can be obtained by the method of step C-1 or a method similar thereto. The compound (16) can be obtained by a method known in the art or a method similar thereto, or a commercially available one can be used. The amount of the compound (16) used in this step is preferably 1 to 5 equivalents with respect to the compound (15). The catalyst used in this step is preferably bis(dibenzylideneacetone)palladium(0). The amount of the catalyst is preferably 0.05 to 0.2 equivalents with respect to the compound (15). The ligand used in this step is preferably 2-dicyclohexylphosphino-2,6'-dimethoxybiphenyl. The amount of the ligand is preferably 0.1 to 0.4 equivalents with respect to the compound (15). The base used in this step is preferably potassium phosphate tribasic. The amount of the base is preferably 2 to 8 equivalents with respect to the compound (15). The solvent used in this step is preferably a 2:1 mixed solvent of toluene and tetrahydrofuran. This step is preferably carried out in a microwave reaction apparatus. The reaction temperature is preferably 120° C. to 150° C. The reaction time is preferably 30 minutes to 4 hours.

Method D:

Step D-1:

This step is the step of condensing compound (1) with maleic acid monomethyl ester to produce compound (18). The compound (1) can be obtained by a method known in the art or a method similar thereto, or a commercially available one can be used. The amount of the maleic acid monomethyl ester used in this step is preferably 1 to 1.2 equivalents with respect to the compound (1) The condensing agent used in this step is preferably 1-ethyl-3-(3-dimethylaminopropyl)carbodiimide hydrochloride. The amount of the condensing agent is preferably 1 to 1.5 equivalents with respect to the compound (1). The catalyst used in this step is preferably 4-dimethylaminopyridine. The amount of the catalyst is preferably 0.1 to 0.15 equivalents with respect to the compound (1). The solvent used in this step is preferably dichloromethane. The reaction temperature of this step is preferably 0° C. to 40° C. The reaction time of this step is preferably 30 minutes to 4 hours.

Step D-2:

This step is the step of constructing a triazole ring by the condensation of compound (18) with compound (4) according to a method described in the reference (Org. Lett., 2015, 17, 1184-1187) to produce compound (19). The compound (18) used can be obtained by the method of step D-1 or a method similar thereto. The compound (4) can be obtained by the method of step A-2 or a method similar thereto, or a commercially available one can be used. The amount of the compound (4) used in this step is preferably 0.9 to 1.1 equivalents with respect to the compound (18). In this step, 2-fluoropyridine is used, and the amount thereof is preferably 1 to 1.2 equivalents with respect to the compound (18). In this step, trifluoromethanesulfonic anhydride is used, and the amount thereof is preferably 1 to 1.2 equivalents with respect to the compound (18). The solvent used in this step is preferably 1,2-dichloroethane. This step is preferably carried out in a microwave reaction apparatus. The reaction temperature is preferably 120° C. to 150° C. The reaction time is preferably 30 minutes to 4 hours.

Method E:

Step E-1:

This step is the step of condensing compound (1) with N-(tert-butoxycarbonyl)glycine to produce compound (20). The compound (1) can be obtained by a method known in the art or a method similar thereto, or a commercially available one can be used. The amount of the N-(tert-butoxycarbonyl)glycine used in this step is preferably 1 to 1.2 equivalents with respect to the compound (1). The condensing agent used in this step is preferably 4-(4,6-dimethoxy-1,3,5-triazin-2-yl)-4-methylmorpholinium chloride. The amount of the condensing agent is preferably 1 to 1.2 equivalents with respect to the compound (1). The solvent used in this step is preferably methanol. The reaction temperature of this step is preferably 0° C. to 40° C. The reaction time of this step is preferably 1 hour to 12 hours.

Step E-2:

This step is the step of contacting compound (20) with Lawesson's Reagent to produce compound (21). The compound (20) used can be obtained by the method of step E-1 or a method similar thereto. The solvent used in this step is preferably tetrahydrofuran. The amount of the Lawesson's Reagent used in this step is preferably 1 to 1.2 equivalents with respect to the compound (20). The reaction temperature of this step is preferably 0° C. to 40° C. The reaction time of this step is preferably 1 hour to 24 hours.

Step E-3:

This step is the step of deprotecting the tert-butoxycarbonyl group in compound (21) with an acid to produce compound (22). The compound (21) used can be obtained by the method of step E-2 or a method similar thereto. The acid used in this step is preferably trifluoroacetic acid. The solvent used in this step is preferably dichloromethane. The ratio between the trifluoroacetic acid and the solvent is preferably 1:6. The reaction temperature of this step is preferably 0° C. to 40° C. The reaction time of this step is preferably 30 minutes to 4 hours.

Step E-4:

This step is the step of converting compound (3) to acid chloride (step E-4-1) and further condensing the acid chloride with compound (22) (step E-4-2) to produce compound (23). The compound (22) used can be obtained by the method of step E-3 or a method similar thereto. The compound (3) can be obtained by a method known in the art or a method similar thereto, or a commercially available one can be used. The reagent used in step E-4-1 is preferably thionyl chloride. The reaction temperature of step E-4-1 is preferably 80° C. to 100° C. The reaction time of step E-4-1 is preferably 30 minutes to 4 hours. The base used in step E-4-2 is preferably N,N-diisopropylethylamine. The amount of the base is preferably 3 to 6 equivalents with respect to the compound (22). The solvent used in step E-4-2 is preferably tetrahydrofuran. The reaction temperature of step E-4-2 is preferably −20° C. to 20° C. The reaction time of step E-4-2 is preferably 30 minutes to 4 hours.

Step E-5:

This step is the step of constructing an imidazole ring by the treatment of compound (23) with phosphoryl chloride to produce compound (24). The amount of the phosphoryl chloride used in this step is preferably 15 to 30 equivalents with respect to the compound (23). The solvent used in this step is preferably toluene. The reaction temperature of this step is preferably 90° C. to 110° C. The reaction time of this step is preferably 30 minutes to 4 hours.

Step E-6:

This step is the step of contacting compound (24) with compound (7) to produce compound (25). The compound (24) used can be obtained by the method of step E-5 or a method similar thereto. The compound (7) can be obtained by a method known in the art or a method similar thereto, or a commercially available one can be used. The amount of the compound (7) used in this step is preferably 1 to 5 equivalents with respect to the compound (24). This step preferably employs a base. The base is preferably sodium hydride. The amount of the base is preferably 1 to 5 equivalents with respect to the compound (24). The solvent used in this step is preferably tetrahydrofuran. The reaction temperature of this step is preferably 0° C. to 40° C. The reaction time of this step is preferably 1 hour to 12 hours.

When the compound represented by formula (I) or (II) of the present invention or the pharmacologically acceptable salt thereof is used as a pharmaceutical drug, the compound or the salt can be administered (i) alone as a bulk (ii) orally as a preparation such as a tablet, a capsule, granules, a powder, or a syrup produced by mixing with an appropriate pharmacologically acceptable excipient, diluent, or the like, or (iii) parenterally as an preparation such as an injection or a suppository produced in the same way as above. Preferably, the compound or the salt is orally administered.

These preparations are produced by well-known methods using additives such as excipients, binders, disintegrants, lubricants, emulsifiers, stabilizers, corrigents, diluents, and solvents for injections.

The excipients can be, for example, organic excipients or inorganic excipients. Examples of the organic excipients can include: sugar derivatives such as lactose, saccharose, glucose, mannitol, and sorbitol; starch derivatives such as corn starch; cellulose derivatives such as crystalline cellulose; gum arabic; dextran; and pullulan. Examples of the inorganic excipients can include: light anhydrous silicic acid and silicate derivatives such as synthetic aluminum silicate; and sulfates such as calcium sulfate.

Examples of the binders can include: the compounds exemplified as the excipients; gelatin; polyvinylpyrrolidone; and polyethylene glycol.

Examples of the disintegrants can include: the compounds exemplified as the excipients; chemically modified starch or cellulose derivatives such as croscarmellose sodium and carboxymethyl starch sodium; and cross-linked polyvinylpyrrolidone.

Examples of the lubricants can include: talc; colloidal silica; waxes such as bees wax and spermaceti; glycol; D,L-leucine; sulfates such as sodium sulfate; and the starch derivatives listed as the excipients.

Examples of the emulsifiers can include: colloidal clay such as bentonite and veegum; anionic surfactants such as sodium lauryl sulfate; cationic surfactants such as benzalkonium chloride; and nonionic surfactants such as polyoxyethylene alkyl ether.

Examples of the stabilizers can include: p-hydroxybenzoic acid esters such as methylparaben; alcohols such as chlorobutanol; benzalkonium chloride; phenol; and thimerosal.

Examples of the corrigents can include sweeteners, acidulants, and flavors usually used.

Examples of the diluents can include water, ethanol, and propylene glycol.

Examples of the solvents for injections can include water, ethanol, and glycerin.

The dose of the compound represented by formula (I) or (II) or the pharmacologically acceptable salt thereof as the active ingredient of the present invention differs depending on the symptoms and age of a patient, etc. The single dose of the compound represented by formula (I) or (II) or the pharmacologically acceptable salt thereof is 0.01 mg/kg (preferably 0.05 mg/kg) as the lower limit and 500 mg/kg (preferably 50 mg/kg) as the upper limit for oral administration and 0.001 mg/kg (preferably 0.005 mg/kg) as the lower limit and 50 mg/kg (preferably 5 mg/kg) as the upper limit for parenteral administration and can be administered to an adult once to six times a day according to the symptoms.

The compound represented by formula (I) or (II) of the present invention or the pharmacologically acceptable salt thereof exhibited excellent apelin receptor agonist activity. Thus, the present invention can provide a method for treating or preventing a disease such as cardiovascular disease, coronary heart disease, stroke, heart failure, systolic heart failure, diastolic heart failure, diabetic heart failure, heart failure with preserved ejection fraction, cardiomyopathy, myocardial infarction, left ventricular dysfunction, left ventricular dysfunction after myocardial infarction, cardiac hypertrophy, myocardial remodeling, myocardial remodeling after infarction, myocardial remodeling after cardiac surgery, valvular heart disease, metabolic disease, metabolic syndrome, insulin resistance, diabetes mellitus, diabetic late complications, diabetic macrovasculopathy, diabetic microvasculopathy, diabetic nephropathy, diabetic retinopathy, diabetic neuropathies, cardiac autonomic neuropathy, CNS-dependent disturbed fluid homeostasis, CNS-independent disturbed fluid homeostasis, acute renal failure, chronic renal failure, hypertension, pulmonary hypertension, portal hypertension, systolic hypertension, vascular disease, vascular hypertrophy, vascular remodeling, vascular stiffness, atherosclerosis, peripheral arterial occlusive disease (PAOD), restenosis, thrombosis, vascular permeability disorder, cardiac, renal, or retinal disorder caused by ischemia, or cardiac, renal, or retinal disorder caused by reperfusion using the compound represented by formula (I) or (II) of the present invention or the pharmacologically acceptable salt thereof.

DETAILED DESCRIPTION OF THE PREFERRED EMBODIMENTS

Hereinafter, the present invention will be described in detail with reference to Examples, etc. However, the scope of the present invention is not intended to be limited by them.

Elution in column chromatography in Examples was carried out under observation by thin layer chromatography (TLC). In the TLC observation, silica gel 60F$_{254}$ (Merck KGaA) was used as a TLC plate; a solvent used as an eluting solvent in column chromatography was used as a developing solvent; and a UV detector or a chromogenic method using a coloring agent (e.g., a ninhydrin coloring solution, an anisaldehyde coloring solution, an ammonium phosphomolybdate coloring solution, a cerium ammonium nitrate coloring solution, or an alkaline permanganate coloring solution) was used as a detection method.

Silica gel SK-85 (230-400 mesh) (Merck KGaA), silica gel 60 N (40-50 µm) (Kanto Chemical Co., Inc.), or Chromatorex NH (200-350 mesh) (Fuji Silysia Chemical Ltd.) was used as silica gel for columns.

In addition to general column chromatography, an automatic chromatography apparatus such as Purif-α2 or Purif-espoir2 (Shoko Scientific Co., Ltd.), W-Prep 2XY (Yamazen Corp.), Isolera One (Biotage Japan Ltd.), or CombiFlash Rf (Teledyne Isco, Inc.) was appropriately used. The eluting solvent was determined on the basis of the TLC observation.

In Examples, nuclear magnetic resonance (H NMR) spectra were indicated by chemical shift δ values (ppm) determined with tetramethylsilane (TMS) as a standard. CDCl$_3$, DMSO-d$_6$, and CD$_3$OD in the parentheses means deuterated chloroform, deuterated dimethylsulfoxide, and deuterated methanol used as a measurement solvent. Multiplicity in $^1$H-NMR means s=singlet, d=doublet, t=triplet, q=quartet, m=multiplet, br s=broad singlet, and br m=broad multiplet.

Mass spectrometry (MS) was conducted by electron spray ionization (ESI), or atmospheric pressure chemical ionization (APCI) method by using liquid chromatography mass spectrometry (LCMS) device.

In each step of Examples, the preparation of a reaction solution and reaction were carried out at room temperature unless the temperature is otherwise specified.

EXAMPLES

Example 1

4-(2,6-Dimethoxyphenyl)-5-(5-methylfuran-2-yl)-4H-1,2,4-triazole-3-thiol

Step 1

2-Isothiocyanato-1,3-dimethoxybenzene

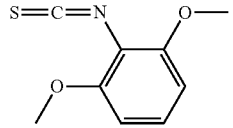

To a mixed solution of dichloromethane (500 mL) and water (500 mL), 2,6-dimethoxyaniline (75.8 g, 495 mmol) and sodium hydrogen carbonate (83.1 g, 990 mmol) were added, and thiophosgene (62.6 g, 544 mmol) was added in small portions with stirring under ice cooling. The mixture was stirred for 10 minutes under ice cooling and then stirred at room temperature for 1 hour. An organic layer was separated, and dichloromethane was added to the aqueous layer to extract organic matter. The organic layers were combined, washed with saturated saline, and then dried over anhydrous magnesium sulfate. The solvent was distilled off under reduced pressure. Then, n-hexane was added to the obtained solid, and the resulting solid was collected by filtration to obtain the title compound (88.5 g, 454 mmol, 92%) as a white solid.

$^1$H-NMR (400 MHz, CDCl$_3$) δ (ppm): 3.89 (6H, s), 6.54 (2H, d, J=8.5 Hz), 7.14 (1H, t, J=8.5 Hz). MS (APCI): m/z 182 [M+H]$^+$.

Step 2

N-(2,6-Dimethoxyphenyl)-2-[(5-methylfuran-2-yl)carbonyl]hydrazinecarbothioamide

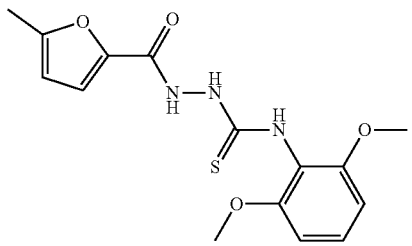

To a suspension of 2-isothiocyanato-1,3-dimethoxy-benzene (62.7 g, 321 mmol) in tetrahydrofuran (642 mL), 5-methylfuran-2-carbohydrazide (45.0 g, 321 mmol) was added at room temperature, and the mixture was heated to reflux for 1.5 hours. The solvent in the reaction solution was distilled off under reduced pressure to obtain the partially purified title compound (107.7 g, 321 mmol, quantitative) as a faint yellow amorphous form. The obtained faint yellow amorphous form was used in the next reaction without being purified.

MS (APCI): m/z 336 [M+H]$^+$.

Step 3

4-(2,6-Dimethoxyphenyl)-5-(5-methylfuran-2-yl)-4H-1,2,4-triazole-3-thiol

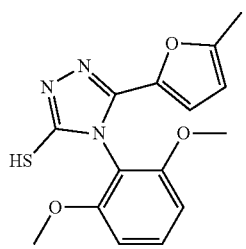

To N-(2,6-dimethoxyphenyl)-2-[(5-methylfuran-2-yl)carbonyl]hydrazinecarbothioamide (107.7 g, 321 mmol), 1 mol/L aqueous sodium hydroxide solution (642 mL, 642 mmol) was added at room temperature, and the mixture was heated to reflux for 1 hour. The reaction solution was ice-cooled, 1 mol/L hydrochloric acid (642 mL, 642 mmol) was added in small portions thereto with stirring, and the mixture was stirred at room temperature for 30 minutes. The resulting white precipitate was collected by filtration, fully washed with water and n-hexane, and then dried under reduced pressure at 50° C. to obtain the title compound (96.2 g, 303 mmol, 94%) as a white solid.

$^1$H-NMR (400 MHz, CDCl$_3$) δ (ppm): 2.32 (3H, s), 3.78 (6H, s), 5.79 (1H, d, J=3.6 Hz), 5.88-5.92 (1H, m), 6.73 (2H, d, J=8.5 Hz), 7.49 (1H, t, J=8.5 Hz), 10.63 (1H, s). MS (APCI): m/z 318 [M+H]$^+$.

Example 2

2-({[4-(2,6-Dimethoxyphenyl)-5-(5-methylfuran-2-yl)-4H-1,2,4-triazol-3-yl]sulfanyl}methyl)-7-methyl-4H-pyrido[1,2-a]pyrimidin-4-one

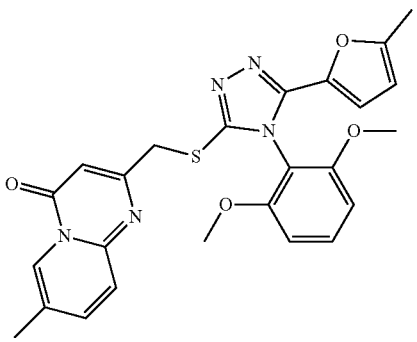 [SMILES: COc1cccc(OC)c1-n1c(SCc2cc(=O)n3cc(C)ccc3n2)nnc1-c1ccc(C)o1]

To a mixture of 2-(chloromethyl)-7-methyl-pyrido[1,2-a]pyrimidin-4-one (44.0 mg, 0.208 mmol), 4-(2,6-dimethoxyphenyl)-5-(5-methylfuran-2-yl)-4H-1,2,4-triazole-3-thiol (60.0 mg, 0.189 mmol), and potassium carbonate (33.0 mg, 0.236 mmol), acetone (1.0 mL) was added, and the mixture was stirred at 65° C. for 1.5 hours. The reaction solution was filtered through celite, and the solvent was distilled off under reduced pressure. The obtained residue was purified by silica gel column chromatography [elution solvent: n-hexane/ethyl acetate/methanol=30/70/0-0/100/0-0/90/10 (V/V)] to obtain the title compound (82 mg, 0.168 mmol, 89%) as a white solid.

$^1$H-NMR (400 MHz, CDCl$_3$) δ (ppm): 2.27 (3H, s), 2.42 (3H, s), 3.71 (6H, s), 4.41 (2H, s), 5.87-5.90 (1H, m), 5.91 (1H, d, J=3.6 Hz), 6.51 (1H, s), 6.66 (2H, d, J=8.5 Hz), 7.43 (1H, t, J=8.5 Hz), 7.52 (1H, d, J=9.1 Hz), 7.58 (1H, dd, J=9.1, 1.8 Hz), 8.81 (1H, s). MS (APCI): m/z 490 [M+H]$^+$.

Example 3

7-Chloro-2-({[4-(2,6-dimethoxyphenyl)-5-(5-methylfuran-2-yl)-4H-1,2,4-triazol-3-yl]sulfanyl}methyl)-4H-pyrido[1,2-a]pyrimidin-4-one

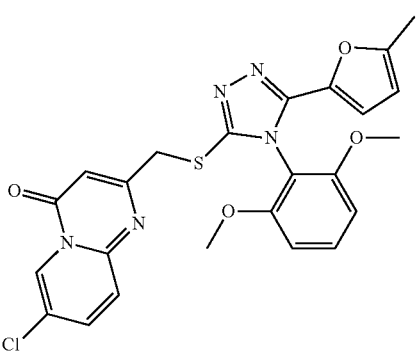 [SMILES: COc1cccc(OC)c1-n1c(SCc2cc(=O)n3cc(Cl)ccc3n2)nnc1-c1ccc(C)o1]

The title compound (92 mg, 0.181 mmol, 96%) was obtained as a white solid from 7-chloro-2-(chloromethyl)pyrido[1,2-a]pyrimidin-4-one (47.6 mg, 0.208 mmol) and 4-(2,6-dimethoxyphenyl)-5-(5-methylfuran-2-yl)-4H-1,2,4-triazole-3-thiol (60.0 mg, 0.189 mmol) in the same way as in Example 2.

$^1$H-NMR (400 MHz, CDCl$_3$) δ (ppm): 2.27 (3H, s), 3.71 (6H, s), 4.38 (2H, s), 5.88-5.90 (1H, m), 5.92 (1H, d, J=3.6 Hz), 6.56 (1H, s), 6.67 (2H, d, J=8.5 Hz), 7.44 (1H, t, J=8.5 Hz), 7.53 (1H, d, J=9.1 Hz), 7.64 (1H, dd, J=9.4, 2.1 Hz), 9.01 (1H, d, J=1.8 Hz). MS (APCI): m/z 510 [M+H]$^+$.

Example 4

Ethyl {[4-(2,6-Dimethoxyphenyl)-5-(5-methylfuran-2-yl)-4H-1,2,4-triazol-3-yl]sulfanyl}acetate

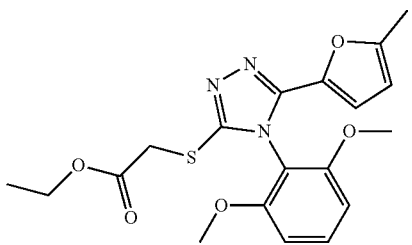 [SMILES: CCOC(=O)CSc1nnc(-c2ccc(C)o2)n1-c1c(OC)cccc1OC]

To a mixture of bromoacetic acid ethyl ester (40 μL, 0.352 mmol), 4-(2,6-dimethoxyphenyl)-5-(5-methylfuran-2-yl)-4H-1,2,4-triazole-3-thiol (93 mg, 0.294 mmol), and potassium carbonate (51 mg, 0.367 mmol), acetone (1.0 mL) was added, and the mixture was stirred at room temperature for 1 hour. The reaction solution was filtered through celite to remove insoluble matter. The solvent was distilled off under reduced pressure, and the obtained residue was purified by silica gel column chromatography [elution solvent: n-hexane/ethyl acetate=60/40-30/70 (V/V)] to obtain the title compound (110 mg, 0.273 mmol, 93%) as a white solid.

$^1$H-NMR (400 MHz, CDCl$_3$) δ (ppm): 1.26 (3H, t, J=7.1 Hz), 2.27 (3H, s), 3.73 (6H, s), 4.05 (2H, s), 4.18 (2H, q, J=7.1 Hz), 5.88-5.90 (1H, m), 5.92 (1H, d, J=3.0 Hz), 6.68 (2H, d, J=8.5 Hz), 7.46 (1H, t, J=8.5 Hz). MS (APCI): m/z 404 [M+H]$^+$.

Example 5

{[4-(2,6-Dimethoxyphenyl)-5-(5-methylfuran-2-yl)-4H-1,2,4-triazol-3-yl]sulfanyl}acetic acid

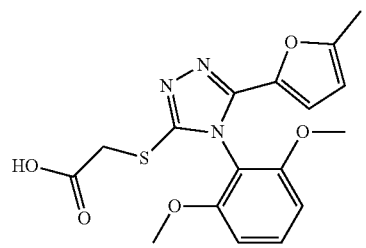 [SMILES: COc1cccc(OC)c1-n1c(SCC(=O)O)nnc1-c1ccc(C)o1]

To ethyl {[4-(2,6-dimethoxyphenyl)-5-(5-methylfuran-2-yl)-4H-1,2,4-triazol-3-yl]sulfanyl}acetate (101 mg, 0.251 mmol), ethanol was added, then 1 mol/L aqueous sodium hydroxide solution (0.50 mL, 0.50 mmol) was added at room temperature, and the mixture was stirred at room temperature for 1.5 hours. Ethanol in the reaction solution was distilled off, then the residue was diluted by the addition of water, and 1 mol/L hydrochloric acid (0.50 mL, 0.50 mmol) was added to the mixture. Ethyl acetate was added thereto for extraction, and the organic layer was dried over anhydrous magnesium sulfate. The solvent was distilled off under reduced pressure to obtain the title compound (83 mg, 0.221 mmol, 88%) as a white solid.

$^1$H-NMR (400 MHz, CDCl$_3$) δ (ppm): 2.28 (3H, s), 3.75 (6H, s), 4.12 (2H, s), 5.92-5.95 (1H, m), 6.02 (1H, d, J=3.0 Hz), 6.70 (2H, d, J=8.5 Hz), 7.50 (1H, t, J=8.5 Hz). MS (APCI): m/z 376 [M+H]$^+$.

Example 6

4-(2,6-Dimethoxyphenyl)-3-(5-methylfuran-2-yl)-4H-1,2,4-triazole

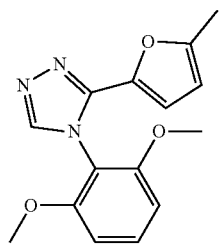

To a solution of 4-(2,6-dimethoxyphenyl)-5-(5-methylfuran-2-yl)-4H-1,2,4-triazole-3-thiol (96.1 g, 303 mmol) in dichloromethane (388 mL), a solution of hydrogen peroxide (62.4 mL, 757 mmol) in acetic acid (173 mL, 3029 mmol) was added dropwise with stirring under ice cooling. After the completion of the dropwise addition, the mixture was stirred at room temperature for 1 hour. The reaction mixture was stirred under ice cooling. The pH of the aqueous layer was rendered neutral by the addition of 1 mol/L aqueous sodium hydroxide solution (500 mL) and 28% aqueous ammonia solution, and the mixture was stirred at room temperature for 30 minutes (the disappearance of peroxide was confirmed using potassium iodide starch paper). An organic layer was separated, followed by further extraction twice by the addition of dichloromethane. The organic layers were combined, washed with an aqueous sodium hydrogensulfite solution (approximately 500 mL) and saturated saline, and dried over anhydrous magnesium sulfate. The reaction solution was concentrated under reduced pressure, and the obtained residue was purified by NH silica gel column chromatography [elution solvent: dichloromethane] to obtain a light brown solid. The solid was crystallized from dichloromethane-ethyl acetate to obtain the title compound (46.1 g, 161 mmol, 53%) as a white solid.

$^1$H-NMR (400 MHz, CDCl$_3$) δ (ppm): 2.28 (3H, s), 3.71 (6H, s), 5.91-5.93 (1H, m), 6.02 (1H, d, J=3.0 Hz), 6.68 (2H, d, J=8.5 Hz), 7.44 (1H, t, J=8.5 Hz), 8.04 (1H, s). MS (APCI): m/z 286 [M+H]$^+$.

Example 7

[4-(2,6-Dimethoxyphenyl)-5-(5-methylfuran-2-yl)-4H-1,2,4-triazol-3-yl]methanol

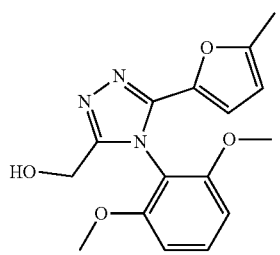 [SMILES: COc1cccc(OC)c1-n1c(CO)nnc1-c1ccc(C)o1]

To 4-(2,6-dimethoxyphenyl)-3-(5-methylfuran-2-yl)-4H-1,2,4-triazole (38.8 g, 136 mmol), a 36% aqueous formaldehyde solution (131 mL, 2720 mmol) was added, and the mixture was heated and stirred at 90° C. for 1 hour under the nitrogen atmosphere. The reaction solution was diluted by the addition of dichloromethane and washed with 1 mol/L aqueous sodium hydroxide solution. After drying over anhydrous magnesium sulfate, the solvent was distilled off under reduced pressure, and the obtained residue was purified by silica gel column chromatography [elution solvent: dichloromethane/ethyl acetate=70/30-30/70 (V/V)] to obtain the title compound (26.9 g, 85.3 mmol, 63%) as a white solid.

$^1$H-NMR (400 MHz, CDCl$_3$) δ (ppm): 2.29 (3H, s), 2.37 (1H, t, J=6.4 Hz, —OH), 3.73 (6H, s), 4.56 (2H, d, J=6.4 Hz), 5.87 (1H, d, J=3.6 Hz), 5.89-5.92 (1H, m), 6.71 (2H, d, J=8.5 Hz), 7.48 (1H, t, J=8.5 Hz). MS (APCI): m/z 316 [M+H]$^+$.

Example 8

Ethyl (2E)-3-[4-(2,6-dimethoxyphenyl)-5-(5-methylfuran-2-yl)-4H-1,2,4-triazol-3-yl]prop-2-enoate

Step 1

4-(2,6-Dimethoxyphenyl)-5-(5-methylfuran-2-yl)-4H-1,2,4-triazole-3-carbaldehyde

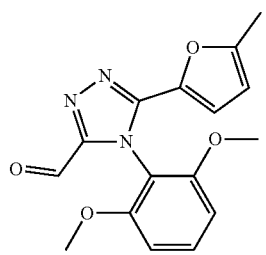 [SMILES: COc1cccc(OC)c1-n1c(C=O)nnc1-c1ccc(C)o1]

To a solution of [4-(2,6-dimethoxyphenyl)-5-(5-methylfuran-2-yl)-4H-1,2,4-triazol-3-yl]methanol (33.3 g, 106 mmol) in dichloromethane (530 mL), Dess-Martin periodinane (53.8 g, 127 mmol) was added in small portions with stirring under ice cooling, and the mixture was then stirred for 1 hour. A saturated aqueous solution of sodium bicarbonate was added to the reaction solution under ice cooling, and the mixture was stirred for 15 minutes. Insoluble matter was filtered off through celite, and an organic layer was separated. Dichloromethane was added to the aqueous layer for extraction, and the organic layers were combined and dried over anhydrous magnesium sulfate. The solvent was distilled off under reduced pressure, and the obtained residue was purified by silica gel column chromatography [elution solvent: dichloromethane/ethyl acetate=95/5-50/50 (V/V)] to obtain the title compound (19.4 g, 62.1 mmol, 59%) as a white solid.

$^1$H-NMR (400 MHz, CDCl$_3$) δ (ppm): 2.33 (3H, s), 3.69 (6H, s), 5.96-5.98 (1H, m), 6.05 (1H, d, J=3.6 Hz), 6.69 (2H, d, J=8.5 Hz), 7.48 (1H, t, J=8.5 Hz), 10.04 (1H, s). MS (APCI): m/z 314 [M+H]$^+$ and 332, [M+H$_2$O+H]$^+$.

Step 2

Ethyl (2E)-3-[4-(2,6-dimethoxyphenyl)-5-(5-methylfuran-2-yl)-4H-1,2,4-triazol-3-yl]prop-2-enoate

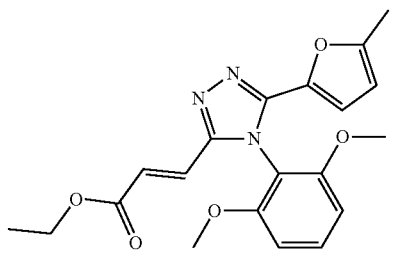 [SMILES: CCOC(=O)/C=C/c1nnc(-c2ccc(C)o2)n1-c1c(OC)cccc1OC]

To a solution of 4-(2,6-dimethoxyphenyl)-5-(5-methyl-2-furyl)-1,2,4-triazole-3-carbaldehyde (19.38 g, 61.86 mmol) in toluene (620 mL), ethyl (triphenylphosphoranylidene)acetate (25.86 g, 74.23 mmol) was added, and the mixture was stirred at 90° C. for 2 hours. The solvent in the reaction solution was distilled off under reduced pressure, and the obtained residue was purified by silica gel column chromatography [elution solvent: dichloromethane/ethyl acetate=100/0-80/20 (V/V)] to obtain the title compound (18.8 g, 49.0 mmol, 79%) as a white solid.

$^1$H-NMR (400 MHz, CDCl$_3$) δ (ppm): 1.28 (3H, t, J=7.0 Hz), 2.29 (3H, s), 3.70 (6H, s), 4.20 (2H, q, J=7.0 Hz), 5.89-5.93 (2H, m), 6.70 (2H, d, J=8.5 Hz), 6.86 (1H, d, J=15.8 Hz), 7.10 (1H, d, J=15.8 Hz), 7.49 (1H, t, J=8.5 Hz). MS (APCI): m/z 384 [M+H]$^+$.

Example 9

(2E)-3-[4-(2,6-Dimethoxyphenyl)-5-(5-methylfuran-2-yl)-4H-1,2,4-triazol-3-yl]prop-2-enoic acid

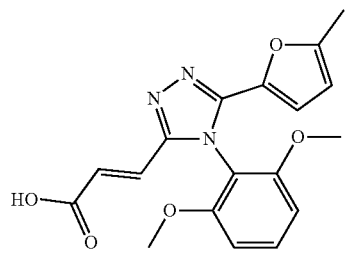 [SMILES: COc1cccc(OC)c1-n1c(/C=C/C(=O)O)nnc1-c1ccc(C)o1]

To a solution of ethyl (2E)-3-[4-(2,6-dimethoxyphenyl)-5-(5-methylfuran-2-yl)-4H-1,2,4-triazol-3-yl]prop-2-enoate (469 mg, 1.22 mmol) in ethanol, 1 mol/L aqueous sodium hydroxide solution (2.50 mL, 2.50 mmol) was added, and the mixture was stirred for 1.5 hours. 1 mol/L hydrochloric acid (2.50 mL, 2.50 mmol) was added thereto under ice cooling, and ethanol was then distilled off under reduced pressure. The resulting white solid was collected by filtration to obtain the title compound (389 mg, 1.10 mmol, 90%).

$^{1}$H-NMR (400 MHz, CDCl$_3$) δ (ppm): 2.28 (3H, s), 3.71 (6H, s), 5.91-5.94 (1H, m), 5.98 (1H, d, J=3.6 Hz), 6.71 (2H, d, J=8.5 Hz), 7.14 (2H, br s), 7.50 (1H, t, J=8.5 Hz). MS (APCI): m/z 356 [M+H]$^{+}$.

Example 10

4-(2,6-Dimethoxyphenyl)-5-(thiophen-2-yl)-4H-1,2,4-triazole-3-thiol

Step 1

N-(2,6-Dimethoxyphenyl)-2-(thiophen-2-ylcarbonyl)hydrazinecarbothioamide

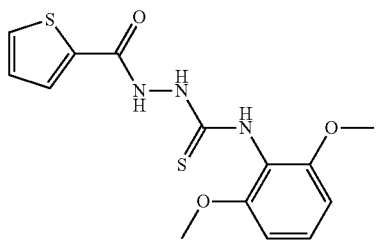 [SMILES: COc1cccc(OC)c1NC(=S)NNC(=O)c1cccs1]

The partially purified title compound (1.32 g, 3.90 mmol, quantitative) was obtained as a white amorphous form from 2-thiophenecarboxylic hydrazide (554 mg, 3.90 mmol) in the same way as in step 2 of Example 1. The obtained white solid was used in the next reaction without being purified. MS (APCI): m/z 338 [M+H]$^{+}$.

Step 2

4-(2,6-Dimethoxyphenyl)-5-(thiophen-2-yl)-4H-1,2,4-triazole-3-thiol

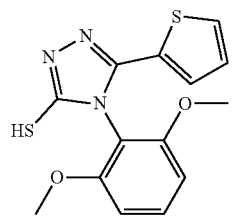 [SMILES: COc1cccc(OC)c1-n1c(S)nnc1-c1cccs1]

The title compound (1.00 g, 80%) was obtained as a white solid from N-(2,6-dimethoxyphenyl)-2-(thiophen-2-ylcarbonyl)hydrazinecarbothioamide (1.32 g, 3.90 mmol) in the same way as in step 3 of Example 1.

$^{1}$H-NMR (400 MHz, DMSO-d$_6$) δ (ppm): 3.70 (6H, s), 6.88 (2H, d, J=8.5 Hz), 6.98 (1H, dd, J=3.7, 1.2 Hz), 7.04 (1H, dd, J=4.9, 3.7 Hz), 7.55 (1H, t, J=8.5 Hz), 7.65-7.68 (1H, m), 14.01 (1H, s). MS (APCI): m/z 320 [M+H]$^{+}$.

Example 11

[2-({[4-(2,6-Dimethoxyphenyl)-5-(thiophen-2-yl)-4H-1,2,4-triazol-3-yl]sulfanyl}methyl)-7-methyl-4H-pyrido[1,2-a]pyrimidin-4-one

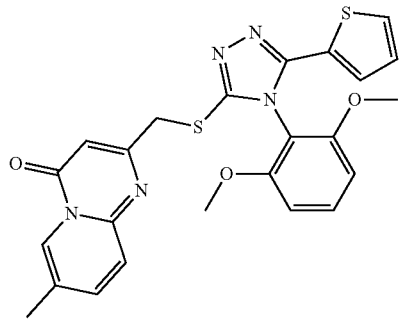 [SMILES: COc1cccc(OC)c1-n1c(SCc2cc(=O)n3cc(C)ccc3n2)nnc1-c1cccs1]

The title compound (124.3 mg, 0.253 mmol, 79%) was obtained as a white solid from 2-(chloromethyl)-7-methyl-pyrido[1,2-a]pyrimidin-4-one (73.0 mg, 0.350 mmol) and 4-(2,6-dimethoxyphenyl)-5-(thiophen-2-yl)-4H-1,2,4-triazole-3-thiol (102 mg, 0.318 mmol) in the same way as in Example 2.

$^{1}$H-NMR (400 MHz, CDCl$_3$) δ (ppm): 2.41 (3H, s), 3.71 (6H, s), 4.42 (2H, s), 6.55 (1H, s), 6.67 (2H, d, J=8.5 Hz), 6.89-6.95 (1H, m), 7.12 (1H, d, J=3.0 Hz), 7.25 (1H, d, J=4.9 Hz), 7.46 (1H, t, J=8.5 Hz), 7.52 (1H, d, J=9.1 Hz), 7.59 (1H, d, J=9.1 Hz), 8.81 (1H, s). MS (APCI): m/z 492 [M+H]$^{+}$.

Example 12

Ethyl 3-[4-(2,6-dimethoxyphenyl)-5-(5-methylfuran-2-yl)-4H-1,2,4-triazol-3-yl]propanoate

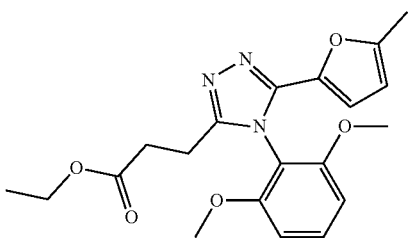 [SMILES: CCOC(=O)CCc1nnc(-c2ccc(C)o2)n1-c1c(OC)cccc1OC]

To a solution of ethyl (2E)-3-[4-(2,6-dimethoxyphenyl)-5-(5-methylfuran-2-yl)-4H-1,2,4-triazol-3-yl]prop-2-enoate (469 mg, 1.22 mmol) in methanol (20 mL), a 10% palladium carbon catalyst (112 mg, 0.1223 mmol) was added, and the mixture was stirred at room temperature for 5 hours under the hydrogen atmosphere. The reaction mixture was filtered through celite and concentrated under reduced pressure. The obtained residue was purified by silica gel column chromatography [elution solvent: dichloromethane/ethyl acetate=90/10-30/70 (V/V)] to obtain the title compound (223 mg, 0.579 mmol, 47%) as a white solid.

$^{1}$H-NMR (400 MHz, DMSO-d$_6$) δ (ppm): 1.16 (3H, t, J=7.1 Hz), 2.23 (3H, s), 2.56-2.62 (2H, m), 2.64-2.71 (2H, m), 3.71 (6H, s), 4.03 (2H, q, J=7.1 Hz), 5.81 (1H, d, J=3.0 Hz), 6.07-6.09 (1H, m), 6.92 (2H, d, J=8.5 Hz), 7.57 (1H, t, J=8.5 Hz). MS (APCI): m/z 386 [M+H]$^{+}$.

Example 13

3-[4-(2,6-Dimethoxyphenyl)-5-(5-methylfuran-2-yl)-4H-1,2,4-triazol-3-yl]propanoic acid The title compound 3-[4-(2,6-dimethoxyphenyl)-5-(5-methyl-2-furyl)-4H-1,2,4-triazol-3-yl]propanoic acid (176 mg, 0.493 mmol, 89%) was obtained as a white solid from ethyl 3-[4-(2,6-dimethoxyphenyl)-5-(5-methylfuran-2-yl)-4H-1,2,4-triazol-3-yl]propanoate (214 mg, 0.556 mmol) in the same way as in Example 9.

$^1$H-NMR (400 MHz, CDCl$_3$) δ (ppm): 2.26 (3H, s), 2.82 (2H, t, J=7.3 Hz), 2.97 (2H, t, J=7.3 Hz), 3.73 (6H, s), 5.87-5.91 (2H, m), 6.70 (2H, d, J=8.5 Hz), 7.48 (1H, t, J=8.5 Hz). MS (APCI): m/z 358 [M+H]$^+$.

Example 14

6-({[4-(2,6-Dimethoxyphenyl)-5-(5-methylfuran-2-yl)-4H-1,2,4-triazol-3-yl]sulfanyl}methyl)pyrimidine-2,4(1H,3H)-dione The title compound (31 mg, 0.071 mmol, 45%) was obtained as a white solid from 4-(2,6-dimethoxyphenyl)-5-(5-methylfuran-2-yl)-4H-1,2,4-triazole-3-thiol (51 mg, 0.159 mmol) and 6-chloromethyluracil (31 mg, 0.191 mmol) in the same way as in Example 2.

$^1$H-NMR (400 MHz, CDCl$_3$) δ (ppm): 2.28 (3H, s), 3.74 (6H, s), 3.96 (2H, s), 5.52 (1H, s), 5.92-5.94 (1H, m), 6.01 (1H, d, J=3.0 Hz), 6.69 (2H, d, J=8.5 Hz), 7.49 (1H, t, J=8.5 Hz), 7.90 (1H, br s), 11.49 (1H, br s). MS (APCI): m/z 442 [M+H]$^+$.

Example 15

6-({[4-(2,6-Dimethoxyphenyl)-5-(5-methylfuran-2-yl)-4H-1,2,4-triazol-3-yl]sulfanyl}methyl)-1,3-dimethylpyrimidine-2,4(1H,3H)-dione The title compound (37 mg, 0.079 mmol, 50%) was obtained as a pale yellow solid from 4-(2,6-dimethoxyphenyl)-5-(5-methylfuran-2-yl)-4H-1,2,4-triazole-3-thiol (50 mg, 0.157 mmol) and 6-(chloromethyl)-1,3-dimethylpyrimidine-2,4(1H,3H)-dione (36 mg, 0.188 mmol) in the same way as in Example 2.

$^1$H-NMR (400 MHz, CDCl$_3$) δ (ppm): 2.27 (3H, s), 3.30 (3H, s), 3.42 (3H, s), 3.72 (6H, s), 4.21 (2H, s), 5.74 (1H, s), 5.90-5.93 (1H, m), 5.97 (1H, d, J=3.6 Hz), 6.69 (2H, d, J=8.5 Hz), 7.48 (1H, t, J=8.5 Hz). MS (APCI): m/z 470 [M+H]$^+$.

Example 16

5-({[4-(2,6-Dimethoxyphenyl)-5-(5-methylfuran-2-yl)-4H-1,2,4-triazol-3-yl]sulfanyl}methyl)pyrazolo[1,5-a]pyrimidin-7(4H)-one The title compound (53 mg, 0.114 mmol, 74%) was obtained as a white solid from 4-(2,6-dimethoxyphenyl)-5-(5-methylfuran-2-yl)-4H-1,2,4-triazole-3-thiol (49 mg, 0.154 mmol) and 5-(chloromethyl)-4H,7H-pyrazolo[1,5-a]pyrimidin-7-one (34 mg, 0.185 mmol) in the same way as in Example 2.

$^1$H-NMR (400 MHz, CDCl$_3$) δ (ppm): 2.31 (3H, s), 3.73 (6H, s), 4.13 (2H, s), 5.72 (1H, s), 5.92-5.98 (2H, m), 6.21 (1H, d, J=1.2 Hz), 6.70 (2H, d, J=8.5 Hz), 7.50 (1H, t, J=8.5 Hz), 7.88 (1H, s). MS (APCI): m/z 465 [M+H]$^+$.

Example 17

4-(2,6-Dimethoxyphenyl)-3-ethyl-5-(5-methylfuran-2-yl)-4H-1,2,4-triazole

Step 1

4-(2,6-Dimethoxyphenyl)-3-ethenyl-5-(5-methyl-furan-2-yl)-4H-1,2,4-triazole

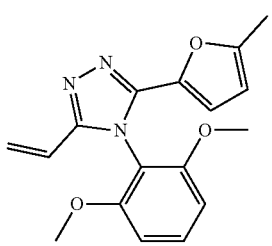 [SMILES: C=Cc1nnc(-c2ccc(C)o2)n1-c1c(OC)cccc1OC]

A suspension of methyltriphenylphosphonium bromide (89 mg, 0.249 mmol) in tetrahydrofuran (2.0 mL) was stirred under ice cooling, and potassium tert-butoxide (28 mg, 0.249 mmol) was added thereto. After stirring for 1 hour, a solution of 4-(2,6-dimethoxyphenyl)-5-(5-methylfuran-2-yl)-4H-1,2,4-triazole-3-carbaldehyde (60 mg, 0.192 mmol) in tetrahydrofuran (2.0 mL) was added dropwise thereto, and the mixture was stirred at room temperature for 1 hour. The solvent in the reaction mixture was distilled off under reduced pressure, and the obtained residue was purified by silica gel column chromatography [elution solvent: dichloromethane/methanol=100/0-95/5 (V/V)] to obtain the title compound (58 mg, 0.187 mmol, 98%) as a colorless oil.

$^1$H-NMR (400 MHz, CDCl$_3$) δ (ppm): 2.29 (3H, s), 3.70 (6H, s), 5.41 (1H, dd, J=10.9, 1.8 Hz), 5.84-5.87 (1H, m), 5.88-5.90 (1H, m), 6.13 (1H, dd, J=18.2, 1.8 Hz), 6.23 (1H, dd, J=18.2, 10.9 Hz), 6.69 (2H, d, J=8.5 Hz), 7.47 (1H, t, J=8.5 Hz). MS (APCI): m/z 312 [M+H]$^+$.

Step 2

4-(2,6-Dimethoxyphenyl)-3-ethyl-5-(5-methylfuran-2-yl)-4H-1,2,4-triazole

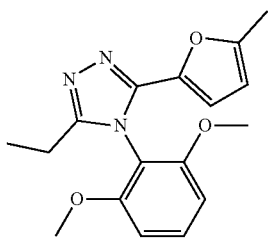 [SMILES: CCc1nnc(-c2ccc(C)o2)n1-c1c(OC)cccc1OC]

The title compound (44 mg, 0.141 mmol, 76%) was obtained as a white solid from 4-(2,6-dimethoxyphenyl)-3-ethenyl-5-(5-methylfuran-2-yl)-4H-1,2,4-triazole (58 mg, 0.187 mmol) in the same way as in Example 12.

$^1$H-NMR (400 MHz, CDCl$_3$) δ (ppm): 1.20 (3H, t, J=7.5 Hz), 2.28 (3H, s), 2.52 (2H, q, J=7.5 Hz), 3.71 (6H, s), 5.78 (1H, d, J=3.0 Hz), 5.85-5.88 (1H, m), 6.69 (2H, d, J=8.5 Hz), 7.46 (1H, t, J=8.5 Hz). MS (APCI): m/z 314 [M+H]$^+$.

Example 18

4-({[4-(2,6-Dimethoxyphenyl)-5-(5-methylfuran-2-yl)-4H-1,2,4-triazol-3-yl]sulfanyl}methyl)pyridin-2(1H)-one

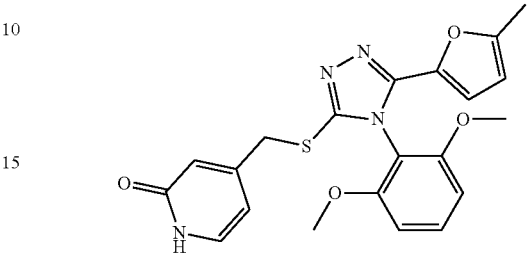

The title compound (55 mg, 0.129 mmol, 79%) was obtained as a white solid from 4-(2,6-dimethoxyphenyl)-5-(5-methylfuran-2-yl)-4H-1,2,4-triazole-3-thiol (52 mg, 0.163 mmol) and 4-(chloromethyl)-1H-pyridin-2-one (28.1 mg, 0.195 mmol) in the same way as in Example 2.

$^1$H-NMR (400 MHz, CDCl$_3$) δ (ppm): 2.27 (3H, s), 3.70 (6H, s), 4.17 (2H, s), 5.88-5.90 (1H, m), 5.92 (1H, d, J=3.0 Hz), 6.30 (1H, dd, J=6.7, 1.8 Hz), 6.42 (1H, s), 6.67 (2H, d, J=8.5 Hz), 7.23 (1H, d, J=7.3 Hz), 7.45 (1H, t, J=8.5 Hz), 12.83 (1H, br s). MS (APCI): m/z 425 [M+H]$^+$.

Example 19

(2E)-3-[4-(2,6-Dimethoxyphenyl)-5-(5-methylfuran-2-yl)-4H-1,2,4-triazol-3-yl]prop-2-enamide

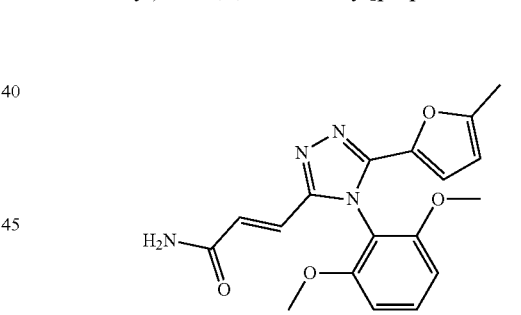

To a suspension of (2E)-3-[4-(2,6-dimethoxyphenyl)-5-(5-methylfuran-2-yl)-4H-1,2,4-triazol-3-yl]prop-2-enoic acid (51 mg, 0.143 mmol) in dichloromethane (2.0 mL), triethylamine (26 μL, 0.186 mmol) was added, and isobutyl chloroformate (24 μL, 0.179 mmol) was added dropwise with stirring under ice cooling. After stirring for 20 minutes, ammonia (ca. 4% in methanol) (0.72 mL, 1.43 mmol) was added thereto, and the mixture was stirred at room temperature for 1 hour. The reaction solution was concentrated under reduced pressure, and the obtained residue was purified by silica gel column chromatography [elution solvent: dichloromethane/methanol=100/0-95/5 (V/V)] to obtain the title compound (42 mg, 0.119 mmol, 83%) as a white solid.

$^1$H-NMR (400 MHz, CD$_3$OD) δ (ppm): 2.27 (3H, s), 3.76 (6H, s), 6.05-6.08 (2H, m), 6.89 (1H, d, J=15.8 Hz), 6.92 (2H, d, J=8.5 Hz), 7.02 (1H, d, J=15.8 Hz), 7.63 (1H, t, J=8.5 Hz). MS (APCI): m/z 355 [M+H]$^+$.

Example 20

(3E)-4-[4-(2,6-Dimethoxyphenyl)-5-(5-methylfuran-2-yl)-4H-1,2,4-triazol-3-yl]but-3-en-2-one

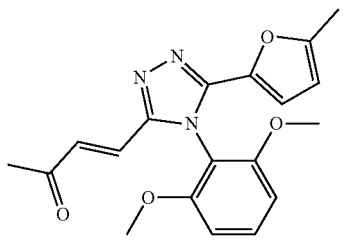 [SMILES: COc1cccc(OC)c1-n1c(/C=C/C(C)=O)nnc1-c1ccc(C)o1]

To a mixture of (acetylmethylene)triphenylphosphorane (196 mg, 0.617 mmol) and 4-(2,6-dimethoxyphenyl)-5-(5-methylfuran-2-yl)-4H-1,2,4-triazole-3-carbaldehyde (149 mg, 0.474 mmol), toluene (5.0 mL) and tetrahydrofuran (1.0 mL) were added, and the mixture was stirred at room temperature for 2 hours. The solvent in the reaction solution was distilled off under reduced pressure, and the obtained residue was purified by silica gel column chromatography [elution solvent: n-hexane/ethyl acetate=30/70-10/90 (V/V)] to obtain the title compound (157 mg, 0.445 mmol, 94%) as a white solid.

$^1$H-NMR (400 MHz, CDCl$_3$) δ (ppm): 2.30 (3H, s), 2.30 (3H, s), 3.70 (6H, s), 5.88-5.93 (2H, m), 6.71 (2H, d, J=8.5 Hz), 6.97 (1H, d, J=15.9 Hz), 7.14 (1H, d, J=15.9 Hz), 7.50 (1H, t, J=8.5 Hz). MS (APCI): m/z 354 [M+H]$^+$.

Example 21

(2E)-3-[4-(2,6-Dimethoxyphenyl)-5-(5-methylfuran-2-yl)-4H-1,2,4-triazol-3-yl]-N,N-dimethylprop-2-enamide

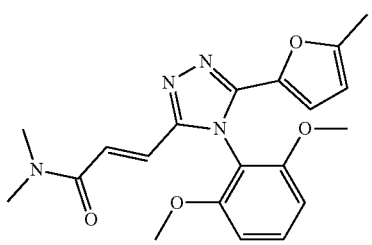

The title compound (49 mg, 0.128 mmol, 84%) was obtained as a white solid from (2E)-3-[4-(2,6-dimethoxyphenyl)-5-(5-methylfuran-2-yl)-4H-1,2,4-triazol-3-yl]prop-2-enoic acid (54 mg, 0.152 mmol) and dimethylamine (2.0 M solution in tetrahydrofuran, 0.76 mL, 1.52 mmol) in the same way as in Example 19.

$^1$H-NMR (400 MHz, CDCl$_3$) δ (ppm): 2.30 (3H, s), 3.02 (3H, s), 3.17 (3H, s), 3.69 (6H, s), 5.86 (1H, d, J=3.1 Hz), 5.89-5.92 (1H, m), 6.68 (2H, d, J=8.5 Hz), 7.00 (1H, d, J=15.3 Hz), 7.46 (1H, t, J=8.5 Hz), 7.61 (1H, d, J=15.3 Hz). MS (APCI): m/z 383 [M+H]$^+$.

Example 22

4-{[4-(2,6-Dimethoxyphenyl)-5-(5-methylfuran-2-yl)-4H-1,2,4-triazol-3-yl]sulfanyl}butanoic acid

Step 1

Ethyl 4-{[4-(2,6-dimethoxyphenyl)-5-(5-methylfuran-2-yl)-4H-1,2,4-triazol-3-yl]sulfanyl}butanoate

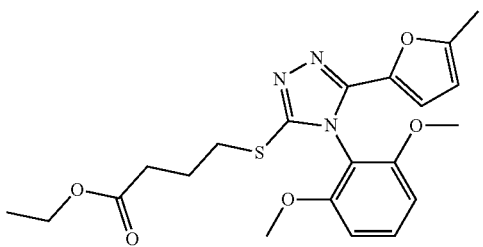 [SMILES: CCOC(=O)CCCSc1nnc(-c2ccc(C)o2)n1-c1c(OC)cccc1OC]

The title compound (66 mg, 0.154 mmol, 58%) was obtained as a colorless oil from 4-(2,6-dimethoxyphenyl)-5-(5-methylfuran-2-yl)-4H-1,2,4-triazole-3-thiol (85 mg, 0.267 mmol) and 4-bromo-n-butyric acid ethyl ester (46 μL, 0.321 mmol) in the same way as in Example 4.

$^1$H-NMR (400 MHz, CDCl$_3$) δ (ppm): 1.23 (3H, t, J=7.0 Hz), 1.98-2.05 (2H, m), 2.28 (3H, s), 2.39 (2H, t, J=7.3 Hz), 3.18 (2H, t, J=7.0 Hz), 3.72 (6H, s), 4.10 (2H, q, J=7.0 Hz), 5.87-5.90 (2H, m), 6.68 (2H, d, J=8.5 Hz), 7.46 (1H, t, J=8.5 Hz). MS (APCI): m/z 432 [M+H]$^+$.

Step 2

4-{[4-(2,6-Dimethoxyphenyl)-5-(5-methylfuran-2-yl)-4H-1,2,4-triazol-3-yl]sulfanyl}butanoic acid

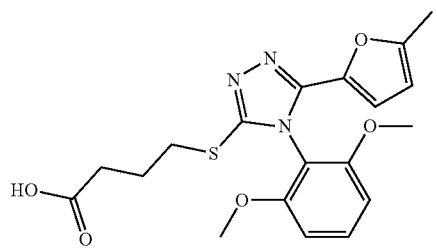 [SMILES: COc1cccc(OC)c1-n1c(SCCCC(=O)O)nnc1-c1ccc(C)o1]

The title compound (58 mg, 0.145 mmol, 97%) was obtained as a white solid from 4-{[4-(2,6-dimethoxyphenyl)-5-(5-methylfuran-2-yl)-4H-1,2,4-triazol-3-yl]sulfanyl}butanoate (64 mg, 0.148 mmol) in the same way as in Example 5.

$^1$H-NMR (400 MHz, CDCl$_3$) δ (ppm): 2.02-2.09 (2H, m), 2.26 (3H, s), 2.54 (2H, t, J=7.0 Hz), 3.23 (2H, t, J=7.0 Hz), 3.73 (6H, s), 5.89-5.92 (1H, m), 5.98 (1H, d, J=3.0 Hz), 6.69 (2H, d, J=8.5 Hz), 7.48 (1H, t, J=8.5 Hz). MS (APCI): m/z 404 [M+H]$^+$.

Example 23

(3E)-4-[4-(2,6-Dimethoxyphenyl)-5-(5-methylfuran-2-yl)-4H-1,2,4-triazol-3-yl]but-3-en-2-ol

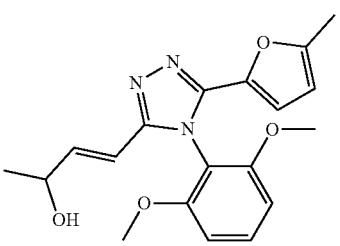 [SMILES: COc1cccc(OC)c1-n1c(/C=C/C(C)O)nnc1-c1ccc(C)o1]

To a solution of (3E)-4-[4-(2,6-dimethoxyphenyl)-5-(5-methylfuran-2-yl)-4H-1,2,4-triazol-3-yl]but-3-en-2-one (66 mg, 0.187 mmol) and cerium chloride anhydrous (55 mg, 0.224 mmol) in methanol (2.0 mL), sodium borohydride (9.2 mg, 0.261 mmol) was added in small portions with stirring under ice cooling, and the mixture was stirred at 0° C. for 15 minutes. The reaction solution was concentrated under reduced pressure, and the obtained residue was purified by silica gel column chromatography [elution solvent: dichloromethane/methanol=100/0-85/15 (V/V)] to obtain the title compound (48 mg, 0.136 mmol, 73%) as a white solid.

$^1$H-NMR (400 MHz, CDCl$_3$) δ (ppm): 1.28 (3H, d, J=6.7 Hz), 2.28 (3H, s), 3.68 (6H, s), 4.39-4.45 (1H, m), 5.82 (1H, d, J=3.6 Hz), 5.88 (1H, d, J=3.6 Hz), 6.08 (1H, d, J=16.4 Hz), 6.69 (2H, d, J=8.5 Hz), 6.82 (1H, dd, J=16.4, 5.2 Hz), 7.46 (1H, t, J=8.5 Hz). MS (APCI): m/z 356 [M+H]$^+$.

Example 24

4-[4-(2,6-Dimethoxyphenyl)-5-(5-methylfuran-2-yl)-4H-1,2,4-triazol-3-yl]butan-2-one

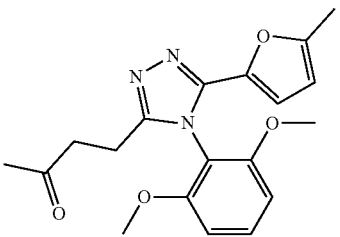 [SMILES: COc1cccc(OC)c1-n1c(CCC(C)=O)nnc1-c1ccc(C)o1]

The title compound (24 mg, 0.069 mmol, 29%) was obtained as a white solid (crystals) from (3E)-4-[4-(2,6-dimethoxyphenyl)-5-(5-methylfuran-2-yl)-4H-1,2,4-triazol-3-yl]but-3-en-2-one (84 mg, 0.237 mmol) in the same way as in Example 12.

$^1$H-NMR (400 MHz, CDCl$_3$) δ (ppm): 2.17 (3H, s), 2.28 (3H, s), 2.66-2.71 (2H, m), 3.03-3.09 (2H, m), 3.71 (6H, s), 5.79 (1H, d, J=3.0 Hz), 5.86-5.88 (1H, m), 6.68 (2H, d, J=8.5 Hz), 7.45 (1H, t, J=8.5 Hz). MS (APCI): m/z 356 [M+H]$^+$.

Example 25

4-[4-(2,6-Dimethoxyphenyl)-5-(5-methylfuran-2-yl)-4H-1,2,4-triazol-3-yl]butan-2-ol

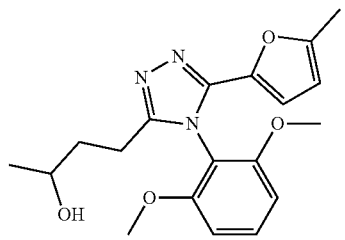 [SMILES: COc1cccc(OC)c1-n1c(CCC(C)O)nnc1-c1ccc(C)o1]

To a solution of 4-[4-(2,6-dimethoxyphenyl)-5-(5-methylfuran-2-yl)-4H-1,2,4-triazol-3-yl]butan-2-one (52 mg, 0.145 mmol) in methanol (3.0 mL), sodium borohydride (7.3 mg, 0.174 mmol) was added with stirring under ice cooling, and the mixture was stirred for 30 minutes. The reaction solution was concentrated under reduced pressure, and the obtained residue was purified by silica gel column chromatography [elution solvent: dichloromethane/methanol=100/0-80/20 (V/V)] to obtain the title compound (45 mg, 0.126 mmol, 87%) as a white solid.

$^1$H-NMR (400 MHz, CDCl$_3$) δ (ppm): 1.16 (3H, d, J=6.7 Hz), 1.72-1.87 (2H, m), 2.27 (3H, s), 2.53-2.70 (2H, m), 3.71 (3H, s), 3.72 (3H, s), 3.80-3.89 (1H, m), 5.81 (1H, d, J=3.0 Hz), 5.86-5.89 (1H, m), 6.70 (2H, dd, J=8.5, 1.8 Hz), 7.47 (1H, t, J=8.5 Hz). MS (APCI): m/z 358 [M+H]$^+$.

Example 26

{[5-(5-Bromofuran-2-yl)-4-(2,6-dimethoxyphenyl)-4H-1,2,4-triazol-3-yl]sulfanyl}acetic acid

Step 1

2-[(5-Bromofuran-2-yl)carbonyl]-N-(2,6-dimethoxyphenyl)hydrazinecarbothioamide

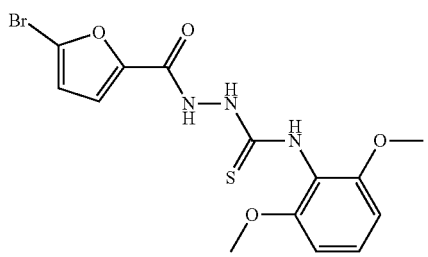 [SMILES: COc1cccc(OC)c1NC(=S)NNC(=O)c1ccc(Br)o1]

The partially purified title compound (4.10 g, 10.3 mmol, quantitative) was obtained as a white amorphous form 5-bromofuran-2-carbohydrazide (2.11 g, 10.3 mmol) and 2-isothiocyanato-1,3-dimethoxy-benzene (2.00 g, 10.3 mmol) in the same way as in step 2 of Example 1. The obtained white amorphous form was used in the next reaction without being purified.

MS (APCI): m/z 400 [M+H]$^+$.

Step 2

5-(5-Bromofuran-2-yl)-4-(2,6-dimethoxyphenyl)-4H-1,2,4-triazole-3-thiol

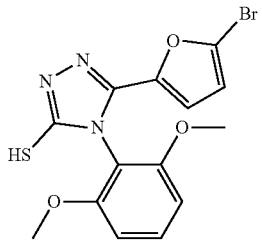 [SMILES: COc1cccc(OC)c1-n1c(S)nnc1-c1ccc(Br)o1]

The title compound (3.88 g, 10.2 mmol, 99%) was obtained from 2-[(5-bromofuran-2-yl)carbonyl]-N-(2,6-dimethoxyphenyl)hydrazinecarbothioamide (4.10 g, 10.3 mmol) in the same way as in step 3 of Example 1.

$^1$H-NMR (400 MHz, CDCl$_3$) δ (ppm): 3.79 (6H, s), 5.93 (1H, d, J=3.6 Hz), 6.25 (1H, d, J=3.6 Hz), 6.73 (2H, d, J=8.5 Hz), 7.50 (1H, t, J=8.5 Hz), 10.90 (1H, s). MS (APCI): m/z 382 [M+H]$^+$.

Step 3

Ethyl {[5-(5-bromofuran-2-yl)-4-(2,6-dimethoxyphenyl)-4H-1,2,4-triazol-3-yl]sulfanyl}acetate

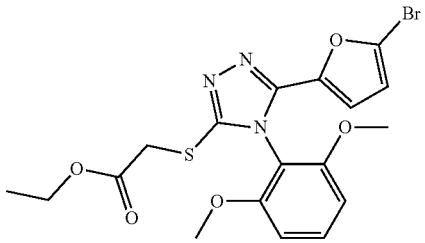 [SMILES: CCOC(=O)CSc1nnc(-c2ccc(Br)o2)n1-c1c(OC)cccc1OC]

The title compound (3.53 g, 7.53 mmol, 93%) was obtained as a white solid from 5-(5-bromofuran-2-yl)-4-(2,6-dimethoxyphenyl)-4H-1,2,4-triazole-3-thiol (3.10 g, 8.11 mmol) and ethyl 2-chloroacetate (1.04 mL, 9.73 mmol) in the same way as in Example 4.

$^1$H-NMR (400 MHz, CDCl$_3$) δ (ppm): 1.26 (3H, t, J=7.3 Hz), 3.75 (6H, s), 4.06 (2H, s), 4.19 (2H, q, J=7.3 Hz), 6.21 (1H, d, J=3.6 Hz), 6.25 (1H, d, J=3.6 Hz), 6.68 (2H, d, J=8.5 Hz), 7.47 (1H, t, J=8.5 Hz). MS (APCI): m/z 468 [M+H]$^+$.

Step 4

{[5-(5-Bromofuran-2-yl)-4-(2,6-dimethoxyphenyl)-4H-1,2,4-triazol-3-yl]sulfanyl}acetic acid

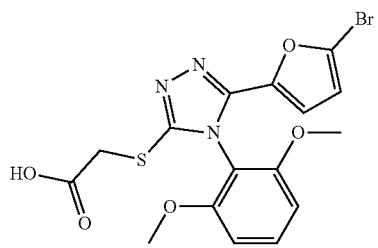 [SMILES: COc1cccc(OC)c1-n1c(SCC(=O)O)nnc1-c1ccc(Br)o1]

To ethyl {[5-(5-bromofuran-2-yl)-4-(2,6-dimethoxyphenyl)-4H-1,2,4-triazol-3-yl]sulfanyl}acetate (90 mg, 0.192 mmol), tetrahydrofuran (1.0 mL) and ethanol (1.0 mL) were added, then 1 mol/L aqueous sodium hydroxide solution (0.384 mL, 0.384 mmol) was added with stirring under ice cooling, and the mixture was stirred at room temperature for 1 hour. 1 mol/L hydrochloric acid (0.38 mL, 0.38 mmol) was added to the reaction solution, and the solvent was concentrated under reduced pressure. The deposited solid was collected by filtration to obtain the title compound (77 mg, 0.174 mmol, 91%) as a white solid.

$^1$H-NMR (400 MHz, CDCl$_3$) δ (ppm): 3.77 (6H, s), 3.93 (2H, s), 6.28-6.31 (2H, m), 6.70 (2H, d, J=8.5 Hz), 7.51 (1H, t, J=8.5 Hz). MS (APCI): m/z 440 [M+H]$^+$.

Example 27

{[4-(2,6-Dimethoxyphenyl)-5-(pyridin-3-yl)-4H-1,2,4-triazol-3-yl]sulfanyl}acetic acid

Step 1

N-(2,6-Dimethoxyphenyl)-2-(pyridin-3-ylcarbonyl)hydrazinecarbothioamide

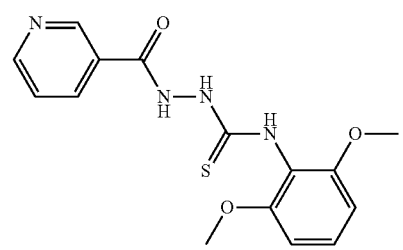 [SMILES: COc1cccc(OC)c1NC(=S)NNC(=O)c1cccnc1]

The partially purified title compound (0.343 g, 1.03 mmol, quantitative) was obtained as a faint yellow solid from nicotinic acid hydrazide (141 mg, 1.03 mmol) and 2-isothiocyanato-1,3-dimethoxy-benzene (201 mg, 1.03 mmol) in the same way as in step 2 of Example 1. The obtained compound was used in the next reaction without being purified.

MS (APCI): m/z 333 [M+H]$^+$.

Step 2

4-(2,6-Dimethoxyphenyl)-5-(pyridin-3-yl)-4H-1,2,4-triazole-3-thiol

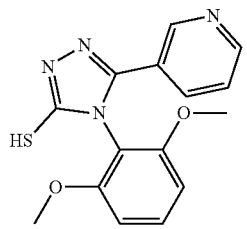 [SMILES: COc1cccc(OC)c1-n1c(S)nnc1-c1cccnc1]

The title compound (296 mg, 0.940 mmol, 91%) was obtained as a white solid from N-(2,6-dimethoxyphenyl)-2-(pyridin-3-ylcarbonyl)hydrazinecarbothioamide (0.343 g, 1.03 mmol) in the same way as in step 3 of Example 1.

$^1$H-NMR (400 MHz, CDCl$_3$) δ (ppm): 3.77 (6H, s), 6.66 (2H, d, J=8.5 Hz), 7.23-7.28 (1H, m), 7.43 (1H, t, J=8.5 Hz), 7.71-7.74 (1H, m), 8.62 (1H, dd, J=4.9, 2.1 Hz), 8.66 (1H, d, J=2.1 Hz), 10.63 (1H, br s). MS (APCI): m/z 315 [M+H]$^+$.

Step 3

Ethyl {[4-(2,6-dimethoxyphenyl)-5-(pyridin-3-yl)-4H-1,2,4-triazol-3-yl]sulfanyl}acetate

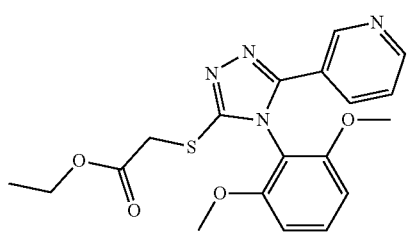 [SMILES: CCOC(=O)CSc1nnc(-c2cccnc2)n1-c1c(OC)cccc1OC]

The title compound (181 mg, 0.451 mmol, 99%) was obtained as a white solid from 4-(2,6-dimethoxyphenyl)-5-(pyridin-3-yl)-4H-1,2,4-triazole-3-thiol (144 mg, 0.458 mmol) and ethyl 2-chloroacetate (0.059 mL, 0.549 mmol) in the same way as in Example 4.

$^1$H-NMR (400 MHz, CDCl$_3$) δ (ppm): 1.27 (3H, t, J=7.0 Hz), 3.71 (6H, s), 4.09 (2H, s), 4.21 (2H, q, J=7.0 Hz), 6.63 (2H, d, J=8.5 Hz), 7.21-7.27 (1H, m), 7.41 (1H, t, J=8.5 Hz), 7.88 (1H, dt, J=7.9, 1.8 Hz), 8.55 (1H, dd, J=4.9, 1.2 Hz), 8.62 (1H, d, J=1.8 Hz). MS (APCI): m/z 401 [M+H]$^+$.

Step 4

{[4-(2,6-Dimethoxyphenyl)-5-(pyridin-3-yl)-4H-1,2,4-triazol-3-yl]sulfanyl}acetic acid

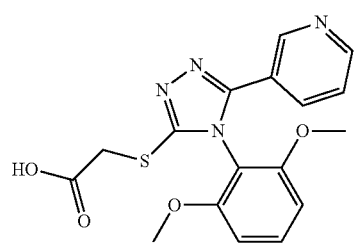 [SMILES: COc1cccc(OC)c1-n1c(SCC(=O)O)nnc1-c1cccnc1]

The title compound (69 mg, 0.185 mmol, 82%) was obtained as a white solid from ethyl {[4-(2,6-dimethoxyphenyl)-5-(pyridin-3-yl)-4H-1,2,4-triazol-3-yl]sulfanyl}acetate (91 mg, 0.226 mmol) in the same way as in step 4 of Example 26.

$^1$H-NMR (400 MHz, CDCl$_3$) δ (ppm): 3.72 (6H, s), 3.95 (2H, s), 6.65 (2H, d, J=8.5 Hz), 7.30 (1H, dd, J=7.9, 4.9 Hz), 7.45 (1H, t, J=8.5 Hz), 7.87 (1H, d, J=7.9 Hz), 8.58-8.63 (2H, br m). MS (APCI): m/z 373 [M+H]$^+$.

Example 28

{[4-(2,6-Dimethoxyphenyl)-5-phenyl-4H-1,2,4-triazol-3-yl]sulfanyl}acetic acid

Step 1

2-Benzoyl-N-(2,6-dimethoxyphenyl)hydrazinecarbothioamide

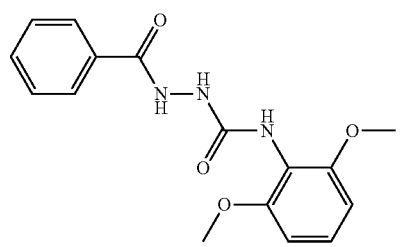

The partially purified title compound (0.339 g, 1.03 mmol, quantitative) was obtained as a white solid from benzohydrazide (139 mg, 1.02 mmol) and 2-isothiocyanato-1,3-dimethoxy-benzene (200 mg, 1.02 mmol) in the same way as in step 2 of Example 1. The obtained compound was used in the next reaction without being purified.

MS (APCI): m/z 332 [M+H]$^+$.

Step 2

4-(2,6-Dimethoxyphenyl)-5-phenyl-4H-1,2,4-triazole-3-thiol

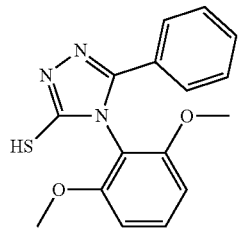 [SMILES: COc1cccc(OC)c1-n1c(S)nnc1-c1ccccc1]

The title compound (285 mg, 0.909 mmol, 89%) was obtained as a white solid from 2-benzoyl-N-(2,6-dimethoxyphenyl)hydrazinecarbothioamide (0.339 g, 1.02 mmol) in the same way as in step 3 of Example 1.

$^1$H-NMR (400 MHz, CDCl$_3$) δ (ppm): 3.75 (6H, s), 6.65 (2H, d, J=8.5 Hz), 7.25-7.32 (2H, m), 7.35-7.44 (4H, m), 10.77 (1H, br s). MS (APCI): m/z 314 [M+H]$^+$.

Step 3

Ethyl {[4-(2,6-dimethoxyphenyl)-5-phenyl-4H-1,2,4-triazol-3-yl]sulfanyl}acetate

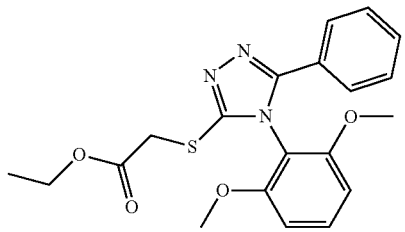 [SMILES: CCOC(=O)CSc1nnc(-c2ccccc2)n1-c1c(OC)cccc1OC]

The title compound (117 mg, 0.293 mmol, 98%) was obtained as a white solid from 4-(2,6-dimethoxyphenyl)-5-phenyl-4H-1,2,4-triazole-3-thiol (94 mg, 0.300 mmol) and ethyl 2-chloroacetate (0.038 mL, 0.360 mmol) in the same way as in Example 4.

$^1$H-NMR (400 MHz, CDCl$_3$) δ (ppm): 1.27 (3H, t, J=7.1 Hz), 3.69 (6H, s), 4.07 (2H, s), 4.20 (2H, q, J=7.1 Hz), 6.62 (2H, d, J=8.5 Hz), 7.23-7.34 (3H, m), 7.39 (1H, t, J=8.5 Hz), 7.44-7.48 (2H, m). MS (APCI): m/z 400 [M+H]$^+$.

Step 4

{[4-(2,6-Dimethoxyphenyl)-5-phenyl-4H-1,2,4-triazol-3-yl]sulfanyl}acetic acid

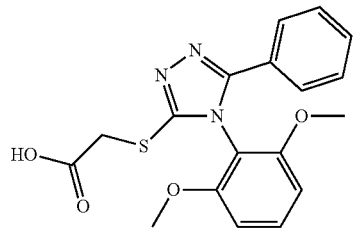 [SMILES: COc1cccc(OC)c1-n1c(SCC(=O)O)nnc1-c1ccccc1]

The title compound (67 mg, 0.180 mmol, 65%) was obtained as a white solid from ethyl 2-[[4-(2,6-dimethoxyphenyl)-5-phenyl-1,2,4-triazol-3-yl]sulfanyl]acetate (110 mg, 0.275 mmol) in the same way as in step 4 of Example 26.

$^1$H-NMR (400 MHz, CDCl$_3$) δ (ppm): 3.70 (6H, s), 3.99 (2H, s), 6.64 (2H, d, J=8.5 Hz), 7.27-7.33 (2H, m), 7.34-7.47 (4H, m). MS (APCI): m/z 372 [M+H]$^+$.

Example 29

{[5-Butyl-4-(2,6-dimethoxyphenyl)-4H-1,2,4-triazol-3-yl]sulfanyl}acetic acid

Step 1

N-(2,6-Dimethoxyphenyl)-2-pentanoylhydrazinecarbothioamide

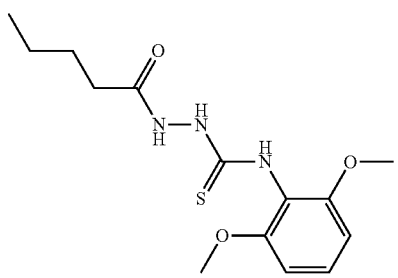 [SMILES: CCCCC(=O)NNC(=S)Nc1c(OC)cccc1OC]

The partially purified title compound (0.324 g, 1.04 mmol, quantitative) was obtained as a white solid from valeric acid hydrazide (121 mg, 1.04 mmol) and 2-isothiocyanato-1,3-dimethoxy-benzene (203.1 mg, 1.04 mmol) in the same way as in step 2 of Example 1. The obtained compound was used in the next reaction without being purified.

MS (APCI): m/z 312 [M+H]$^+$.

Step 2

5-Butyl-4-(2,6-dimethoxyphenyl)-4H-1,2,4-triazole-3-thiol

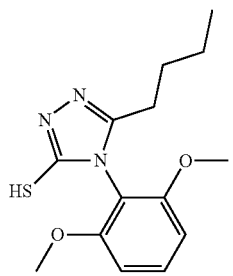 [SMILES: CCCCc1nnc(S)n1-c1c(OC)cccc1OC]

The title compound (222 mg, 0.757 mmol, 73%) was obtained as a white solid from N-(2,6-dimethoxyphenyl)-2-pentanoylhydrazinecarbothioamide (0.324 g, 1.04 mmol) in the same way as in step 3 of Example 1.

$^1$H-NMR (400 MHz, CDCl$_3$) δ (ppm): 0.83 (3H, t, J=7.3 Hz), 1.24-1.35 (2H, m), 1.49-1.57 (2H, m), 2.34 (2H, t, J=7.6 Hz), 3.82 (6H, s), 6.71 (2H, d, J=8.5 Hz), 7.45 (1H, t, J=8.5 Hz), 10.29 (1H, br s). MS (APCI): m/z 294 [M+H]$^+$.

Step 3

Ethyl {[5-butyl-4-(2,6-dimethoxyphenyl)-4H-1,2,4-triazol-3-yl]sulfanyl}acetate

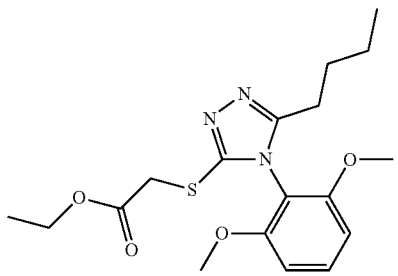 [SMILES: CCCCc1nnc(SCC(=O)OCC)n1-c1c(OC)cccc1OC]

The title compound (57 mg, 0.151 mmol, 50%) was obtained as a white solid from 5-butyl-4-(2,6-dimethoxyphenyl)-1,2,4-triazole-3-thiol (88 mg, 0.300 mmol) and ethyl 2-chloroacetate (0.038 mL, 0.360 mmol) in the same way as in Example 4.

$^1$H-NMR (400 MHz, CDCl$_3$) δ (ppm): 0.81 (3H, t, J=7.6 Hz), 1.22-1.33 (5H, m), 1.53-1.60 (2H, m), 2.45 (2H, t, J=7.9 Hz), 3.77 (6H, s), 3.94 (2H, s), 4.16 (2H, q, J=7.1 Hz), 6.67 (2H, d, J=8.5 Hz), 7.41 (1H, t, J=8.5 Hz). MS (APCI): m/z 380 [M+H]$^+$.

Step 4

{[5-Butyl-4-(2,6-dimethoxyphenyl)-4H-1,2,4-triazol-3-yl]sulfanyl}acetic acid

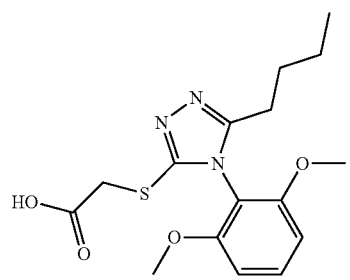 [SMILES: CCCCc1nnc(SCC(=O)O)n1-c1c(OC)cccc1OC]

The title compound (42 mg, 0.120 mmol, 88%) was obtained as a white solid from ethyl 2-[[5-butyl-4-(2,6-dimethoxyphenyl)-4H-1,2,4-triazol-3-yl]sulfanyl]acetate (51 mg, 0.135 mmol) in the same way as in step 4 of Example 26.

$^1$H-NMR (400 MHz, CDCl$_3$) δ (ppm): 0.84 (3H, t, J=7.3 Hz), 1.24-1.36 (2H, m), 1.56-1.63 (2H, m), 2.48 (2H, t, J=7.6 Hz), 3.81 (6H, s), 3.88 (2H, s), 6.70 (2H, d, J=8.5 Hz), 7.47 (1H, t, J=8.5 Hz). MS (APCI): m/z 352 [M+H]$^+$.

Example 30

{[4-(2,6-Dimethoxyphenyl)-5-(thiophen-2-yl)-4H-1,2,4-triazol-3-yl]sulfanyl}acetic acid

Step 1

Ethyl {[4-(2,6-dimethoxyphenyl)-5-(thiophen-2-yl)-4H-1,2,4-triazol-3-yl]sulfanyl}acetate

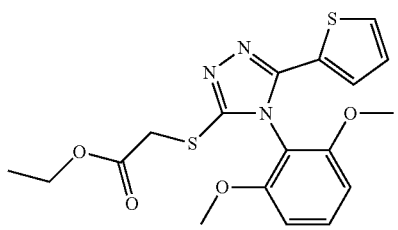 [SMILES: CCOC(=O)CSc1nnc(-c2cccs2)n1-c1c(OC)cccc1OC]

The title compound (18 mg, 0.290 mmol, 94%) was obtained as a white solid from 4-(2,6-dimethoxyphenyl)-5-(thiophen-2-yl)-4H-1,2,4-triazole-3-thiol (99 mg, 0.309 mmol) and ethyl 2-chloroacetate (40 μL, 0.371 mmol) in the same way as in Example 4.

$^1$H-NMR (400 MHz, CDCl$_3$) δ (ppm): 1.27 (3H, t, J=7.0 Hz), 3.73 (6H, s), 4.05 (2H, s), 4.20 (2H, q, J=7.0 Hz), 6.69 (2H, d, J=8.5 Hz), 6.93 (1H, dd, J=5.5, 3.6 Hz), 7.12 (1H, dd, J=3.6, 1.2 Hz), 7.25 (2H, d, J=1.2 Hz), 7.49 (1H, t, J=8.5 Hz). MS (APCI): m/z 406 [M+H]$^+$.

Step 2

{[4-(2,6-Dimethoxyphenyl)-5-(thiophen-2-yl)-4H-1,2,4-triazol-3-yl]sulfanyl}acetic acid

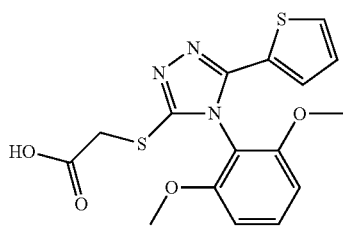 [SMILES: COc1cccc(OC)c1-n1c(SCC(=O)O)nnc1-c1cccs1]

The title compound (98 mg, 0.259 mmol, 94%) was obtained as a white solid from ethyl {[4-(2,6-dimethoxyphenyl)-5-(thiophen-2-yl)-4H-1,2,4-triazol-3-yl]sulfanyl}acetate (112 mg, 0.276 mmol) in the same way as in step 4 of Example 26.

$^1$H-NMR (400 MHz, CDCl$_3$) δ (ppm): 3.75 (6H, s), 3.94 (2H, s), 6.71 (2H, d, J=8.5 Hz), 6.97 (1H, dd, J=4.9, 3.6 Hz), 7.17 (1H, dd, J=3.6, 1.2 Hz), 7.33 (1H, dd, J=4.9, 1.2 Hz), 7.53 (1H, t, J=8.5 Hz). MS (APCI): m/z 378 [M+H]$^+$.

Example 31

{[4-(2,6-Diethylphenyl)-5-(5-methylfuran-2-yl)-4H-1,2,4-triazol-3-yl]sulfanyl}acetic acid

Step 1

N-(2,6-Diethylphenyl)-2-[(5-methylfuran-2-yl)carbonyl]hydrazinecarbothioamide

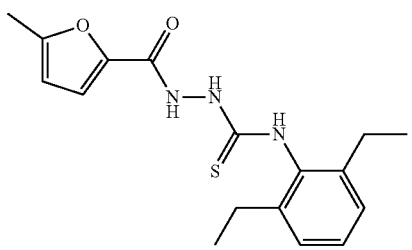 [SMILES: CCc1cccc(CC)c1NC(=S)NNC(=O)c1ccc(C)o1]

The partially purified title compound (0.497 g, 1.50 mmol, quantitative) was obtained as a white solid from 2,6-diethylphenyl isothiocyanate (287 mg, 1.50 mmol) and 5-methylfuran-2-carbohydrazide (210 mg, 1.50 mmol) in the same way as in step 2 of Example 1. The obtained compound was used in the next reaction without being purified.

MS (APCI): m/z 332 [M+H]$^+$.

Step 2

4-(2,6-Diethylphenyl)-5-(5-methylfuran-2-yl)-4H-1,2,4-triazole-3-thiol

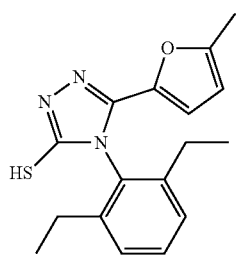 [SMILES: CCc1cccc(CC)c1-n1c(S)nnc1-c1ccc(C)o1]

The title compound (419 mg, 1.34 mmol, 89%) was obtained as a white solid from N-(2,6-diethylphenyl)-2-[(5-methylfuran-2-yl)carbonyl]hydrazinecarbothioamide (497 mg, 1.50 mmol) in the same way as in step 3 of Example 1.

$^1$H-NMR (400 MHz, CDCl$_3$) δ (ppm): 1.14 (6H, t, J=7.3 Hz), 2.30-2.34 (5H, m), 2.44-2.48 (2H, m), 5.43 (1H, d, J=3.0 Hz), 5.87-5.87 (1H, m), 7.32 (2H, d, J=7.3 Hz), 7.51-7.53 (1H, m), 11.01 (1H, br s). MS (APCI): m/z 314 [M+H]$^+$.

Step 3

Ethyl {[4-(2,6-diethylphenyl)-5-(5-methylfuran-2-yl)-4H-1,2,4-triazol-3-yl]sulfanyl}acetate

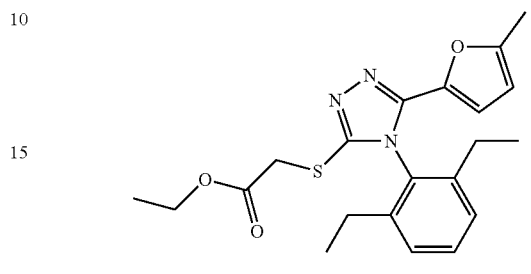

The title compound (114 mg, 0.285 mmol, 95%) was obtained as a colorless oil from 4-(2,6-diethylphenyl)-5-(5-methylfuran-2-yl)-4H-1,2,4-triazole-3-thiol (94 mg, 0.30 mmol) and ethyl 2-chloroacetate (0.038 mL, 0.36 mmol) in the same way as in Example 4.

$^1$H-NMR (400 MHz, CDCl$_3$) δ (ppm): 1.07 (6H, t, J=7.6 Hz), 1.28 (3H, t, J=7.3 Hz), 2.17-2.39 (6H, m), 4.18 (2H, s), 4.21 (2H, q, J=7.3 Hz), 5.63 (1H, d, J=3.0 Hz), 5.84-5.88 (1H, m), 7.29 (2H, d, J=7.3 Hz), 7.49 (1H, t, J=7.3 Hz). MS (APCI): m/z 400 [M+H]$^+$.

Step 4

{[4-(2,6-Diethylphenyl)-5-(5-methylfuran-2-yl)-4H-1,2,4-triazol-3-yl]sulfanyl}acetic acid

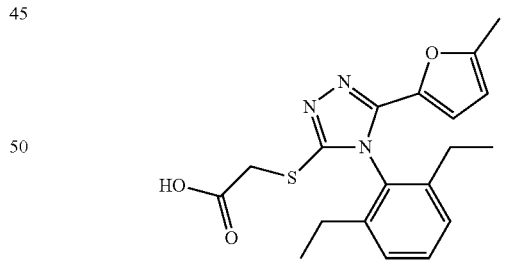

The title compound (86 mg, 0.232 mmol, 85%) was obtained as a white solid from ethyl {[4-(2,6-diethylphenyl)-5-(5-methylfuran-2-yl)-4H-1,2,4-triazol-3-yl]sulfanyl}acetate (110 mg, 0.275 mmol) in the same way as in step 4 of Example 26.

$^1$H-NMR (DMSO-d$_6$) δ (ppm): 0.99 (6H, t, J=7.6 Hz), 2.08-2.28 (7H, m), 4.12 (2H, s), 5.61 (1H, d, J=3.6 Hz), 6.08-6.11 (1H, m), 7.40 (2H, d, J=7.9 Hz), 7.57 (1H, t, J=7.9 Hz). MS (APCI): m/z 372 [M+H]$^+$.

Example 32

{[4-(2,6-Dichlorophenyl)-5-(5-methylfuran-2-yl)-4H-1,2,4-triazol-3-yl]sulfanyl}acetic acid

Step 1

N-(2,6-Dichlorophenyl)-2-[(5-methylfuran-2-yl)carbonyl]hydrazinecarbothioamide

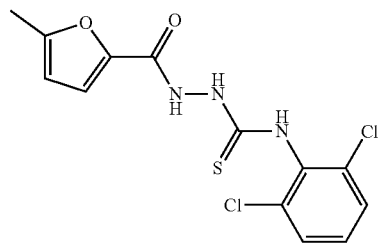 [SMILES: Cc1ccc(C(=O)NNC(=S)Nc2c(Cl)cccc2Cl)o1]

The partially purified title compound (0.516 g, 1.50 mmol, quantitative) was obtained as a white solid from 2,6-dichlorophenyl isothiocyanate (306 mg, 1.50 mmol) and 5-methylfuran-2-carbohydrazide (210 mg, 1.50 mmol) in the same way as in step 2 of Example 1. The obtained compound was used in the next reaction without being purified. MS (APCI): m/z 344 [M+H]$^+$.

Step 2

4-(2,6-Dichlorophenyl)-5-(5-methylfuran-2-yl)-4H-1,2,4-triazole-3-thiol

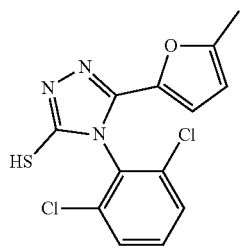 [SMILES: Cc1ccc(-c2nnc(S)n2-c2c(Cl)cccc2Cl)o1]

To N-(2,6-dichlorophenyl)-2-[(5-methylfuran-2-yl)carbonyl]hydrazinecarbothioamide (0.516 g, 1.50 mmol), 1 mol/L aqueous sodium hydroxide solution (3.0 mL, 3.00 mmol) was added, and the mixture was heated to reflux for 1 hour. 5 mol/L hydrochloric acid (0.60 mL, 3.00 mmol) was added to the reaction solution with stirring under ice cooling, and the resulting white precipitate was collected by filtration to obtain the partially purified title compound (549 mg) as a white solid. The obtained compound was purified by silica gel column chromatography [elution solvent: n-hexane/ethyl acetate=90/10-40/60 (V/V)] to obtain the title compound (259 mg, 0.795 mmol, 53%) as a white solid.

$^1$H-NMR (400 MHz, CDCl$_3$) δ (ppm): 2.29 (3H, s), 5.93-5.99 (2H, m), 7.48-7.54 (1H, m), 7.55-7.60 (2H, m), 11.41 (1H, br s). MS (APCI): m/z 326 [M+H]$^+$.

Step 3

Ethyl {[4-(2,6-dichlorophenyl)-5-(5-methylfuran-2-yl)-4H-1,2,4-triazol-3-yl]sulfanyl}acetate

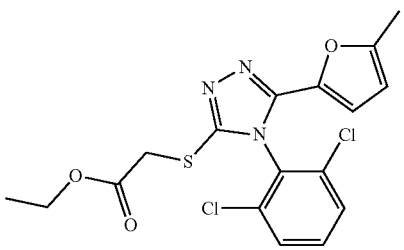 [SMILES: CCOC(=O)CSc1nnc(-c2ccc(C)o2)n1-c1c(Cl)cccc1Cl]

The title compound (113 mg, 0.273 mmol, 91%) was obtained as a colorless oil from 4-(2,6-dichlorophenyl)-5-(5-methylfuran-2-yl)-4H-1,2,4-triazole-3-thiol (98 mg, 0.30 mmol) and ethyl 2-chloroacetate (0.038 mL, 0.360 mmol) in the same way as in Example 4.

$^1$H-NMR (400 MHz, CDCl$_3$) δ (ppm): 1.27 (3H, t, J=7.3 Hz), 2.21 (3H, s), 4.14 (2H, s), 4.21 (2H, q, J=7.3 Hz), 5.95-5.98 (1H, m), 6.19 (1H, d, J=3.6 Hz), 7.46-7.57 (3H, m). MS (APCI): m/z 412 [M+H]$^+$.

Step 4

{[4-(2,6-Dichlorophenyl)-5-(5-methylfuran-2-yl)-4H-1,2,4-triazol-3-yl]sulfanyl}acetic acid

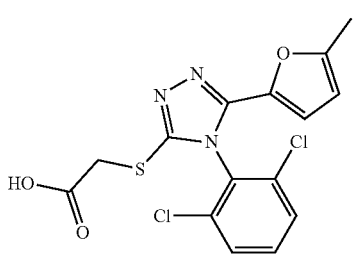 [SMILES: Cc1ccc(-c2nnc(SCC(=O)O)n2-c2c(Cl)cccc2Cl)o1]

The title compound (96 mg, 0.251 mmol, 95%) was obtained as a white solid from ethyl {[4-(2,6-dichlorophenyl)-5-(5-methylfuran-2-yl)-4H-1,2,4-triazol-3-yl]sulfanyl}acetate (109 mg, 0.264 mmol) in the same way as in step 4 of Example 26.

$^1$H-NMR (400 MHz, DMSO-d$_6$) δ (ppm): 2.22 (3H, s), 4.04 (2H, d, J=1.8 Hz), 5.86 (1H, d, J=3.7 Hz), 6.11-6.15 (1H, m), 7.59-7.73 (2H, m), 7.96 (1H, dd, J=7.6, 1.5 Hz), 13.02 (1H, br s). MS (APCI): m/z 384 [M+H]$^+$.

Example 33

{[5-Cyclopentyl-4-(2,6-dimethoxyphenyl)-4H-1,2,4-triazol-3-yl]sulfanyl}acetic acid

Step 1

2-(Cyclopentylcarbonyl)-N-(2,6-dimethoxyphenyl)hydrazinecarbothioamide

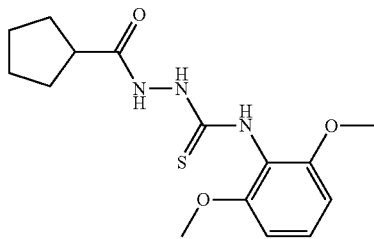 [SMILES: COc1cccc(OC)c1NC(=S)NNC(=O)C1CCCC1]

The partially purified title compound (0.485 g, 1.50 mmol, quantitative) was obtained as a faint yellow solid from 2-isothiocyanato-1,3-dimethoxy-benzene (293 mg, 1.50 mmol) and cyclopentanecarbohydrazide (192 mg, 1.50 mmol) in the same way as in step 2 of Example 1. The obtained compound was used in the next reaction without being purified.

MS (APCI): m/z=324 [M+H]$^+$.

Step 2

5-Cyclopentyl-4-(2,6-dimethoxyphenyl)-4H-1,2,4-triazole-3-thiol

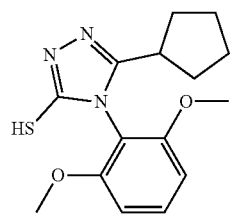 [SMILES: COc1cccc(OC)c1-n1c(S)nnc1C1CCCC1]

The title compound (392 mg, 1.28 mmol, 86%) was obtained as a white solid from 2-(cyclopentylcarbonyl)-N-(2,6-dimethoxyphenyl)hydrazinecarbothioamide (0.485 g, 1.50 mmol) in the same way as in step 3 of Example 1.

$^1$H-NMR (400 MHz, CDCl$_3$) δ (ppm): 1.46-1.56 (2H, m), 1.66-1.86 (6H, m), 2.59-2.66 (1H, m), 3.82 (6H, s), 6.70 (2H, d, J=8.5 Hz), 7.44 (1H, t, J=8.5 Hz), 10.47 (1H, s). MS (APCI): m/z=306 [M+H]$^+$.

Step 3

Ethyl {[5-cyclopentyl-4-(2,6-dimethoxyphenyl)-4H-1,2,4-triazol-3-yl]sulfanyl}acetate

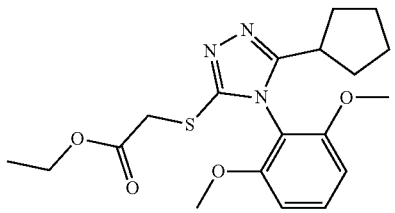 [SMILES: CCOC(=O)CSc1nnc(C2CCCC2)n1-c1c(OC)cccc1OC]

The title compound ethyl 2-[[5-cyclopentyl-4-(2,6-dimethoxyphenyl)-4H-1,2,4-triazol-3-yl]sulfanyl]acetate (81 mg, 0.207 mmol, 69%) was obtained as a colorless oil from 5-cyclopentyl-4-(2,6-dimethoxyphenyl)-4H-1,2,4-triazole-3-thiol (92 mg, 0.300 mmol) and ethyl 2-chloroacetate (0.0384 mL, 0.360 mmol) in the same way as in Example 4.

$^1$H-NMR (400 MHz, CDCl$_3$) δ (ppm): 1.25 (3H, t, J=7.3 Hz), 1.44-1.56 (2H, m), 1.69-1.80 (4H, m), 1.84-1.95 (2H, m), 2.66-2.74 (1H, m), 3.78 (6H, s), 3.96 (2H, s), 4.17 (2H, q, J=7.3 Hz), 6.67 (2H, d, J=8.5 Hz), 7.42 (1H, t, J=8.5 Hz). MS (APCI): m/z=392 [M+H]$^+$.

Step 4

{[5-Cyclopentyl-4-(2,6-dimethoxyphenyl)-4H-1,2,4-triazol-3-yl]sulfanyl}acetic acid

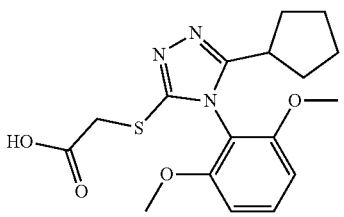 [SMILES: COc1cccc(OC)c1-n1c(SCC(=O)O)nnc1C1CCCC1]

The title compound (56 mg, 0.154 mmol, 74%) was obtained as a white solid from ethyl {[5-cyclopentyl-4-(2,6-dimethoxyphenyl)-4H-1,2,4-triazol-3-yl]sulfanyl}acetate (81 mg, 0.207 mmol) in the same way as in step 4 of Example 26.

$^1$H-NMR (400 MHz, CDCl$_3$) δ (ppm): 1.46-1.60 (2H, m), 1.71-1.93 (6H, m), 2.69-2.79 (1H, m), 3.80 (6H, s), 3.86 (2H, s), 6.69 (2H, d, J=8.5 Hz), 7.47 (1H, t, J=8.5 Hz). MS (APCI): m/z 364 [M+H]$^+$.

Example 34

{[4-(2,4-Dimethoxypyridin-3-yl)-5-(5-methylfuran-2-yl)-4H-1,2,4-triazol-3-yl]sulfanyl}acetic acid

Step 1

3-Isothiocyanato-2,4-dimethoxypyridine

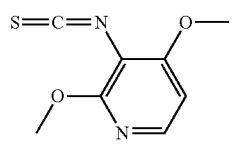

The title compound (563 mg, 2.87 mmol, 89%) was obtained as a white solid from thiophosgene (274 μL, 3.568 mmol) and 2,4-dimethoxypyridin-3-amine (500 mg, 3.24 mmol) in the same way as in step 1 of Example 1.
$^1$H NMR (400 MHz, CDCl$_3$) δ (ppm): 3.94 (3H, s), 4.01 (3H, s), 6.55 (1H, d, J=6.1 Hz), 7.94 (1H, d, J=6.1 Hz). MS (APCI): m/z=197 [M+H]$^+$.

Step 2

N-(2,4-Dimethoxypyridin-3-yl)-2-[(5-methylfuran-2-yl)carbonyl]hydrazinecarbothioamide

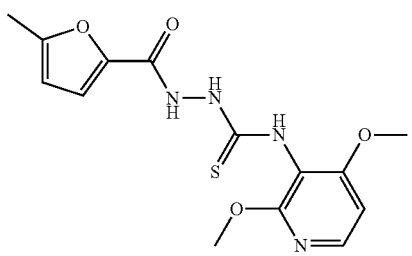

The partially purified title compound (0.506 g, 1.50 mmol, quantitative) was obtained as a faint yellow solid from 3-isothiocyanato-2,4-dimethoxypyridine (294 mg, 1.50 mmol) and 5-methylfuran-2-carbohydrazide (210 mg, 1.50 mmol) in the same way as in step 2 of Example 1.
MS (APCI): m/z=337 [M+H]$^+$.

Step 3

4-(2,4-Dimethoxypyridin-3-yl)-5-(5-methylfuran-2-yl)-4H-1,2,4-triazole-3-thiol

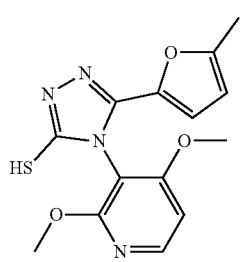 [SMILES: COc1ccnc(OC)c1-n1c(S)nnc1-c1ccc(C)o1]

The title compound (431 mg, 1.36 mmol, 90%) was obtained as a white solid from N-(2,4-dimethoxypyridin-3-yl)-2-[(5-methylfuran-2-yl)carbonyl]hydrazinecarbothioamide (0.506 g, 1.50 mmol) in the same way as in step 3 of Example 1.
$^1$H-NMR (400 MHz, CDCl$_3$) δ (ppm): 2.30 (3H, s), 3.86 (3H, s), 3.91 (3H, s), 5.94-5.97 (1H, m), 6.00 (1H, d, J=3.7 Hz), 6.73 (1H, d, J=6.1 Hz), 8.29 (1H, d, J=6.1 Hz), 10.90 (1H, s). MS (APCI): m/z=319 [M+H]$^+$.

Step 4

Ethyl {[4-(2,4-dimethoxypyridin-3-yl)-5-(5-methylfuran-2-yl)-4H-1,2,4-triazol-3-yl]sulfanyl}acetate

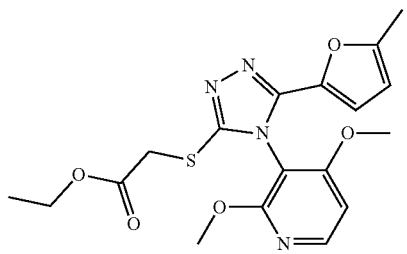 [SMILES: CCOC(=O)CSc1nnc(-c2ccc(C)o2)n1-c1c(OC)ccnc1OC]

The title compound (115 mg, 0.284 mmol, 95%) was obtained as a white solid from 4-(2,4-dimethoxypyridin-3-yl)-5-(5-methylfuran-2-yl)-4H-1,2,4-triazole-3-thiol (96 mg, 0.300 mmol) and ethyl 2-chloroacetate (0.038 mL, 0.360 mmol) in the same way as in Example 4.
$^1$H-NMR (400 MHz, CDCl$_3$) δ (ppm): 1.26 (3H, t, J=7.0 Hz), 2.24 (3H, s), 3.82 (3H, s), 3.87 (3H, s), 4.00-4.11 (2H, m), 4.19 (2H, q, J=7.0 Hz), 5.94-5.96 (1H, m), 6.19 (1H, d, J=3.1 Hz), 6.69 (1H, d, J=6.1 Hz), 8.24 (1H, d, J=6.1 Hz). MS (APCI): m/z=405 [M+H]$^+$.

Step 5

{[4-(2,4-Dimethoxypyridin-3-yl)-5-(5-methylfuran-2-yl)-4H-1,2,4-triazol-3-yl]sulfanyl}acetic acid

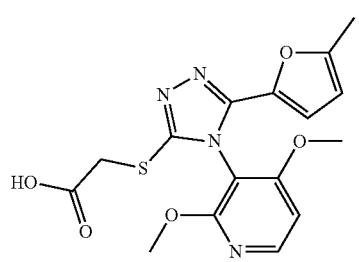 [SMILES: COc1ccnc(OC)c1-n1c(SCC(=O)O)nnc1-c1ccc(C)o1]

The title compound (77 mg, 0.204 mmol, 76%) was obtained as a white solid from ethyl {[4-(2,4-dimethoxypyridin-3-yl)-5-(5-methylfuran-2-yl)-4H-1,2,4-triazol-3-yl]sulfanyl}acetate (109 mg, 0.269 mmol) in the same way as in step 4 of Example 26.
$^1$H-NMR (400 MHz, CDCl$_3$) δ (ppm): 2.24 (3H, s), 3.84 (3H, s), 3.89 (3H, s), 3.98-4.11 (2H, m), 5.98-6.01 (1H, m), 6.28 (1H, d, J=3.0 Hz), 6.71 (1H, d, J=6.1 Hz), 8.27 (1H, d, J=6.1 Hz). MS (APCI): m/z=377 [M+H]$^+$.

Example 35

{[4-(2,6-Dimethoxyphenyl)-5-(5-methylfuran-2-yl)-4H-1,2,4-triazol-3-yl]sulfanyl}(phenyl)acetic acid

Step 1

Methyl {[4-(2,6-dimethoxyphenyl)-5-(5-methylfuran-2-yl)-4H-1,2,4-triazol-3-yl]sulfanyl}(phenyl)acetate

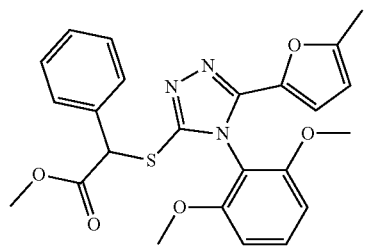

To a solution of 4-(2,6-dimethoxyphenyl)-5-(5-methyl-2-furyl)-1,2,4-triazole-3-thiol (59 mg, 0.186 mmol) in acetone (3.0 mL), potassium carbonate (32 mg, 0.232 mmol) and methyl alpha-bromophenylacetate (51 mg, 0.223 mmol) were added, and the mixture was heated to reflux for 1 hour. The reaction solution was allowed to cool to room temperature and then filtered through celite, and the solvent in the filtrate was distilled off under reduced pressure. The obtained residue was purified by silica gel column chromatography [elution solvent: n-hexane/ethyl acetate=40/60-20/85 (V/V)] to obtain the title compound (85 mg, 0.183 mmol, 99%) as a white solid.

$^1$H-NMR (400 MHz, CDCl$_3$) δ (ppm): 2.26 (3H, s), 3.53 (3H, s), 3.72 and 3.75 (total 6H, each s), 5.61 (1H, s), 5.86-5.88 (1H, m), 5.89-5.92 (1H, m), 6.59 (1H, d, J=8.5 Hz), 6.67 (1H, d, J=8.5 Hz), 7.25-7.31 (3H, m), 7.38-7.45 (3H, m). MS (APCI): m/z 466 [M+H]$^+$.

Step 2

{[4-(2,6-Dimethoxyphenyl)-5-(5-methylfuran-2-yl)-4H-1,2,4-triazol-3-yl]sulfanyl}(phenyl)acetic acid

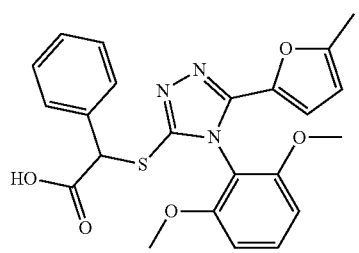 [SMILES: COc1cccc(OC)c1-n1c(SC(C(=O)O)c2ccccc2)nnc1-c1ccc(C)o1]

The title compound (75 mg, 0.166 mmol, 95%) was obtained as a white solid from methyl {[4-(2,6-dimethoxyphenyl)-5-(5-methylfuran-2-yl)-4H-1,2,4-triazol-3-yl]sulfanyl}(phenyl)acetate (81 mg, 0.174 mmol) in the same way as in step 4 of Example 26.

$^1$H-NMR (400 MHz, CDCl$_3$) δ (ppm): 2.20 (3H, s), 3.55 and 3.70 (total 6H, each s), 5.63 (1H, s), 5.86 (1H, m), 5.91 (1H, m), 6.60 (1H, d, J=8.5 Hz), 6.65 (1H, d, J=8.5 Hz), 7.11-7.23 (3H, m), 7.35-7.49 (3H, m). MS (APCI): m/z 452 [M+H]$^+$.

Example 36

2-{[4-(2,6-Dimethoxyphenyl)-5-(5-methylfuran-2-yl)-4H-1,2,4-triazol-3-yl]sulfanyl}-2-methylpropanoic acid

Step 1

Ethyl 2-{[4-(2,6-dimethoxyphenyl)-5-(5-methylfuran-2-yl)-4H-1,2,4-triazol-3-yl]sulfanyl}-2-methylpropanoate

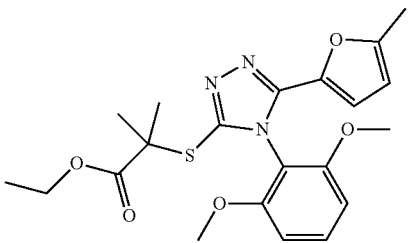 [SMILES: CCOC(=O)C(C)(C)Sc1nnc(-c2ccc(C)o2)n1-c1c(OC)cccc1OC]

The title compound (98 mg, 0.227 mmol, 75%) was obtained as a colorless oil from 4-(2,6-dimethoxyphenyl)-5-(5-methylfuran-2-yl)-4H-1,2,4-triazole-3-thiol (97 mg, 0.305 mmol) and 2-bromoisobutyric acid ethyl ester (54 μL, 0.366 mmol) in the same way as in step 1 of Example 35.

$^1$H-NMR (400 MHz, CDCl$_3$) δ (ppm): 1.23 (3H, t, J=7.0 Hz), 1.53 (6H, s), 2.27 (3H, s), 3.70 (6H, s), 4.12 (2H, q, J=7.0 Hz), 5.88-5.91 (1H, m), 5.96 (1H, d, J=3.0 Hz), 6.66 (2H, d, J=8.5 Hz), 7.45 (1H, t, J=8.5 Hz). MS (APCI): m/z 432 [M+H]$^+$.

Step 2

2-{[4-(2,6-Dimethoxyphenyl)-5-(5-methylfuran-2-yl)-4H-1,2,4-triazol-3-yl]sulfanyl}-2-methylpropanoic acid

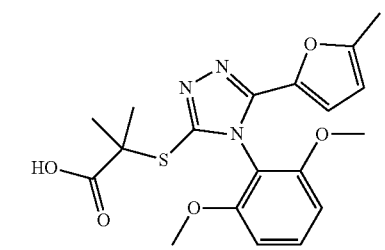 [SMILES: COc1cccc(OC)c1-n1c(SC(C)(C)C(=O)O)nnc1-c1ccc(C)o1]

The title compound (80 mg, 0.197 mmol, 90%) was obtained as a white solid from ethyl 2-{[4-(2,6-dimethoxyphenyl)-5-(5-methylfuran-2-yl)-4H-1,2,4-triazol-3-yl]sulfanyl}-2-methylpropanoate (94 mg, 0.218 mmol) in the same way as in step 4 of Example 26.

$^1$H-NMR (400 MHz, CDCl$_3$) δ (ppm): 1.59 (6H, s), 2.28 (3H, s), 3.73 (6H, s), 5.93 (1H, d, J=3.0 Hz), 6.00 (1H, d, J=3.0 Hz), 6.70 (2H, d, J=8.5 Hz), 7.50 (1H, t, J=8.5 Hz). MS (APCI): m/z 404 [M+H]$^+$.

Example 37

Methyl {[4-(2,6-dimethoxyphenyl)-5-(5-methyl-furan-2-yl)-4H-1,2,4-triazol-3-yl]sulfanyl}(naphthalen-1-yl)acetate

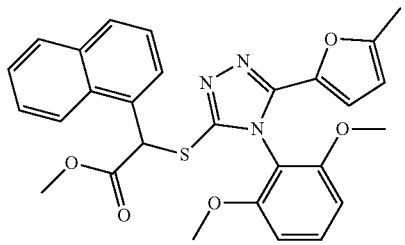 [SMILES: COC(=O)C(Sc1nnc(-c2ccc(C)o2)n1-c1c(OC)cccc1OC)c1cccc2ccccc12]

The title compound (106 mg, 0.206 mmol, 67%) was obtained as a white solid from 4-(2,6-dimethoxyphenyl)-5-(5-methylfuran-2-yl)-4H-1,2,4-triazole-3-thiol (95 mg, 0.300 mmol) and alpha-bromo-1-naphthaleneacetic acid ethyl ester (152 mg, 0.519 mmol) in the same way as in step 1 of Example 35.

$^1$H-NMR (400 MHz, CDCl$_3$) δ (ppm): 2.26 (3H, s), 3.39 (3H, s), 3.73 and 3.76 (total 6H, each s), 5.85-5.89 (1H, m), 5.92 (1H, d, J=3.6 Hz), 6.34 (1H, s), 6.49 (1H, d, J=8.5 Hz), 6.66 (1H, d, J=8.5 Hz), 7.34-7.42 (2H, m), 7.45-7.53 (2H, m), 7.61 (1H, d, J=7.3 Hz), 7.78 (1H, d, J=8.5 Hz), 7.81-7.85 (1H, m), 8.10 (1H, d, J=8.5 Hz). MS (APCI): m/z 516 [M+H]$^+$.

Example 38

{[4-(2,6-Dimethoxyphenyl)-5-(5-methylfuran-2-yl)-4H-1,2,4-triazol-3-yl]sulfanyl}(naphthalen-1-yl)acetic acid

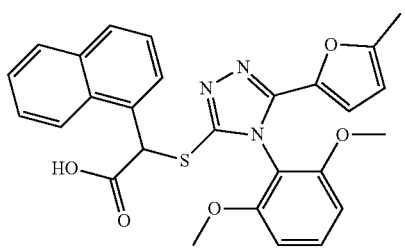 [SMILES: COc1cccc(OC)c1-n1c(SC(C(=O)O)c2cccc3ccccc23)nnc1-c1ccc(C)o1]

The title compound (93 mg, 0.184 mmol, 98%) was obtained as a white solid from methyl {[4-(2,6-dimethoxyphenyl)-5-(5-methylfuran-2-yl)-4H-1,2,4-triazol-3-yl]sulfanyl}(naphthalen-1-yl)acetate (97 mg, 0.189 mmol) in the same way as in step 4 of Example 26.

$^1$H-NMR (400 MHz, CDCl$_3$) δ (ppm): 2.23 (3H, s), 3.52 and 3.56 (total 6H, each s), 5.91 and 5.92 (total 1H, each s), 6.09-6.12 (2H, m), 6.55 (2H, dd, J=12.1, 8.5 Hz), 7.39 (2H, t, J=8.5 Hz), 7.44-7.53 (2H, m), 7.66 (1H, d, J=6.7 Hz), 7.79 (1H, d, J=8.5 Hz), 7.81-7.85 (1H, m), 8.00-8.05 (1H, m). MS (APCI): m/z 502 [M+H]$^+$.

Example 39

2-{[4-(2,6-Dimethoxyphenyl)-5-(5-methylfuran-2-yl)-4H-1,2,4-triazol-3-yl]sulfanyl}-3-phenylpropanoic acid Step 1

Ethyl 2-{[4-(2,6-Dimethoxyphenyl)-5-(5-methylfuran-2-yl)-4H-1,2,4-triazol-3-yl]sulfanyl}-3-phenylpropanoate

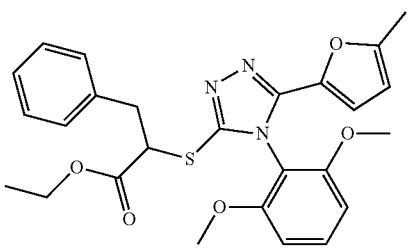 [SMILES: CCOC(=O)C(Cc1ccccc1)Sc1nnc(-c2ccc(C)o2)n1-c1c(OC)cccc1OC]

The title compound (144 mg, 0.291 mmol, 97%) was obtained as a white oil from 4-(2,6-dimethoxyphenyl)-5-(5-methylfuran-2-yl)-4H-1,2,4-triazole-3-thiol (95 mg, 0.300 mmol) and ethyl 2-bromo-3-phenyl-propanoate (93 mg, 0.360 mmol) in the same way as in step 1 of Example 35.

$^1$H-NMR (400 MHz, CDCl$_3$) δ (ppm): 1.07 (3H, t, J=7.0 Hz), 2.28 (3H, s), 3.15-3.30 (2H, m), 3.697 and 3.701 (total 6H, each s), 3.98-4.06 (2H, m), 4.48-4.53 (1H, m), 5.89-5.91 (1H, m), 5.94 (1H, d, J=3.0 Hz), 6.67 (2H, d, J=8.5 Hz), 7.14-7.27 (5H, m), 7.46 (1H, t, J=8.5 Hz). MS (APCI): m/z=494 [M+H]$^+$.

Step 2

2-{[4-(2,6-Dimethoxyphenyl)-5-(5-methylfuran-2-yl)-4H-1,2,4-triazol-3-yl]sulfanyl}-3-phenylpropanoic acid

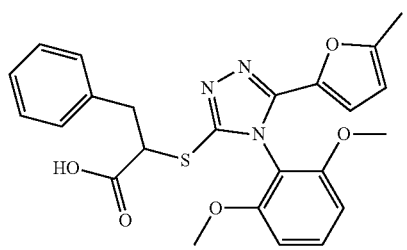 [SMILES: COc1cccc(OC)c1-n1c(SC(Cc2ccccc2)C(=O)O)nnc1-c1ccc(C)o1]

The title compound (118 mg, 0.253 mmol, 90%) was obtained as a white solid from ethyl 2-{[4-(2,6-dimethoxyphenyl)-5-(5-methylfuran-2-yl)-4H-1,2,4-triazol-3-yl]sulfanyl}-3-phenylpropanoate (139 mg, 0.281 mmol) in the same way as in step 4 of Example 26.

$^1$H-NMR (400 MHz, CDCl$_3$) δ (ppm): 2.27 (3H, s), 2.98-3.05 (1H, m), 3.45-3.52 (1H, m), 3.55 and 3.74 (total 6H, each s), 4.37-4.43 (1H, m), 5.93-5.96 (1H, m), 6.14 (1H, d, J=3.0 Hz), 6.61-6.70 (2H, m), 7.16-7.28 (5H, m), 7.48 (1H, t, J=8.5 Hz). MS (APCI): m/z 466 [M+H]$^+$.

Example 40

3-(Benzylsulfanyl)-4-(2,6-dimethoxyphenyl)-5-(5-methylfuran-2-yl)-4H-1,2,4-triazole

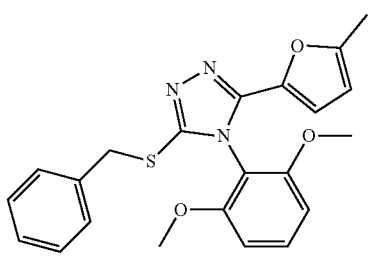 [SMILES: COc1cccc(OC)c1-n1c(SCc2ccccc2)nnc1-c1ccc(C)o1]

The title compound (32 mg, 0.0793 mmol, 39%) was obtained as a white solid from 4-(2,6-dimethoxyphenyl)-5-(5-methylfuran-2-yl)-4H-1,2,4-triazole-3-thiol (64 mg, 0.202 mmol) and benzyl bromide (29 μL, 0.243 mmol) in the same way as in step 1 of Example 35.

$^1$H-NMR (400 MHz, CDCl$_3$) δ (ppm): 2.28 (3H, s), 3.66 (6H, s), 4.41 (2H, s), 5.87-5.90 (2H, m), 6.65 (2H, d, J=8.5 Hz), 7.19-7.32 (5H, m), 7.43 (1H, t, J=8.5 Hz). MS (APCI): m/z 408 [M+H]$^+$.

Example 41

2-{[4-(2,6-Dimethoxyphenyl)-5-(5-methylfuran-2-yl)-4H-1,2,4-triazol-3-yl]sulfanyl}propanoic acid

Step 1

Ethyl 2-{[4-(2,6-dimethoxyphenyl)-5-(5-methyl-furan-2-yl)-4H-1,2,4-triazol-3-yl]sulfanyl}propanoate

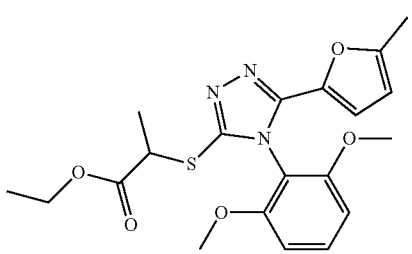 [SMILES: CCOC(=O)C(C)Sc1nnc(-c2ccc(C)o2)n1-c1c(OC)cccc1OC]

The title compound (119 mg, 0.285 mmol, 95%) was obtained as a colorless oil from 4-(2,6-dimethoxyphenyl)-5-(5-methylfuran-2-yl)-4H-1,2,4-triazole-3-thiol (95 mg, 0.300 mmol) and ethyl 2-bromopropionate (65 mg, 0.360 mmol) in the same way as in step 1 of Example 35.

$^1$H-NMR (400 MHz, CDCl$_3$) δ (ppm): 1.23 (3H, t, J=7.3 Hz), 1.56 (3H, d, J=7.3 Hz), 2.28 (3H, s), 3.72 and 3.72 (total 6H, each s), 4.15 (2H, q, J=7.3 Hz), 4.39 (1H, q, J=7.3 Hz), 5.88-5.91 (1H, m), 5.92 (1H, d, J=3.6 Hz), 6.68 (2H, d, J=8.5 Hz), 7.46 (1H, t, J=8.5 Hz). MS (APCI): m/z 418 [M+H]$^+$.

Step 2

2-{[4-(2,6-Dimethoxyphenyl)-5-(5-methylfuran-2-yl)-4H-1,2,4-triazol-3-yl]sulfanyl}propanoic acid

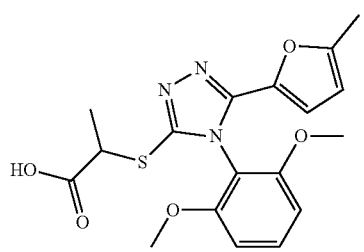 [SMILES: COc1cccc(OC)c1-n1c(SC(C)C(=O)O)nnc1-c1ccc(C)o1]

The title compound (84 mg, 0.215 mmol, 79%) was obtained as a white solid from ethyl 2-{[4-(2,6-dimethoxyphenyl)-5-(5-methylfuran-2-yl)-4H-1,2,4-triazol-3-yl]sulfanyl}propanoate (114 mg, 0.273 mmol) in the same way as in step 4 of Example 26.

$^1$H-NMR (400 MHz, CDCl$_3$) δ (ppm): 1.56 (3H, d, J=7.3 Hz), 2.28 (3H, s), 3.74 and 3.75 (total 6H, each s), 4.19 (1H, q, J=7.3 Hz), 5.92-5.95 (1H, m), 6.01 (1H, d, J=3.6 Hz), 6.70 (2H, d, J=8.5 Hz), 7.50 (1H, t, J=8.5 Hz). MS (APCI): m/z=390 [M+H]$^+$.

Example 42

2-{[4-(2,6-Dimethoxyphenyl)-5-(5-methylfuran-2-yl)-4H-1,2,4-triazol-3-yl]sulfanyl}pentanoic acid

Step 1

Ethyl 2-{[4-(2,6-dimethoxyphenyl)-5-(5-methyl-furan-2-yl)-4H-1,2,4-triazol-3-yl]sulfanyl}pentanoate

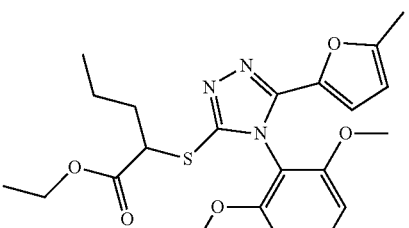

The title compound (121 mg, 0.272 mmol, 91%) was obtained as a colorless oil from 4-(2,6-dimethoxyphenyl)-5-(5-methylfuran-2-yl)-4H-1,2,4-triazole-3-thiol (95 mg, 0.300 mmol) and ethyl 2-bromovalerate (0.360 mmol) in the same way as in step 1 of Example 35.

$^1$H-NMR (400 MHz, CDCl$_3$) δ (ppm): 0.87 (3H, t, J=7.3 Hz), 1.23 (3H, t, J=7.0 Hz), 1.29-1.42 (2H, m), 1.77-1.95 (2H, m), 2.27 (3H, s), 3.71 and 3.72 (total 6H, each s), 4.15 (2H, q, J=7.3 Hz), 4.28 and 4.30 (total 1H, each d, J=6.1 Hz), 5.88-5.90 (1H, m), 5.92 (1H, d, J=3.0 Hz), 6.67 (2H, dd, J=8.5, 1.2 Hz), 7.45 (1H, t, J=8.5 Hz). MS (APCI): m/z 446 [M+H]$^+$.

Step 2

2-{[4-(2,6-Dimethoxyphenyl)-5-(5-methylfuran-2-yl)-4H-1,2,4-triazol-3-yl]sulfanyl}pentanoic acid

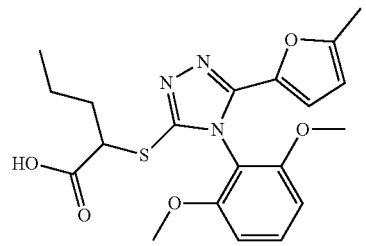 [SMILES: CCCC(Sc1nnc(-c2ccc(C)o2)n1-c1c(OC)cccc1OC)C(=O)O]

The title compound (103 mg, 0.248 mmol, 95%) was obtained as a white solid from ethyl 2-{[4-(2,6-dimethoxyphenyl)-5-(5-methylfuran-2-yl)-4H-1,2,4-triazol-3-yl]sulfanyl}pentanoate (116 mg, 0.261 mmol) in the same way as in step 4 of Example 26.

$^1$H-NMR (400 MHz, CDCl$_3$) δ (ppm): 0.90 (3H, t, J=7.3 Hz), 1.36-1.53 (2H, m), 1.69-1.79 (1H, m), 2.02-2.13 (1H, m), 2.28 (3H, s), 3.74 and 3.75 (total 6H, each s), 4.00-4.06 (1H, m), 5.92-5.95 (1H, m), 5.99-6.02 (1H, m), 6.6 (2H, d, J=8.5 Hz), 7.50 (1H, t, J=8.5 Hz). MS (APCI): m/z=418 [M+H]$^+$.

Example 43

2-{[4-(2,6-Dimethoxyphenyl)-5-(5-methylfuran-2-yl)-4H-1,2,4-triazol-3-yl]sulfanyl}-3-methylbutanoic acid

Step 1

Ethyl 2-{[4-(2,6-dimethoxyphenyl)-5-(5-methylfuran-2-yl)-4H-1,2,4-triazol-3-yl]sulfanyl}-3-methylbutanoate

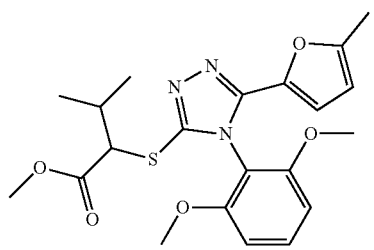

The title compound (130 mg, 0.292 mmol, 97%) was obtained as a white solid from 4-(2,6-dimethoxyphenyl)-5-(5-methylfuran-2-yl)-4H-1,2,4-triazole-3-thiol (95 mg, 0.300 mmol) and ethyl 2-bromo-3-methyl-butanoate (77 mg, 0.360 mmol) in the same way as in step 1 of Example 35.

$^1$H-NMR (400 MHz, CDCl$_3$) δ (ppm): δ: 0.98 and 1.01 (total 6H, each d, J=6.7 Hz), 1.24 (3H, t, J=7.3 Hz), 2.17-2.26 (1H, m), 2.27 (3H, s), 3.72 and 3.72 (total 6H, each s), 4.15 (2H, q, J=7.3 Hz), 4.29 (1H, d, J=6.1 Hz), 5.87-5.90 (1H, m), 5.91 (1H, d, J=3.6 Hz), 6.68 (2H, d, J=8.5 Hz), 7.45 (1H, t, J=8.5 Hz). MS (APCI): m/z=446 [M+H]$^+$.

Step 2

2-{[4-(2,6-Dimethoxyphenyl)-5-(5-methylfuran-2-yl)-4H-1,2,4-triazol-3-yl]sulfanyl}-3-methylbutanoic acid

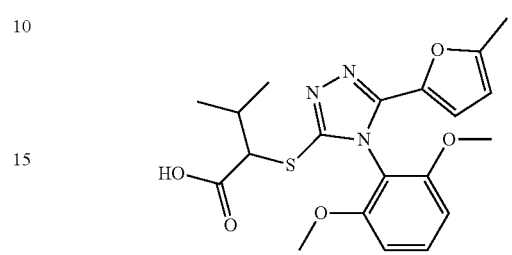

The title compound (84 mg, 0.200 mmol, 71%) was obtained as a white solid from ethyl 2-{[4-(2,6-dimethoxyphenyl)-5-(5-methylfuran-2-yl)-4H-1,2,4-triazol-3-yl]sulfanyl}-3-methylbutanoate (125 mg, 0.281 mmol) in the same way as in step 4 of Example 26.

$^1$H-NMR (400 MHz, CDCl$_3$) δ (ppm): 0.98 and 1.11 (total 6H, each d, J=6.7 Hz), 2.29 (3H, s), 2.39-2.48 (1H, m), 3.61 (1H, d, J=8.5 Hz), 3.72 and 3.75 (total 6H, each s), 5.92-5.95 (1H, m), 6.00 (1H, d, J=3.0 Hz), 6.71 (2H, dd, J=8.5, 3.0 Hz), 7.51 (1H, t, J=8.5 Hz). MS (APCI): m/z 418 [M+H]$^+$.

Example 44

3-Bromo-4-(2,6-dimethoxyphenyl)-5-(5-methylfuran-2-yl)-4H-1,2,4-triazole

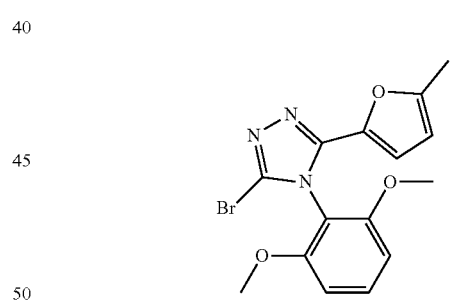

To a solution of 4-(2,6-dimethoxyphenyl)-3-(5-methylfuran-2-yl)-4H-1,2,4-triazole (202 mg, 0.708 mmol) in tetrahydrofuran (3.5 mL), N-bromosuccinimide (151 mg, 0.850 mmol) was added at room temperature, and the mixture was heated to reflux for 1 hour. The solvent was distilled off under reduced pressure, and the obtained residue was purified by silica gel column chromatography [elution solvent: n-hexane/ethyl acetate=60/40-30/70 (V/V)] to obtain the title compound (245 mg, 0.672 mmol, 95%) as a white solid.

$^1$H-NMR (400 MHz, CDCl$_3$) δ (ppm): δ: 2.29 (3H, s), 3.74 (6H, s), 5.90-5.92 (1H, m), 5.93-5.95 (1H, m), 6.70 (2H, d, J=8.5 Hz), 7.50 (1H, t, J=8.5 Hz). MS (APCI): m/z 364 [M+H]$^+$.

Example 45

Methyl 3-[4-(2,6-dimethoxyphenyl)-5-(5-methyl-furan-2-yl)-4H-1,2,4-triazol-3-yl]benzoate

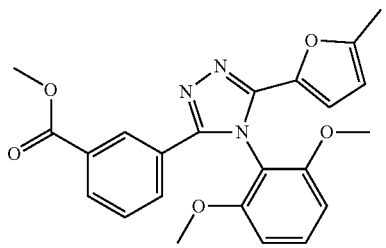 [SMILES: COC(=O)c1cccc(-c2nnc(-c3ccc(C)o3)n2-c2c(OC)cccc2OC)c1]

To a mixed solution of 3-bromo-4-(2,6-dimethoxyphenyl)-5-(5-methylfuran-2-yl)-4H-1,2,4-triazole (120 mg, 0.330 mmol) in toluene (1.90 mL) and tetrahydrofuran (0.95 mL), 3-(methoxycarbonyl)phenylboronic acid (119 mg, 0.659 mmol), potassium phosphate tribasic (200 mg, 0.989 mmol), bis(dibenzylideneacetone)palladium(0) (9.5 mg, 0.0165 mmol), and 2-dicyclohexylphosphino-2,6'-dimethoxybiphenyl (27 mg, 0.0659 mmol) were added, and the mixture was heated and stirred at 130° C. for 1 hour in a microwave reaction apparatus. Potassium phosphate tribasic (210 mg, 0.989 mmol), bis(dibenzylideneacetone)palladium(0) (20 mg, 0.0330 mmol), 2-dicyclohexylphosphino-2,6'-dimethoxybiphenyl (54 mg, 0.132 mmol), and 3-(methoxycarbonyl)phenylboronic acid (237 mg, 1.32 mmol) were further added thereto, and the mixture was heated and stirred at 140° C. for 2 hours using a microwave reaction apparatus. Ethyl acetate was added to the reaction solution. Insoluble matter was filtered off, and the solvent was distilled off under reduced pressure. The obtained residue was purified by silica gel column chromatography [elution solvent: n-hexane/ethyl acetate=20/80-0/100 (V/V)] to obtain the title compound (69 mg, 0.164 mmol, 50%) as a white solid.

$^1$H-NMR (400 MHz, CDCl$_3$) δ (ppm): 2.31 (3H, s), 3.67 (6H, s), 3.86 (3H, s), 5.87-5.88 (1H, m), 5.91-5.92 (1H, m), 6.64 (2H, d, J=8.5 Hz), 7.37-7.45 (2H, m), 7.82-7.84 (1H, m), 7.98-8.00 (1H, m), 8.16-8.16 (1H, m). MS (APCI): m/z 420 [M+H]$^+$.

Example 46

3-[4-(2,6-Dimethoxyphenyl)-5-(5-methylfuran-2-yl)-4H-1,2,4-triazol-3-yl]benzoic acid

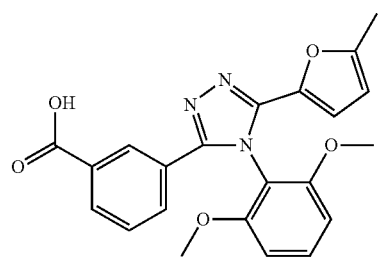 [SMILES: COc1cccc(OC)c1-n1c(-c2cccc(C(=O)O)c2)nnc1-c1ccc(C)o1]

To methyl 3-[4-(2,6-dimethoxyphenyl)-5-(5-methylfuran-2-yl)-4H-1,2,4-triazol-3-yl]benzoate (61 mg, 0.145 mmol), tetrahydrofuran (2.0 mL), methanol (2.0 mL), and a 5 mol/L aqueous sodium hydroxide solution (0.145 mL, 0.726 mmol) were added, and the mixture was heated and stirred at 65° C. for 1 hour. The reaction solution was allowed to cool to room temperature, and 5 mol/L hydrochloric acid (0.145 mL, 0.726 mmol) was added thereto. The reaction mixture was concentrated under reduced pressure, and the resulting solid was collected by filtration to obtain the title compound (54 mg, 0.133 mmol, 92%) as a white solid.

$^1$H-NMR (400 MHz, CDCl$_3$) δ (ppm): 2.27 (3H, s), 3.67 (6H, s), 5.86 (1H, d, J=3.0 Hz), 6.12-6.14 (1H, m), 6.88 (2H, d, J=8.5 Hz), 7.49-7.57 (2H, m), 7.65-7.69 (1H, m), 7.95 (1H, dt, J=7.9, 1.5 Hz), 8.04 (1H, t, J=1.5 Hz). MS (APCI): m/z 406 [M+H]$^+$.

Example 47

Methyl 4-[4-(2,6-dimethoxyphenyl)-5-(5-methyl-furan-2-yl)-4H-1,2,4-triazol-3-yl]benzoate

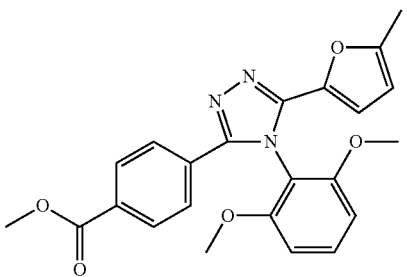

The title compound (79 mg, 0.189 mmol, 47%) was obtained as a faint yellow solid in the same way as in Example 45 by heating and stirring at 140° C. for 1 hour in a microwave reaction apparatus using 3-bromo-4-(2,6-dimethoxyphenyl)-5-(5-methyl-2-furyl)-1,2,4-triazole (146 mg, 0.40 mmol), 4-(methoxycarbonyl)phenylboronic acid (216 mg, 1.20 mmol), potassium phosphate tribasic (255 mg, 1.20 mmol), bis(dibenzylideneacetone)palladium(0) (9.5 mg, 0.040 mmol), and 2-dicyclohexylphosphino-2,6'-dimethoxybiphenyl (65.7 mg, 0.1600 mmol).

$^1$H-NMR (400 MHz, CDCl$_3$) δ (ppm): 2.31 (3H, s), 3.64 (6H, s), 3.89 (3H, s), 5.89-5.94 (2H, m), 6.63 (2H, d, J=8.5 Hz), 7.44 (1H, t, J=8.5 Hz), 7.60 (2H, d, J=8.5 Hz), 7.95 (2H, d, J=8.5 Hz). MS (APCI): m/z=420 [M+H]$^+$.

Example 48

4-[4-(2,6-Dimethoxyphenyl)-5-(5-methylfuran-2-yl)-4H-1,2,4-triazol-3-yl]benzoic acid

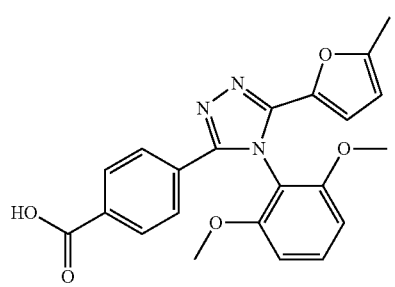 [SMILES: COc1cccc(OC)c1-n1c(-c2ccc(C(=O)O)cc2)nnc1-c1ccc(C)o1]

The title compound (58 mg, 0.144 mmol, 90%) was obtained as a white solid from methyl 4-[4-(2,6-dimethoxyphenyl)-5-(5-methylfuran-2-yl)-4H-1,2,4-triazol-3-yl]benzoate (67 mg, 0.160 mmol) in the same way as in Example 46.

$^1$H-NMR (400 MHz, DMSO-$d_6$) δ (ppm): 2.24 (3H, s), 3.63 (6H, s), 5.85 (1H, d, J=3.6 Hz), 6.10-6.13 (1H, m), 6.86 (2H, d, J=8.5 Hz), 7.49-7.57 (3H, m), 7.88 (2H, d, J=8.5 Hz), 13.09 (1H, s). MS (APCI): m/z 406 [M+H]$^+$.

Example 49

5-{[4-(2,6-Dimethoxyphenyl)-5-(5-methylfuran-2-yl)-4H-1,2,4-triazol-3-yl]sulfanyl}pentanoic acid

Step 1

Ethyl 5-{[4-(2,6-dimethoxyphenyl)-5-(5-methylfuran-2-yl)-4H-1,2,4-triazol-3-yl]sulfanyl}pentanoate

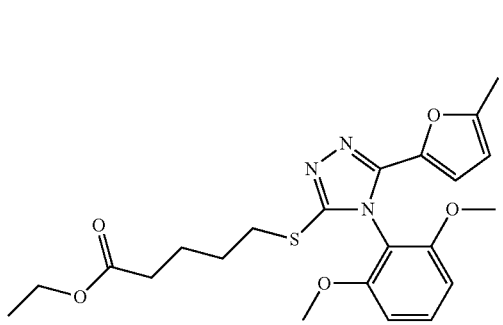 [SMILES: CCOC(=O)CCCCSc1nnc(-c2ccc(C)o2)n1-c1c(OC)cccc1OC]

The title compound (131 mg, 0.295 mmol, 98%) was obtained as a colorless oil from 4-(2,6-dimethoxyphenyl)-5-(5-methylfuran-2-yl)-4H-1,2,4-triazole-3-thiol (95 mg, 0.300 mmol) and ethyl 5-bromopentanoate (57 µL, 0.360 mmol) in the same way as in Example 4.

$^1$H-NMR (400 MHz, CDCl$_3$) δ (ppm): 1.24 (3H, t, J=7.1 Hz), 1.60-1.77 (4H, m), 2.26-2.31 (5H, m), 3.13 (2H, t, J=7.0 Hz), 3.72 (6H, s), 4.10 (2H, q, J=7.1 Hz), 5.87-5.90 (2H, m), 6.68 (2H, d, J=8.5 Hz), 7.46 (1H, t, J=8.5 Hz). MS (APCI): m/z 446 [M+H]$^+$.

Step 2

5-{[4-(2,6-Dimethoxyphenyl)-5-(5-methylfuran-2-yl)-4H-1,2,4-triazol-3-yl]sulfanyl}pentanoic acid

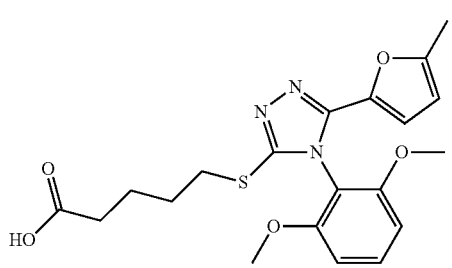 [SMILES: COc1cccc(OC)c1-n1c(SCCCCC(=O)O)nnc1-c1ccc(C)o1]

The title compound (109 mg, 0.262 mmol, 92%) was obtained as a white solid from ethyl 5-[[4-(2,6-dimethoxyphenyl)-5-(5-methyl-2-furyl)-4H-1,2,4-triazol-3-yl]sulfanyl]pentanoate (126.8 mg, 0.2846 mmol) and tetrahydrofuran (1.50 mL) in the same way as in Example 5.

$^1$H-NMR (400 MHz, CDCl$_3$) δ (ppm): 1.69-1.80 (4H, m), 2.26 (3H, s), 2.39 (2H, t, J=7.0 Hz), 3.13 (2H, t, J=7.0 Hz), 3.72 (6H, s), 5.88-5.90 (1H, m), 5.93 (1H, d, J=3.6 Hz), 6.69 (2H, d, J=8.5 Hz), 7.47 (1H, t, J=8.5 Hz). MS (APCI): m/z 418 [M+H]$^+$.

Example 50

6-{[4-(2,6-Dimethoxyphenyl)-5-(5-methylfuran-2-yl)-4H-1,2,4-triazol-3-yl]sulfanyl}hexanoic acid

Step 1

Ethyl 6-{[4-(2,6-dimethoxyphenyl)-5-(5-methylfuran-2-yl)-4H-1,2,4-triazol-3-yl]sulfanyl}hexanoate

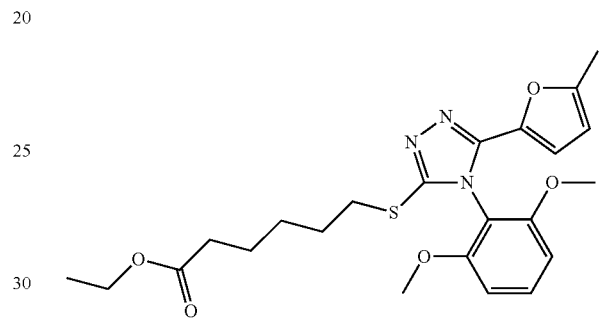

The title compound (131 mg, 0.286 mmol, 95%) was obtained as a colorless oil from 4-(2,6-dimethoxyphenyl)-5-(5-methylfuran-2-yl)-4H-1,2,4-triazole-3-thiol (95 mg, 0.300 mmol) and 6-bromohexanoic acid ethyl ester (64 µL, 0.360 mmol) in the same way as in Example 4.

$^1$H-NMR (400 MHz, CDCl$_3$) δ (ppm): 1.24 (3H, t, J=7.3 Hz), 1.34-1.43 (2H, m), 1.55-1.74 (4H, m), 2.26 (2H, t, J=7.3 Hz), 2.28 (3H, s), 3.11 (2H, t, J=7.3 Hz), 3.72 (6H, s), 4.11 (2H, q, J=7.3 Hz), 5.87-5.90 (2H, m), 6.69 (2H, d, J=8.5 Hz), 7.46 (1H, t, J=8.5 Hz). MS (APCI): m/z 460 [M+H]$^+$.

Step 2

6-{[4-(2,6-Dimethoxyphenyl)-5-(5-methylfuran-2-yl)-4H-1,2,4-triazol-3-yl]sulfanyl}hexanoic acid

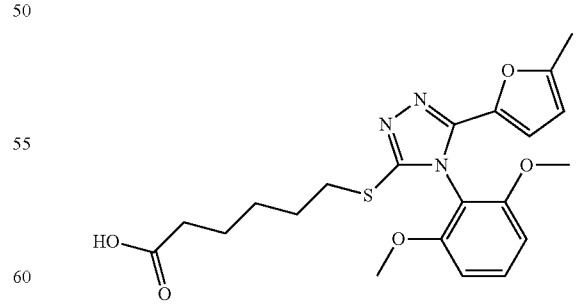

The title compound (91 mg, 0.210 mmol, 77%) was obtained as a white solid from ethyl 6-{[4-(2,6-dimethoxyphenyl)-5-(5-methylfuran-2-yl)-4H-1,2,4-triazol-3-yl]sulfanyl}hexanoate (125 mg, 0.273 mmol) in the same way as in Example 5.

¹H-NMR (400 MHz, CDCl₃) δ (ppm): 1.39-1.49 (2H, m), 1.60-1.74 (4H, m), 2.27 (3H, s), 2.36 (2H, t, J=7.3 Hz), 3.09 (2H, t, J=7.3 Hz), 3.72 (6H, s), 5.88-5.90 (1H, m), 5.92 (1H, d, J=3.0 Hz), 6.69 (2H, d, J=8.5 Hz), 7.47 (1H, t, J=8.5 Hz). MS (APCI): m/z=432 [M+H]⁺.

Example 51

Ethyl (3E)-4-[4-(2,6-dimethoxyphenyl)-5-(5-methyl-furan-2-yl)-4H-1,2,4-triazol-3-yl]-2-oxobut-3-enoate

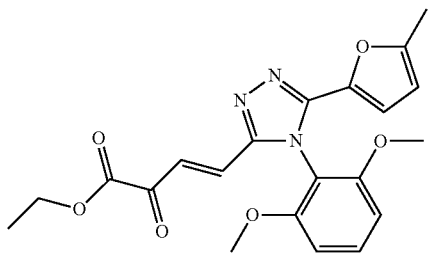 [SMILES: CCOC(=O)C(=O)/C=C/c1nnc(-c2ccc(C)o2)n1-c1c(OC)cccc1OC]

The title compound (277 mg, 0.672 mmol, 67%) was obtained as a yellow solid from 4-(2,6-dimethoxyphenyl)-5-(5-methylfuran-2-yl)-4H-1,2,4-triazole-3-carbaldehyde (313 mg, 1.000 mmol) and ethyl (triphenylphosphoranylidene)pyruvate (1.200 mmol) in the same way as in step 2 of Example 8.

¹H-NMR (400 MHz, CDCl₃) δ (ppm): 1.37 (3H, t, J=7.1 Hz), 2.30 (3H, s), 3.70 (6H, s), 4.35 (2H, q, J=7.1 Hz), 5.91-5.96 (1H, m), 5.96-6.00 (1H, m), 6.73 (2H, d, J=8.5 Hz), 7.22 (1H, d, J=16.1 Hz), 7.52 (1H, t, J=8.5 Hz), 7.77 (1H, d, J=16.1 Hz). MS (APCI): m/z 412 [M+H]⁺.

Example 52

2-{(E)-2-[4-(2,6-Dimethoxyphenyl)-5-(5-methyl-furan-2-yl)-4H-1,2,4-triazol-3-yl]ethenyl}-7-methyl-4H-pyrido[1,2-a]pyrimidin-4-one

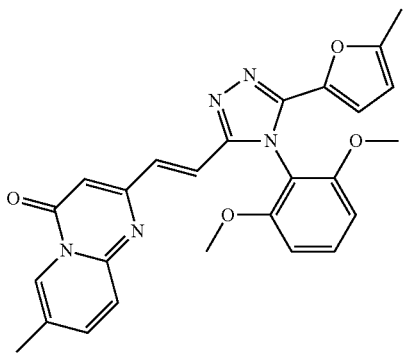 [SMILES: COc1cccc(OC)c1-n1c(/C=C/c2cc(=O)n3cc(C)ccc3n2)nnc1-c1ccc(C)o1]

To a solution of (7-methyl-4-oxo-pyrido[1,2-a]pyrimidin-2-yl)methyl-triphenyl-phosphonium chloride (reference: Journal of Heterocyclic Chemistry, 1983, vol. 20, #4, p. 1053-1057; 471 mg, 1.000 mmol) in dimethyl sulfoxide (2.50 mL), potassium tert-butoxide (112 mg, 1.000 mmol) was added in small portions at room temperature, and the mixture was stirred for 30 minutes. A solution of 4-(2,6-dimethoxyphenyl)-5-(5-methylfuran-2-yl)-4H-1,2,4-triazole-3-carbaldehyde (57 mg, 0.500 mmol) in dimethyl sulfoxide (2.5 mL) was added to the reaction solution at room temperature, and the mixture was stirred for 3 hours. A saturated aqueous solution of ammonium chloride was added thereto, followed by the extraction of organic matter with dichloromethane. The organic layer was washed with water and saturated saline and dried over anhydrous magnesium sulfate. The solvent was distilled off under reduced pressure, and the obtained residue was purified by silica gel chromatography (elution solvent: dichloromethane/methanol=100/0-90/10) to obtain the title compound (177 mg, 0.3768 mmol, 75%) as a pale yellow solid.

¹H-NMR (400 MHz, CDCl₃) δ (ppm): 2.30 (3H, s), 2.40 (3H, s), 3.71 (6H, s), 5.90-5.93 (2H, m), 6.37 (1H, s), 6.74 (2H, d, J=8.5 Hz), 7.28 (1H, d, J=15.8 Hz), 7.43 (1H, d, J=15.8 Hz), 7.47-7.56 (3H, m), 8.78 (1H, s). MS (APCI): m/z 470 [M+H]⁺.

Example 53

(2E)-3-[4-(2,6-Dimethoxyphenyl)-5-(5-methylfuran-2-yl)-4H-1,2,4-triazol-3-yl]prop-2-enenitrile

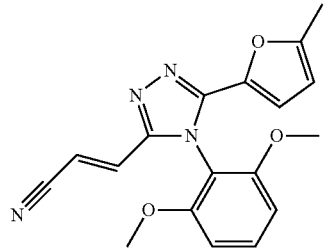 [SMILES: COc1cccc(OC)c1-n1c(/C=C/C#N)nnc1-c1ccc(C)o1]

The title compound (783 mg, 2.33 mmol, 93%) was obtained as a white solid from 4-(2,6-dimethoxyphenyl)-5-(5-methylfuran-2-yl)-4H-1,2,4-triazole-3-carbaldehyde (783 mg, 2.50 mmol) and cyanomethylenetributylphosphorane (0.787 mL, 3.000 mmol) in the same way as in step 2 of Example 8.

¹H-NMR (400 MHz, CDCl₃) δ (ppm): 2.29 (3H, s), 3.72 (6H, s), 5.92-5.95 (1H, m), 6.00 (1H, d, J=3.0 Hz), 6.42 (1H, d, J=16.4 Hz), 6.73 (2H, d, J=8.5 Hz), 6.76 (1H, d, J=16.4 Hz), 7.53 (1H, t, J=8.5 Hz). MS (APCI): m/z 337 [M+H]⁺.

Example 54

(2E)-3-[4-(2,6-Dimethoxyphenyl)-5-(5-methylfuran-2-yl)-4H-1,2,4-triazol-3-yl]-N-methoxy-N-methyl-prop-2-enamide

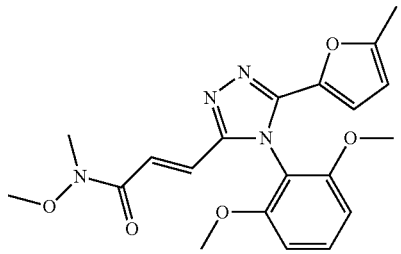

The title compound (107 mg, 0.268 mmol, 54%) was obtained as a white solid from 4-(2,6-dimethoxyphenyl)-5-

(5-methylfuran-2-yl)-4H-1,2,4-triazole-3-carbaldehyde (157 mg, 0.500 mmol) and N-methoxy-N-methyl-2-(triphenylphosphoranylidene)acetamide (218 mg, 0.600 mmol) in the same way as in step 2 of Example 8.

$^1$H-NMR (400 MHz, CDCl$_3$) δ (ppm): 2.30 (3H, s), 3.26 (3H, s), 3.69 (6H, s), 3.73 (3H, s), 5.87-5.92 (2H, m), 6.69 (2H, d, J=8.5 Hz), 7.08 (1H, d, J=15.8 Hz), 7.47 (1H, t, J=8.5 Hz), 7.58 (1H, d, J=15.8 Hz). MS (APCI): m/z=399 [M+H]$^+$.

Example 55

Methyl (2Z)-3-[4-(2,6-dimethoxyphenyl)-5-(5-methylfuran-2-yl)-4H-1,2,4-triazol-3-yl]prop-2-enoate Step 1

Methyl (2Z)-4-[(2,6-dimethoxyphenyl)amino]-4-oxobut-2-enoate

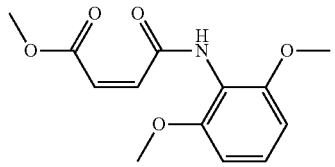

To a solution of 2,6-dimethoxyaniline (2.00 g, 13.1 mmol) and maleic acid monomethyl ester (1.87 g, 14.4 mmol) in dichloromethane (39 mL), 1-ethyl-3-(3-dimethylaminopropyl)carbodiimide hydrochloride (3.13 g, 16.3 mmol) and 4-dimethylaminopyridine (16 mg, 0.1306 mmol) were added, and the mixture was stirred at room temperature for 1 hour. The reaction solution was diluted with dichloromethane, washed with a 1 N aqueous hydrochloric acid solution, a saturated aqueous solution of sodium bicarbonate, and saturated saline, and dried over anhydrous magnesium sulfate. The solvent was distilled off under reduced pressure, and the obtained residue was purified by silica gel column chromatography [elution solvent: n-hexane/ethyl acetate=40/60-10/90 (V/V)] to obtain the title compound (897 mg, 3.38 mmol, 26%) as a white solid.

$^1$H-NMR (400 MHz, CDCl$_3$) δ (ppm): 3.81 (3H, br s), 3.84 (6H, s), 6.10-6.31 (1H, br m), 6.37-6.53 (1H, br m), 6.60 (2H, d, J=8.5 Hz), 7.19 (1H, t, J=8.5 Hz), 9.43 (1H, br s). MS (APCI): m/z 266 [M+H]$^+$.

Step 2

Methyl (2Z)-3-[4-(2,6-dimethoxyphenyl)-5-(5-methylfuran-2-yl)-4H-1,2,4-triazol-3-yl]prop-2-enoate

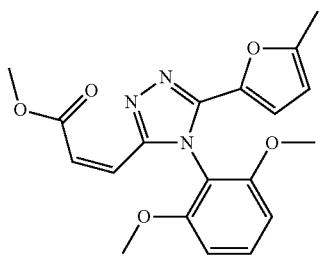

The title compound was obtained as follows according to the reference (Org. Lett., 2015, 17, 1184-1187). (2Z)-4-[(2,6-dimethoxyphenyl)amino]-4-oxobut-2-enoate (890.0 mg, 3.355 mmol) and a stirrer bar were placed in a 20 mL glass vial for microwave reaction (Biotage 10-20 mL), which was then capped. 1,2-Dichloroethane (10 mL) was added thereto using a syringe, and then 2-fluoropyridine (317 μL, 3.691 mmol) was added thereto using a syringe. Trifluoromethanesulfonic anhydride (621 μL, 3.69 mmol) was gradually added dropwise thereto using a syringe with stirring under ice cooling, and the mixture was stirred for 10 minutes. The cap was temporarily removed, 5-methylfuran-2-carbohydrazide (470 mg, 3.36 mmol) was quickly added thereto, and the mixture was then heated and stirred at 140° C. for 2 hours using a microwave reaction apparatus. The reaction solution was directly purified by silica gel column chromatography [elution solvent: n-hexane/ethyl acetate=60/40-35/65 (V/V)] to obtain the title compound (96 mg, 0.259 mmol, 7.7%) as a faint brown solid.

$^1$H-NMR (400 MHz, CDCl$_3$) δ (ppm): 2.29 (3H, s), 3.70 (6H, s), 3.75 (3H, s), 5.90-5.93 (2H, m), 6.71 (2H, d, J=8.5 Hz), 6.87 (1H, d, J=15.8 Hz), 7.10 (1H, d, J=15.8 Hz), 7.50 (1H, t, J=8.5 Hz). MS (APCI): m/z 370 [M+H]$^+$.

Example 56

(2Z)-3-[4-(2,6-Dimethoxyphenyl)-5-(5-methylfuran-2-yl)-4H-1,2,4-triazol-3-yl]prop-2-enoic acid

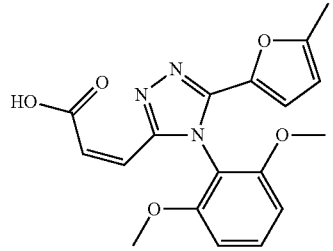 [SMILES: COc1cccc(OC)c1-n1c(/C=C\C(=O)O)nnc1-c1ccc(C)o1]

The title compound (64 mg, 0.181 mmol, 78%) was obtained as a white solid from methyl (2Z)-3-[4-(2,6-dimethoxyphenyl)-5-(5-methylfuran-2-yl)-4H-1,2,4-triazol-3-yl]prop-2-enoate (85 mg, 0.231 mmol) in the same way as in Example 9.

$^1$H-NMR (400 MHz, CDCl$_3$) δ (ppm): 2.28 (3H, s), 3.71 (6H, s), 5.92-5.94 (1H, m), 5.98 (1H, d, J=3.0 Hz), 6.71 (2H, d, J=8.5 Hz), 7.15 (2H, br s), 7.50 (1H, t, J=8.5 Hz). MS (APCI): m/z 356 [M+H]$^+$.

Example 57

4-(2,6-Dimethoxyphenyl)-3-(5-methylfuran-2-yl)-5-phenyl-4H-1,2,4-triazole

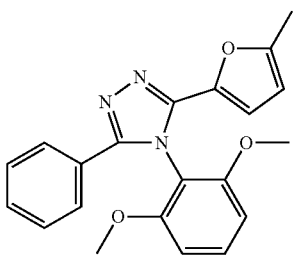 [SMILES: COc1cccc(OC)c1-n1c(-c2ccccc2)nnc1-c1ccc(C)o1]

To 3-bromo-4-(2,6-dimethoxyphenyl)-5-(5-methyl-2-furyl)-1,2,4-triazole (0.080 g, 0.220 mmol), phenylboronic acid (0.120 g, 0.879 mmol), potassium phosphate tribasic (0.191 g, 0.879 mmol), bis(dibenzylideneacetone)palladium (0) (0.023 g, 0.0329 mmol), and 2-dicyclohexylphosphino-2,6'-dimethoxybiphenyl (0.0570 g, 0.132 mmol), toluene (1.50 mL) and tetrahydrofuran (0.75 mL) were added, and the mixture was heated and stirred at 140° C. for 1 hour under microwave. The reaction solution was concentrated under reduced pressure, and the obtained residue was then purified by silica gel column chromatography [elution solvent: n-hexane/ethyl acetate=50/50-30/70 (V/V)] to obtain the title compound (0.0600 g, 0.166 mmol, 76%) as a pale yellow solid.

$^1$H-NMR (500 MHz, CDCl$_3$) δ (ppm): 2.30 (3H, s), 3.63 (6H, s), 5.86-5.89 (1H, m), 5.89-5.91 (1H, m), 6.62 (2H, d, J=8.5 Hz), 7.25-7.33 (3H, m), 7.41 (1H, t, J=8.5 Hz), 7.49-7.54 (2H, m). MS (ESI): m/z 362 [M+H]$^+$.

Example 58

Methyl 2-[4-(2,6-dimethoxyphenyl)-5-(5-methyl-2-furyl)-4H-1,2,4-triazol-3-yl]benzoate

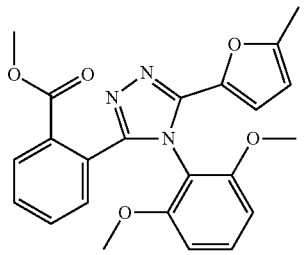 [SMILES: COC(=O)c1ccccc1-c1nnc(-c2ccc(C)o2)n1-c1c(OC)cccc1OC]

The title compound (0.0240 g, 0.0572 mmol, 26%) was obtained as a pale yellow solid using 3-bromo-4-(2,6-dimethoxyphenyl)-5-(5-methyl-2-furyl)-1,2,4-triazole (0.0800 g, 0.220 mmol) in the same way as in Example 57.

$^1$H-NMR (500 MHz, CDCl$_3$) δ (ppm): 2.30 (3H, s), 3.61 (6H, s), 3.72 (3H, s), 5.92-5.94 (1H, m), 5.95-5.98 (1H, m), 6.52 (2H, d, J=8.5 Hz), 7.31 (1H, t, J=8.5 Hz), 7.41-7.45 (3H, m), 7.84-7.86 (1H, m). MS (ESI): m/z 420 [M+H]$^+$.

Example 59

2-[4-(2,6-Dimethoxyphenyl)-5-(5-methylfuran-2-yl)-4H-1,2,4-triazol-3-yl]benzoic acid

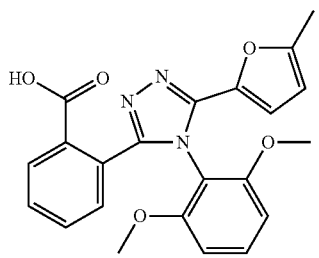 [SMILES: COc1cccc(OC)c1-n1c(-c2ccc(C)o2)nnc1-c1ccccc1C(=O)O]

The title compound (0.0130 g, 0.0321 mmol, 56%) was obtained as a pale yellow solid using methyl 2-[4-(2,6-dimethoxyphenyl)-5-(5-methyl-2-furyl)-4H-1,2,4-triazol-3-yl]benzoate (0.0240 g, 0.0572 mmol) in the same way as in Example 5.

$^1$H-NMR (500 MHz, CD$_3$OD) δ (ppm): 2.28 (3H, s), 3.65 (6H, s), 6.04-6.07 (1H, m), 6.08-6.10 (1H, m), 6.65 (2H, d, J=8.5 Hz), 7.38 (1H, t, J=8.5 Hz), 7.44-7.48 (1H, m), 7.52-7.60 (2H, m), 7.89-7.93 (1H, m). MS (ESI): m/z 406 [M+H]$^+$.

Example 60

{[1-(2,6-Dimethoxyphenyl)-2-(5-methylfuran-2-yl)-1H-imidazol-5-yl]sulfanyl}acetic acid Step 1 tert-Butyl {2-[(2,6-dimethoxyphenyl)amino]-2-oxoethyl}carbamate

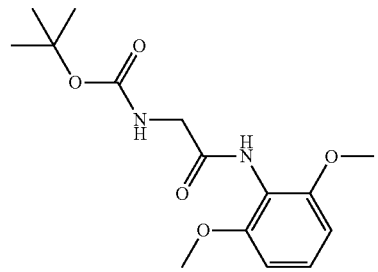 [SMILES: COc1cccc(OC)c1NC(=O)CNC(=O)OC(C)(C)C]

N-(tert-Butoxycarbonyl)glycine (6.29 g, 35.9 mmol) and 2,6-dimethoxyaniline (5.00 g, 32.6 mmol) were dissolved in methanol (100 mL). To the solution, 4-(4,6-dimethoxy-1,3,5-triazin-2-yl)-4-methylmorpholinium chloride (9.93 g, 35.9 mmol) was added at room temperature, and the mixture was stirred for 5 hours. The reaction solution was concentrated under reduced pressure, and water was then added to the residue, followed by extraction with dichloromethane. The organic layer was concentrated under reduced pressure, and the obtained solid was collected by filtration using diisopropyl ether to obtain the partially purified title compound (8.25 g, 26.6 mmol, 81%) as a light gray solid.

$^1$H-NMR (500 MHz, CD$_3$OD) δ (ppm): 1.46 (9H, s), 3.83 (6H, s), 4.05 (2H, s), 6.59 (2H, d, J=8.5 Hz), 7.22 (1H, t, J=8.5 Hz). MS (ESI): m/z 311 [M+H]$^+$.

Step 2 tert-Butyl {2-[(2,6-dimethoxyphenyl)amino]-2-thioxoethyl}carbamate

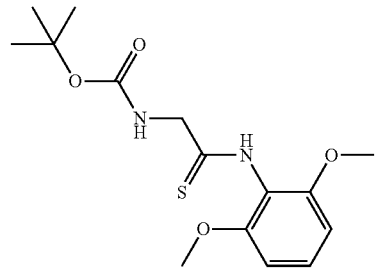 [SMILES: COc1cccc(OC)c1NC(=S)CNC(=O)OC(C)(C)C]

To a solution of tert-butyl {2-[(2,6-dimethoxyphenyl)amino]-2-oxoethyl}carbamate (1.12 g, 3.20 mmol) in tetrahydrofuran (45 mL), Lawesson's Reagent (0.820 g, 1.90 mmol) was added at room temperature, and the mixture was stirred for 2 hours. Lawesson's Reagent (0.820 g, 1.90 mmol) was further added thereto, and the mixture was stirred for 12 hours. The reaction solution was concentrated under reduced pressure, and the obtained residue was purified by silica gel column chromatography [elution solvent: n-hexane/ethyl acetate=75/25-30/70 (V/V)] to obtain the title compound (1.04 g, 3.10 mmol, 95%) as a pale yellow solid.

MS (ESI): m/z 327 [M+H]⁺.

Step 3

2-Amino-N-(2,6-dimethoxyphenyl)ethanethioamide trifluoroacetic acid

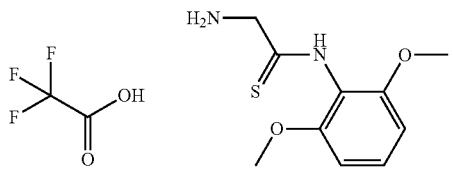

To a solution of tert-butyl {2-[(2,6-dimethoxyphenyl)amino]-2-thioxoethyl}carbamate (0.352 g, 1.07 mmol) in dichloromethane (6.0 mL), trifluoroacetic acid (1 mL, 1.0 ml) was added at room temperature, and the mixture was stirred for 1 hour. The reaction solution was concentrated under reduced pressure to obtain the partially purified title compound (0.340 g, 1.00 mmol, 93%) as a pale yellow oil. The obtained title compound was used in the next reaction without being purified.

MS (ESI): m/z 227 [M+H]⁺ (free form).

Step 4

N-{2-[(2,6-Dimethoxyphenyl)amino]-2-thioxoethyl}-5-methylfuran-2-carboxamide

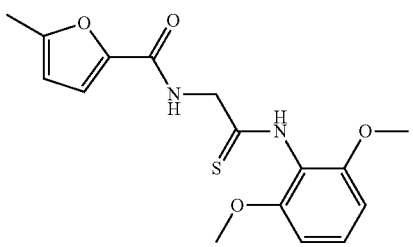

To 5-methyl-2-furancarboxylic acid (0.160 g, 1.20 mmol), thionyl chloride (4.2 mL) was added, and the mixture was stirred at 90° C. for 2 hours. Then, the reaction solution was concentrated under reduced pressure to prepare 5-methylfuran-2-carbonyl chloride. A solution of 2-amino-N-(2,6-dimethoxyphenyl)ethanethioamide trifluoroacetic acid (0.340 g, 1.00 mmol) in tetrahydrofuran (15 mL) was cooled to 0° C., a solution of N,N-diisopropylethylamine (0.870 ml, 5.00 mmol) and the preliminarily prepared solution of 5-methylfuran-2-carbonyl chloride in tetrahydrofuran (15 mL) were added dropwise thereto, and the mixture was stirred at 0° C. for 1 hour. The reaction solution was concentrated under reduced pressure, and the obtained residue was purified by silica gel column chromatography [elution solvent: n-hexane/ethyl acetate=80/20-50/50 (V/V)] to obtain the title compound (0.230 g, 0.688 mmol, 69%) as a yellow oil.

MS (ESI): m/z 335 [M+H]⁺.

Step 5

1-(2,6-Dimethoxyphenyl)-2-(5-methylfuran-2-yl)-1H-imidazole-5-thiol

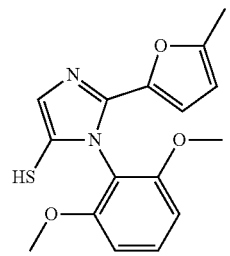 [SMILES: COc1cccc(OC)c1-n1c(S)cnc1-c1ccc(C)o1]

To a solution of N-{2-[(2,6-dimethoxyphenyl)amino]-2-thioxoethyl}-5-methylfuran-2-carboxamide (0.180 g, 0.538 mmol) in toluene (2.0 mL), phosphoryl chloride (1.00 mL, 11.0 mmol) was added at room temperature, and the mixture was stirred at 100° C. for 2 hours. The reaction solution was concentrated under reduced pressure, and the residue was diluted by the addition of ethyl acetate. Then, a saturated aqueous solution of sodium bicarbonate was added thereto, followed by extraction with ethyl acetate. The organic layer was concentrated under reduced pressure, and the obtained residue was purified by silica gel column chromatography [elution solvent: n-hexane/ethyl acetate=75/25-30/70 (V/V)] to obtain the title compound (0.0850 g, 0.269 mmol, 50%) as a pale yellow oil.

¹H-NMR (500 MHz, CD₃OD) δ (ppm): 2.32 (3H, s), 3.82 (6H, s), 6.03-6.06 (1H, m), 6.58-6.61 (1H, m), 6.59 (2H, d, J=8.5 Hz), 7.03 (1H, t, J=8.5 Hz), 7.13 (1H, s). MS (ESI): m/z 317 [M+H]⁺.

Step 6

Ethyl {[1-(2,6-dimethoxyphenyl)-2-(5-methylfuran-2-yl)-1H-imidazol-5-yl]sulfanyl}acetate

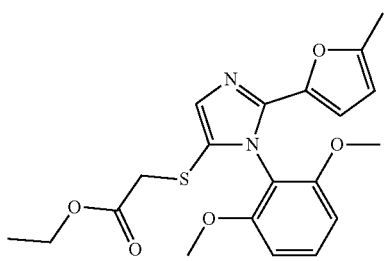 [SMILES: CCOC(=O)CSc1cnc(-c2ccc(C)o2)n1-c1c(OC)cccc1OC]

A solution of 1-(2,6-dimethoxyphenyl)-2-(5-methylfuran-2-yl)-1H-imidazole-5-thiol (0.0850 g, 0.269 mmol) and ethyl 2-chloroacetate (0.067 mL, 0.537 mmol) in tetrahydrofuran (10 mL) was cooled to 0° C., sodium hydride (60% in oil. 0.0260 g, 0.537 mmol) was added thereto, and the mixture was stirred at 0° C. for 10 minutes. After stirring at room temperature for 4 hours, sodium hydride (60% in oil, 0.0260 g, 0.537 mmol) and ethyl 2-chloroacetate (0.067 mL, 0.537 mmol) were added thereto again, and the mixture was stirred at room temperature for 4 hours. A saturated aqueous solution of ammonium chloride was added to the reaction solution, followed by extraction with ethyl acetate. The organic layer was concentrated under reduced pressure, and the obtained residue was purified by silica gel column chromatography [elution solvent: n-hexane/ethyl acetate=80/20-0/100 (V/V)] to obtain the title compound (0.0240 g, 0.0596 mmol, 22%) as a brown oil.

$^1$H-NMR (500 MHz, CDCl$_3$) δ (ppm): 1.27 (3H, t, J=7.3 Hz), 2.31 (3H, s), 3.82 (6H, s), 4.20 (2H, q, J=7.3 Hz), 4.25 (2H, s), 6.04-6.07 (1H, m), 6.62-6.64 (1H, m), 6.62 (2H, d, J=8.3 Hz), 6.82 (1H, s), 7.26 (1H, t, J=8.3 Hz). MS (ESI): m/z 403 [M+H]$^+$.

Step 7

{[1-(2,6-Dimethoxyphenyl)-2-(5-methylfuran-2-yl)-1H-imidazol-5-yl]sulfanyl}acetic acid

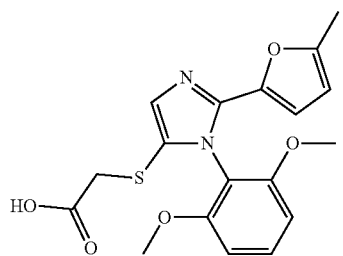 [SMILES: COc1cccc(OC)c1-n1c(SCC(=O)O)cnc1-c1ccc(C)o1]

The title compound (0.0180 g, 0.0487 mmol, 82%) was obtained as a light brown solid from ethyl {[1-(2,6-dimethoxyphenyl)-2-(5-methylfuran-2-yl)-1H-imidazol-5-yl]sulfanyl}acetate (0.0240 g, 0.0596 mmol) in the same way as in Example 5.

$^1$H-NMR (500 MHz, CD$_3$OD) δ (ppm): 2.29 (3H, s), 3.82 (6H, s), 4.22 (2H, s), 6.10 (1H, d, J=3.4 Hz), 6.59 (1H, d, J=3.4 Hz), 6.70 (1H, s), 6.75 (2H, d, J=8.3 Hz), 7.32 (1H, t, J=8.3 Hz). MS (ESI): m/z 375 [M+H]$^+$.

Example 61

{[4-(2,6-Dimethoxyphenyl)-5-(furan-2-yl)-4H-1,2,4-triazol-3-yl]sulfanyl}acetic acid Step 1

Ethyl {[4-(2,6-dimethoxyphenyl)-5-(furan-2-yl)-4H-1,2,4-triazol-3-yl]sulfanyl}acetate

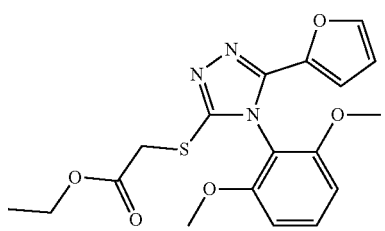 [SMILES: CCOC(=O)CSc1nnc(-c2ccco2)n1-c1c(OC)cccc1OC]

To a solution of ethyl 2-[[5-(5-bromo-2-furyl)-4-(2,6-dimethoxyphenyl)-4H-1,2,4-triazol-3-yl]sulfanyl]acetate (0.0510 g, 0.107 mmol) in ethanol (2.0 mL), a 10% palladium carbon catalyst (0.0550 g) was added, and the mixture was stirred at room temperature for 3 hours under the hydrogen atmosphere. Insoluble matter was filtered off through celite, and the filtrate was concentrated under reduced pressure. The obtained residue was purified by silica gel column chromatography [elution solvent: n-hexane/ethyl acetate=60/40-30/70 (V/V)] to obtain the title compound (0.0130 g, 0.0342 mmol, 32%) as a colorless oil.

$^1$H-NMR (400 MHz, CDCl$_3$) δ (ppm): 1.26 (3H, t, J=7.2 Hz), 3.73 (6H, s), 4.06 (2H, s), 4.19 (2H, q, J=7.2 Hz), 6.17-6.18 (1H, m), 6.32-6.33 (1H, m), 6.68 (2H, d, J=8.6 Hz), 7.38-7.39 (1H, m), 7.46 (1H, t, J=8.6 Hz). MS (ESI): m/z 362 [M+H]$^+$.

Step 2

{[4-(2,6-Dimethoxyphenyl)-5-(furan-2-yl)-4H-1,2,4-triazol-3-yl]sulfanyl}acetic acid

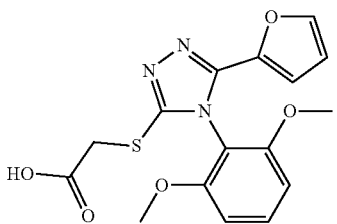 [SMILES: COc1cccc(OC)c1-n1c(SCC(=O)O)nnc1-c1ccco1]

The title compound (0.0097 g, 0.027 mmol, 79%) was obtained as a pale yellow solid using ethyl {[4-(2,6-dimethoxyphenyl)-5-(furan-2-yl)-4H-1,2,4-triazol-3-yl]sulfanyl}acetate (0.0130 g, 0.0342 mmol) in the same way as in Example 5.

$^1$H-NMR (500 MHz, CD$_3$OD) δ (ppm): 3.77 (6H, s), 3.97 (2H, s), 6.22 (1H, d, J=3.4 Hz), 6.44 (1H, dd, J=1.5 Hz, 3.4 Hz), 6.88 (2H, d, J=8.3 Hz), 7.57 (1H, d, J=1.5 Hz), 7.58 (1H, t, J=8.3 Hz). MS (ESI): m/z 362 [M+H]$^+$.

Example 62

{[4-(2,6-Dimethoxyphenyl)-5-(furan-3-yl)-4H-1,2,4-triazol-3-yl]sulfanyl}acetic acid Step 1

Furan-3-carbohydrazide

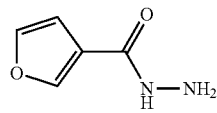

To a solution of furan-3-carboxylic acid (10.5 g, 89.2 mmol) in methanol (100 mL), sulfuric acid (0.500 mL, 8.92 mmol) was added, and the mixture was stirred at 60° C. for 3 hours. The reaction solution was concentrated under reduced pressure, and the obtained residue was diluted with ethanol (70 mL). Hydrazine monohydrate (21.5 mL, 446 mmol) was added thereto, and the mixture was stirred at 100° C. for 5 hours. The reaction solution was concentrated under reduced pressure, and the deposited solid was collected by filtration using diisopropyl ether. The obtained solid was dried under reduced pressure at 50° C. to obtain the title compound (5.95 g, 47.2 mmol, 52.9%) as a yellow solid.

$^1$H-NMR (500 MHz, CDCl$_3$) δ (ppm): 4.06 (2H, s, NH$_2$), 6.62 (1H, s), 7.21 (1H, s, NH), 7.46 (1H, s), 7.96 (1H, s). MS (ESI): m/z 127 [M+H]$^+$.

Step 2

N-(2,6-Dimethoxyphenyl)-2-(furan-3-ylcarbonyl)hydrazinecarbothioamide

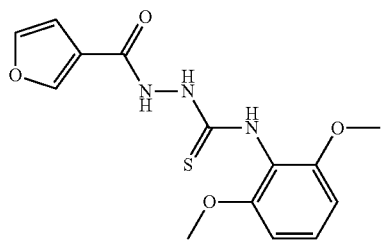 [SMILES: COc1cccc(OC)c1NC(=S)NNC(=O)c1ccoc1]

The title compound (1.27 g, 3.96 mmol, quantitative) was obtained as a pale yellow solid using furan-3-carbohydrazide (0.510 g, 3.96 mmol) in the same way as in step 2 of Example 1.

MS (ESI): m/z 322 [M+H]$^+$.

Step 3

4-(2,6-Dimethoxyphenyl)-5-(furan-3-yl)-4H-1,2,4-triazole-3-thiol

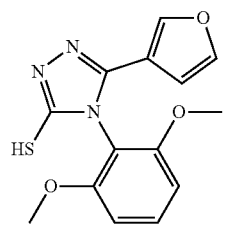 [SMILES: COc1cccc(OC)c1-n1c(S)nnc1-c1ccoc1]

The title compound (1.01 g, 3.33 mmol, 84%) was obtained as a pale yellow solid using N-(2,6-dimethoxyphenyl)-2-(furan-3-ylcarbonyl)hydrazinecarbothioamide (1.27 g, 3.96 mmol) in the same way as in step 3 of Example 1.

$^1$H-NMR (400 MHz, CDCl$_3$) δ (ppm): 3.74 (6H, s), 6.60-6.61 (1H, m), 6.74 (2H, d, J=8.6 Hz), 7.03 (1H, s), 7.36-7.37 (1H, m), 7.51 (1H, t, J=8.6 Hz), 10.28 (1H, s, SH). MS (ESI): m/z 304 [M+H]$^+$.

Step 4

Ethyl {[4-(2,6-dimethoxyphenyl)-5-(furan-3-yl)-4H-1,2,4-triazol-3-yl]sulfanyl}acetate

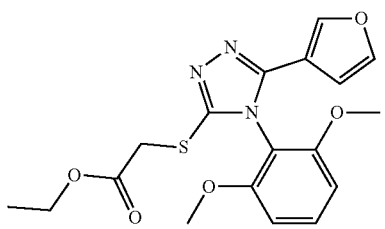 [SMILES: CCOC(=O)CSc1nnc(-c2ccoc2)n1-c1c(OC)cccc1OC]

The title compound (0.107 g, 0.276 mmol, 84%) was obtained as a colorless oil using 4-(2,6-dimethoxyphenyl)-5-(furan-3-yl)-4H-1,2,4-triazole-3-thiol (0.100 g, 0.330 mmol) in the same way as in Example 2.

$^1$H-NMR (400 MHz, CDCl$_3$) δ (ppm): 1.23 (3H, t, J=7.2 Hz), 3.70 (6H, s), 4.00 (2H, s), 4.15 (2H, q, J=7.2 Hz), 6.63-6.64 (1H, m), 6.65 (2H, d, J=8.6 Hz), 7.11-7.12 (1H, m), 7.29-7.30 (1H, m), 7.43 (1H, t, J=8.6 Hz). MS (ESI): m/z 390 [M+H]$^+$.

Step 5

{[4-(2,6-Dimethoxyphenyl)-5-(furan-3-yl)-4H-1,2,4-triazol-3-yl]sulfanyl}acetic acid

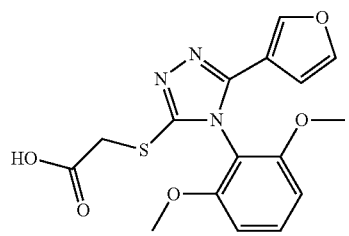 [SMILES: COc1cccc(OC)c1-n1c(SCC(=O)O)nnc1-c1ccoc1]

The title compound (0.0902 g, 0.250 mmol, 91%) was obtained as a pale yellow solid using ethyl {[4-(2,6-dimethoxyphenyl)-5-(furan-3-yl)-4H-1,2,4-triazol-3-yl]sulfanyl}acetate (0.107 g, 0.276 mmol) in the same way as in Example 5.

$^1$H-NMR (500 MHz, CD$_3$OD) δ (ppm): 3.75 (6H, s), 3.91 (2H, s), 6.54-6.55 (1H, m), 6.86 (2H, d, J=8.5 Hz), 7.22-7.23 (1H, m), 7.48-7.49 (1H, m), 7.57 (1H, t, J=8.5 Hz). MS (ESI): m/z 362 [M+H]$^+$.

Example 63

{[4-(2,6-Dimethoxyphenyl)-5-(4,5-dimethylfuran-2-yl)-4H-1,2,4-triazol-3-yl]sulfanyl}acetic acid Step 1

Methyl 4,5-dimethylfuran-2-carboxylate

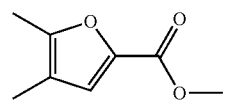

To a solution of 4,5-dimethyl-2-furancarboxylic acid (5.01 g, 36.0 mmol) in dichloromethane (30 mL), N,N-dimethylformamide (0.0200 mL, 0.260 mmol) was added, the mixture was cooled to 0° C., and oxalyl chloride (6.10 mL, 71.0 mmol) was then added dropwise thereto. After the dropwise addition, the reaction solution was heated to room temperature and stirred for 3 hours. The reaction solution was concentrated under reduced pressure. Methanol (50 mL) was added to the obtained residue at room temperature, and the mixture was stirred for 1 hour. The reaction solution was concentrated under reduced pressure, and water was added to the obtained residue followed by extraction with ethyl acetate. The organic layer was concentrated under reduced pressure to obtain the title compound (5.41 g, 35.0 mmol, 97%) as a yellow oil.

MS (ESI): m/z 155 [M+H]$^+$.

Step 2

4,5-Dimethylfuran-2-carbohydrazide

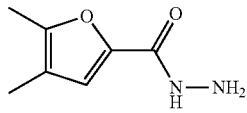

To a solution of methyl 4,5-dimethylfuran-2-carboxylate (5.41 g, 35.0 mmol) in ethanol (100 mL), hydrazine monohydrate (3.40 mL, 70.0 mmol) was added, and the mixture was stirred at 110° C. for 4 hours. Hydrazine monohydrate (100 mL, 210 mmol) was further added to the reaction solution, and the mixture was stirred at 100° C. for 4 hours. The reaction solution was concentrated under reduced pressure, and the deposited solid was collected by filtration using diisopropyl ether. The obtained solid was dried under reduced pressure at 50° C. to obtain the title compound (5.0 g, 32.7 mmol, 94%) as a pale yellow solid.

$^1$H-NMR (500 MHz, CDCl$_3$) δ (ppm): 1.97 (3H, s), 2.24 (3H, s), 3.98 (2H, s, NH$_2$), 6.91 (1H, s), 7.41 (1H, s, NH). MS (ESI) m/z 155 [M+H]$^+$.

Step 3

N-(2,6-Dimethoxyphenyl)-2-[(4,5-dimethylfuran-2-yl)carbonyl]hydrazinecarbothioamide

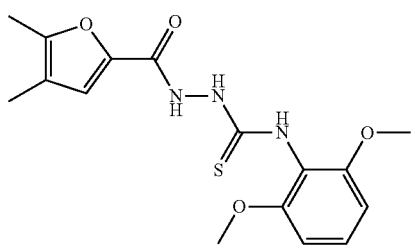

The title compound (1.13 g, 3.24 mmol, quantitative) was obtained as a pale yellow solid from 4,5-dimethylfuran-2-carbohydrazide (0.505 g, 3.24 mmol) in the same way as in step 2 of Example 5.

MS (ESI): m/z 350 [M+H]$^+$.

Step 4

4-(2,6-Dimethoxyphenyl)-5-(4,5-dimethylfuran-2-yl)-4H-1,2,4-triazole-3-thiol

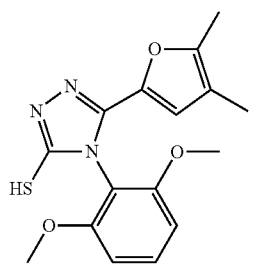 [SMILES: COc1cccc(OC)c1-n1c(S)nnc1-c1cc(C)c(C)o1]

The title compound (1.00 g, 3.00 mmol, 93%) was obtained as a pale yellow solid from N-(2,6-dimethoxyphenyl)-2-[(4,5-dimethylfuran-2-yl)carbonyl]hydrazinecarbothioamide (1.13 g, 3.24 mmol) in the same way as in step 3 of Example 1.

$^1$H-NMR (400 MHz, CDCl$_3$) δ (ppm): 1.83 (3H, s), 2.23 (3H, s), 3.79 (6H, s), 5.67 (1H, s), 6.74 (2H, d, J=8.5 Hz), 7.51 (1H, t, J=8.5 Hz), 10.74 (1H, s). MS (ESI): m/z 350 [M+H]$^+$.

Step 5

Ethyl {[4-(2,6-dimethoxyphenyl)-5-(4,5-dimethylfuran-2-yl)-4H-1,2,4-triazol-3-yl]sulfanyl}acetate

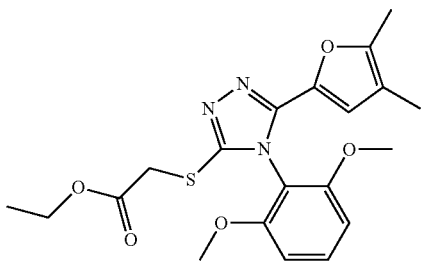 [SMILES: CCOC(=O)CSc1nnc(-c2cc(C)c(C)o2)n1-c1c(OC)cccc1OC]

The title compound (0.0965 g, 0.231 mmol, 77%) was obtained as a colorless oil from 4-(2,6-dimethoxyphenyl)-5-(4,5-dimethylfuran-2-yl)-4H-1,2,4-triazole-3-thiol (0.100 g, 0.302 mmol) in the same way as in Example 4.

$^1$H-NMR (400 MHz, CDCl$_3$) δ (ppm): 1.26 (3H, t, J=7.0 Hz), 1.83 (3H, s), 2.17 (3H, s), 3.74 (6H, s), 4.03 (2H, s), 4.18 (2H, q, J=7.0 Hz), 5.84 (1H, s), 6.69 (2H, d, J=8.6 Hz), 7.46 (1H, t, J=8.6 Hz). MS (ESI): m/z 418 [M+H]$^+$.

Step 6

{[4-(2,6-Dimethoxyphenyl)-5-(4,5-dimethylfuran-2-yl)-4H-1,2,4-triazol-3-yl]sulfanyl}acetic acid

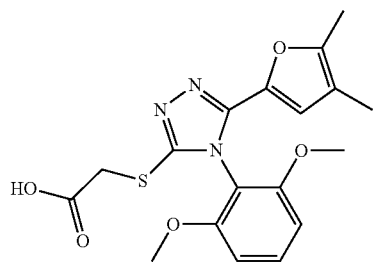 [SMILES: COc1cccc(OC)c1-n1c(SCC(=O)O)nnc1-c1cc(C)c(C)o1]

The title compound (0.0772 g, 0.198 mmol, 86%) was obtained as a colorless solid from ethyl {[4-(2,6-dimethoxyphenyl)-5-(4,5-dimethylfuran-2-yl)-4H-1,2,4-triazol-3-yl]sulfanyl}acetate (0.0965 g, 0.231 mmol) in the same way as in Example 5.

$^1$H-NMR (500 MHz, CD$_3$OD) δ (ppm): 1.84 (3H, s), 2.15 (3H, s), 3.77 (6H, s), 3.93 (2H, s), 5.93 (1H, s), 6.87 (2H, d, J=8.3 Hz), 7.58 (1H, t, J=8.3 Hz). MS (ESI): m/z 375 [M+H]$^+$.

Example 64

Ammonium (2E)-3-[4-(2,6-dimethoxyphenyl)-5-(5-methylfuran-2-yl)-4H-1,2,4-triazol-3-yl]prop-2-enoate

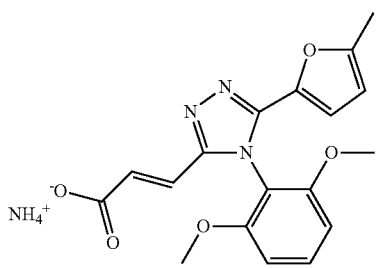

To a solution of (2E)-3-[4-(2,6-dimethoxyphenyl)-5-(5-methylfuran-2-yl)-4H-1,2,4-triazol-3-yl]prop-2-enoic acid (43.6 mg, 0.123 mmol) in methanol, ammonia (ca. 4% in methanol, ca. 2.0 mol/L) (0.61 mL, 1.23 mmol) was added, and the mixture was stirred at room temperature for 15 minutes. The solvent was evaporated to dryness under reduced pressure to obtain the title compound (43.4 mg, 0.117 mmol, 95%) as a white solid.

$^1$H-NMR (400 MHz, CD$_3$OD) δ (ppm): 2.26 (3H, s), 3.77 (6H, s), 6.05-6.08 (1H, m), 6.10 (1H, d, J=3.6 Hz), 6.67 (1H, d, J=15.8 Hz), 6.93 (2H, d, J=8.5 Hz), 6.99 (1H, d, J=15.8 Hz), 7.64 (1H, t, J=8.5 Hz). MS (APCI): m/z 356 [M+H]$^+$ (free form).

Example 65

Sodium (2E)-3-[4-(2,6-dimethoxyphenyl)-5-(5-methylfuran-2-yl)-4H-1,2,4-triazol-3-yl]prop-2-enoate

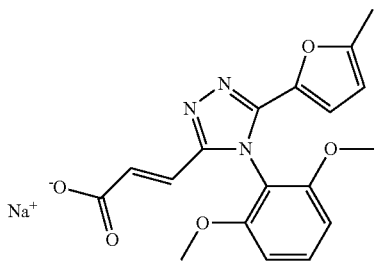

To a solution of (2E)-3-[4-(2,6-dimethoxyphenyl)-5-(5-methylfuran-2-yl)-4H-1,2,4-triazol-3-yl]prop-2-enoic acid (63.7 mg, 0.179 mmol) in ethanol (1.80 mL), a 1.00 mol/L aqueous sodium hydroxide solution (0.179 mmol) was added, and the mixture was stirred at room temperature for 30 minutes. The solvent was distilled off under reduced pressure. Ethanol was added to the obtained residue, and the mixture was azeotropically dried to obtain the partially purified title compound (65.1 mg, 0.173 mmol, 96%) as a white solid.

$^1$H-NMR (400 MHz, CD$_3$OD) δ (ppm): 2.26 (3H, s), 3.75 (6H, s), 5.99-6.01 (1H, m), 6.02-6.04 (1H, m), 6.78 (1H, d, J=15.8 Hz), 6.83 (1H, d, J=15.8 Hz), 6.89 (2H, d, J=8.5 Hz), 7.60 (1H, t, J=8.5 Hz). MS (APCI): m/z 356 [M+H]$^+$.

Example 66

Ethyl {[4-(2,6-dimethoxyphenyl)-5-(5-methylfuran-2-yl)-4H-1,2,4-triazol-3-yl]methoxy}acetate

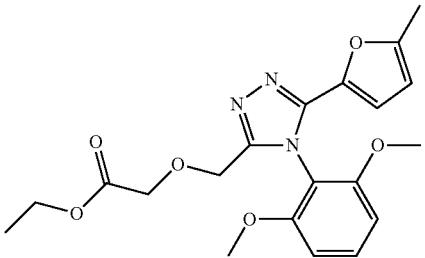 [SMILES: CCOC(=O)COCc1nnc(-c2ccc(C)o2)n1-c1c(OC)cccc1OC]

[4-(2,6-Dimethoxyphenyl)-5-(5-methylfuran-2-yl)-4H-1,2,4-triazol-3-yl]methanol (0.115 g, 0.317 mmol) was dissolved in N,N-dimethylformamide (4.0 mL). To the solution, sodium hydride in oil (35.0 mg, 0.634 mmol) was added at room temperature, and the mixture was stirred for 10 minutes. Chloroacetic acid ethyl ester (0.078 g, 0.634 mmol) was added to the reaction solution, and the mixture was stirred for 8 hours. A saturated aqueous solution of ammonium chloride was added to the reaction solution. Ethyl acetate was added thereto for extraction, and the organic layer was dried over anhydrous magnesium sulfate. The solvent was distilled off under reduced pressure, and the obtained residue was purified by silica gel column chromatography [elution solvent: n-hexane/ethyl acetate=50/50-0/100 (V/V))] to obtain the title compound (0.118 g, 0.294 mmol, 93%) as a yellow oil.

¹H-NMR (500 MHz, CDCl₃) δ (ppm): 1.21 (3H, t, J=7.1 Hz), 2.26 (3H, s), 3.67 (6H, s), 3.98 (2H, s), 4.13 (2H, q, J=7.1 Hz), 4.60 (2H, s), 5.83 (1H, d, J=3.4 Hz), 5.86-5.88 (1H, m), 6.65 (2H, d, J=8.8 Hz), 7.42 (1H, t, J=8.8 Hz). MS (ESI): m/z 402 [M+H]⁺.

Example 67

{[4-(2,6-Dimethoxyphenyl)-5-(5-methylfuran-2-yl)-4H-1,2,4-triazol-3-yl]methoxy}acetic acid

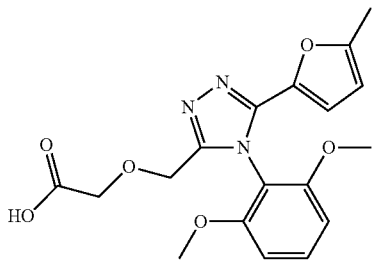 [SMILES: COc1cccc(OC)c1-n1c(COCC(=O)O)nnc1-c1ccc(C)o1]

The title compound (0.0215 g, 0.0576 mmol, 39%) was obtained as a white solid using ethyl {[4-(2,6-dimethoxyphenyl)-5-(5-methylfuran-2-yl)-4H-1,2,4-triazol-3-yl]methoxy}acetate (0.060 g, 0.149 mmol) in the same way as in Example 5.

¹H-NMR (500 MHz, DMSO-d₆) δ (ppm): 2.24 (3H, s), 3.69 (6H, s), 3.82 (2H, s), 4.44 (2H, s), 5.86 (1H, d, J=3.4 Hz), 6.09-6.11 (1H, m), 6.89 (2H, d, J=8.8 Hz), 7.55 (1H, t, J=8.8 Hz). MS (ESI): m/z 374 [M+H]⁺.

Example 68

4-(2,6-Dimethoxyphenyl)-3-(5-methylfuran-2-yl)-5-[(4H-1,2,4-triazol-3-ylsulfanyl)methyl]-4H-1,2,4-triazole Step 1

[4-(2,6-Dimethoxyphenyl)-5-(5-methylfuran-2-yl)-4H-1,2,4-triazol-3-yl]methyl methanesulfonate

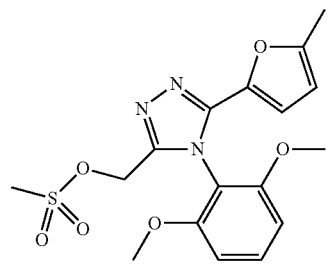

[4-(2,6-Dimethoxyphenyl)-5-(5-methyl-2-furyl)-1,2,4-triazol-3-yl]methanol (0.750 g, 2.38 mmol) was dissolved in dichloromethane (25 mL), and the solution was cooled to 0° C. Then, triethylamine (0.66 mL, 4.76 mmol) and methanesulfonyl chloride (0.370 mL, 4.76 mmol) were added thereto, and the mixture was stirred at the same temperature as above for 1 hour. Ice water was added to the reaction solution, followed by extraction with dichloromethane. The organic layer was concentrated under reduced pressure to obtain the title compound as a yellow oil. The obtained residue was directly used in the next reaction without being purified.

¹H-NMR (500 MHz, DMSO-d₆) δ (ppm): 2.29 (3H, s), 2.93 (3H, s), 3.74 (6H, s), 5.18 (2H, s), 5.93-5.95 (1H, m), 5.99 (1H, d, J=3.4 Hz), 6.72 (2H, d, J=8.5 Hz), 7.50 (1H, t, J=8.5 Hz).

Step 2

4-(2,6-Dimethoxyphenyl)-3-(5-methylfuran-2-yl)-5-[(4H-1,2,4-triazol-3-ylsulfanyl)methyl]-4H-1,2,4-triazole

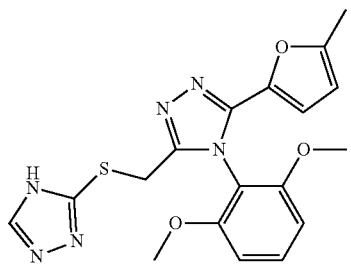 [SMILES: COc1cccc(OC)c1-n1c(CSc2nnc[nH]2)nnc1-c1ccc(C)o1]

The title compound (60.0 mg, 0.151 mmol, 49%) was obtained as a yellow solid from [4-(2,6-dimethoxyphenyl)-5-(5-methylfuran-2-yl)-4H-1,2,4-triazol-3-yl]methyl methanesulfonate (0.122 g, 0.310 mmol) and 4H-1,2,4-triazole-3-thiol (50.0 mg, 0.465 mmol) in the same way as in Example 2.

¹H-NMR (500 MHz, DMSO-d₆) δ (ppm): 2.29 (3H, s), 3.75 (6H, s), 4.14 (2H, s), 5.93-5.95 (1H, m), 5.98-6.00 (1H, m), 6.73 (2H, d, J=8.5 Hz), 7.52 (1H, t, J=8.5 Hz). MS (ESI): m/z 399 [M+H]⁺.

Example 69

4-(2,6-Dimethoxyphenyl)-3-(5-methylfuran-2-yl)-5-[(4H-1,2,4-triazol-3-ylsulfanyl)methyl]-4H-1,2,4-triazole

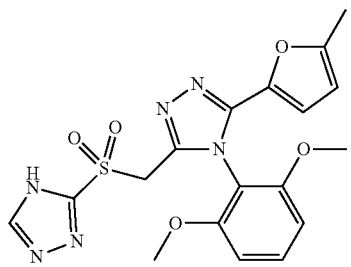 [SMILES: COc1cccc(OC)c1-n1c(CS(=O)(=O)c2nnc[nH]2)nnc1-c1ccc(C)o1]

4-(2,6-Dimethoxyphenyl)-3-(5-methylfuran-2-yl)-5-[(4H-1,2,4-triazol-3-ylsulfanyl)methyl]-4H-1,2,4-triazole (60.0 mg, 0.151 mmol) was dissolved in dichloromethane (10 mL). To the solution, 3-chloroperoxybenzoic acid (contains ca. 30% water) (82.0 mg, 0.301 mmol) was added at room temperature, and the mixture was stirred at room temperature for 12 hours. Dimethyl sulfoxide (0.10 mL) was added to the reaction solution, and then a saturated aqueous solution of sodium bicarbonate was added thereto, followed by extraction with dichloromethane. The organic layer was concentrated under reduced pressure, and the obtained residue was purified by silica gel column chromatography [elution solvent: ethyl acetate/methanol=100/0-75/25 (V/V))] to obtain the title compound (32.5 mg, 0.0743 mmol, 49%) as a yellow solid.

$^1$H-NMR (500 MHz, CDCl$_3$) δ (ppm): 2.29 (3H, s), 3.80 (6H, s), 4.78 (2H, s), 5.94-5.95 (1H, m), 5.99-6.01 (1H, m), 6.76 (2H, d, J=8.5 Hz), 7.55 (1H, t, J=8.5 Hz), 8.46 (1H, s). MS (ESI): m/z 431 [M+H]$^+$.

Example 70

1-[4-(2,6-Dimethoxyphenyl)-5-(5-methylfuran-2-yl)-4H-1,2,4-triazol-3-yl]methanamine

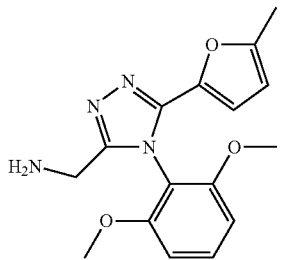 [SMILES: COc1cccc(OC)c1-n1c(CN)nnc1-c1ccc(C)o1]

To a solution of [4-(2,6-dimethoxyphenyl)-5-(5-methylfuran-2-yl)-4H-1,2,4-triazol-3-yl]methyl methanesulfonate (350 mg, 0.890 mmol) in acetone (0.30 mL), 28% aqueous ammonia solution (0.50 mL, 30 mmol) was added, and the mixture was stirred at room temperature for 12 hours. Water was added to the reaction solution, followed by extraction with ethyl acetate. Then, the organic layer was concentrated under reduced pressure. The obtained residue was purified by NH silica gel column chromatography [elution solvent: ethyl acetate/methanol=100/0-50/50 (V/V))] to obtain the title compound (150 mg, 0.477 mmol, 54%) as a light brown oil.

$^1$H-NMR (500 MHz, CDCl$_3$) δ (ppm): 2.27 (3H, s), 3.69 (2H, s), 3.73 (6H, s), 5.82-5.85 (1H, m), 5.88-5.89 (1H, m), 6.71 (2H, d, J=8.5 Hz), 7.47 (1H, t, J=8.5 Hz). MS (ESI): m/z 315 [M+H]$^+$.

Example 71

N-{[4-(2,6-Dimethoxyphenyl)-5-(5-methylfuran-2-yl)-4H-1,2,4-triazol-3-yl]methyl}methanesulfonamide

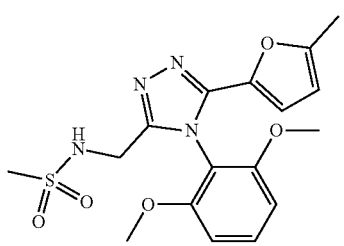

To a solution of 1-[4-(2,6-dimethoxyphenyl)-5-(5-methylfuran-2-yl)-4H-1,2,4-triazol-3-yl]methanamine (23.0 mg, 0.0732 mmol) in dichloromethane (5.0 mL), N,N-diisopropylethylamine (0.050 mL, 0.220 mmol) and methanesulfonyl chloride (0.020 mL, 0.220 mmol) were added at room temperature, and the mixture was stirred for 2 hours. The reaction solution was purified by silica gel column chromatography [elution solvent: ethyl acetate/methanol=100/0-80/20 (V/V))] to obtain the title compound (18.3 mg, 0.0466 mmol, 64%) as a pale yellow solid.

$^1$H-NMR (500 MHz, DMSO-d$_6$) δ (ppm): 2.25 (3H, s), 2.81 (3H, s), 3.72 (6H, s), 4.02 (2H, d, J=6.3 Hz), 5.85-5.88 (1H, m), 6.11-6.13 (1H, m), 6.91 (2H, d, J=8.5 Hz), 7.57 (1H, t, J=8.5 Hz), 7.61 (1H, t, J=6.3 Hz). MS (ESI): m/z 393 [M+H]$^+$.

Example 72

N-{[4-(2,6-Dimethoxyphenyl)-5-(5-methylfuran-2-yl)-4H-1,2,4-triazol-3-yl]methyl}-4-methyl-N-(4-methylbenzoyl)benzamide

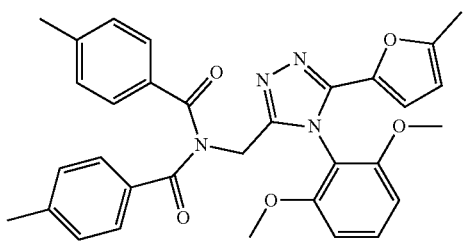

The title compound (18.0 mg, 0.0416 mmol, 40%) was obtained as a pale yellow solid using 1-[4-(2,6-dimethoxyphenyl)-5-(5-methylfuran-2-yl)-4H-1,2,4-triazol-3-yl]methanamine (26.0 mg, 0.0827 mmol) and p-toluoyl chloride (0.022 mL, 0.165 mmol) in the same way as in Example 71.

$^1$H-NMR (500 MHz, CDCl$_3$) δ (ppm): 2.23 (3H, s), 2.24 (3H, s), 3.70 (6H, s), 5.02 (2H, s), 5.87-5.90 (1H, m), 5.99-6.01 (1H, m), 6.67 (2H, d, J=8.5 Hz), 6.97 (2H, d, J=7.8 Hz), 7.44 (1H, t, J=8.5 Hz), 7.52 (2H, d, J=7.8 Hz). MS (ESI): m/z 433 [M+H]$^+$.

Example 73

[4-(2,6-Dimethoxyphenyl)-5-(5-methylfuran-2-yl)-4H-1,2,4-triazol-3-yl]acetonitrile

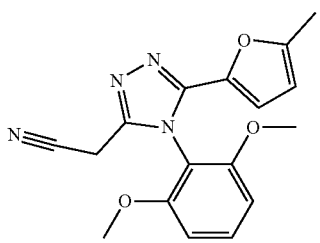 [SMILES: COc1cccc(OC)c1-n1c(CC#N)nnc1-c1ccc(C)o1]

To a solution of [4-(2,6-dimethoxyphenyl)-5-(5-methylfuran-2-yl)-4H-1,2,4-triazol-3-yl]methyl methanesulfonate (304 mg, 0.763 mmol) in dimethyl sulfoxide (5.5 mL), sodium cyanide (233 mg, 3.81 mmol) was added, and the mixture was stirred at 90° C. for 3 hours. Water was added to the reaction solution, followed by extraction with ethyl acetate. Then, the organic layer was concentrated under reduced pressure. The obtained residue was purified by silica gel column chromatography [elution solvent: n-hexane/ethyl acetate=30/70-0/100 (V/V))] to obtain the title compound (22 mg, 0.068 mmol, 8.9%) as a light brown oil.

$^1$H-NMR (500 MHz, CDCl$_3$) δ (ppm): 2.31 (3H, s), 3.78 (2H, s), 3.79 (6H, s), 5.94-5.96 (1H, m), 5.99 (1H, d, J=3.4 Hz), 6.76 (2H, d, J=8.5 Hz), 7.55 (1H, t, J=8.5 Hz). MS (ESI): m/z 325 [M+H]$^+$.

Example 74

5-({[4-(2,6-Dimethoxyphenyl)-5-(5-methylfuran-2-yl)-4H-1,2,4-triazol-3-yl]sulfanyl}methyl)-1H-tetrazole Step 1

5-({[4-(2,6-Dimethoxyphenyl)-5-(5-methylfuran-2-yl)-4H-1,2,4-triazol-3-yl]sulfanyl}methyl)-2-trityl-2H-tetrazole

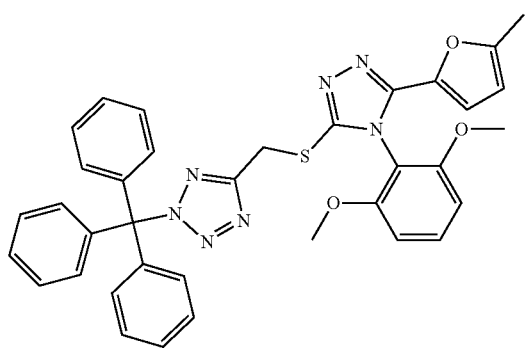 [SMILES: COc1cccc(OC)c1-n1c(SCc2nnn(C(c3ccccc3)(c3ccccc3)c3ccccc3)n2)nnc1-c1ccc(C)o1]

To a solution of 4-(2,6-dimethoxyphenyl)-5-(5-methyl-2-furyl)-1,2,4-triazole-3-thiol (172 mg, 0.473 mmol) in acetone (10.0 mL), 5-(chloromethyl)-2-trityl-2H-tetrazole (reference: U.S. Pat. No. 6,046,227; 376 mg, 0.945 mmol) and a fine potassium carbonate powder (230 mg, 1.42 mmol) were added, and the mixture was stirred at 60° C. for 1 hour. 3-Pentanone (5.0 mL) was further added to the reaction solution, and the mixture was stirred at 100° C. for 1 hour. Then, the solvent was distilled off under reduced pressure. The obtained residue was purified by silica gel column chromatography [elution solvent: n-hexane/ethyl acetate=50/50-0/100 (V/V)] to obtain the title compound (360 mg, 0.560 mmol, quantitative) as a colorless oil.

$^1$H-NMR (500 MHz, CDCl$_3$) δ (ppm): 2.28 (3H, s), 3.61 (6H, s), 4.60 (2H, s), 5.89-5.91 (1H, m), 5.93 (1H, d, J=3.4 Hz), 6.63 (2H, d, J=8.5 Hz), 7.04-7.06 (6H, m), 7.30-7.33 (9H, m), 7.42 (1H, t, J=8.5 Hz).

Step 2

5-({[4-(2,6-Dimethoxyphenyl)-5-(5-methylfuran-2-yl)-4H-1,2,4-triazol-3-yl]sulfanyl}methyl)-1H-tetrazole

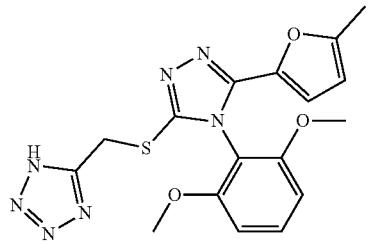 [SMILES: COc1cccc(OC)c1-n1c(SCc2nnn[nH]2)nnc1-c1ccc(C)o1]

5-({[4-(2,6-Dimethoxyphenyl)-5-(5-methylfuran-2-yl)-4H-1,2,4-triazol-3-yl]sulfanyl}methyl)-2-trityl-2H-tetrazole (120 mg, 0.189 mmol) was dissolved in dichloromethane (5.0 mL) and methanol (5.0 mL). To the solution, a 10% palladium carbon catalyst (M) wet (100 mg) was added, and the mixture was stirred at room temperature for 2 hours under the hydrogen atmosphere. Trifluoroacetic acid (2.0 mL, 26.14 mmol) was added to the reaction solution, and the mixture was stirred at room temperature for 30 minutes. Insoluble matter was filtered off through celite, and the filtrate was concentrated under reduced pressure. The obtained residue was purified by silica gel column chromatography [elution solvent: ethyl acetate/methanol=100/0-75/25 (V/V)] to obtain the title compound (67.0 mg, 0.168 mmol, 90%) as a colorless oil.

$^1$H-NMR (500 MHz, CDCl$_3$) δ (ppm): 2.30 (3H, s), 3.72 (6H, s), 4.56 (2H, s), 5.94-5.96 (1H, m), 6.02 (1H, d, J=3.4 Hz), 6.70 (2H, d, J=8.5 Hz), 7.50 (1H, t, J=8.5 Hz). MS (ESI): m/z 400 [M+H]$^+$.

Example 75

3-({[4-(2,6-Dimethoxyphenyl)-5-(5-methylfuran-2-yl)-4H-1,2,4-triazol-3-yl]sulfanyl}methyl)pyridazine

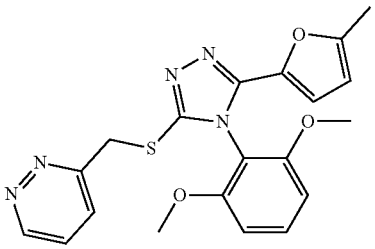 [SMILES: COc1cccc(OC)c1-n1c(SCc2cccnn2)nnc1-c1ccc(C)o1]

The title compound (123 mg, 0.300 mmol, 95%) was obtained as a light brown solid using 4-(2,6-dimethoxyphenyl)-5-(5-methylfuran-2-yl)-4H-1,2,4-triazole-3-thiol (100 mg, 0.315 mmol) and 3-(chloromethyl)pyridazine hydrochloride (110 mg, 0.630 mmol) in the same way as in Example 2.

$^1$H-NMR (500 MHz, CDCl$_3$) δ (ppm): 2.28 (3H, s), 3.66 (6H, s), 4.70 (2H, s), 5.88-5.92 (2H, m), 6.65 (2H, d, J=8.5 Hz), 7.40 (1H, dd, J=8.3, 4.9 Hz), 7.44 (1H, t, J=8.5 Hz), 7.88 (1H, dd, J=8.3, 1.5 Hz), 9.06 (1H, dd, J=4.9, 1.5 Hz). MS (ESI): m/z 410 [M+H]$^+$.

Example 76

4-(2,6-Dimethoxyphenyl)-3-(5-methylfuran-2-yl)-5-[(1,3-thiazol-2-ylmethyl)sulfanyl]-4H-1,2,4-triazole

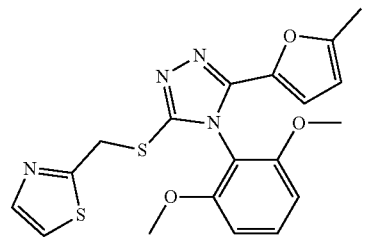 [SMILES: COc1cccc(OC)c1-n1c(SCc2nccs2)nnc1-c1ccc(C)o1]

The title compound (240 mg, 0.579 mmol, 61%) was obtained as a yellow solid using 4-(2,6-dimethoxyphenyl)-5-(5-methylfuran-2-yl)-4H-1,2,4-triazole-3-thiol (300 mg, 0.945 mmol) and 1,3-thiazol-2-ylmethyl methanesulfonate (reference: WO2007/34277; 376 mg, 0.945 mmol) in the same way as in Example 2.

$^1$H-NMR (500 MHz, CDCl$_3$) δ (ppm): 2.29 (3H, s), 3.69 (6H, s), 4.78 (2H, s), 5.90-5.91 (1H, m), 5.94 (1H, d, J=2.9 Hz), 6.66 (2H, d, J=8.5 Hz), 7.24 (1H, d, J=3.4 Hz), 7.45 (1H, t, J=8.5 Hz), 7.68 (1H, d, J=3.4 Hz). MS (ESI): m/z 415 [M+H]$^+$.

Example 77

Methyl 2-({[4-(2,6-dimethoxyphenyl)-5-(5-methyl-furan-2-yl)-4H-1,2,4-triazol-3-yl]sulfanyl}methyl)benzoate

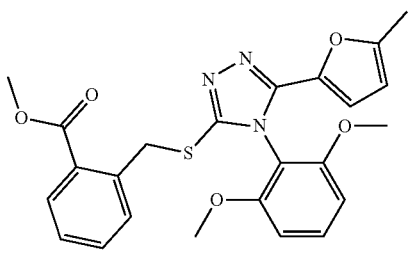

The title compound (87.0 mg, 0.187 mmol, 40%) was obtained as a white solid using 4-(2,6-dimethoxyphenyl)-5-(5-methyl-2-furyl)-1,2,4-triazole-3-thiol (150 mg, 0.473 mmol) and methyl 2-bromomethylbenzoate (220 mg, 0.945 mmol) in the same way as in Example 2.

$^1$H-NMR (500 MHz, CDCl$_3$) δ (ppm): 2.27 (3H, s), 3.60 (6H, s), 3.84 (3H, s), 4.78 (2H, s), 5.86-5.88 (2H, m), 6.61 (2H, d, J=8.5 Hz), 7.29 (1H, td, J=7.6, 1.3 Hz), 7.40 (1H, t, J=8.5 Hz), 7.41 (1H, td, J=7.6, 1.3 Hz), 7.61 (1H, dd, J=7.6, 1.3 Hz), 7.91 (1H, dd, J=7.6, 1.3 Hz). MS (ESI): m/z 466 [M+H]$^+$.

Example 78

2-({[4-(2,6-Dimethoxyphenyl)-5-(5-methylfuran-2-yl)-4H-1,2,4-triazol-3-yl]sulfanyl}methyl)benzoic acid

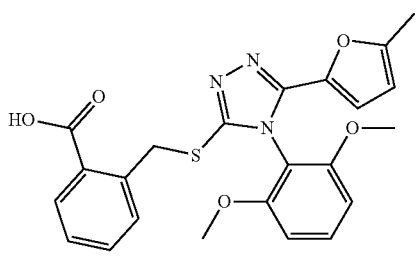 [SMILES: COc1cccc(OC)c1-n1c(SCc2ccccc2C(=O)O)nnc1-c1ccc(C)o1]

The title compound (65.0 mg, 0.144 mmol, 77%) was obtained as a white solid using methyl 2-({[4-(2,6-dimethoxyphenyl)-5-(5-methylfuran-2-yl)-4H-1,2,4-triazol-3-yl]sulfanyl}methyl)benzoate (87.0 mg, 0.187 mmol) in the same way as in Example 5.

$^1$H-NMR (500 MHz, CDCl$_3$) δ (ppm): 2.24 (3H, s), 3.70 (6H, s), 4.48 (2H, s), 5.85-5.86 (2H, m), 6.69 (2H, d, J=8.5 Hz), 7.28-7.31 (1H, m), 7.33-7.37 (1H, m), 7.47-7.52 (2H, m), 7.64-7.67 (1H, m) MS (ESI): m/z 452 [M+H]$^+$.

Example 79

Methyl 3-({[4-(2,6-dimethoxyphenyl)-5-(5-methyl-furan-2-yl)-4H-1,2,4-triazol-3-yl]sulfanyl}methyl)benzoate

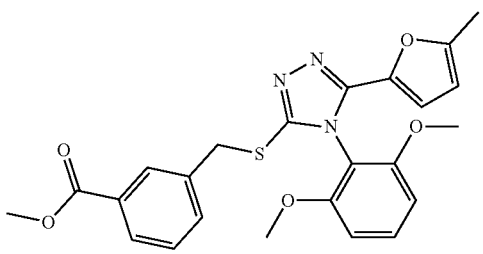

The title compound (134 mg, 0.288 mmol, 61%) was obtained as a white solid using 4-(2,6-dimethoxyphenyl)-5-(5-methyl-2-furyl)-1,2,4-triazole-3-thiol (165 mg, 0.473 mmol) and methyl 2-bromomethylbenzoate (220 mg, 0.945 mmol) in the same way as in Example 2.

$^1$H-NMR (500 MHz, CDCl$_3$) δ (ppm): 2.27 (3H, s), 3.66 (6H, s), 3.89 (3H, s), 4.42 (2H, s), 5.87-5.92 (2H, m), 6.65 (2H, d, J=8.3 Hz), 7.33 (1H, t, J=7.8 Hz), 7.43 (1H, t, J=8.3 Hz), 7.56 (1H, dd, J=7.8, 1.7 Hz), 7.90 (1H, dd, J=7.8, 1.7 Hz), 7.95 (1H, t, J=1.7 Hz). MS (ESI): m/z 466 [M+H]$^+$.

Example 80

3-({[4-(2,6-Dimethoxyphenyl)-5-(5-methylfuran-2-yl)-4H-1,2,4-triazol-3-yl]sulfanyl}methyl)benzoic acid

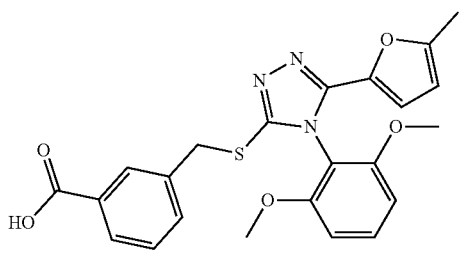 [SMILES: COc1cccc(OC)c1-n1c(SCc2cccc(C(=O)O)c2)nnc1-c1ccc(C)o1]

The title compound (100 mg, 0.222 mmol, 77%) was obtained as a white solid using methyl 3-({[4-(2,6-dimethoxyphenyl)-5-(5-methylfuran-2-yl)-4H-1,2,4-triazol-3-yl]sulfanyl}methyl)benzoate (134 mg, 0.288 mmol) in the same way as in Example 5.

$^1$H-NMR (500 MHz, CDCl$_3$) δ (ppm): 2.28 (3H, s), 3.69 (6H, s), 4.45 (2H, s), 5.90-5.91 (1H, m), 5.96 (1H, d, J=3.4 Hz), 6.67 (2H, d, J=8.5 Hz), 7.38 (1H, t, J=7.8 Hz), 7.46 (1H, t, J=8.5 Hz), 7.61 (1H, d, J=7.8 Hz), 7.98 (1H, d, J=7.8 Hz), 8.05 (1H, s). MS (ESI): m/z 452 [M+H]$^+$.

Example 81

Methyl 4-({[4-(2,6-dimethoxyphenyl)-5-(5-methylfuran-2-yl)-4H-1,2,4-triazol-3-yl]sulfanyl}methyl)benzoate

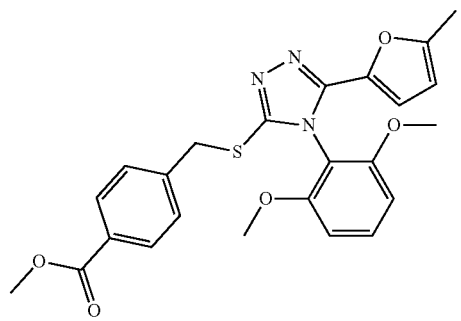

The title compound (115 mg, 0.247 mmol, 52%) was obtained as a white solid using 4-(2,6-dimethoxyphenyl)-5-(5-methyl-2-furyl)-1,2,4-triazole-3-thiol (150 mg, 0.473 mmol) and methyl 2-bromomethylbenzoate (220 mg, 0.945 mmol) in the same way as in Example 2.

$^1$H-NMR (500 MHz, CDCl$_3$) δ (ppm): 2.27 (3H, s), 3.64 (6H, s), 3.89 (3H, s), 4.42 (2H, s), 5.87-5.90 (1H, m), 5.91 (1H, d, J=3.4 Hz), 6.64 (2H, d, J=8.5 Hz), 7.37 (2H, d, J=8.3 Hz), 7.43 (1H, t, J=8.5 Hz), 7.91 (2H, d, J=8.3 Hz). MS (ESI): m/z 466 [M+H]$^+$.

Example 82

4-({[4-(2,6-Dimethoxyphenyl)-5-(5-methylfuran-2-yl)-4H-1,2,4-triazol-3-yl]sulfanyl}methyl)benzoic acid

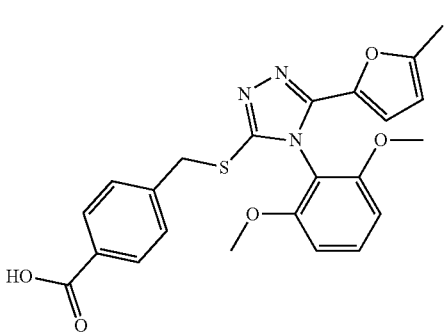 [SMILES: COc1cccc(OC)c1-n1c(SCc2ccc(C(=O)O)cc2)nnc1-c1ccc(C)o1]

The title compound (88.9 mg, 0.147 mmol, 80%) was obtained as a white solid using methyl 4-({[4-(2,6-dimethoxyphenyl)-5-(5-methylfuran-2-yl)-4H-1,2,4-triazol-3-yl]sulfanyl}methyl)benzoate (115 mg, 0.247 mmol) in the same way as in Example 5.

$^1$H-NMR (500 MHz, CDCl$_3$) δ (ppm): 2.27 (3H, s), 3.65 (6H, s), 4.43 (2H, s), 5.88-5.91 (1H, m), 5.92 (1H, d, J=3.4 Hz), 6.64 (2H, d, J=8.5 Hz), 7.40 (2H, d, J=8.3 Hz), 7.44 (1H, t, J=8.5 Hz), 7.97 (2H, d, J=8.3 Hz). MS (ESI): m/z 452 [M+H]$^+$.

Example 83

2-{[4-(2,6-Dimethoxyphenyl)-5-(5-methylfuran-2-yl)-4H-1,2,4-triazol-3-yl]sulfanyl}acetamide

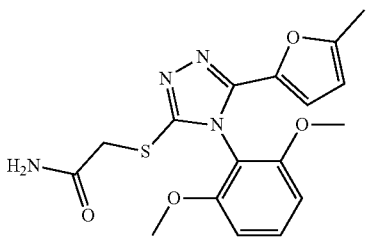 [SMILES: COc1cccc(OC)c1-n1c(SCC(N)=O)nnc1-c1ccc(C)o1]

The title compound (200 mg, 0.534 mmol, 57%) was obtained as a pale yellow solid using 4-(2,6-dimethoxyphenyl)-5-(5-methyl-2-furyl)-1,2,4-triazole-3-thiol (300 mg, 0.945 mmol) and 2-bromoacetamide (400 mg, 2.84 mmol) in the same way as in Example 2.

$^1$H-NMR (500 MHz, CDCl$_3$) δ (ppm): 2.28 (3H, s), 3.72 (2H, s), 3.74 (6H, s), 5.90-5.93 (1H, m), 5.96 (1H, d, J=3.4 Hz), 6.69 (2H, d, J=8.5 Hz), 7.48 (1H, t, J=8.5 Hz). MS (ESI): m/z 375 [M+H]$^+$.

Example 84

{[4-(2,6-Dimethoxyphenyl)-5-(5-methylfuran-2-yl)-4H-1,2,4-triazol-3-yl]sulfanyl}acetonitrile

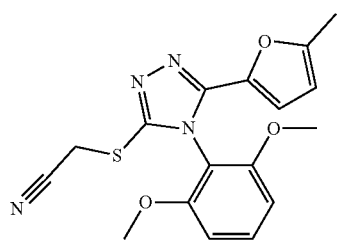 [SMILES: COc1cccc(OC)c1-n1c(SCC#N)nnc1-c1ccc(C)o1]

The title compound (250 mg, 0.701 mmol, 74%) was obtained as a pale yellow solid using 4-(2,6-dimethoxyphenyl)-5-(5-methyl-2-furyl)-1,2,4-triazole-3-thiol (300 mg, 0.945 mmol) and bromoacetonitrile (227 mg, 1.89 mmol) in the same way as in Example 2.

$^1$H-NMR (500 MHz, CDCl$_3$) δ (ppm): 2.28 (3H, s), 3.74 (6H, s), 3.96 (2H, s), 5.91-5.93 (1H, m), 5.99 (1H, d, J=3.4 Hz), 6.70 (2H, d, J=8.5 Hz), 7.49 (1H, t, J=8.5 Hz). MS (ESI): m/z 357 [M+H]$^+$.

Example 85

4-(2,6-Dimethoxyphenyl)-3-(5-methylfuran-2-yl)-5-(methylsulfanyl)-4H-1,2,4-triazole

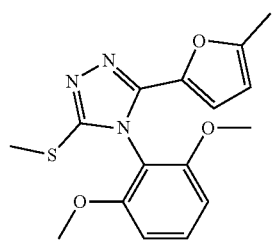

4-(2,6-Dimethoxyphenyl)-5-(5-methylfuran-2-yl)-4H-1,2,4-triazole-3-thiol (3.18 g, 10.0 mmol) was dissolved in tetrahydrofuran (100 mL). To the solution, a fine potassium carbonate powder (4.50 g, 30.1 mmol) and iodomethane (stabilized with copper chip) (0.60 ml, 15.0 mmol) were added, and the mixture was stirred at room temperature for 5 hours. Water was added to the reaction solution, followed by extraction with ethyl acetate. The organic layer was washed with saturated saline and then concentrated under reduced pressure, and the deposited solid was washed with n-hexane and diisopropyl ether. The obtained solid was dried under reduced pressure to obtain the partially purified title compound (2.50 g, 7.54 mmol, 75%) as a light brown solid.

$^1$H-NMR (500 MHz, CDCl$_3$) δ (ppm): 2.28 (3H, s), 2.64 (3H, s), 3.73 (6H, s), 5.87-5.91 (2H, m), 6.69 (2H, d, J=8.5 Hz), 7.46 (1H, t, J=8.5 Hz). MS (ESI): m/z 332 [M+H]$^+$.

Example 86

4-(2,6-Dimethoxyphenyl)-3-(5-methylfuran-2-yl)-5-(methylsulfonyl)-4H-1,2,4-triazole

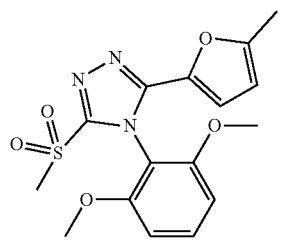 [SMILES: COc1cccc(OC)c1-n1c(-c2ccc(C)o2)nnc1S(C)(=O)=O]

The title compound (1.60 g, 4.4 mmol, 70%) was obtained as a yellow solid using 4-(2,6-dimethoxyphenyl)-3-(5-methylfuran-2-yl)-5-(methylsulfanyl)-4H-1,2,4-triazole (2.10 g, 6.30 mmol) in the same way as in Example 69.

$^1$H-NMR (500 MHz, CDCl$_3$) δ (ppm): 2.30 (3H, s), 3.33 (3H, s), 3.75 (6H, s), 5.95 (1H, d, J=3.4 Hz), 6.02 (1H, d, J=3.4 Hz), 6.70 (2H, d, J=8.5 Hz), 7.49 (1H, t, J=8.5 Hz). MS (ESI): m/z 364 [M+H]$^+$.

Example 87

3-(2,2-Dimethoxyethoxy)-4-(2,6-dimethoxyphenyl)-5-(5-methylfuran-2-yl)-4H-1,2,4-triazole

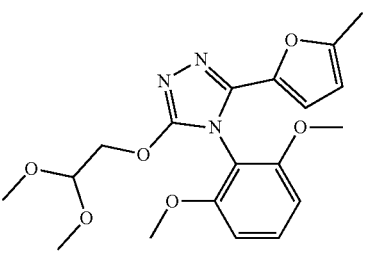

Glycolaldehyde dimethyl acetal (253 mg, 2.20 mmol) was dissolved in N,N-dimethylformamide (5.0 mL). To the solution, sodium hydride in oil (101 mg, 2.20 mmol) was added, and the mixture was stirred at room temperature for 10 minutes. 4-(2,6-Dimethoxyphenyl)-3-(5-methylfuran-2-yl)-5-(methylsulfonyl)-4H-1,2,4-triazole (393 mg, 1.10 mmol) was added to the reaction solution, and the mixture was stirred at 120° C. for 2 hours. A saturated aqueous solution of ammonium chloride was added to the reaction solution, followed by extraction with dichloromethane. The organic layer was concentrated under reduced pressure, and the obtained residue was purified by silica gel column chromatography [elution solvent: n-hexane/ethyl acetate=70/30-0/100 (V/V)] to obtain the title compound (244 mg, 0.627 mmol, 57%) as a yellow oil.

$^1$H-NMR (500 MHz, CDCl$_3$) δ (ppm): 2.27 (3H, s), 3.36 (6H, s), 3.72 (6H, s), 4.46 (1H, d, J=5.4 Hz), 4.74 (1H, t, J=5.4 Hz), 5.84-5.88 (2H, m), 6.65 (2H, d, J=8.5 Hz), 7.41 (1H, t, J=8.5 Hz). MS (ESI): m/z 390 [M+H]$^+$.

Example 88

{[4-(2,6-Dimethoxyphenyl)-5-(5-methylfuran-2-yl)-4H-1,2,4-triazol-3-yl]oxy}acetic acid

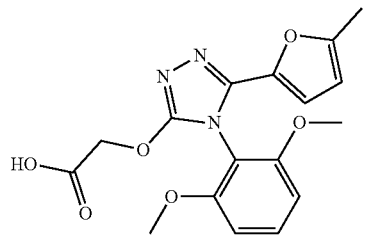 [SMILES: COc1cccc(OC)c1-n1c(OCC(=O)O)nnc1-c1ccc(C)o1]

3-(2,2-Dimethoxyethoxy)-4-(2,6-dimethoxyphenyl)-5-(5-methylfuran-2-yl)-4H-1,2,4-triazole (200 mg, 0.582 mmol) was dissolved in formic acid (10 ml), and the solution was stirred at 50° C. for 48 hours. Water was added to the reaction solution, followed by extraction with ethyl acetate and subsequently with dichloromethane/methanol. Then, the extracted organic layers were mixed and concentrated under reduced pressure. t-Butyl alcohol (5.0 mL), 2-methyl-2-butene (5.0 mL), and water (2.0 mL) were added to the obtained residue, sodium dihydrogen phosphate (212 mg, 1.75 mmol) and sodium chlorite (105 mg, 1.12 mmol) were added thereto at room temperature, and the mixture was stirred for 3 hours. Water was added to the reaction solution, followed by extraction with ethyl acetate. The aqueous layer was purified by ODS column chromatography [elution solvent: 0.1% formic acid water/0.1% formic acid acetonitrile=100/0-20/80 (V/V)] to obtain the title compound (6.5 mg, 0.0180 mmol, 3.1%) as a pale yellow solid.

$^1$H-NMR (500 MHz, CDCl$_3$) δ (ppm): 2.27 (3H, s), 3.74 (6H, s), 4.93 (2H, s), 5.88-5.97 (2H, m), 6.68 (2H, d, J=8.5 Hz), 7.44 (1H, t, J=8.5 Hz). MS (ESI): m/z 360 [M+H]$^+$.

Example 89

Methyl {[4-(2,6-dimethoxyphenyl)-5-(5-methyl-furan-2-yl)-4H-1,2,4-triazol-3-yl]sulfanyl}(pyridin-2-yl)acetate

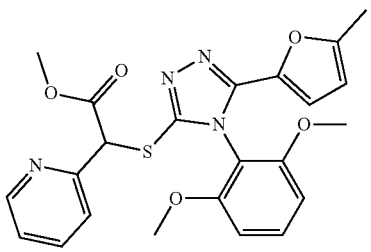 [SMILES: COC(=O)C(Sc1nnc(-c2ccc(C)o2)n1-c1c(OC)cccc1OC)c1ccccn1]

The title compound (diastereomeric mixture, 200 mg, 0.429 mmol, 45%) was obtained as a yellow solid using 4-(2,6-dimethoxyphenyl)-5-(5-methyl-2-furyl)-1,2,4-triazole-3-thiol (300 mg, 0.945 mmol) and methyl 2-bromo-2-(2-pyridyl)acetate (reference: WO2006/44602; 435 mg, 1.89 mmol) in the same way as in Example 2.

$^1$H-NMR (500 MHz, CDCl$_3$) δ (ppm): 2.29 (3H, s), 3.58 (3H, s), 3.77 (3H, s), 3.78 (3H, s), 5.90-5.93 (2H, m), 5.92 (1H, s), 6.61 (1H, d, J=8.5 Hz), 6.69 (1H, d, J=8.5 Hz), 7.20-7.22 (1H, m), 7.43 (1H, t, J=8.5 Hz), 7.57-7.60 (1H, m), 7.65-7.69 (1H, m), 8.53-8.56 (1H, m). MS (ESI): m/z 467 [M+H]$^+$.

Example 90

Methyl 1-{(2E)-3-[4-(2,6-dimethoxyphenyl)-5-(5-methylfuran-2-yl)-4H-1,2,4-triazol-3-yl]prop-2-enoyl}-L-prolinate

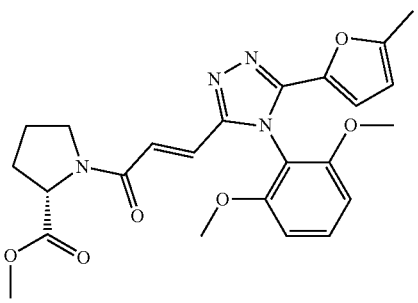 [SMILES: COC(=O)[C@@H]1CCCN1C(=O)/C=C/c1nnc(-c2ccc(C)o2)n1-c1c(OC)cccc1OC]

The title compound (197 mg, 0.421 mmol, 83%) was obtained as a yellow solid using (2E)-3-[4-(2,6-dimethoxyphenyl)-5-(5-methylfuran-2-yl)-4H-1,2,4-triazol-3-yl]prop-2-enoic acid (161 mg, 0.453 mmol), triethylamine (0.199 mL, 1.43 mmol), isobutyl chloroformate (84 µL, 0.6374 mmol), and methyl L-prolinate hydrochloride (127 mg, 0.765 mmol) in the same way as in Example 19.

$^1$H-NMR (400 MHz, CDCl$_3$) δ (ppm): 1.98-2.28 (4H, m), 2.30 (3H, s), 3.67-3.76 (1H, m), 3.68 (3H, s), 3.69 (3H, s), 3.72 (3H, s), 3.83-3.90 (1H, m), 4.52 (1H, dd, J=8.5, 4.3 Hz), 5.85-5.92 (2H, m), 6.65-6.69 (2H, m), 7.03 (1H, d, J=15.2 Hz), 7.42-7.49 (2H, m). MS (APCI): m/z 467 [M+H]$^+$.

Example 91

Methyl (4R)-1-{(2E)-3-[4-(2,6-dimethoxyphenyl)-5-(5-methylfuran-2-yl)-4H-1,2,4-triazol-3-yl]prop-2-enoyl}-4-hydroxy-L-prolinate

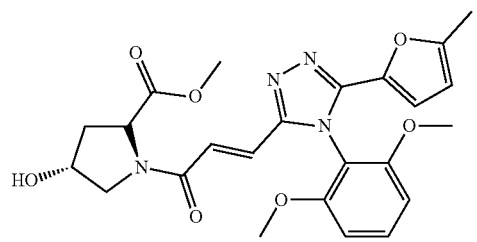

The title compound (197 mg, 0.409 mmol, 90%) was obtained as a white solid using (2E)-3-[4-(2,6-dimethoxyphenyl)-5-(5-methylfuran-2-yl)-4H-1,2,4-triazol-3-yl]prop-2-enoic acid (161 mg, 0.453 mmol), triethylamine (0.177 mL, 1.27 mmol), isobutyl chloroformate (0.074 mL, 0.566 mmol), and methyl (4R)-4-hydroxy-L-prolinate hydrochloride (123 mg, 0.680 mmol) in the same way as in Example 19.

$^1$H-NMR (400 MHz, CDCl$_3$) δ (ppm): 2.07-2.18 (1H, m), 2.29 (3H, s), 2.32-2.40 (1H, m), 3.67 (3H, s), 3.69 (3H, s), 3.73 (3H, s), 3.86-3.89 (1H, br m), 3.98 (2H, d, J=3.0 Hz), 4.65-4.67 (1H, m), 5.90-5.91 (2H, m), 6.66 (2H, dd, J=8.5, 3.0 Hz), 7.01 (1H, d, J=15.8 Hz), 7.42-7.52 (2H, m). MS (APCI): m/z 483 [M+H]$^+$.

Example 92

(4R)-1-{(2E)-3-[4-(2,6-Dimethoxyphenyl)-5-(5-methylfuran-2-yl)-4H-1,2,4-triazol-3-yl]prop-2-enoyl}-4-hydroxy-L-proline

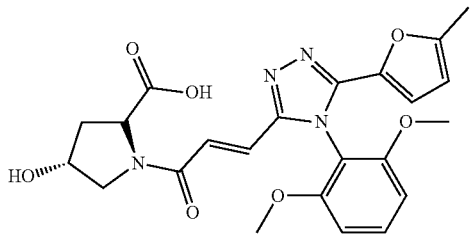

The title compound (56.2 mg, 0.120 mmol, 76%) was obtained as a white solid using methyl (4R)-1-{(2E)-3-[4-(2,6-dimethoxyphenyl)-5-(5-methylfuran-2-yl)-4H-1,2,4-triazol-3-yl]prop-2-enoyl}-4-hydroxy-L-prolinate (76.1 mg, 0.158 mmol) in the same way as in Example 5.

$^1$H-NMR (400 MHz, CD$_3$OD) δ (ppm): 2.04-2.12 (1H, m), 2.27 (3H, s), 2.28-2.44 (1H, m), 3.62-3.68 (1H, m), 3.76 (6H, s), 3.81 (1H, dd, J=10.6, 3.9 Hz), 4.36-4.69 (2H, m), 6.04-6.10 (2H, m), 6.89-7.29 (4H, m), 7.63 (1H, t, J=8.5 Hz). MS (APCI): m/z 469 [M+H]$^+$.

Example 93

1-{(2E)-3-[4-(2,6-Dimethoxyphenyl)-5-(5-methylfuran-2-yl)-4H-1,2,4-triazol-3-yl]prop-2-enoyl}-L-proline

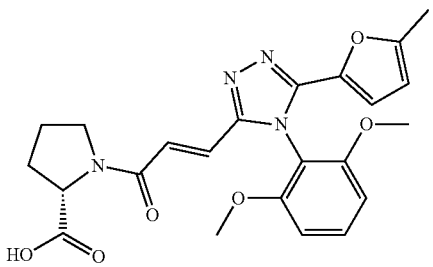 [SMILES: COc1cccc(OC)c1-n1c(/C=C/C(=O)N2CCC[C@H]2C(=O)O)nnc1-c1ccc(C)o1]

The title compound (57.3 mg, 0.127 mmol, 83%) was obtained as a yellow solid using 1-{(2E)-3-[4-(2,6-dimethoxyphenyl)-5-(5-methylfuran-2-yl)-4H-1,2,4-triazol-3-yl]prop-2-enoyl}-L-prolinate (71.0 mg, 0.152 mmol) in the same way as in Example 5.

$^1$H-NMR (400 MHz, CDCl$_3$) δ (ppm): 1.90-2.13 (3H, m), 2.27 and 2.30 (total 3H, each s), 2.41-2.56 (1H, m), 3.50-3.74 (1H, m), 3.67 and 3.69 (total 3H, each s), 3.70 and 3.71 (total 3H, each s), 3.74-3.83 (1H, m), 4.66-4.70 and 4.89-4.94 (total 1H, each m), 5.86-5.94 (2H, m), 6.64-6.74 (2H, m), 6.98 and 7.08 (total 1H, each d, J=15.2 Hz), 7.41-7.63 (2H, m). MS (APCI): m/z 453 [M+H]$^+$.

Example 94

3-({[4-(2,6-Dimethoxyphenyl)-5-(5-methylfuran-2-yl)-4H-1,2,4-triazol-3-yl]sulfanyl}methyl)-1,2,4-oxadiazol-5(2H)-one

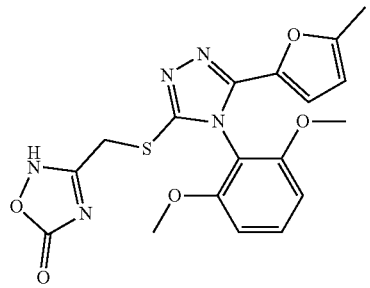 [SMILES: COc1cccc(OC)c1-n1c(SCc2nc(=O)o[nH]2)nnc1-c1ccc(C)o1]

{[4-(2,6-Dimethoxyphenyl)-5-(5-methylfuran-2-yl)-4H-1,2,4-triazol-3-yl]sulfanyl}acetonitrile (120 mg, 0.337 mmol) was dissolved in ethanol (5.4 ml). To the solution, 50% aqueous hydroxylamine solution (45 mg, 0.673 mmol) was added, and the mixture was stirred at 90° C. for 5 hours. Then, the solvent was distilled off under reduced pressure to obtain partially purified 2-{[4-(2,6-dimethoxyphenyl)-5-(5-methylfuran-2-yl)-4H-1,2,4-triazol-3-yl]sulfanyl}-N-hydroxyethanimidamide as a colorless amorphous form.

Then, obtained 2-{[4-(2,6-dimethoxyphenyl)-5-(5-methylfuran-2-yl)-4H-1,2,4-triazol-3-yl]sulfanyl}-N-hydroxyethanimidamide was dissolved in 1,4-dioxane (5.5 mL). To the solution, 1,1'-carbonyldiimidazole (65.2 mg, 0.403 mmol) and 1,8-diazabicyclo[5.4.0]-7-undecene (0.062 mL, 0.403 mmol) were added, and the mixture was stirred at 90° C. for 5 hours. Then, the solvent was concentrated under reduced pressure. The obtained residue was purified by silica gel column chromatography [elution solvent: ethyl acetate/methanol=100/0-67/33 (V/V)], and washed with 1 mol/L hydrochloric acid to obtain the title compound (123 mg, 0.296 mmol, 88%) as a white solid.

$^1$H-NMR (500 MHz, CDCl$_3$) δ (ppm): 2.25 (3H, s), 3.72 (6H, s), 4.02 (2H, s), 5.90-5.93 (1H, m), 5.99-6.02 (1H, m), 6.68 (2H, d, J=8.5 Hz), 7.47 (1H, t, J=8.5 Hz), 11.48 (1H, br s). MS (ESI): m/z 416 [M+H]$^+$.

Example 95

2-{[4-(2,6-Dimethoxyphenyl)-5-(5-methylfuran-2-yl)-4H-1,2,4-triazol-3-yl]sulfanyl}-N-(phenylsulfonyl)acetamide

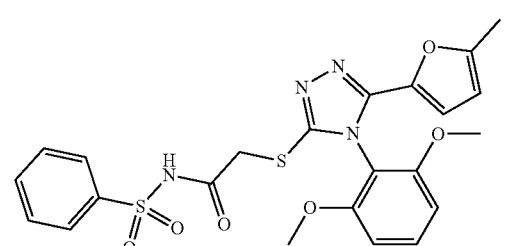

To a solution of {[4-(2,6-Dimethoxyphenyl)-5-(5-methylfuran-2-yl)-4H-1,2,4-triazol-3-yl]sulfanyl}acetic acid (38 mg, 0.101 mmol) in dichloromethane (10 mL), benzenesulfonamide (17 mg, 0.111 mmol), 4-dimethylaminopyridine (15 mg, 0.121 mmol) and 1-ethyl-3-(3-dimethylaminopropyl)carbodiimide hydrochloride were added at room temperature, and the mixture was stirred for 10 hours. Water was added to the reaction solution, followed by extraction with dichloromethane and ethyl acetate. The organic layer was concentrated under reduced pressure, and the obtained residue was purified by silica gel column chromatography [elution solvent: ethyl acetate/methanol=100/0-70/30 (V/V)] to obtain the title compound (21 mg, 0.041 mmol, 40%) as a pale yellow solid.

$^1$H-NMR (500 MHz, CDCl$_3$) δ (ppm): 2.28 (3H, s), 3.64 (2H, s), 3.66 (6H, s), 5.90-5.92 (1H, m), 5.99-6.01 (1H, m), 6.66 (2H, d, J=8.5 Hz), 7.21-7.32 (3H, m), 7.45 (1H, t, J=8.5 Hz), 7.89-7.96 (2H, m). MS (ESI): m/z 515 [M+H]$^+$.

Example 96

Dipropan-2-yl ({[4-(2,6-dimethoxyphenyl)-5-(5-methylfuran-2-yl)-4H-1,2,4-triazol-3-yl]sulfanyl}methyl)phosphonate

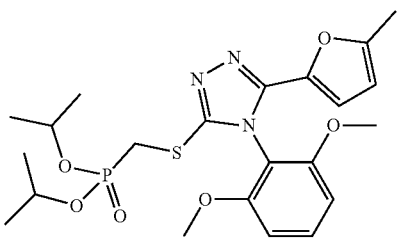 [SMILES: COc1cccc(OC)c1-n1c(SCP(=O)(OC(C)C)OC(C)C)nnc1-c1ccc(C)o1]

The title compound (230 mg, 0.464 mmol, 98%) was obtained as a pale yellow oil using 4-(2,6-dimethoxyphenyl)-5-(5-methyl-2-furyl)-1,2,4-triazole-3-thiol (150 mg, 0.473 mmol) and diisopropyl bromomethylphosphonate (245 mg, 0.945 mmol) in the same way as in Example 2.

$^1$H-NMR (500 MHz, CDCl$_3$) δ (ppm): 1.28 (6H, d, J=5.9 Hz), 1.31 (6H, d, J=5.9 Hz), 2.28 (3H, s), 3.60 (2H, d, J=14.6 Hz), 3.72 (6H, s), 4.67-4.76 (2H, m), 5.89-5.92 (2H, m), 6.68 (2H, d, J=8.5 Hz), 7.46 (1H, t, J=8.5 Hz). MS (ESI): m/z 496 [M+H]$^+$.

Example 97

Ethyl ({[4-(2,6-dimethoxyphenyl)-5-(5-methylfuran-2-yl)-4H-1,2,4-triazol-3-yl]methyl}amino)(oxo)acetate

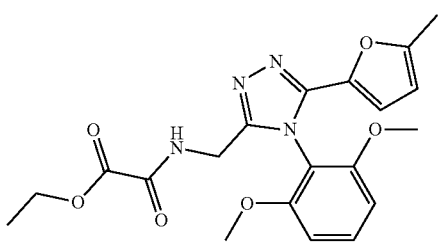 [SMILES: CCOC(=O)C(=O)NCc1nnc(-c2ccc(C)o2)n1-c1c(OC)cccc1OC]

To a solution of 1-[4-(2,6-Dimethoxyphenyl)-5-(5-methylfuran-2-yl)-4H-1,2,4-triazol-3-yl]methanamine (100 mg, 0.318 mmol) in tetrahydrofuran (10 mL), triethylamine (0.100 mL, 0.636 mmol) and ethyl chloroglyoxylate (0.053 mL, 0.477 mmol) were added at room temperature, and the mixture was stirred for 3 hours. Then, the solvent was concentrated under reduced pressure, and the obtained residue was purified by silica gel column chromatography [elution solvent: ethyl acetate/methanol=100/0-80/20 (V/V)] to obtain the title compound (46 mg, 0.111 mmol, 35%) as a yellow oil.

$^1$H-NMR (500 MHz, CDCl$_3$) δ (ppm): 1.37 (3H, t, J=7.1 Hz), 2.29 (3H, s), 3.73 (6H, s), 4.33 (2H, q, J=7.1 Hz), 4.48 (2H, d, J=5.4 Hz), 5.88-5.93 (2H, m), 6.68 (2H, d, J=8.5 Hz), 7.47 (1H, t, J=8.5 Hz), 7.63-7.70 (1H, m). MS (ESI): m/z 415 [M+H]$^+$.

Example 98

({[4-(2,6-Dimethoxyphenyl)-5-(5-methylfuran-2-yl)-4H-1,2,4-triazol-3-yl]methyl}amino)(oxo)acetic acid

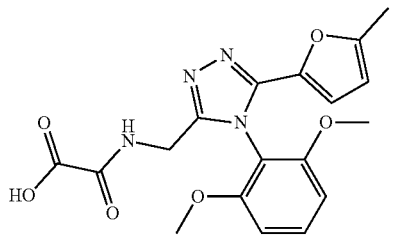 [SMILES: COc1cccc(OC)c1-n1c(CNC(=O)C(=O)O)nnc1-c1ccc(C)o1]

To a solution of Ethyl ({[4-(2,6-dimethoxyphenyl)-5-(5-methylfuran-2-yl)-4H-1,2,4-triazol-3-yl]methyl}amino)(oxo)acetate (40 mg, 0.0965 mmol) in ethanol (5.0 mL), 1 mol/L aqueous sodium hydroxide solution (1.0 mL) was added at room temperature, and the mixture was stirred for 4 hours. Then, 1 mol/L hydrochloric acid (1.0 mL) was added, and the resulting precipitate was removed by filtration. The solvent was concentrated under reduced pressure, and the obtained residue was purified by ODS column chromatography [elution solvent: 0.1% formic acid water/0.1% formic acid acetonitrile=100/0-30/70 (V/V)], and lyophilized to obtain the title compound (20 mg, 0.0518 mmol, 54%) as a white solid.

$^1$H-NMR (500 MHz, CDCl$_3$) δ (ppm): 2.28 (3H, s), 3.74 (6H, s), 4.52 (2H, s), 5.89-5.92 (2H, m), 6.69 (2H, d, J=8.3 Hz), 7.48 (1H, t, J=8.3 Hz), 7.76 (1H, br s). MS (ESI): m/z 469 [M+H]$^+$.

Example 99

N-{[4-(2,6-Dimethoxyphenyl)-5-(5-methylfuran-2-yl)-4H-1,2,4-triazol-3-yl]methyl}-4-methylbenzamide

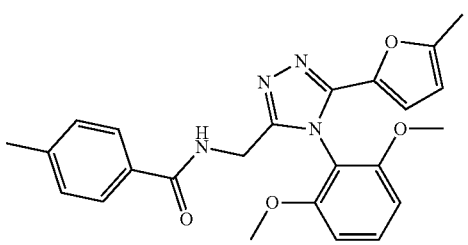

The title compound (78.0 mg, 0.180 mmol, 34%) was obtained as a white solid using 1-[4-(2,6-dimethoxyphenyl)-5-(5-methylfuran-2-yl)-4H-1,2,4-triazol-3-yl]methanamine (166 mg, 0.528 mmol) and p-toluoyl chloride (0.070 mL, 0.528 mmol) in the same way as in Example 71.

$^1$H-NMR (500 MHz, CDCl$_3$) δ (ppm): 2.30 (3H, s), 2.40 (3H, s), 3.67 (6H, s), 4.56 (2H, d, J=4.4 Hz), 5.88-5.92 (2H, m), 6.65 (2H, d, J=8.5 Hz), 6.91 (1H, br s), 7.23 (2H, d, J=8.3 Hz), 7.45 (1H, t, J=8.5 Hz), 7.65 (2H, d, J=8.3 Hz). MS (ESI): m/z 433 [M+H]$^+$.

Example 100

5-({[4-(2,6-Dimethoxyphenyl)-5-(5-methylfuran-2-yl)-4H-1,2,4-triazol-3-yl]sulfanyl}methyl)-2,4-dihydro-3H-1,2,4-triazol-3-one Step 1

Ethyl 2-(2-chloroethanimidoyl)hydrazinecarboxylate

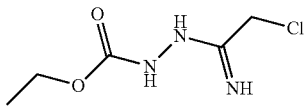

A solution of Chloroacetonitrile (1.26 mL, 19.9 mmol) in methanol (15 mL) was cooled to 0° C. To the solution, 1 mol/L sodium methoxide methanol solution (0.72 mL, 0.72 mmol) was added dropwise, and the mixture was stirred at room temperature for 30 minutes. To the reaction solution, acetic acid (0.034 mL) was added, and ethyl carbazate (2.00 g, 19.5 mmol) was added, and the mixture was stirred at room temperature for 1 hour. The reaction solution was concentrated under reduced pressure to obtain the partially purified title compound (3.58 g, 20 mmol, quantitative) as a pale yellow solid.

$^1$H-NMR (500 MHz, CDCl$_3$) δ (ppm): 1.34 (3H, t, J=7.1 Hz), 3.51 (2H, s), 4.29 (2H, q, J=7.1 Hz), 5.07 (2H, br s). MS (ESI): m/z 180 [M+H]$^+$.

Step 2

5-({[4-(2,6-Dimethoxyphenyl)-5-(5-methylfuran-2-yl)-4H-1,2,4-triazol-3-yl]sulfanyl}methyl)-2,4-dihydro-3H-1,2,4-triazol-3-one

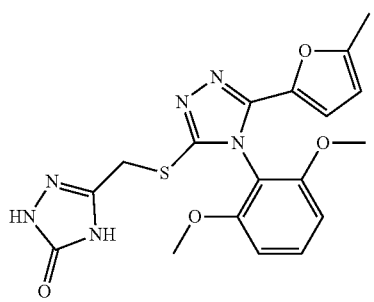 [SMILES: COc1cccc(OC)c1-n1c(SCc2n[nH]c(=O)[nH]2)nnc1-c1ccc(C)o1]

To a solution of 4-(2,6-dimethoxyphenyl)-5-(5-methyl-2-furyl)-1,2,4-triazole-3-thiol (200 mg, 0.630 mmol) in acetone (15 mL), potassium carbonate (400 mg, 1.89 mmol) and ethyl 2-(2-chloroethanimidoyl)hydrazinecarboxylate (220 mg, 1.26 mmol) were added, and the mixture was stirred at 60° C. for 5 hours. Then, the solvent was concentrated under reduced pressure, the obtained residue was added N,N-dimethylformamide (15 mL), and the mixture was stirred at 140° C. for 3 hours. Water was added to the reaction solution, followed by extraction with ethyl acetate. The organic layer was concentrated under reduced pressure, and the obtained residue was purified by silica gel column chromatography [elution solvent: n-hexane/ethyl acetate/methanol=50/50/0-0/100/0-0/80/20 (V/V/V)] and ODS column chromatography [elution solvent: 0.1% formic acid water/0.1% formic acid acetonitrile=100/0-30/70 (V/V)] to obtain the title compound (35 mg, 0.0845 mmol, 13%) as a white solid.

$^1$H-NMR (500 MHz, CDCl$_3$) δ (ppm): 2.34 (3H, s), 3.79 (6H, s), 5.40 (2H, s), 5.83-5.86 (1H, m), 5.93-5.96 (1H, m), 6.75 (2H, d, J=8.5 Hz), 7.53 (1H, d, J=8.5 Hz), 8.61 (1H, br s), 9.67 (1H, br s). MS (ESI): m/z 415 [M+H]$^+$.

Example 101

5-({[4-(2,6-Dimethoxyphenyl)-5-(5-methylfuran-2-yl)-4H-1,2,4-triazol-3-yl]sulfanyl}methyl)-1,3,4-oxadiazol-2(3H)-one Step 1

2-{[4-(2,6-Dimethoxyphenyl)-5-(5-methylfuran-2-yl)-4H-1,2,4-triazol-3-yl]sulfanyl}acetohydrazide

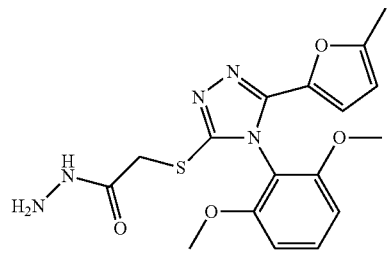 [SMILES: COc1cccc(OC)c1-n1c(SCC(=O)NN)nnc1-c1ccc(C)o1]

To a solution of Ethyl {[4-(2,6-dimethoxyphenyl)-5-(5-methylfuran-2-yl)-4H-1,2,4-triazol-3-yl]sulfanyl}acetate (250 mg, 0.620 mmol) in ethanol (5.0 mL), hydrazine monohydrate (150 mg, 3.10 mmol) was added, and the mixture was stirred at 70° C. for 5 hours. Then, the solvent was concentrated under reduced pressure, the obtained residue was purified by silica gel column chromatography [elution solvent: ethyl acetate/methanol=100/0-80/20 (V/V)] to obtain the title compound (288 mg, 0.740 mmol, quantitative) as a white solid.

$^1$H-NMR (500 MHz, CDCl$_3$) δ (ppm): 2.28 (3H, s), 3.75 (6H, s), 3.78 (2H, s), 3.91 (2H, br s), 5.91-5.93 (1H, m), 5.97 (1H, d, J=3.4 Hz), 6.70 (2H, d, J=8.5 Hz), 7.48 (1H, d, J=8.5 Hz), 9.16 (1H, br s). MS (ESI): m/z 390 [M+H]$^+$.

Step 2

5-({[4-(2,6-Dimethoxyphenyl)-5-(5-methylfuran-2-yl)-4H-1,2,4-triazol-3-yl]sulfanyl}methyl)-1,3,4-oxadiazol-2(3H)-one

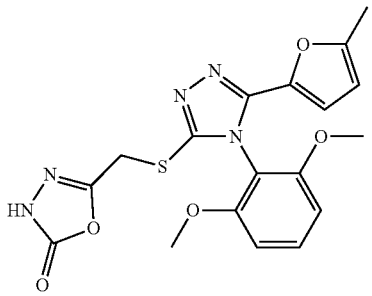 [SMILES: COc1cccc(OC)c1-n1c(SCc2n[nH]c(=O)o2)nnc1-c1ccc(C)o1]

To a solution of 2-{[4-(2,6-Dimethoxyphenyl)-5-(5-methylfuran-2-yl)-4H-1,2,4-triazol-3-yl]sulfanyl}acetohydrazide (230 mg, 0.591 mmol) in tetrahydrofuran (20 mL), 1,1-carbonyldiimidazole (145 mg, 0.886 mmol) was added at room temperature, and the mixture was stirred for 6 hours. Then, the solvent was concentrated under reduced pressure, the obtained residue was purified by silica gel column chromatography [elution solvent: n-hexane/ethyl acetate=30/70-0/100 (V/V)] to obtain the title compound (142 mg, 0.342 mmol, 58%) as a white solid.

$^1$H-NMR (500 MHz, CDCl$_3$) δ (ppm): 2.27 (3H, s), 3.74 (6H, s), 4.16 (2H, s), 5.89-5.93 (1H, m), 5.99 (1H, d, J=3.4 Hz), 6.71 (2H, d, J=8.5 Hz), 7.49 (1H, d, J=8.5 Hz). MS (ESI): m/z 416 [M+H]$^+$.

Example 102

({[4-(2,6-Dimethoxyphenyl)-5-(5-methylfuran-2-yl)-4H-1,2,4-triazol-3-yl]sulfanyl}methyl)phosphonic acid

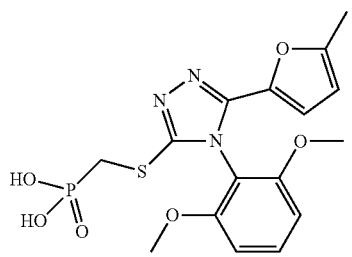 [SMILES: COc1cccc(OC)c1-n1c(SCP(=O)(O)O)nnc1-c1ccc(C)o1]

Dipropan-2-yl ({[4-(2,6-dimethoxyphenyl)-5-(5-methylfuran-2-yl)-4H-1,2,4-triazol-3-yl]sulfanyl}methyl)phosphonate (270 mg, 0.545 mmol) was dissolved in acetonitrile (15 mL). To the solution, bromotrimethylsilane (1.5 mL, 11 mmol) was added at room temperature, and the mixture was stirred for 12 hours. Then, the solvent was added a small amount of methanol, and concentrated under reduced pressure. The obtained residue was purified by ODS column chromatography [elution solvent: 0.1% formic acid water/0.1% formic acid acetonitrile=100/0-30/70 (V/V)], and lyophilized to obtain the title compound (80 mg, 0.194 mmol, 36%) as a white solid.

$^1$H-NMR (500 MHz, CDCl$_3$) δ (ppm): 2.26 (3H, s), 3.26 (2H, d, J=12.2 Hz), 3.73 (6H, s), 5.92-5.94 (1H, m), 6.01-6.04 (1H, m), 6.69 (2H, d, J=8.5 Hz), 7.49 (1H, t, J=8.5 Hz). MS (ESI): m/z 412 [M+H]$^+$.

Example 103

3-({[4-(2,6-Dimethoxyphenyl)-5-(5-methylfuran-2-yl)-4H-1,2,4-triazol-3-yl]sulfanyl}methyl)-1,2-oxazol-5(4H)-one

Step 1

Ethyl 4-{[4-(2,6-dimethoxyphenyl)-5-(5-methylfuran-2-yl)-4H-1,2,4-triazol-3-yl]sulfanyl}-3-oxobutanoate

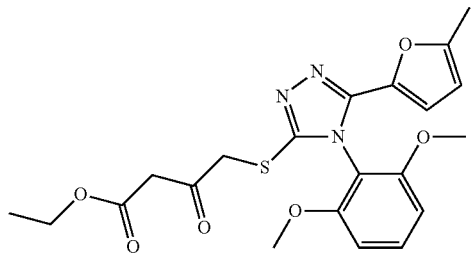 [SMILES: CCOC(=O)CC(=O)CSc1nnc(-c2ccc(C)o2)n1-c1c(OC)cccc1OC]

The title compound (398 mg, 0.893 mmol, 71%) was obtained as a pale yellow oil using 4-(2,6-dimethoxyphenyl)-5-(5-methyl-2-furyl)-1,2,4-triazole-3-thiol (400 mg, 1.26 mmol) and 4-chloroacetoacetic acid ethyl ester (0.240 mL, 1.89 mmol) in the same way as in Example 2.

$^1$H-NMR (500 MHz, CDCl$_3$) δ (ppm): 1.27 (3H, t, J=7.3 Hz), 2.27 (3H, s), 3.72 (2H, s), 3.73 (6H, s), 4.18 (2H, q, J=7.3 Hz), 4.19 (2H, s), 5.87-5.92 (1H, m), 5.94 (1H, d, J=3.4 Hz), 6.68 (2H, d, J=8.5 Hz), 7.47 (1H, t, J=8.5 Hz). MS (ESI): m/z 446 [M+H]$^+$.

Step 2

3-({[4-(2,6-Dimethoxyphenyl)-5-(5-methylfuran-2-yl)-4H-1,2,4-triazol-3-yl]sulfanyl}methyl)-1,2-oxazol-5(4H)-one

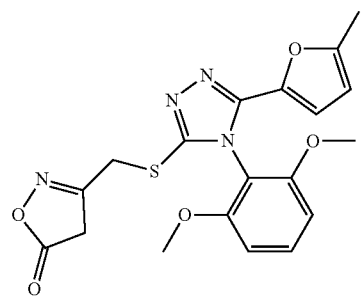 [SMILES: COc1cccc(OC)c1-n1c(SCC2=NOC(=O)C2)nnc1-c1ccc(C)o1]

To a solution of Ethyl 4-[[4-(2,6-dimethoxyphenyl)-5-(5-methyl-2-furyl)-1,2,4-triazol-3-yl]sulfanyl]-3-oxo-butanoate (105 mg, 0.236 mmol) in ethanol (3.0 mL), potassium carbonate (37 mg, 0.236 mmol) and hydroxylammonium chloride (25 mg, 0.260 mmol) were added, and the mixture was stirred at room temperature for 10 hours. Then, the solvent was concentrated under reduced pressure, the obtained residue was purified by silica gel column chromatography [elution solvent: ethyl acetate/methanol=100/0-80/20 (V/V)] and ODS column chromatography [elution solvent: 0.1% formic acid water/0.1% formic acid acetonitrile=100/0-30/70 (V/V)], and lyophilized to obtain the title compound (35 mg, 0.084 mmol, 36%) as a white solid.

$^1$H-NMR (500 MHz, CDCl$_3$) δ (ppm): 2.28 (3H, s), 3.51 (2H, s), 3.73 (6H, s), 4.15 (2H, s), 5.91-5.94 (1H, m), 5.96-5.99 (1H, m), 6.70 (2H, d, J=8.5 Hz), 7.49 (1H, t, J=8.5 Hz). MS (ESI): m/z 415 [M+H]$^+$.

Example 104

5-({[4-(2,6-Dimethoxyphenyl)-5-(5-methylfuran-2-yl)-4H-1,2,4-triazol-3-yl]sulfanyl}methyl)-1,2-dihydro-3H-pyrazol-3-one

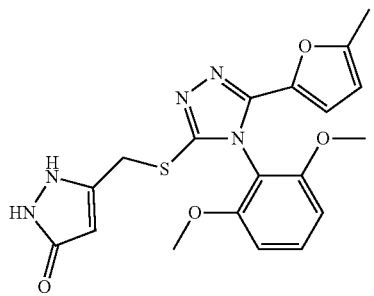 [SMILES: COc1cccc(OC)c1-n1c(SCc2cc(=O)[nH][nH]2)nnc1-c1ccc(C)o1]

To a solution of Ethyl 4-[[4-(2,6-dimethoxyphenyl)-5-(5-methyl-2-furyl)-1,2,4-triazol-3-yl]sulfanyl]-3-oxo-butanoate (146 mg, 0.328 mmol) in ethanol (3.0 mL), hydrazine monohydrate (0.020 mL, 0.393 mmol) was added, and the mixture was stirred at room temperature for 10 hours. Then, the solvent was concentrated under reduced pressure, the obtained residue was purified by silica gel column chromatography [elution solvent: ethyl acetate/methanol=100/0-80/20 (V/V)] to obtain the title compound (55 mg, 0.133 mmol, 41%) as a white solid.

$^1$H-NMR (500 MHz, DMSO-d$_6$) δ (ppm): 2.24 (3H, s), 3.69 (6H, s), 4.20 (2H, s), 5.32 (1H, s), 5.87-5.89 (1H, m), 6.09-6.12 (1H, m), 6.89 (2H, d, J=8.5 Hz), 7.56 (1H, t, J=8.5 Hz). MS (ESI): m/z 414 [M+H]$^+$.

Example 105

4-({[4-(2,6-Dimethoxyphenyl)-5-(5-methylfuran-2-yl)-4H-1,2,4-triazol-3-yl]sulfanyl}methyl)benzamide

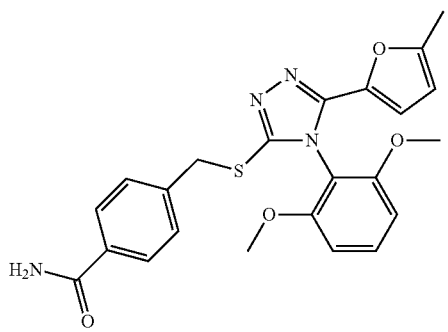 [SMILES: COc1cccc(OC)c1-n1c(SCc2ccc(C(N)=O)cc2)nnc1-c1ccc(C)o1]

To 4-({[4-(2,6-Dimethoxyphenyl)-5-(5-methylfuran-2-yl)-4H-1,2,4-triazol-3-yl]sulfanyl}methyl)benzoic acid (30 mg, 0.0664 mmol), 28% aqueous ammonia solution (0.20 mL, 0.133 mmol) and methanol (3.0 mL) were added, and 4-(4,6-dimethoxy-1,3,5-triazin-2-yl)-4-methylmorpholinium chloride (38 mg, 0.133 mmol) was added at room temperature, and the mixture was stirred for 12 hours. Further, 28% aqueous ammonia solution (0.20 mL, 0.133 mmol) and 4-(4,6-dimethoxy-1,3,5-triazin-2-yl)-4-methylmorpholinium chloride (38 mg, 0.133 mmol) were added, and the mixture was stirred at room temperature for 12 hours. Then, the solvent was concentrated under reduced pressure, the obtained residue was purified by NH silica gel column chromatography [elution solvent: ethyl acetate/methanol=100/0-80/20 (V/V)] to obtain the title compound (12 mg, 0.0266 mmol, 40%) as a pale yellow solid.

$^1$H-NMR (500 MHz, CDCl$_3$) δ (ppm): 2.28 (3H, s), 3.65 (6H, s), 4.41 (2H, s), 5.89-5.92 (2H, m), 6.66 (2H, d, J=8.5 Hz), 7.40 (2H, d, J=8.3 Hz), 7.45 (1H, t, J=8.5 Hz), 7.71 (2H, d, J=8.3 Hz). MS (ESI): m/z 451 [M+H]$^+$.

Example 106

3-({[4-(2,6-Dimethoxyphenyl)-5-(5-methylfuran-2-yl)-4H-1,2,4-triazol-3-yl]sulfanyl}methyl)benzamide

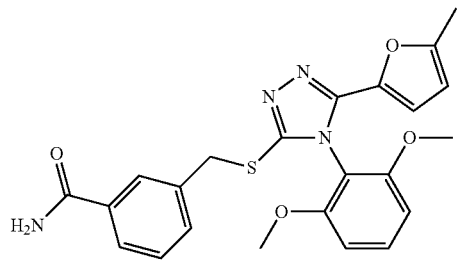 [SMILES: COc1cccc(OC)c1-n1c(SCc2cccc(C(N)=O)c2)nnc1-c1ccc(C)o1]

The title compound (25.0 mg, 0.055 mmol, 83%) was obtained as a pale yellow solid using 3-({[4-(2,6-dimethoxyphenyl)-5-(5-methylfuran-2-yl)-4H-1,2,4-triazol-3-yl]sulfanyl}methyl)benzoic acid (30 mg, 0.0664 mmol) in the same way as in Example 105.

$^1$H-NMR (500 MHz, CDCl$_3$) δ (ppm): 2.27 (3H, s), 3.64 (6H, s), 4.36 (2H, s), 5.87-5.90 (2H, m), 6.65 (2H, d, J=8.5 Hz), 7.34 (1H, t, J=7.8 Hz), 7.44 (1H, t, J=8.5 Hz), 7.47 (1H, d, J=7.8 Hz), 7.72 (1H, d, J=7.8 Hz), 7.75 (1H, s). MS (ESI): m/z 451 [M+H]$^+$.

Example 107

N-{[4-(2,6-Dimethoxyphenyl)-5-(5-methylfuran-2-yl)-4H-1,2,4-triazol-3-yl]methyl}-4-methylbenzenesulfonamide

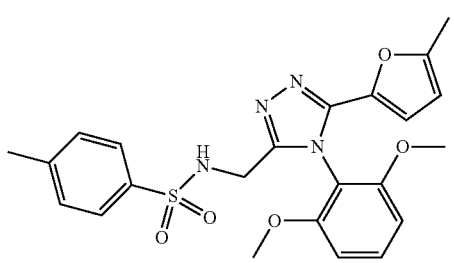

The title compound (14.0 mg, 0.0388 mmol, 36%) was obtained as a pale yellow solid using 1-[4-(2,6-dimethoxyphenyl)-5-(5-methylfuran-2-yl)-4H-1,2,4-triazol-3-yl]methanamine (26.0 mg, 0.083 mmol) and p-toluenesulfonyl chloride (31.0 mg, 0.165 mmol) in the same way as in Example 71.

$^1$H-NMR (500 MHz, CDCl$_3$) δ (ppm): 2.27 (3H, s), 2.41 (3H, s), 3.71 (6H, s), 4.06 (2H, d, J=5.4 Hz), 5.09 (1H, t, J=5.4 Hz), 5.86-5.88 (1H, m), 5.89-5.91 (1H, m), 6.61 (2H, d, J=8.5 Hz), 7.26 (2H, d, J=8.5 Hz), 7.50 (1H, t, J=8.5 Hz), 7.67 (2H, d, J=8.5 Hz). MS (ESI): m/z 469 [M+H]$^+$.

Test Example 1

Measurement of Apelin Receptor Agonist Activity

The apelin receptor agonist activity of the compound represented by formula (I) or (II) of the present invention was measured by cell-based assay for determining the amount of intracellular cAMP.

CHO cells (DiscoveRx Corp.) stably expressing the human apelin receptor were inoculated to wells of a microtiter plate and cultured overnight at 37° C. under conditions of 5% CO$_2$.

Each test compound and Forskolin were added to the wells at the same time. Specifically, the test compound dissolved in DMSO was diluted with a Forskolin-containing buffer [DMEM/F-12, HEPES, no phenol red (#11039, GIBCO)] to prepare a mixed solution containing the test compound at a final concentration of 0 to 10 M (common ratio: 3, serial dilution: 11), Forskolin at a final concentration of 10 µM, and DMSO at a final concentration of 0.3% v/v, which was then added to the wells (N=4).

After 30 minutes, the cells were lysed, and HitHunter cAMP XS+ Assay #90-0075L (DiscoveRx Corp.) was added to the cell lysate. The mixture was left overnight, and the resulting chemiluminescence signals were then detected using Analyst GT (Molecular Devices LLC.) to determine the amount of cAMP.

The amount of cAMP determined by the addition of a positive control [Pyr1]-apelin-13 (final concentration: 0.300 µM) and Forskolin (final concentration: 10 µM) at the same time was used as an index to define 100% efficacy. The amount of cAMP determined by the addition of Forskolin (final concentration: 10 µM) alone was used as an index to define 0% efficacy.

A dose response curve was prepared from the final concentration of the test compound and the determined amount of cAMP using Sigmaplot 12.0. The concentration at which the test compound exhibited 50% efficacy was calculated as an EC$_{50}$ value (µM).

The test results of the compound represented by formula (I) or (II) of the present invention are shown in Table 1.

TABLE 1

| Example No. | EC$_{50}$ value (µM) |
|---|---|
| 1 | 0.031 |
| 2 | 0.001 |
| 3 | 0.002 |
| 4 | 0.122 |
| 5 | 0.026 |
| 6 | 0.703 |
| 7 | 0.815 |
| 8 | 1.57 |
| 9 | 0.018 |
| 10 | 0.192 |
| 11 | 0.005 |
| 12 | 0.701 |

TABLE 1-continued

| Example No. | EC$_{50}$ value (µM) |
|---|---|
| 13 | 0.159 |
| 14 | 0.424 |
| 15 | 0.164 |
| 16 | 0.314 |
| 17 | 1.41 |
| 18 | 0.561 |
| 19 | 0.171 |
| 20 | 0.729 |
| 21 | 0.539 |
| 22 | 0.087 |
| 23 | 0.271 |
| 24 | 0.751 |
| 25 | 1.72 |
| 26 | 0.057 |
| 27 | 2.87 |
| 28 | 1.42 |
| 29 | 0.812 |
| 30 | 0.332 |
| 31 | 0.174 |
| 32 | 3.98 |
| 33 | 2.44 |
| 34 | 0.152 |
| 35 | 0.010 |
| 36 | 0.108 |
| 37 | 0.825 |
| 38 | 0.009 |
| 39 | 0.011 |
| 40 | 1.11 |
| 41 | 0.045 |
| 42 | 0.012 |
| 43 | 0.039 |
| 44 | 1.21 |
| 45 | 1.32 |
| 46 | 0.096 |
| 47 | 0.419 |
| 48 | 0.022 |
| 49 | 0.393 |
| 50 | 1.32 |
| 51 | 0.111 |
| 52 | 0.217 |
| 53 | 2.65 |
| 54 | 1.20 |
| 55 | 1.92 |
| 56 | 0.048 |
| 57 | 1.21 |
| 58 | 2.80 |
| 59 | 0.349 |
| 60 | 1.30 |
| 61 | 0.412 |
| 62 | 0.808 |
| 63 | 0.716 |
| 64 | 0.052 |
| 65 | 0.075 |
| 66 | 0.817 |
| 67 | 0.774 |
| 68 | 1.33 |
| 69 | 0.696 |
| 70 | 0.384 |
| 71 | 1.07 |
| 72 | 0.095 |
| 73 | 1.02 |
| 74 | 0.098 |
| 75 | 0.128 |
| 76 | 0.158 |
| 77 | 0.557 |
| 78 | 0.034 |
| 79 | 0.208 |
| 80 | 1.53 |
| 81 | 0.071 |
| 82 | 5.46 |
| 83 | 0.219 |
| 84 | 0.267 |
| 85 | 0.253 |
| 86 | 2.02 |
| 87 | 0.744 |
| 88 | 0.035 |
| 89 | 0.261 |
| 90 | 0.503 |

TABLE 1-continued

| Example No. | EC$_{50}$ value (μM) |
|---|---|
| 91 | 0.351 |
| 92 | 0.166 |
| 93 | 0.364 |
| 94 | 0.071 |
| 95 | 0.006 |
| 96 | 0.605 |
| 97 | 0.273 |
| 98 | 1.17 |
| 99 | 0.338 |
| 100 | 0.957 |
| 101 | 0.587 |
| 102 | 0.103 |
| 103 | 0.046 |
| 104 | 0.048 |
| 105 | 1.20 |
| 106 | 0.793 |
| 107 | 0.668 |

The present invention has demonstrated a novel azole derivative as an apelin receptor agonist, and a method for treating cardiovascular disease, diabetic disease, renal disease, hypertension, and arteriosclerosis, etc., using the same. The present invention is useful in the treatment of cardiovascular disease, diabetic disease, renal disease, hypertension, and arteriosclerosis, etc.

What is claimed is:

1. A compound represented by formula (I), or a pharmacologically acceptable salt thereof:

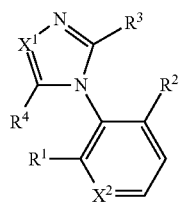

(I)

wherein $X^1$ represents —CH=, $X^2$ represents —CH=, $R^1$ and $R^2$ each independently represent a $C_1$ to $C_6$ alkyl group, a $C_1$ to $C_6$ alkoxy group, or a halogeno group (the $C_1$ to $C_6$ alkyl group and the $C_1$ to $C_6$ alkoxy group are each optionally substituted by 1 to 3 fluoro groups), $R^3$ is a furyl group, a thienyl group, a pyridyl group, a phenyl group, a n-butyl group, or a cyclopentyl group (the furyl group, the thienyl group, the pyridyl group, and the phenyl group are each optionally substituted by 1 or 2 identical or different groups selected from a methyl group and a halogeno group); and

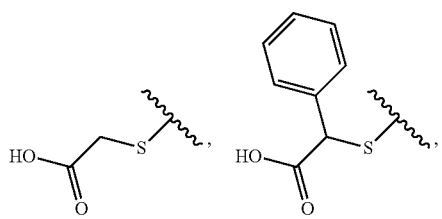

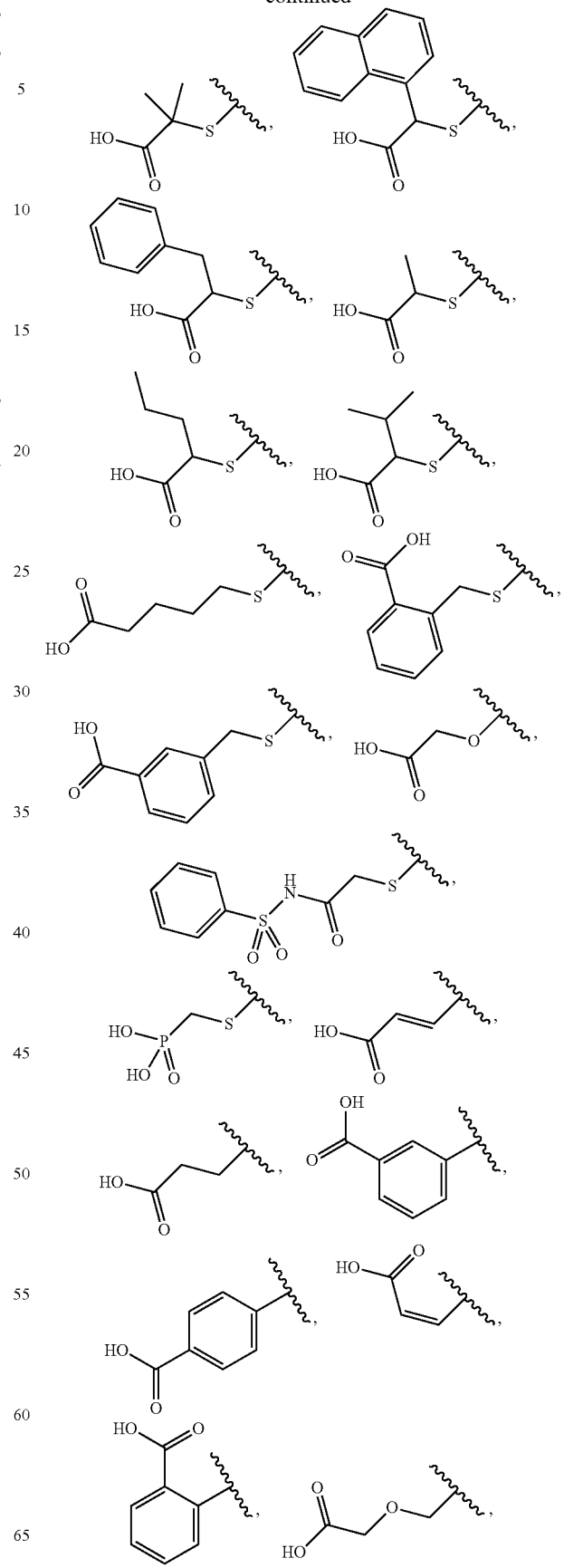

-continued

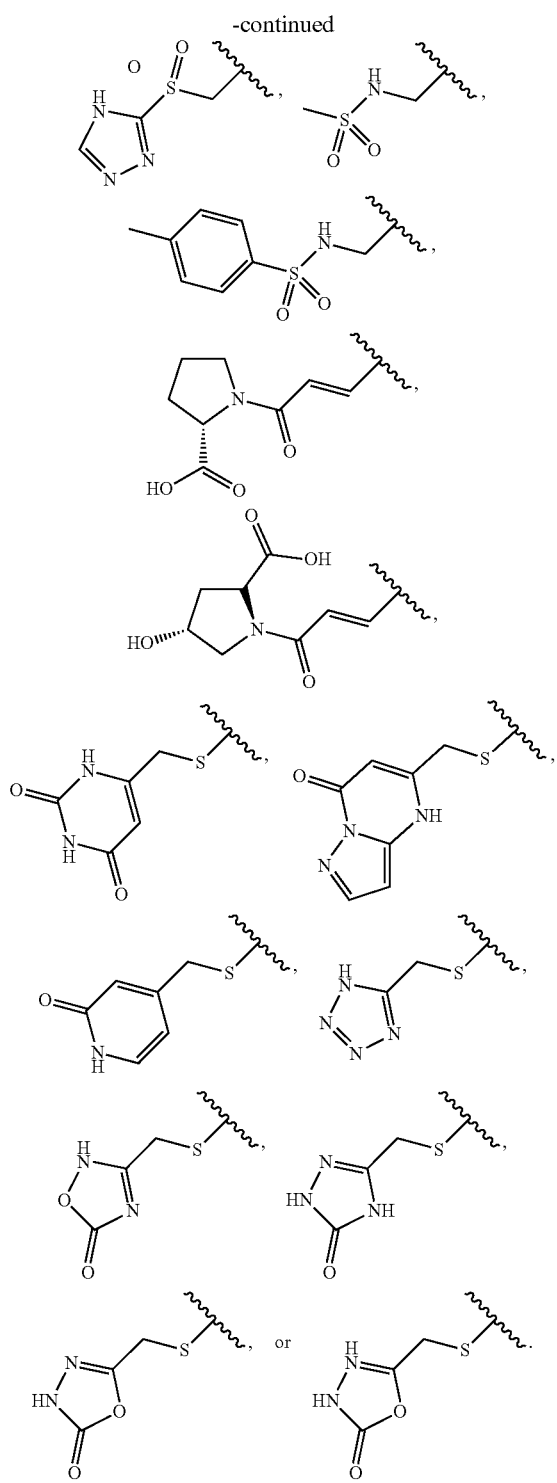

2. The compound according to claim 1, or a pharmacologically acceptable salt thereof, wherein $R^1$ and $R^2$ are each independently a $C_1$ to $C_6$ alkoxy group or a $C_1$ to $C_6$ alkyl group.

3. The compound according to claim 1, or a pharmacologically acceptable salt thereof, wherein $R^3$ is a furyl group or a thienyl group (the furyl group or the thienyl group are each optionally substituted by 1 or 2 identical or different groups selected from a methyl group and a halogeno group).

4. The compound according to claim 1, or a pharmacologically acceptable salt thereof, wherein $R^3$ is a 5-methyl-furan-2-yl group.

5. The compound according to claim 1, or a pharmacologically acceptable salt thereof, wherein $R^4$ is

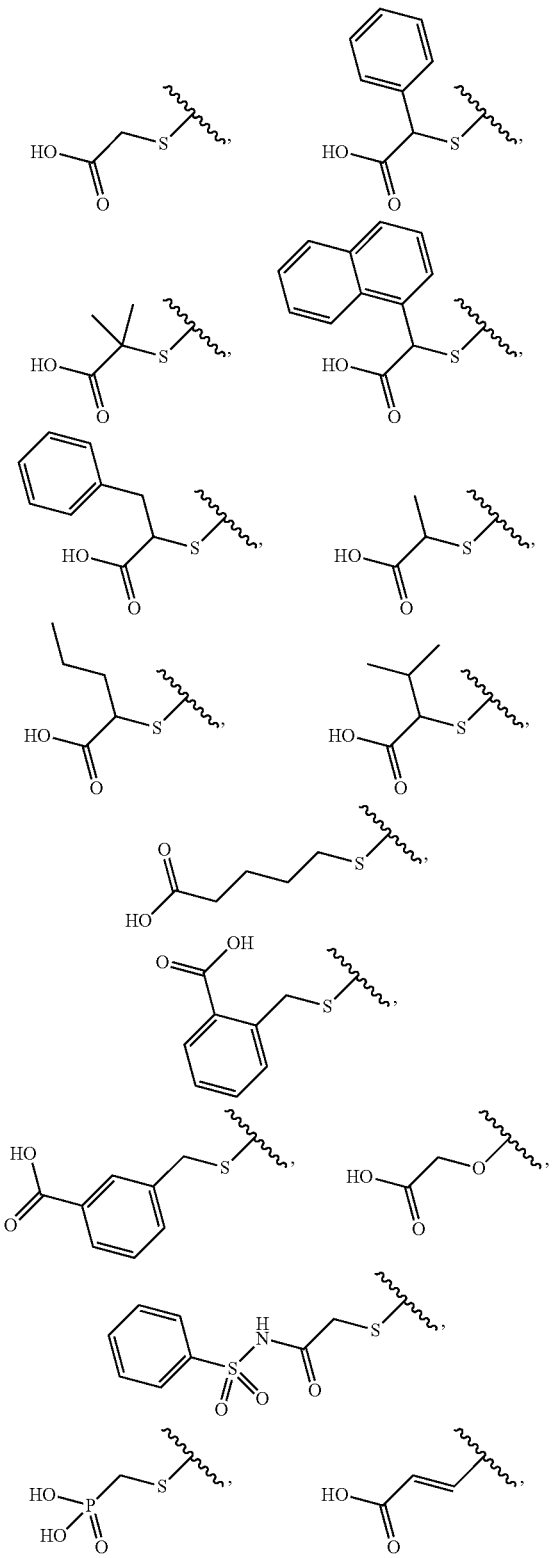

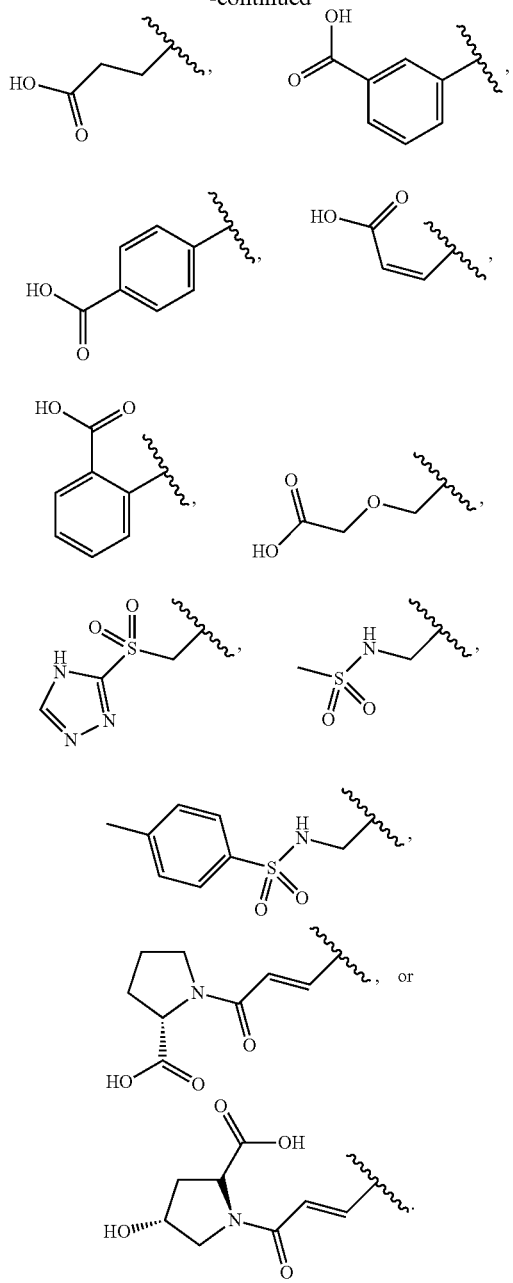
6. The compound according to claim 1, or a pharmacologically acceptable salt thereof, wherein R⁴ is
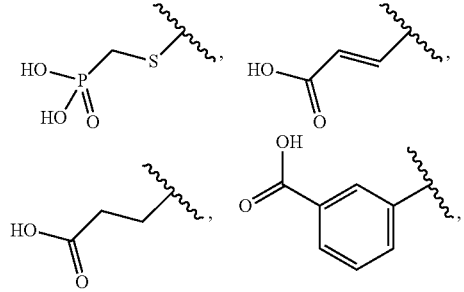
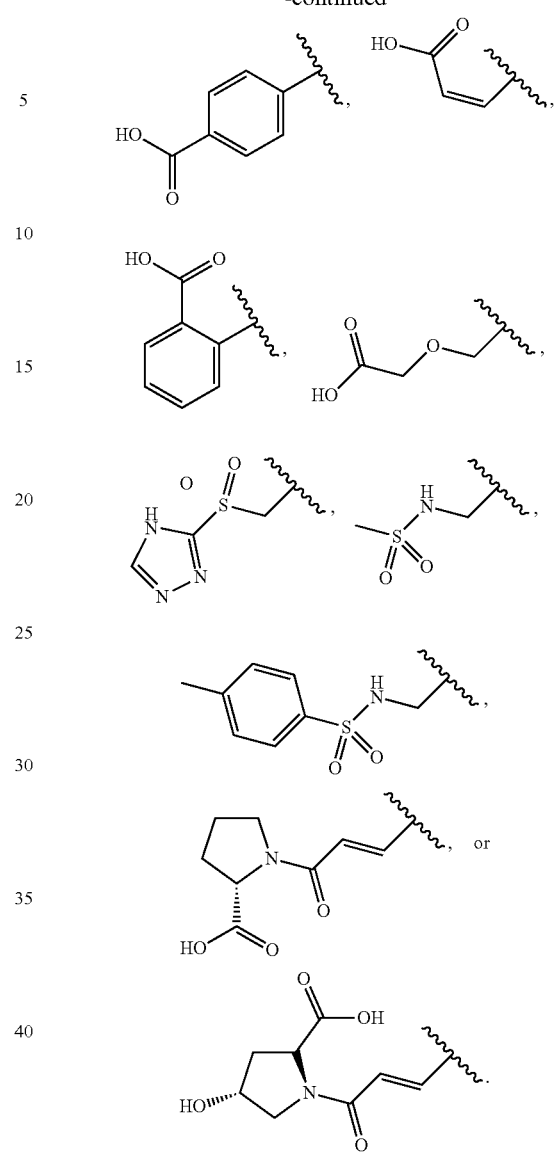
7. The compound according to claim 1, or a pharmacologically acceptable salt thereof, wherein R⁴ is
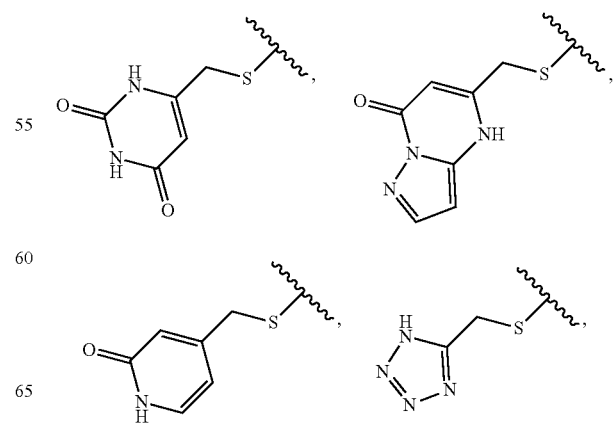

-continued

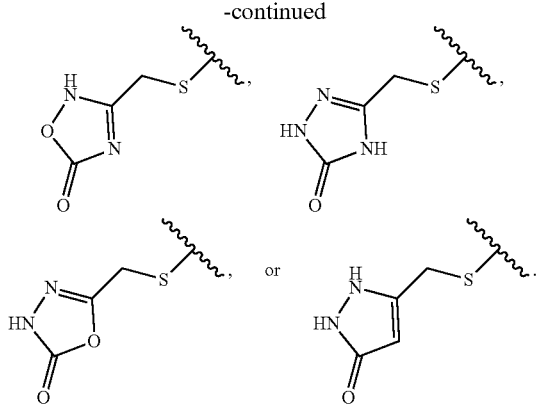

8. The compound according to claim 1, or a pharmacologically acceptable salt thereof, wherein $R^4$ is

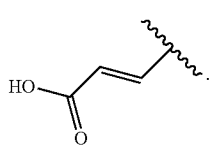

9. The compound according to claim 1, or a pharmacologically acceptable salt thereof, wherein $R^4$ is

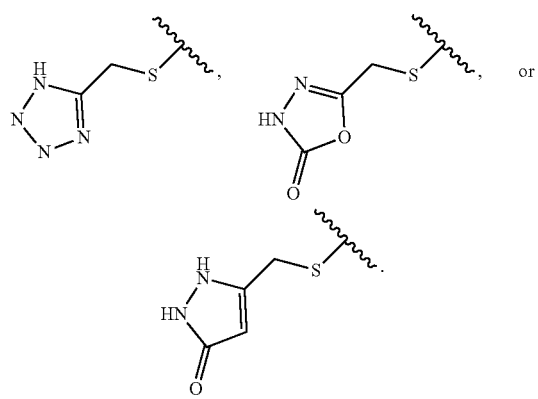

10. A pharmaceutical composition comprising a compound according to claim 1, or a pharmacologically acceptable salt thereof, as an active ingredient.

11. A method for treating a disease, comprising administering a pharmacologically effective amount of a compound according to claim 1, or a pharmacologically acceptable salt thereof.

12. The method according to claim 11, wherein the disease comprises cardiovascular disease, coronary heart disease, stroke, heart failure, systolic heart failure, diastolic heart failure, diabetic heart failure, heart failure with preserved ejection fraction, cardiomyopathy, myocardial infarction, left ventricular dysfunction, left ventricular dysfunction after myocardial infarction, cardiac hypertrophy, myocardial remodeling, myocardial remodeling after infarction, myocardial remodeling after cardiac surgery, valvular heart disease, metabolic disease, metabolic syndrome, insulin resistance, diabetes mellitus, diabetic late complications, diabetic macrovasculopathy, diabetic microvasculopathy, diabetic nephropathy, diabetic retinopathy, diabetic neuropathies, cardiac autonomic neuropathy, CNS-dependent disturbed fluid homeostasis, CNS-independent disturbed fluid homeostasis, acute renal failure, chronic renal failure, hypertension, pulmonary hypertension, portal hypertension, systolic hypertension, vascular disease, vascular hypertrophy, vascular remodeling, vascular stiffness, atherosclerosis, peripheral arterial occlusive disease (PAOD), restenosis, thrombosis, vascular permeability disorder, cardiac, renal, or retinal disorder caused by ischemia, or cardiac, renal, or retinal disorder caused by reperfusion.

13. The method according to claim 11, wherein the disease comprises cardiovascular disease, coronary heart disease, stroke, heart failure, systolic heart failure, diastolic heart failure, diabetic heart failure, heart failure with preserved ejection fraction, cardiomyopathy, myocardial infarction, left ventricular dysfunction, left ventricular dysfunction after myocardial infarction, cardiac hypertrophy, myocardial remodeling, myocardial remodeling after infarction, myocardial remodeling after cardiac surgery, or valvular heart disease.

14. The method according to claim 11, wherein the disease comprises metabolic disease, metabolic syndrome, insulin resistance, diabetes mellitus, diabetic late complications, diabetic macrovasculopathy, diabetic microvasculopathy, diabetic nephropathy, diabetic retinopathy, diabetic neuropathies, or cardiac autonomic neuropathy.

15. The method according to claim 11, wherein the disease comprises CNS-dependent disturbed fluid homeostasis, CNS-independent disturbed fluid homeostasis, acute renal failure, chronic renal failure, hypertension, pulmonary hypertension, portal hypertension, or systolic hypertension.

16. The method according to claim 11, wherein the disease comprises vascular disease, vascular hypertrophy, vascular remodeling, vascular stiffness, atherosclerosis, peripheral arterial occlusive disease (PAOD), restenosis, thrombosis, vascular permeability disorder, cardiac, renal, or retinal disorder caused by ischemia, or cardiac, renal, or retinal disorder caused by reperfusion.

17. The method according to claim 11, wherein the disease comprises pulmonary hypertension.

18. A method for agonizing apelin receptor activity in a subject, comprising administering a compound according to claim 1, or a pharmacologically acceptable salt thereof, to a subject.

19. A method for treating a disease or condition treatable by agonizing apelin receptor, comprising administering to a subject in need thereof a therapeutically effective amount of a compound according to claim 1, or a pharmacologically acceptable salt thereof, wherein the disease or condition is cardiovascular disease, coronary heart disease, stroke, heart failure, systolic heart failure, diastolic heart failure, diabetic heart failure, heart failure with preserved ejection fraction, cardiomyopathy, myocardial infarction, left ventricular dysfunction, left ventricular dysfunction after myocardial infarction, cardiac hypertrophy, myocardial remodeling, myocardial remodeling after infarction, myocardial remodeling after cardiac surgery, valvular heart disease, metabolic disease, metabolic syndrome, insulin resistance, diabetes mellitus, diabetic late complications, diabetic macrovasculopathy, diabetic microvasculopathy, diabetic nephropathy, diabetic retinopathy, diabetic neuropathies, cardiac autonomic neuropathy, CNS-dependent disturbed fluid homeostasis, CNS-independent disturbed fluid homeostasis, acute renal failure, chronic renal failure, hypertension, pulmonary hypertension, portal hypertension, systolic hypertension, vascular disease, vascular hypertrophy, vascular remodeling, vascular stiffness, atherosclerosis, peripheral arterial occlusive disease (PAOD), restenosis, thrombosis, vascular permeability disorder, cardiac, renal, or retinal disorder caused by ischemia, or cardiac, renal, or retinal disorder caused by reperfusion.

* * * * *

UNITED STATES PATENT AND TRADEMARK OFFICE
CERTIFICATE OF CORRECTION

PATENT NO.         : 11,155,525 B2                               Page 1 of 1
APPLICATION NO.    : 16/853604
DATED              : October 26, 2021
INVENTOR(S)        : Takuya Ikeda et al.

It is certified that error appears in the above-identified patent and that said Letters Patent is hereby corrected as shown below:

In the Claims

• Column 121, Line 57:
Claim 1, preceding the list of chemical groups, the claim should read -- $R^4$ is: --

Signed and Sealed this
First Day of March, 2022

Drew Hirshfeld
*Performing the Functions and Duties of the
Under Secretary of Commerce for Intellectual Property and
Director of the United States Patent and Trademark Office*